US011090491B2

(12) United States Patent
Mishra et al.

(10) Patent No.: US 11,090,491 B2
(45) Date of Patent: Aug. 17, 2021

(54) APPARATUS WITH ENHANCED STIMULATION WAVEFORMS

(71) Applicant: Nalu Medical, Inc., Carlsbad, CA (US)

(72) Inventors: Lakshmi Narayan Mishra, Carlsbad, CA (US); James C. Makous, Encinitas, CA (US); Lee Fason Hartley, Carlsbad, CA (US); Daniel M. Pivonka, Encinitas, CA (US); J. Christopher Flaherty, Auburndale, FL (US)

(73) Assignee: Nalu Medical, Inc., Carlsbad, CA (US)

( * ) Notice: Subject to any disclaimer, the term of this patent is extended or adjusted under 35 U.S.C. 154(b) by 162 days.

(21) Appl. No.: 16/104,829

(22) Filed: Aug. 17, 2018

(65) Prior Publication Data
US 2019/0001139 A1   Jan. 3, 2019

Related U.S. Application Data

(63) Continuation of application No. PCT/US2017/017978, filed on Feb. 15, 2017.
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36146* (2013.01); *A61N 1/0556* (2013.01); *A61N 1/0558* (2013.01);
(Continued)

(58) Field of Classification Search
CPC ................ A61N 1/36146; A61N 1/36071
See application file for complete search history.

(56) References Cited

U.S. PATENT DOCUMENTS

| 7,734,340 | B2 | 6/2010 | De Ridder et al. |
| 8,170,675 | B2 | 5/2012 | Alataris et al. |
| (Continued) | | | |

FOREIGN PATENT DOCUMENTS

| WO | WO-2009045297 A1 | 4/2009 |
| WO | WO-2014205129 A1 | 12/2014 |
| (Continued) | | |

OTHER PUBLICATIONS

EP17753756.0 Extended Search Report dated Nov. 11, 2019.
(Continued)

*Primary Examiner* — William J Levicky
(74) *Attorney, Agent, or Firm* — Wilson Sonsini Goodrich and Rosati, P.C.

(57) ABSTRACT

A medical apparatus for a patient comprises an implantable system. The implantable system comprises a first implantable device comprising: at least one implantable functional element configured to deliver stimulation energy to tissue of the patient; and an implantable controller configured to provide a stimulation waveform to the at least one implantable functional element, the stimulation waveform comprising one or more stimulation parameters. The apparatus is configured to randomly vary at least one of the one or more stimulation parameters. Methods of providing stimulation energy with randomly varying stimulation parameters are also provided.

34 Claims, 27 Drawing Sheets

Related U.S. Application Data

(60) Provisional application No. 62/417,907, filed on Nov. 4, 2016, provisional application No. 62/297,679, filed on Feb. 19, 2016.

(52) U.S. Cl.
CPC ..... *A61N 1/36071* (2013.01); *A61N 1/36075* (2013.01); *A61N 1/37205* (2013.01); *A61N 1/37229* (2013.01)

(56) References Cited

U.S. PATENT DOCUMENTS

| | | | |
|---|---|---|---|
| 8,224,453 B2 | 7/2012 | De Ridder et al. | |
| 8,359,102 B2 | 1/2013 | Alataris et al. | |
| 8,401,655 B2 | 3/2013 | De Ridder et al. | |
| 8,712,533 B2 | 4/2014 | Alataris et al. | |
| 8,768,472 B2 | 7/2014 | Fang et al. | |
| 8,792,988 B2 | 7/2014 | Alataris et al. | |
| 8,868,192 B2 | 10/2014 | Alataris et al. | |
| 8,874,222 B2 | 10/2014 | Alataris et al. | |
| 8,886,326 B2 | 11/2014 | Alataris et al. | |
| 8,897,870 B2 | 11/2014 | De Ridder et al. | |
| 8,934,981 B2 | 1/2015 | De Ridder et al. | |
| 9,327,125 B2 | 5/2016 | Alataris et al. | |
| 9,327,126 B2 | 5/2016 | Alataris et al. | |
| 9,327,127 B2 | 5/2016 | Alataris et al. | |
| 9,333,357 B2 | 5/2016 | Alataris et al. | |
| 9,333,358 B2 | 5/2016 | Alataris et al. | |
| 9,480,842 B2 | 11/2016 | Alataris et al. | |
| 9,764,135 B2 | 9/2017 | De Ridder et al. | |
| 2006/0074458 A1 | 4/2006 | Imran et al. | |
| 2007/0049986 A1 | 3/2007 | Imran et al. | |
| 2009/0088817 A1 | 4/2009 | Starkebaum et al. | |
| 2009/0088819 A1* | 4/2009 | Starkebaum | A61N 1/36007 607/40 |
| 2009/0216296 A1* | 8/2009 | Meskens | A61N 1/36036 607/57 |
| 2009/0319005 A1* | 12/2009 | Lineaweaver | A61N 1/36038 607/57 |
| 2010/0036454 A1 | 2/2010 | Bennett et al. | |
| 2010/0114189 A1* | 5/2010 | Donofrio | A61N 1/36114 607/2 |
| 2010/0274316 A1 | 10/2010 | Alataris et al. | |
| 2010/0274318 A1* | 10/2010 | Walker | A61N 1/36175 607/46 |
| 2011/0093032 A1 | 4/2011 | Boggs, II et al. | |
| 2011/0184488 A1* | 7/2011 | De Ridder | A61N 1/36171 607/46 |
| 2011/0218593 A1* | 9/2011 | Rubinstein | A61N 1/36038 607/57 |
| 2011/0264163 A1* | 10/2011 | Tracey | A61N 1/36021 607/41 |
| 2014/0222106 A1 | 8/2014 | Sharma et al. | |
| 2014/0288616 A1* | 9/2014 | Rawat | A61N 1/36067 607/46 |
| 2015/0321000 A1 | 11/2015 | Rosenbluth et al. | |
| 2016/0166835 A1 | 6/2016 | De Ridder et al. | |
| 2016/0331956 A1 | 11/2016 | Yakovlev et al. | |
| 2016/0346546 A1* | 12/2016 | Zhu | A61N 1/37247 |
| 2017/0001003 A1 | 1/2017 | Pivonka et al. | |
| 2017/0095667 A1 | 4/2017 | Yakovlev et al. | |
| 2017/0252552 A1* | 9/2017 | Cook | A61N 1/36025 |
| 2017/0368339 A1 | 12/2017 | De Ridder et al. | |
| 2018/0028824 A1 | 2/2018 | Pivonka et al. | |
| 2018/0256906 A1 | 9/2018 | Pivonka et al. | |
| 2018/0368875 A1 | 12/2018 | Castillo et al. | |
| 2019/0009097 A1 | 1/2019 | Hartley et al. | |
| 2019/0151659 A1 | 5/2019 | Mishra et al. | |
| 2019/0269913 A1 | 9/2019 | Pivonka et al. | |
| 2019/0374776 A1 | 12/2019 | Mishra et al. | |
| 2020/0101291 A1 | 4/2020 | Anatoly et al. | |
| 2020/0139138 A1 | 5/2020 | Sit et al. | |
| 2020/0306528 A1 | 10/2020 | Linden et al. | |
| 2020/0398058 A1 | 12/2020 | Pivonka et al. | |

FOREIGN PATENT DOCUMENTS

| | | |
|---|---|---|
| WO | WO-2015139053 A1 | 9/2015 |
| WO | WO-2015179177 A1 | 11/2015 |
| WO | WO-2015196164 | 12/2015 |
| WO | WO-2016127130 A1 | 8/2016 |
| WO | WO-2016191055 A1 | 12/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |
| WO | WO-2021003439 | 1/2021 |

OTHER PUBLICATIONS

Lenssen et al. Bimodal listeners are not sensitive to interaural time differences in unmodulated low-frequency stimuli (L). J. Acoust. Soc. Am. 129(6):3457-3460 (2011).

PCT/US17/17978 International Search Report dated May 5, 2017.

* cited by examiner

APPARATUS WITH ENHANCED STIMULATION WAVEFORMS

CROSS REFERENCE

This application is a continuation of PCT Application No. PCT/US2017/017978, titled "Apparatus with Enhanced Stimulation Waveforms", filed Feb. 15, 2017, which claims priority to U.S. Provisional Application Ser. No. 62/297,679, titled "Apparatus with Enhanced Stimulation Waveforms", filed Feb. 19, 2016, and U.S. Provisional Application Ser. No. 62/417,907, titled "Apparatus with Enhanced Stimulation Waveforms", filed Nov. 4, 2016, the content of each of which is incorporated herein by reference in its entirety for all purposes.

DESCRIPTION OF THE INVENTION

Related Applications

This application is related to: U.S. patent application Ser. No. 14/975,358, titled "Method and Apparatus for Minimally Invasive Implantable Modulators", filed Dec. 18, 2015; U.S. patent application Ser. No. 15/264,864, titled "Method and Apparatus for Versatile Minimally Invasive Neuromodulators", filed Sep. 14, 2016; U.S. patent application Ser. No. 15/38,729, titled "Method and Apparatus for Neuromodulation Treatments of Pain and Other Conditions", filed Dec. 20, 2016; International PCT Patent Application Serial Number PCT/US2016/016888, titled "Medical Apparatus including an Implantable System and an External System", filed Feb. 5, 2016; International PCT Patent Application Serial Number PCT/US2016/051177, titled "Apparatus for Peripheral or Spinal Stimulation", filed Sep. 9, 2016; the content of each of which is incorporated herein by reference in its entirety for all purposes.

Field of the Invention

The present invention relates generally to medical apparatus for a patient, and in particular, apparatus that deliver enhanced stimulation waveforms to effectively treat pain while avoiding undesired effects.

BACKGROUND OF THE INVENTION

Implantable devices that treat a patient and/or record patient data are known. For example, implants that deliver energy such as electrical energy, or deliver agents such as pharmaceutical agents are commercially available. Implantable electrical stimulators can be used to pace or defibrillate the heart, as well as modulate nerve tissue (e.g. to treat pain). Most implants are relatively large devices with batteries and long conduits, such as implantable leads configured to deliver electrical energy or implantable tubes (i.e. catheters) to deliver an agent. These implants require a fairly invasive implantation procedure, and periodic battery replacement, which requires additional surgery. The large sizes of these devices and their high costs have prevented their use in a variety of applications.

Nerve stimulation treatments have shown increasing promise recently, showing potential in the treatment of many chronic diseases including drug-resistant hypertension, motility disorders in the intestinal system, metabolic disorders arising from diabetes and obesity, and both chronic and acute pain conditions among others. Many of these implantable device configurations have not been developed effectively because of the lack of miniaturization and power efficiency, in addition to other limitations.

There is a need for apparatus, systems, devices and methods that provide one or more implantable devices and are designed to provide enhanced treatment of pain and other enhanced benefits.

SUMMARY

According to an aspect of the present inventive concepts, a medical apparatus for a patient comprises an implantable system. The implantable system comprises a first implantable device comprising at least one implantable functional element configured to deliver stimulation energy to tissue of the patient, and an implantable controller configured to provide a stimulation waveform to the at least one implantable functional element, the stimulation waveform comprising one or more stimulation parameters. The apparatus can be configured to randomly vary at least one of the one or more stimulation parameters.

In some embodiments, the apparatus is configured to treat pain. The apparatus can be configured to treat pain selected from the group consisting of: back pain; joint pain; neuropathic pain; tennis elbow; muscle pain; shoulder pain; chronic, intractable pain of the back; chronic intractable pain of the lower limbs; unilateral pain; bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations thereof. The apparatus can be configured to stimulate tissue selected from the group consisting of: spinal cord tissue; spinal cord nerves; spinal cord ganglia; tissue associated with the spinal cord; nerves associated with the spinal cord; ganglia associated with the spinal cord; and combinations thereof. The apparatus can be configured to stimulate dorsal root ganglia. The apparatus can be configured to stimulate one or more peripheral nerves.

In some embodiments, the apparatus is configured to treat a disease or disorder selected from the group consisting of: chronic pain; acute pain; migraine; cluster headaches; urge incontinence; overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations thereof.

In some embodiments, the apparatus is configured to treat heart disease. The apparatus can be configured to stimulate the spinal cord.

In some embodiments, the first implantable device comprises an implantable energy storage assembly, and at least a portion of the stimulation energy is provided by the implantable energy storage assembly. The implantable energy storage assembly can comprise at least one of a battery or a capacitor. The implantable energy storage assembly can provide continuous and/or intermittent stimulation energy over a time period of at least 1 hour, at least one day, at least 1 month and/or at least 1 year. In some embodiments, the first implantable device does not receive power from an external source during at least a portion of the time period in which the stimulation energy is delivered. The implantable energy storage assembly can be configured to store at least 1 mWh of energy. The implantable energy storage assembly can be configured to store at least 1 Wh of energy. The implantable energy storage assembly can provide continuous and/or intermittent stimulation energy for at least one charge-balanced pulse.

In some embodiments, the first implantable device further comprises at least one implantable antenna configured to receive the first transmission signal from the first external device, an implantable receiver configured to receive the first transmission signal from the at least one implantable antenna, an implantable energy storage assembly configured to provide power to an element selected from the group consisting of: the at least one implantable functional element; the implantable controller; the implantable receiver; and combinations thereof, and an implantable housing surrounding at least the implantable controller and the implantable receiver. The implantable housing can further surround the at least one implantable antenna.

In some embodiments the medical apparatus further comprises an external system configured to transmit one or more transmission signals, each transmission signal comprising at least power or data, and the external system comprises a first external device comprising: at least one external antenna configured to transmit a first transmission signal to the implantable system, the first transmission signal comprising at least power or data; an external transmitter configured to drive the at least one external antenna; an external power supply configured to provide power to at least the external transmitter; and an external controller configured to control the external transmitter; and the implantable system can be configured to receive the one or more transmission signals from the external system.

In some embodiments, the apparatus is configured to reduce paresthesia by performing a function selected from the group consisting of: incorporating patient feedback; monitoring evoked potentials; using data provided by positional sensors; adjusting stimulation based upon known heuristics; and combinations thereof.

In some embodiments, the at least one functional element comprises at least two electrodes, and the first implantable device is configured to deliver stimulation energy to the at least two electrodes to stimulate target tissue and reduce stimulation to non-target tissue. The stimulation waveform can comprise pulses including at least 3 phases.

In some embodiments, the apparatus is configured to perform charge constancy. The first implantable device can provide a normalizing pulse that charge balances one or more pulses that include one or more randomly varied stimulation parameters. The first implantable device can further comprise a DC charge recovery mechanism configured to perform the charge constancy. The charge constancy can comprise passive charge recovery. The charge constancy can comprise exponential charge recovery. The charge constancy can comprise active charge recovery. The charge constancy can comprise active charge recovery and passive charge recovery.

In some embodiments, the apparatus is configured to provide therapeutic constancy. The therapeutic constancy can be based on strength-duration information. The therapeutic constancy can be related to a cumulative stimulation pulse comprising the amount of charge delivered in a time period. The first implantable device can be configured to deliver a residual therapy pulse that achieves the desired therapeutic constancy. The residual stimulation energy delivered can comprise one or more randomly varied stimulation parameters.

In some embodiments, the apparatus is configured to provide compliance optimization. The compliance optimization can comprise voltage compliance. The compliance optimization can be configured to maintain a minimum voltage during one or more stimulation pulses. The compliance optimization can be configured to reduce pulse width of one or more stimulation pulses such that current levels required are increased to deliver a target amount of charge. The compliance optimization can be configured to select pulse width and current of one or more stimulation pulses to optimize compliance voltage. The first implantable device can further comprise a sensor configured to measure tissue impedance, and the first implantable device can be configured to automatically adjust the pulse width and/or current of one or more stimulation pulses to provide compliance optimization.

In some embodiments, the apparatus is configured to provide a compliance optimized burst. The stimulation waveform can comprise an element selected from the group consisting of: monophasic pulses; biphasic pulses; triphasic pulses; train-on period between 1 μsec and 100 msec; train-off period between 1 μsec and 100 msec; burst-on period comprising between 2 and 1000 trains; two similar trains; two dissimilar trains; burst-off period between 1 μsec and 10 seconds; delivery of non-zero energy during quiescent period; and combinations thereof. The stimulation waveform can comprise an element selected from the group consisting of: one or more train-on periods with a duration of approximately 790 μsec; one or more pulses each comprising at least two phases of approximately 10 μsec each; one or more inter-phase gaps each with a duration of approximately 10 μsec; one or more inter-pulse gaps each with a duration of approximately 10 μsec; a train-off period with a duration of approximately 910 μsec; an inter-pulse gap with a duration of approximately 10 μsec; a pulse width of approximately 30 μsec; a pulse train comprising approximately 10 pulses; a burst-on period of approximately 8.5 msec; a burst-off period of approximately 16.5 msec; and combinations thereof.

In some embodiments, the stimulation energy delivered comprises energy selected from the group consisting of: electrical energy; magnetic energy; electromagnetic energy; light energy; infrared light energy; visible light energy; ultraviolet light energy; mechanical energy; thermal energy; heat energy; cryogenic energy; sound energy; ultrasonic sound energy; high intensity focused ultrasound energy; low intensity focused ultrasound energy; subsonic sound energy; chemical energy; and combinations thereof.

In some embodiments, the stimulation energy delivered comprises energy selected from the group consisting of: electrical energy; constant or otherwise controlled electrical current and/or voltage applied to tissue; magnetic energy; magnetic field energy provided by applying controlled current or voltage to a coil or other magnetic field generating element positioned proximate tissue; electromagnetic energy provided by applying both current to tissue and a magnetic field to tissue; and combinations thereof. The stimulation energy delivered can comprise electrical energy. The stimulation energy delivered can comprise energy delivered in a multiphasic waveform configured to minimize stimulation of non-target tissue. The apparatus can be configured to deliver the stimulation energy while avoiding undesired charge accumulation.

In some embodiments, the stimulation waveform comprises an element selected from the group consisting of: a combination of low frequency stimulation and burst stimulation; burst stimulation; a combination of low frequency stimulation and high frequency stimulation; a combination of low frequency stimulation, high frequency stimulation and burst stimulation; and combinations thereof.

In some embodiments, the at least one functional element comprises a first functional element configured to deliver a first stimulation waveform and a second functional element configured to deliver a second stimulation waveform. The first stimulation waveform and the second stimulation waveform can be delivered simultaneously and/or sequentially.

In some embodiments, the stimulation waveform comprises a high frequency carrier signal modulated with a low frequency envelope. The low frequency envelope can comprise a frequency between 0.1 Hz and 1500 Hz. The high frequency carrier can comprise a frequency between 1 Hz and 10 kHz. The low frequency envelope can comprise a frequency of approximately 40 Hz and the high frequency carrier can comprise a frequency of approximately 10 kHz. The stimulation waveform can comprise pulses with a shape selected from the group consisting of: square; rectangle; triangle; symmetric triangle; asymmetric triangle; trapezoid; sawtooth; ramp; and combinations thereof. The stimulation waveform can comprise a biphasic pulse, a high frequency carrier signal of approximately 10 kHz and a low frequency envelope with a frequency of between 40 Hz and 100 Hz.

In some embodiments, the stimulation waveform comprises amplitude modulated signals comprising a high frequency carrier with low frequency modulation.

In some embodiments, the stimulation waveform comprises a series of amplitude modulated pulses. The amplitude of the stimulation waveform can be varied continuously. The amplitude modulated pulses can sweep from 2 mA to 3 mA. The amplitude of the stimulation waveform can be varied between 2 mA and 3 mA every second. The amplitude of the stimulation waveform can be varied between 1 mA and 3 mA. The stimulation waveform can be varied between 0 mA and 3 mA. The stimulation waveform can comprise a component selected from the group consisting of: a carrier frequency between 1 kHz and 50 kHz; a modulation frequency between 0.1 Hz and carrier frequency; a depth of modulation between 0.1% and 100%; and combinations thereof. The stimulation waveform can be modulated with a square wave. The stimulation waveform can be modulated with a signal selected from the group consisting of: sinusoid; square; rectangle; triangle; symmetric triangle; asymmetric triangle; trapezoid; sawtooth; ramp; piece-wise step function; and combinations thereof. The stimulation waveform can comprise a carrier signal with a frequency between 0.01 Hz and 1500 Hz. The stimulation waveform can comprise an amplitude modulated signal with a frequency between 1 Hz and 100 kHz.

In some embodiments, the stimulation waveform comprises frequency modulated signals configured to avoid accommodation by creating a continuously varying pulse train.

In some embodiments, the stimulation waveform comprises a series of frequency modulated pulses. The stimulation waveform can comprise a component selected from the group consisting of: a signal that modulates between 2.0 kHz and 3.0 kHz every second; a carrier frequency between 1 kHz and 50 kHz; a modulation frequency between 0.1 Hz and 10 kHz; a modulation range between 1 Hz and the carrier frequency; and combinations thereof. The stimulation waveform can comprise a pulse shape selected from the group consisting of: rectangle; triangle; symmetric triangle; asymmetric triangle; trapezoid; sawtooth; ramp; and combinations thereof. The stimulation waveform can comprise an amplitude that is varied. The amplitude can be modulated independent of the frequency modulation.

In some embodiments, the stimulation waveform comprises pulses modulated by a wave selected from the group consisting of: rectangle wave; triangle wave; symmetric triangle wave; asymmetric triangle wave; trapezoid wave; sawtooth wave; ramp wave; and combinations thereof. The stimulation waveform can comprise a signal with a frequency greater than 1 kHz. The stimulation waveform can comprise pulses with a pulse width between 1 μsec and 10 msec. The stimulation waveform can comprise pulses with a pulse width between 10 μsec and 300 μsec. The stimulation waveform can comprise cathodic pulses and anodic pulses. The stimulation waveform can be charge balanced.

In some embodiments, the at least one implantable functional element comprises a first functional element and a second functional element, and the first functional element is configured to deliver stimulation energy at a first frequency, and the second functional element is configured to deliver stimulation energy at a second frequency different than the first frequency. The first frequency can be a high frequency and the second frequency can be a low frequency. The first functional element and the second functional element can deliver stimulation energy simultaneously.

In some embodiments, the stimulation waveform comprises a first burst at a first frequency and a first amplitude, a second burst at a second frequency and a second amplitude, and at least one of: the first frequency and the second frequency are different or the first amplitude and the second amplitude are different.

In some embodiments, the medical apparatus further comprises a first external device, and the first implantable device receives a power transmission from the first external device, and the stimulation waveform is independent of the power transmission.

In some embodiments, the stimulation waveform comprises a current amplitude between 0.01 mA and 15 mA, such as between 0.1 mA and 15 mA. The stimulation waveform can comprise a current amplitude between 0.1 mA and 12 mA. The stimulation waveform can comprise a current amplitude between 0.1 mA and 10 mA.

In some embodiments, the stimulation waveform comprises at least low frequency stimulation (e.g. electrical energy comprising a low frequency signal). The stimulation waveform can further comprise at least a high frequency signal. The lower frequency signal can be delivered to elicit patient feedback and the high frequency signal can be delivered to treat pain. The low frequency signal can comprise a frequency between 1 Hz and 1 kHz. The low frequency signal can be configured to stimulate motor nerves to improve tone, improve structural support and/or induce paresthesia. The stimulation waveform can further comprise a high frequency signal configured to treat pain. The stimulation waveform can further comprise burst stimulation. The low frequency signal and the burst stimulation can be delivered simultaneously and/or sequentially. The at least one functional element can comprise a first functional element configured to deliver the low frequency signal, and a second functional element configured to deliver the burst stimulation.

In some embodiments, the stimulation waveform comprises at least one high frequency signal. The stimulation waveform can further comprise at least one low frequency signal. The high frequency signal can comprise a frequency between 600 Hz and 50 kHz. The high frequency signal can comprise a frequency between 1 kHz and 20 kHz. The high frequency signal can comprise a signal of at least 600 Hz, 1.0 kHz, 1.2 kHz, 5 kHz, 10 kHz and/or 25 kHz.

In some embodiments, the stimulation waveform is void of a low frequency signal below 100 Hz, 500 Hz, 1000 Hz, 1200 Hz and/or 1500 Hz.

In some embodiments, the stimulation waveform comprises a high frequency signal modulated with a low frequency signal. The modulation can comprise a modulation selected from the group consisting of: frequency modulation; amplitude modulation; phase modulation; pulse width modulation; and combinations thereof.

In some embodiments, the stimulation waveform comprises a waveform selected from the group consisting of: pseudo random binary sequence (PRBS) non-return to zero waveform; pseudo random binary sequence (PRBS) return to zero waveform; and combinations thereof. The stimulation waveform can comprise pulses with a fixed pulse width and/or fixed frequency. The stimulation waveform can comprise pulses with varying pulse width and/or varying frequency.

In some embodiments, the stimulation waveform comprises a variation in a parameter selected from the group consisting of: frequency; amplitude; a time period; a time period between pulses; a time period between pulse trains; pulse width; multiple piecewise or continuous variations of one of more stimulation parameters in a single pulse; pulse symmetry; stimulation energy over a time window and/or overlapping time windows; power in the frequency spectrum of the stimulation waveform; and combinations thereof. The variation can comprise a random variation.

In some embodiments, the stimulation waveform comprises a biphasic pulse.

In some embodiments, the stimulation waveform comprises a triphasic pulse.

In some embodiments, the stimulation waveform comprises a multiphasic pulse train. The multiphasic pulse train can be configured to maintain charge balance.

In some embodiments, the stimulation waveform comprises a biphasic pulse train.

In some embodiments, the stimulation waveform comprises a pulse with an exponential portion. The stimulation waveform can comprise a dynamic return pulse including a current of at least 1 mA. The dynamic return pulse can comprise a duration of approximately 1 μsec. The dynamic return pulse can decay to a current of approximately 100 nA. The dynamic return pulse can decay with a time constant between 1 μsec and 100 sec.

In some embodiments, the medical apparatus further comprises a sensor configured to produce a sensor signal, and the apparatus is configured to adjust the stimulation waveform based on the sensor signal. The first implantable device can comprise the sensor. The apparatus can be configured to automatically adjust the waveform based on the sensor signal.

In some embodiments, the stimulation waveform comprises pulses of varying shape. The stimulation waveform can comprise pulses with a shape selected from the group consisting of: a sinusoidal geometry; a square geometry; a rectangular geometry; a triangular geometry; a symmetric triangular geometry; an asymmetric triangle geometry; a trapezoidal geometry; a sawtooth geometry; a ramped geometry; an exponential geometry; a piece-wise step function geometry; a root-raised cosine geometry; and combinations thereof.

In some embodiments, the stimulation waveform comprises a charge recovery phase. The charge recovery phase can be varied over time.

In some embodiments, the stimulation waveform comprises continuously balanced analog current waveforms. The implantable controller can comprise at least one current source configured to provide the stimulation energy to the at least one implantable functional element. The at least one current source can comprise at least one differential Howland current source. The at least one implantable functional element can comprise multiple functional elements, and the at least one current source can comprise a first current source, and the implantable controller can further comprise a switch matrix connecting the first current source to the multiple functional elements. The implantable controller can further comprise a capacitor attached to the at least one current source and configured to receive a stimulation waveform signal and provide DC balance.

In some embodiments, the stimulation waveform comprises a current between 100 nA and 40 mA. The stimulation waveform can comprise a current between 0.5 mA and 10 mA.

In some embodiments, the stimulation waveform comprises a voltage less than or equal to 20V. The stimulation waveform can comprise a voltage between 0.1V and 15V, such as between 1V and 15V.

In some embodiments, the stimulation waveform comprises asymmetric pulses. The asymmetric pulses can comprise amplitude ratios between 1:1 and 10,000:1. The asymmetric pulses can comprise pulse width ratios between 1:1 and 10,000:1. The asymmetric pulses can comprise a pulse width between 1 μsec and 10 msec. The asymmetric pulses can comprise a pulse width between 10 μsec and 300 μsec.

In some embodiments, the stimulation waveform comprises pulses with a shape configured to influence the onset and/or patient perception of neural activation. The shape can comprise a triangle wave. The pulses can comprise a pulse width between 1 μsec and 10 msec. The pulses can comprise a pulse width between 10 μsec and 300 μsec.

In some embodiments, the stimulation waveform comprises a planned series of pulses from which at least one pulse is randomly removed. The medical apparatus can further comprise a probability distribution, and the at least one pulse can be removed based on the probability distribution. The stimulation waveform can further comprise a randomly varying stimulation parameter. The stimulation waveform can further comprise a pulse randomly added to the planned series of pulses.

In some embodiments, the stimulation waveform comprises a planned series of pulses to which at least one pulse is randomly added. The medical apparatus can further comprise a probability distribution, and the at least one pulse can be added based on the probability distribution. The stimulation waveform can further comprise a randomly varying stimulation parameter. The stimulation waveform can further comprise a pulse randomly removed from the planned series of pulses.

In some embodiments, the stimulation waveform comprises a train. The train can comprise high frequency signals. The train can comprise low frequency signals. The train can comprise pulses with a pulse width between 5 μsec and 1 msec. The train can comprise a stimulation parameter that is randomly varied. The randomly varied stimulation parameter can comprise a parameter selected from the group consisting of: amplitude; average amplitude; peak amplitude; frequency; average frequency; period; phase; polarity; pulse shape; a duty cycle parameter; inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations thereof. The train can comprise pulses with a pulse shape selected from the group consisting of: sinusoid; square, rectangle; triangle; symmetric triangle; asymmetric triangle; trapezoid; sawtooth; ramp; linear ramp; exponential curve; piece-wise step function; and combinations thereof. The train can comprise an inter-pulse gap with a first duration and an inter-train period with a second duration, and the first duration can be less than the second duration. The train can comprise an inter-pulse gap with a first duration and an inter-train period with a second duration, and the first duration comprises a time between 0.1 µsec and the second duration. The train can comprise an inter-pulse gap with a duration between 1 µsec and 1 second. The train can comprise an inter-train period with a duration between 1 µsec and 24 hours. The train can comprise a train-on period with a duration between 10 µsec and 24 hours. The train can comprise an envelope with a shape selected from the group consisting of: cosine; cosine-squared; sine; square; rectangle; triangle; symmetric triangle; asymmetric triangle; trapezoid: sawtooth; ramp; linear ramp; and combinations thereof. The train can comprise a train ramp duration between 1 µsec and 10 minutes. The train can comprise a depth of modulation between 1% and 99%. The train can comprise pulses with a first amplitude and pulses with a second amplitude, and the second amplitude can be greater than the first amplitude. The pulses at the first amplitude and/or the pulses at the second amplitude can be delivered at a high frequency. The high frequency can comprise a frequency greater than 1 kHz. The pulses at the first amplitude can be delivered at a first frequency, and the pulses at the second amplitude can be delivered at a second frequency, and the first frequency can be different than the second frequency. The second frequency can be lower than the first frequency. The second frequency can be greater than the first frequency. The pulses at the first amplitude and/or the pulses at the second amplitude can comprise a pulse width between 1 µsec and 10 msec. The pulses at the first amplitude and/or the pulses at the second amplitude can comprise a pulse width between 10 µsec and 300 µsec.

In some embodiments, the stimulation waveform comprises a burst. The burst can comprise low frequency signals. The burst can comprise high frequency signals. The burst can comprise pulses with a pulse width between 5 µsec and 1 msec. The burst can comprise a stimulation parameter that is randomly varied. The randomly varied stimulation parameter can comprise a parameter selected from the group consisting of: amplitude; average amplitude; peak amplitude; frequency; average frequency; period; phase; polarity; pulse shape; a duty cycle parameter; inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations thereof. The burst can comprise pulses with a pulse shape selected from the group consisting of: sinusoid; square, rectangle; triangle; symmetric triangle; asymmetric triangle; trapezoid; sawtooth; ramp; linear ramp; exponential curve; piece-wise step function; and combinations thereof. The burst can comprise an inter-pulse gap with a first duration and an inter-train period with a second duration, and the first duration can be less than the second duration. The burst can comprise an inter-pulse gap with a first duration and an inter-train period with a second duration, and the first duration can comprise a time between 0.1 µsec and the second duration. The burst can comprise an inter-pulse gap with a duration between 1 µsec and 1 second. The burst can comprise an inter-train period with a duration between 1 µsec and 24 hours. The burst can comprise an inter-burst period with a duration between 20 µsec and 24 hours. The burst can comprise an inter-train period with a duration between 1 µsec and 24 hours. The burst can comprise a train-on period between 10 µsec and 24 hours. The burst can comprise a train envelope and/or burst envelope with a shape selected from the group consisting of: cosine; cosine-squared; sine; square; rectangle; triangle; symmetric triangle; asymmetric triangle; trapezoid: sawtooth; ramp; linear ramp; and combinations thereof. The burst can comprise a train ramp duration and/or burst ramp duration between 1 µsec and 10 minutes. The burst can comprise a depth of modulation between 1% and 99%. The burst can comprise pulses with a shape selected from the group consisting of: sinusoid; square; rectangle; triangle; symmetric triangle; asymmetric triangle; trapezoid; sawtooth; ramp; and combinations thereof. The burst can comprise a repeated pulse train comprising a stimulation parameter selected from the group consisting of: 3 to 6 pulses in each train; pulse widths of approximately 1 msec; inter-pulse gap of approximately 4 msec; inter-train period of approximately 25 msec; a train-on period of approximately 16 msec; and combinations thereof. The burst can comprise pulses with a pulse width between 5 µsec and 1 msec. The burst can comprise an inter-pulse gap with a duration between 20 µsec and 1 sec. The inter-pulse gap can vary with a variation magnitude between 0.1 µsec and 1 msec. The burst can comprise an inter-burst period with a duration between 20 µsec and 24 hours. The inter-burst period can vary with a variation magnitude between 1 µsec and 24 hours. The burst can comprise a shaped burst envelope. The burst envelope can comprise a shape selected from the group consisting of: cosine; cosine-squared; sine; trapezoid; ramp; square; rectangular; triangular; and combinations thereof. The burst can comprise a burst ramp duration between 1 µsec and 10 minutes.

In some embodiments, the stimulation parameters comprise a parameter selected from the group consisting of: amplitude; voltage amplitude; current amplitude; average amplitude; peak amplitude; frequency; average frequency; period; phase; polarity; pulse shape; a duty cycle parameter; inter-pulse gap; polarity; burst-on period; burst-off period; inter-burst period; pulse train; train-on period; train-off period; inter-train period; drive impedance; duration of pulse; duration of amplitude level; duration of stimulation waveform; repetition of stimulation waveform; an amplitude modulation parameter; a frequency modulation parameter; a burst parameter; a power spectral density parameter; an anode/cathode configuration parameter; amount of energy to be delivered; amount of power to be delivered; rate of energy delivery; rate of power delivery; time of energy delivery initiation; method of charge recovery; and combinations thereof.

In some embodiments, the apparatus is configured to randomly vary at least one of the one or more stimulation parameters to at least one of avoid accommodation or reduce synchrony of neuronal firing. The medical apparatus can further comprise a probability distribution, and the apparatus can be configured to randomly vary at least one of the one or more stimulation parameters based on the probability distribution. The apparatus can be configured to randomly vary at least one of the one or more stimulation parameters to reduce at least one of paresthesia or patient discomfort. The apparatus can be configured to randomly vary at least one of the one or more stimulation parameters to improve pain relief. The apparatus can randomly vary a parameter selected from the group consisting of: inter-pulse gap; pulse width; amplitude; and combinations thereof. The apparatus can randomly vary a parameter selected from the group consisting of: amplitude; voltage amplitude; current amplitude; average amplitude; peak amplitude; frequency; average frequency; period; phase; polarity; pulse shape; a duty cycle parameter; duty cycle frequency, duty cycle pulse width; duty cycle off time; inter-pulse gap; polarity; burst-on period; burst-off period; inter-burst period; pulse train; train-on period; train-off period; inter-train period; drive impedance; duration of pulse; duration of amplitude level; duration of stimulation waveform; repetition of stimulation waveform; an amplitude modulation parameter; a frequency modulation parameter; a burst parameter; a power spectral density parameter; an anode/cathode configuration parameter; amount of energy to be delivered; amount of power to be delivered; rate of energy delivery; rate of power delivery; time of energy delivery initiation; method of charge recovery; and combinations thereof. The stimulation waveform can comprise an FM modulated signal.

In some embodiments, the apparatus is configured to randomly vary at least one of the one or more stimulation parameters to reduce an undesired patient condition. The apparatus can be configured to randomly vary at least one of the one or more stimulation parameters to reduce paresthesia. The apparatus can randomly vary a parameter selected from the group consisting of: amplitude; voltage amplitude; current amplitude; average amplitude; peak amplitude; frequency; average frequency; period; phase; polarity; pulse shape; a duty cycle parameter; duty cycle frequency, duty cycle pulse width; duty cycle off time; inter-pulse gap; polarity; burst-on period; burst-off period; inter-burst period; pulse train; train-on period; train-off period; inter-train period; drive impedance; duration of pulse; duration of amplitude level; duration of stimulation waveform; repetition of stimulation waveform; an amplitude modulation parameter; a frequency modulation parameter; a burst parameter; a power spectral density parameter; an anode/cathode configuration parameter; amount of energy to be delivered; amount of power to be delivered; rate of energy delivery; rate of power delivery; time of energy delivery initiation; method of charge recovery; and combinations thereof.

In some embodiments, the apparatus is configured to randomly vary at least one of the one or more stimulation parameters to elicit a neurostimulation effect selected from the group consisting of: synchronized superthreshold neuronal activation; stochastic activation; sub-paresthesia neuronal stimulation; and combinations thereof.

In some embodiments, the medical apparatus further comprises a probability distribution, and the apparatus is configured to randomly vary at least one of the one or more stimulation parameters based on the probability distribution. The probability distribution can comprise a distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations thereof. The apparatus can be configured to shift the probability distribution during use. The apparatus can be configured to shift the probability distribution based on patient position. The apparatus can be configured to shift the probability distribution based on patient feedback. The apparatus can be configured to shift the probability distribution based on an assessment of patient comfort. The apparatus can be configured to shift the probability distribution based on an assessment of paresthesia. The apparatus can be configured to shift the probability distribution based on an assessment of treatment efficacy. The apparatus can be configured to shift the probability distribution based on an assessment of pain relief.

In some embodiments, the apparatus is configured to randomly vary the inter-pulse gap of the delivered stimulation energy. The medical apparatus can further comprise a probability distribution, and the inter-pulse gap can be varied based on the probability distribution.

In some embodiments, the apparatus is configured to randomly vary frequency of the delivered stimulation energy. The medical apparatus can further comprise a probability distribution, and the frequency can be varied based on the probability distribution. The probability distribution can comprise a low frequency peak and a high frequency peak. The probability distribution can comprise a low frequency peak between 10 Hz and 1000 Hz, such as between 100 Hz and 300 Hz. The probability distribution can comprise a high frequency peak between 1 kHz and 15 kHz, such as between 5 kHz and 15 kHz. The probability distribution can comprise multiple high frequency peaks. The varied frequency can comprise the carrier frequency of energy delivery.

In some embodiments, the apparatus is configured to randomly vary one or more stimulation parameters of a stimulation energy type selected from the group consisting of: electrical energy, magnetic energy, sound energy; ultrasound energy, light energy, thermal energy; heat energy; cryogenic energy; chemical energy; and combinations thereof.

In some embodiments, the apparatus randomly varies at least one of the one or more stimulation parameters based on a patient interrogation.

In some embodiments, the apparatus is configured to continue a random variation of at least one of the one or more stimulation parameters based on a patient interrogation.

In some embodiments, the medical apparatus further comprises a waveform generator configured to produce the stimulation waveform. The first implantable device can comprise the waveform generator. The medical apparatus can further comprise a first external device configured to transmit data and/or power to the first implantable device, and the first external device can comprise the waveform generator. The waveform generator can be configured to randomly vary the stimulation waveform. The waveform generator can perform the random variation based on a probability distribution. The waveform generator can be configured to produce a stimulation waveform comprising elements selected from the group consisting of: pulses with relatively constant amplitude and pulse width; amplitude modulated pulses; pulse width modulated pulses; amplitude and pulse width modulated pulses; multiple pulses with random inter-pulse gaps between two or more pulses; waveforms with a stimulation parameter varied based on a probability distribution; and combinations thereof. The waveform generator can be configured to produce a stimulation waveform comprising pulse width modulated pulses with overall charge held constant. The waveform generator can be configured to produce a stimulation waveform comprising one or more random pulses, and the timing of the one or more pulses can be maintained within a constrained and predetermined range. The medical apparatus can further comprise a probability distribution, and the one or more random pulses can be included based on the probability distribution. The medical apparatus can further comprise a first external device configured to deliver data to the first implantable device, and waveform information can be transmitted to the first implantable device from the first external device. The medical apparatus can further comprise a memory module, and the stimulation waveform can be based on information stored in the memory module. The medical apparatus can further comprise a first external device configured to transmit data and/or power to the first implantable device, and the stimulation waveform can be further based on information received from the first external device.

In some embodiments, the medical apparatus further comprises a charge monitor configured to track total charge delivered to tissue and recovered from tissue and to produce charge status information. The first implantable device can be configured to perform charge balancing based on the charge status information, and the charge balancing can comprise a function selected from the group consisting of: active charge recovery; passive charge recovery; and combinations thereof.

In some embodiments, the implantable system further comprises at least a second implantable device.

In some embodiments, the medical apparatus further comprises a first external device, and the first implantable device receives wireless power transmissions from the first external device. The first implantable device can further receive data from the first external device. The first implantable device can receive the power and data simultaneously from the first external device. The apparatus can be configured to adjust the power transmissions from the external device. The apparatus can be configured to adjust the power transmissions from the external device in real time. The power transmission can be adjusted to improve the efficiency of transmissions between the first external device and the first implantable device. The apparatus can adjust a parameter selected from the group consisting of: power transmission amplitude; duty cycle; frequency; phase; periodicity; and combinations thereof. The first implantable device can be configured to transmit data to the first external device.

In some embodiments, the first implantable device further comprises at least one implantable antenna. The at least one implantable antenna can comprise multiple implantable antennas. The at least one implantable antenna can comprise one or more antennas selected from the group consisting of: loop antenna; multiple-turn loop antenna; planar loop antenna; coil antenna; dipole antenna; electric dipole antenna; magnetic dipole antenna; patch antenna; elongated loop antenna; loaded dipole antenna; concentric loop antenna; loop antenna with ferrite core; and combinations thereof. The at least one implantable antennas can comprise one or more multi-turn spiral loop antennas.

In some embodiments, the apparatus is configured to control charge balance. The apparatus can be configured to actively control charge balance. The apparatus can be configured to passively control charge balance.

In some embodiments, the medical apparatus further comprises an implantable energy storage assembly and clamping circuit, and the clamping circuit is configured to allow at least one of fast charging or fast discharging of the implantable energy storage assembly.

In some embodiments, the at least one implantable functional element comprises multiple functional elements. At least two of the multiple functional elements can be configured to delivery bipolar electrical stimulation energy.

In some embodiments, the at least one implantable functional element comprises a sensor configured to record patient information.

In some embodiments, the at least one implantable functional element comprises at least one electrode. The at least one electrode can be configured to deliver energy to tissue and sense a patient parameter. The at least one electrode can comprise one or more electrodes selected from the group consisting of: microelectrode; cuff electrode; array of electrodes; linear array of electrodes; circular array of electrodes; paddle-shaped array of electrodes; bifurcated electrodes; and combinations thereof.

In some embodiments, the medical apparatus further comprises a lead, and the lead comprises the at least one functional element.

In some embodiments, the medical apparatus further comprises an external controller configured to control the first implantable device. The external controller can be configured to adjust a parameter of the first implantable device selected from the group consisting of: a stimulation parameter; a stimulation waveform parameter; a sensing parameter; a therapy parameter; a data recording parameter; a patient data recording parameter; an implantable device data recording parameter; power transfer; data rate; activity of one or more external transmitters; activity of one or more external antennas; an implantable functional element parameter; an external functional element parameter; and combinations thereof.

In some embodiments, the medical apparatus further comprises a sensor configured to produce a sensor signal. The at least one implantable functional element can comprise the sensor. The sensor can be configured to record data representing a physiologic parameter of the patient. The physiologic parameter can comprise a parameter selected from the group consisting of: blood glucose; blood pressure; EKG; heart rate; cardiac output; oxygen level; pH level; pH of blood; pH of a bodily fluids; tissue temperature; inflammation level; bacteria level; type of bacteria present; gas level; blood gas level; neural activity; neural spikes (also referred to as "action potential" or "neuronal action potential"); neural spike shape; action potential; local field potential (LFP); EEG; muscular activity; skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations thereof. The sensor can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor; bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations thereof. The sensor can comprise a sensor selected from the group consisting of: an energy sensor; a voltage sensor; a current sensor; a temperature sensor; a contamination detector; an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations thereof. The sensor can be configured to record data representing a parameter of the first implantable device.

In some embodiments, the apparatus is configured to maintain charge constancy comprising maintaining a minimum level of charge delivered in a predetermined time period. The apparatus can be configured to vary at least one stimulation parameter randomly and to vary at least one other stimulation parameter to maintain the charge constancy.

In some embodiments, the stimulation waveform comprises two or more sequential pulses in one phase followed by one or more pulses in the opposite phase.

In some embodiments, the stimulation waveform comprises a train including an inter-pulse gap of at least 1 msec, and the stimulation waveform can be configured to cause synchronous firing of one or more neurons.

In some embodiments, the stimulation waveform comprises a train including an inter-pulse gap less than at least one of 1 msec or 0.67 msec, and the stimulation waveform can be configured to cause stochastic firing of one or more neurons. The apparatus can be configured to deliver the stimulation energy to spinal cord neurons to reduce pain.

In some embodiments, the apparatus is configured to set a stimulation parameter to zero time, and the stimulation parameter can be selected from the group consisting of: an inter-phase gap; an inter-pulse gap; a train-off period; a burst-off period; and combinations thereof. The apparatus can be configured to randomly set the stimulation parameter to zero time.

In some embodiments, the stimulation waveform comprises an element selected from the group consisting of: one or more train-on periods with a duration of approximately 8 msec; one or more pulses each comprising at least two phases of approximately 10 μsec each; one or more pulses each with a pulse width of approximately 30 μsec; one or more inter-phase gaps each with a duration of approximately 10 μsec; one or more inter-pulse gaps each with a duration of approximately 90 μsec; a burst-on period of approximately 8 msec; a burst-off period of approximately 17 msec; and combinations thereof.

In some embodiments, the stimulation waveform comprises an element selected from the group consisting of: one or more train-on periods with a duration of approximately 1.45 msec; one or more pulses each comprising at least two phases of approximately 10 μsec each; one or more pulses each with a pulse width of approximately 90 μsec; one or more inter-phase gaps each with a duration of approximately 20 μsec; one or more inter-pulse gaps each with a duration of approximately 90 μsec; a train-off period of approximately 1.55 msec; a burst-on period of approximately 12 msec; a burst-off period of approximately 18 msec; and combinations thereof.

In some embodiments, the stimulation waveform comprises an element selected from the group consisting of: one or more train-on periods with a duration of approximately 1.45 msec; one or more pulses each comprising at least two phases of approximately 10 μsec each; one or more pulses each with a pulse width of approximately 90 μsec; one or more inter-phase gaps each with a duration of approximately 20 μsec; one or more inter-pulse gaps each with a duration of approximately 90 μsec; a train-off period of approximately 1.55 msec; a burst-on period of approximately 12 msec; a burst-off period of approximately 13 msec; and combinations thereof.

In some embodiments, the stimulation waveform comprises an element selected from the group consisting of: one or more train-on periods with a duration between 700 μsec and 1.1 msec; one or more pulses each comprising at least two phases of between 5 μsec and 15 μsec each; one or more pulses each with a pulse width of between 30 μsec and 90 μsec; one or more inter-phase gaps each with a duration of between 10 μsec and 30 μsec; one or more inter-pulse gaps each with a duration of between 1 μsec and 100 μsec; a train-off period of between 900 μsec and 1.7 msec; a burst-on period of between 8 msec and 12 msec; a burst-off period of between 8 msec and 18 msec; and combinations thereof.

In some embodiments, the stimulation waveform comprises a burst including at least one burst-off period during which sub-threshold energy is delivered.

In some embodiments, the stimulation waveform comprises two or more sequential pulses in a single phase followed by at least one pulse in an opposite phase. The two or more sequential phases in a single phase can comprise at least one of the same amplitude or the same pulse width. The two or more sequential phases in a single phase can comprise at least one of different amplitudes or different pulse widths. The two or more sequential phases can comprise a quantity of sequential pulses that is determined randomly.

In some embodiments, the apparatus is configured to provide a stimulation waveform comprising one or more optimized stimulation parameters. The one or more optimized stimulation parameters can comprise one or more parameters selected from the group consisting of: one or more pulses each with a pulse width of approximately 30 μsec; one or more inter-pulse gaps each with a duration of approximately 30 μsec; one or more train-on periods with a duration of approximately 2 msec; one or more train-off periods with a duration of approximately 0.9 msec; one or more burst-on periods with a duration of approximately 13.5 msec; one or more burst-off periods with a duration of approximately 11.5 msec; and combinations thereof. The one or more stimulation parameters can comprise: one or more pulses each with a pulse width of approximately 30 μsec; one or more inter-pulse gaps each with a duration of approximately 30 μsec; one or more train-on periods with a duration of approximately 2 msec; one or more train-off periods with a duration of approximately 0.9 msec; one or more burst-on periods with a duration of approximately 13.5 msec; one or more burst-off periods with a duration of approximately 11.5 msec; and combinations thereof. The one or more optimized stimulation parameters can comprise one or more parameters selected from the group consisting of: one or more pulses each with a pulse width of approximately 30 μsec; one or more inter-pulse gaps each with a duration of approximately 310 μsec; one or more train-on periods with a duration of approximately 1.33 msec; one or more train-off periods with a duration of approximately 0.9 msec; one or more burst-on periods with a duration of approximately 10.2 msec; one or more burst-off periods with a duration of approximately 14.8 msec; and combinations thereof. The one or more optimized stimulation parameters can comprise: one or more pulses each with a pulse width of approximately 30 μsec; one or more inter-pulse gaps each with a duration of approximately 310 μsec; one or more train-on periods with a duration of approximately 1.33 msec; one or more train-off periods with a duration of approximately 0.9 msec; one or more burst-on periods with a duration of approximately 10.2 msec; one or more burst-off periods with a duration of approximately 14.8 msec; and combinations thereof. The one or more optimized stimulation parameters can comprise one or more parameters selected from the group consisting of: one or more pulses each with a pulse width of approximately 100 μsec; one or more inter-pulse gaps each with a duration of approximately 50 μsec; one or more train-on periods with a duration of approximately 1.5 msec; one or more train-off periods with a duration of approximately 0.9 msec; one or more burst-on periods with a duration of approximately 11.1 msec; one or more burst-off periods with a duration of approximately 13.9 msec; and combinations thereof. The one or more optimized stimulation parameters can comprise: one or more pulses each with a pulse width of approximately 100 μsec; one or more inter-pulse gaps each with a duration of approximately 50 μsec; one or more train-on periods with a duration of approximately 1.5 msec; one or more train-off periods with a duration of approximately 0.9 msec; one or more burst-on periods with a duration of approximately 11.1 msec; one or more burst-off periods with a duration of approximately 13.9 msec; and combinations thereof.

In some embodiments, the apparatus is configured to vary one or more of the stimulation parameters to optimize at least one of: therapeutic benefit; system efficiency; avoidance of paresthesia; reduction of paresthesia; reduction of charge; and combinations thereof.

In some embodiments, the apparatus is configured to deliver a stimulation waveform comprising a series of monophasic pulses. The monophasic pulses can comprise an amplitude of between approximately 0.01 mA and 20 mA, such as between 0.05 mA and 20 mA. The monophasic pulses can comprise an amplitude of between approximately 0.01 mA and 2.5 mA, such as between 0.5 mA and 2.5 mA. The stimulation waveform can comprise a charge recovery pulse in an opposite phase to the monophasic pulses. The charge recovery pulse can comprise passive charge recovery.

In some embodiments, the medical apparatus is configured to vary at least one of the one or more stimulation parameters to increase charge to be delivered to a patient. The medical apparatus can be configured to allow a patient and/or other operator to vary the at least one of the one or more stimulation parameters. The apparatus can be configured to deliver a stimulation waveform comprising a predetermined pulse width and amplitude. The apparatus can be configured to increase the stimulation waveform amplitude until a minimum system compliance voltage is reached. The apparatus can be configured to increase the stimulation waveform pulse width until a therapeutic benefit is achieved or a first pulse width threshold is reached. The apparatus can be configured to: increase the system compliance voltage by an increment $\Delta CV$; increase the stimulation waveform amplitude by an increment $\Delta A$; and decrease the stimulation waveform pulse width by an increment $\Delta PW$. The increment $\Delta CV$ can comprise an increase in the system compliance voltage of between approximately 0.2V and 1.5V. The increment $\Delta CV$ can comprise an increase in the system compliance voltage of between approximately 0.5V and 1.0V. The increment $\Delta A$ can comprise an increase in amplitude configured to correlate with the increased system compliance voltage. The increment $\Delta PW$ can comprise a decrease in pulse width configured to keep charge constant for the increased amplitude. The apparatus can be configured to increase pulse width until a therapeutic benefit is achieved or a second pulse width threshold is reached. The apparatus can be configured to notify the patient and/or other operator when a maximum system charge level has been reached. The apparatus can be configured to provide a prompt to the patient and/or other operator to increase and/or decrease the one or more stimulation parameters. The apparatus can be configured to indicate to the patient and/or other operator that an alternate therapeutic program should be selected.

In some embodiments, the apparatus comprises a system compliance voltage comprising a minimum voltage of between approximately 1V and 5V, and a maximum voltage of approximately 15V.

In some embodiments, the apparatus comprises a stimulation waveform pulse width comprising a minimum of approximately 10 μsec. The apparatus can comprise one or more pulse width thresholds. A first pulse width threshold can be approximately 100 μsec. A second pulse width threshold can be approximately 200 μsec.

In some embodiments, the apparatus is configured to provide multiple stimulation waveforms, the multiple stimulation waveforms collectively configured to deliver therapies for multiple patient conditions. The multiple stimulation waveforms can comprise a common set of one or more stimulation parameters. The apparatus can be configured to allow the patient and/or other operator to select one or more of the multiple stimulation waveforms to be delivered.

In some embodiments, the apparatus is configured to provide a user interface program comprising one or more sub-programs, each sub-program comprising one or more stimulation parameters. The one or more sub-programs can each be configured to treat an anatomical location. A first sub-program can be configured to treat a first anatomical location, a second sub-program can be configured to treat a second anatomical location, and the first sub-program and the second sub-program can comprise similar stimulation parameters. The user interface program can be configured to allow the patient and/or other operator to adjust one or more stimulation parameters. The apparatus can comprise a program configured to cycle through the one or more sub-programs. The program can be configured to automatically cycle through the one or more sub-programs. The apparatus can be configured to switch between the one or more sub-programs rapidly. The apparatus can be configured to switch between the one or more sub-programs within a time period of between approximately 50 μsec and 1 second. The apparatus can be configured to switch between the one or more sub-programs at a rate of between approximately 10 Hz and 10 kHz.

In some embodiments, the stimulation waveform comprises a series of narrow pulses. The series of narrow pulses can comprise between approximately 2 and 1000 pulses. The series of narrow pulses can comprise a train-on period of between approximately 1 μsec and 100 msec. The train-on period can be followed by a train-off period of between approximately 1 μsec and 100 msec. The train-on period can comprise a series of monophasic pulses. The series of monophasic pulses can be followed by the delivery of a passive charge recovery pulse.

In some embodiments, the apparatus is configured to provide a stimulation waveform comprising a compliance optimized burst. The compliance optimized burst can comprise one or more stimulation waveforms comprising a cycle of one or more burst-on periods followed by one or more burst-off periods. The one or more burst-on periods can comprise one or more sets of one or more train-on periods and one or more train-off periods. The one or more burst-on periods can comprise between approximately 2 and 1000 of the train-on and train-off periods. The one or more burst-off periods can comprise a period between approximately 1 μsec and 10 seconds. The one or more burst off periods can comprise a charge recovery slot. The charge recovery slot can comprise a charge recovery pulse in the opposite phase to one or more stimulation pulses. The charge recovery slot can comprise a passive charge recovery.

In some embodiments, the medical apparatus is configured to increase charge to be delivered to a patient by increasing at least one of: (1) the amplitude of a first pulse in a series of pulse trains to be delivered; (2) the number of pulses in a series of pulse trains to be delivered; (3) the amplitude of a second pulse in a series of pulse trains to be delivered; (4) the pulse width of a set of pulses in a series of pulse trains to be delivered; or (5) the amplitude of a set of pulses in a series of pulse trains to be delivered. The variations (1) through (5) can be performed in order to increase the charge delivered. A decrease in any of the stimulation parameters of (5) through (1) causes a decrease in charge delivered.

According to another aspect of the present inventive concepts, a method of treating a patient disease or disorder comprises providing a medical apparatus for a patient, the medical apparatus comprising an implantable system and the implantable system comprises a first implantable device. The first implantable device comprises at least one implantable functional element configured to deliver stimulation energy to tissue of the patient, and an implantable controller configured to provide a stimulation waveform to the at least one implantable functional element, the stimulation waveform comprising one or more stimulation parameters, and randomly varying at least one of the one or more stimulation parameters.

In some embodiments, the randomly varying at least one of the one or more stimulation parameters is performed based on a probability distribution.

In some embodiments, the medical apparatus is configured to treat pain. The pain can comprise back pain.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE DRAWINGS

Figure 1:
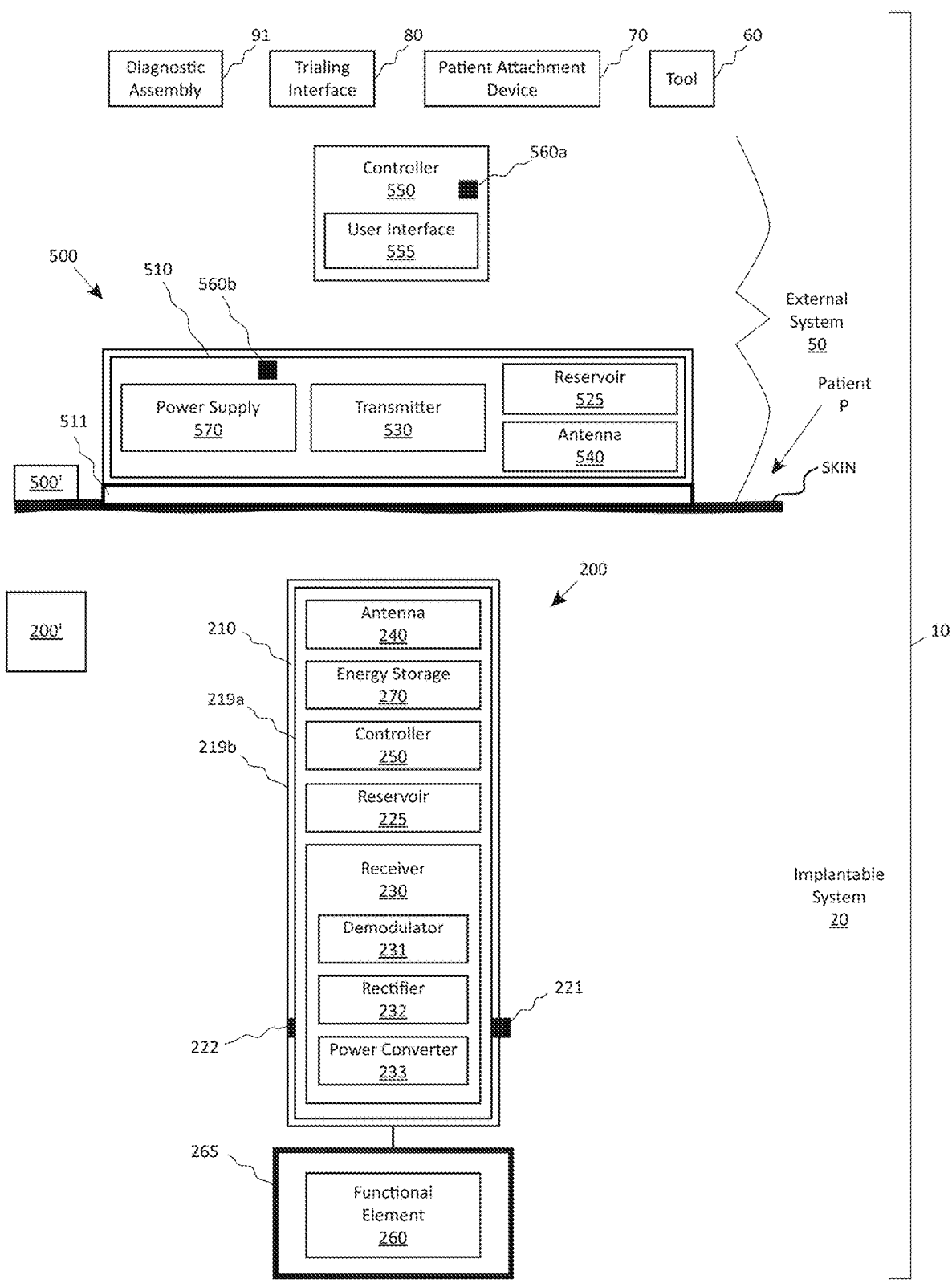
FIG. 1 is a schematic anatomical view of a medical apparatus comprising an external system and an implantable system, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.). A first component (e.g. a device, assembly, housing or other component) can be "attached", "connected" or "coupled" to another component via a connecting filament (as defined below). In some embodiments, an assembly comprising multiple components connected by one or more connecting filaments is created during a manufacturing process (e.g. pre-connected at the time of an implantation procedure of the system of the present inventive concepts). Alternatively or additionally, a connecting filament can comprise one or more connectors (e.g. a connectorized filament comprising a connector on one or both ends), and a similar assembly can be created by a user (e.g. a clinician) operably attaching the one or more connectors of the connecting filament to one or more mating connectors of one or more components of the assembly.

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); thermal energy to tissue (e.g. heat energy and/or cryogenic energy); chemical energy; electromagnetic energy; magnetic energy; and combinations of one or more of these.

The term "transmission signal" where used herein is to be taken to include any signal transmitted between two components, such as via a wired or wireless communication pathway. For example, a transmission signal can comprise a power and/or data signal wirelessly transmitted between a component external to the patient and one or more components implanted in the patient. A transmission signal can include one or more signals transmitted using body conduction. Alternatively or additionally, a transmission signal can comprise reflected energy, such as energy reflected from any power and/or data signal.

The term "data signal" where used herein is to be taken to include a transmission signal including at least data. For example, a data signal can comprise a transmission signal including data and sent from a component external to the patient and one or more components implanted in the patient. Alternatively, a data signal can comprise a transmission signal including data sent from an implanted component to one or more components external to the patient. A data signal can comprise a radiofrequency signal including data (e.g. a radiofrequency signal including both power and data) and/or a data signal sent using body conduction.

The term "implantable" where used herein is to be taken to define a component which is constructed and arranged to be fully or partially implanted in a patient's body and/or a component that has been fully or partially implanted in a patient. The term "external" where used herein is to be taken to define a component which is constructed and arranged to be positioned outside of the patient's body.

The terms "connection", "connected", "connecting" and the like, where used herein, are to be taken to include any type of connection between two or more components. The connection can include an operable connection which allows multiple connected components to operate together such as to transfer information, power and/or material (e.g. an agent to be delivered) between the components. An operable connection can include a physical connection, such as a physical connection including one or more wires, optical fibers, wave guides, tubes such as fluid transport tubes and/or linkages such as translatable rods or other mechanical linkages. Alternatively or additionally, an operable connection can include a non-physical or "wireless" connection, such as a wireless connection in which information and/or power is transmitted between components using electromagnetic energy. A connection can include a connection selected from the group consisting of: a wired connection; a wireless connection; an electrical connection; a mechanical connection; an optical connection; a sound propagating connection; a fluid connection; and combinations of one or more of these.

The term "connecting filament" where used herein is to be taken to define a filament connecting a first component to a second component. The connecting filament can include a connector on one or both ends, such as to allow a user to operably attach at least one end of the filament to a component. A connecting filament can comprise one or more elements selected from the group consisting of: wires; optical fibers; fluid transport tubes; mechanical linkages; wave guides; flexible circuits; and combinations of one or more of these. A connecting filament can comprise rigid filament, a flexible filament or it can comprise one or more flexible portions and one or more rigid portions.

The term "connectorized" where used herein is to be taken to refer to a filament, housing or other component that includes one or more connectors (e.g. clinician or other user-attachable connectors) for operably connecting that component to a mating connector (e.g. of the same or different component).

The terms "stimulation parameter", "stimulation signal parameter" or "stimulation waveform parameter" where used herein can be taken to refer to one or more parameters of a stimulation waveform (also referred to as stimulation signal). Applicable stimulation parameters of the present inventive concepts shall include but are not limited to: amplitude (e.g. amplitude of voltage and/or current); average amplitude; peak amplitude; frequency; average frequency; period; phase; polarity; pulse shape; a duty cycle parameter (e.g. frequency, pulse width and/or off time); inter-pulse gap; polarity; burst-on period; burst-off period; inter-burst period; pulse train; train-on period; train-off period; inter-train period; drive impedance; duration of pulse and/or amplitude level; duration of stimulation waveform; repetition of stimulation waveform; an amplitude modulation parameter; a frequency modulation parameter; a burst parameter; a power spectral density parameter; an anode/cathode configuration parameter; amount of energy and/or power to be delivered; rate of energy and/or power delivery; time of energy delivery initiation; method of charge recovery; and combinations of one or more of these. A stimulation parameter can refer to a single stimulation pulse, multiple stimulation pulses, or a portion of a stimulation pulse. The term "amplitude" where used herein can refer to an instantaneous or continuous amplitude of one or more stimulation pulses (e.g. the instantaneous voltage level or current level of a pulse). The term "pulse" where used herein can refer to a period of time during which stimulation energy is relatively continuously being delivered. In some embodiments, stimulation energy delivered during a pulse comprises energy selected from the group consisting of: electrical energy; magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, stimulation energy comprises electrical energy and a pulse comprises a phase change in current and/or voltage. In these embodiments, an inter-phase gap can be present within a single pulse. The term "quiescent period" where used herein can refer to a period of time during which zero energy or minimal energy is delivered (e.g. insufficient energy to elicit an action potential and/or other neuronal response). The term "inter-pulse gap" where used herein can refer to a quiescent period between the end of one pulse to the onset of the next (sequential) pulse. The terms "pulse train" or "train" where used herein can refer to a series of pulses. The terms "burst", "burst of pulses" or "burst stimulation" where used herein can refer to a series of pulse trains, each separated by a quiescent period. The term "train-on period" where used herein can refer to a period of time from the beginning of the first pulse to the end of the last pulse of a single train. The term "train-off period" where used herein can refer to a quiescent period between the end of one train and the beginning of the next train. The term "burst-on period" where used herein can refer to a period of time from the beginning of the first pulse of the first train to the end of the last pulse of the last train of a single burst. The term "burst-off period" where used herein can refer to a quiescent period between the end of one burst and the beginning of the next burst. The term "inter-train period" where used herein can refer to a quiescent period between the end of one train and the beginning of the next train. The term "inter-burst period" where used herein can refer to a quiescent period between the end of one burst and the beginning of the next burst. The term "train envelope" where used herein can refer to a curve outlining the amplitude extremes of a series of pulses in a train. The term "burst envelope" where used herein can refer to a curve outlining the amplitude extremes of a series of pulses in a burst. The term "train ramp duration" where used herein can refer to the time from the onset of a train until its train envelope reaches a desired target magnitude. The term "burst ramp duration" where used herein can refer to the time from the onset of a burst until its burst envelope reaches a desired target magnitude.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present inventive concepts include a medical apparatus and clinical methods for treating a patient, such as to treat pain. The patient can comprise a human or other mammalian patient. The medical apparatus can comprise a stimulation apparatus. The medical apparatus can comprise an implantable system and an external system. The implantable system can comprise one or more similar and/or dissimilar implantable devices. Each implantable device can comprise one or more implantable antennas configured to receive power and/or data. Each implantable device can comprise an implantable receiver configured to receive the power and/or data from the one or more implantable antennas. Each implantable device can comprise one or more implantable functional elements. An implantable functional element can be configured to interface with the patient (e.g. interface with tissue of the patient or interface with any patient location). Alternatively or additionally, an implantable functional element can interface with a portion of an implantable device (e.g. to measure an implantable device parameter). In some embodiments, the one or more implantable functional elements can comprise one or more transducers, electrodes, and/or other elements configured to deliver energy to tissue. Alternatively or additionally, the one or more implantable functional elements can comprise one or more sensors, such as a sensor configured to record a physiologic parameter of the patient. In some embodiments, one or more implantable functional elements are configured to record device information and/or patient information (e.g. patient physiologic or patient environment information).

Each implantable device can comprise an implantable controller configured to control (e.g. modulate power to, send a signal to and/or receive a signal from) the one or more implantable functional elements. In some embodiments, an implantable controller of a first implantable device is configured to control one or more other implantable devices. Each implantable device can comprise an implantable energy storage assembly configured to provide power to the implantable controller (e.g. a controller comprising a stimulation waveform generator), the implantable receiver and/or the one or more implantable functional elements. In some embodiments, an implantable energy storage assembly is further configured to provide power to an assembly that transmits signals via the implantable antenna (e.g. when the implantable device is further configured to transmit data to one or more external devices). Each implantable device can comprise an implantable housing surrounding the implantable controller and the implantable receiver. In some embodiments, one or more implantable antennas are positioned within the implantable housing. Alternatively or additionally, one or more implantable antennas and/or implantable functional elements can be tethered (e.g. electrically tethered) to the implantable housing. In some embodiments, one or more implantable functional elements are positioned on an implantable lead, such as a flexible lead mechanically fixed or attachable to the implantable housing and operably connected (e.g. electrically, fluidly, optically and/or mechanically) to one or more components internal to the implantable housing. The implantable lead can be inserted (e.g. tunneled) through tissue of the patient, such that its one or more functional elements are positioned proximate tissue to be treated and/or positioned at an area in which data is to be recorded.

The external system of the medical apparatus of the present inventive concepts can comprise one or more similar and/or dissimilar external devices. Each external device can comprise one or more external antennas configured to transmit power and/or data to one or more implanted components of the implantable system. Each external device can comprise an external transmitter configured to drive the one or more external antennas. Each external device can comprise an external power supply configured to provide power to at least the external transmitter. Each external device can comprise an external programmer configured to control the external transmitter and/or an implantable device (e.g. when an external power transmitter is not included in the apparatus or otherwise not present during use). Each external device can comprise an external housing that surrounds at least the external transmitter. In some embodiments, the external housing surrounds the one or more external antennas, the external power supply and/or the external programmer.

The external programmer can comprise a discrete controller separate from the one or more external devices, and/or a controller integrated into one or more external devices. The external programmer can comprise a user interface, such as a user interface configured to set and/or modify one or more treatment and/or data recording settings of the medical apparatus of the present inventive concepts. In some embodiments, the external programmer can be configured to collect and/or diagnose recorded patient information, such as to provide the information and/or diagnosis to a clinician of the patient, to a patient family member and/or to the patient themselves. The collected information and/or diagnosis can be used to adjust treatment or other operating parameters of the medical apparatus.

In some embodiments, a medical apparatus comprises a stimulation apparatus for activating, blocking, affecting or otherwise stimulating (hereinafter "stimulate" or "stimulating") tissue of a patient, such as nerve tissue or nerve root tissue (hereinafter "nerve", "nerves", "nerve tissue" or "nervous system tissue"). The stimulation apparatus comprises an external system configured to transmit power, and an implanted system configured to receive the power from the external system and to deliver stimulation energy to tissue. The delivered stimulation energy can comprise one or more stimulation waveforms, such as a stimulation waveform configured to enhance treatment of pain while minimizing undesired effects. The stimulation signal (also referred to as "stimulation energy") delivered by the implanted system can be independent of the power received from the external system, such as to be independent of one or more of: the position of one or more components of the external system; the changing position of one or more components of the external system; the frequency of the power received from the external system; the amplitude of the power received from the external system; changes in amplitude of the power received from the external system; duty cycle of the power received from the external system; envelope of the power received from the external system; and combinations of one or more of these.

Referring now to FIG. 1, a schematic anatomical view of a medical apparatus for treating and/or diagnosing a patient is illustrated, consistent with the present inventive concepts. Apparatus 10 comprises implantable system 20 and external system 50. Implantable system 20 comprises implantable device 200 shown implanted beneath the skin of patient P. In some embodiments, implantable system 20 comprises multiple implantable devices 200 (singly or collectively implantable device 200), such as is described in applicant's co-pending application International PCT Patent Serial Number PCT/US2016/051177, titled "Apparatus for Peripheral or Spinal Stimulation", filed Sep. 9, 2016, the content of which is incorporated herein in its entirety for all purposes. In some embodiments, implantable system 20 comprises at least two implantable devices, such as implantable device 200 and implantable device 200' shown in FIG. 1. Implantable device 200' can be of similar construction and arrangement to implantable device 200, and it can include components of different configuration.

External system 50 can comprise an external device 500, which includes housing 510. In some embodiments, external system 50 comprises multiple external devices 500 (singly or collectively external device 500), also as is described in applicant's co-pending application International PCT Patent Serial Number PCT/US2016/051177, titled "Apparatus for Peripheral or Spinal Stimulation", filed Sep. 9, 2016. In some embodiments, external system 50 comprises at least two external devices (e.g. at least two external devices configured to deliver power and/or data to one or more implantable devices 200), such as external device 500 and external device 500' shown in FIG. 1. External device 500' can be of similar construction and arrangement to external device 500, and it can include components of different configuration.

External system 50 can comprise external programmer 550, which can comprise a user interface, such as user interface 555. External programmer 550 can be configured to control one or more external devices 500. Alternatively or additionally, external programmer 550 can be configured to control one or more implantable devices 200 (e.g. when no external device 500 is included in apparatus 10 or otherwise no external device 500 is available to communicate with an implantable device 200.

Apparatus 10 can be configured as a patient treatment apparatus, such as a stimulation apparatus configured to stimulate tissue (e.g. stimulate nerve tissue such as tissue of the central nervous system or tissue of the peripheral nervous system, such as to neuromodulate nerve tissue), such as by having one or more implantable devices 200 deliver and/or provide energy (hereinafter "deliver energy") and/or deliver an agent (e.g. a pharmaceutical compound or other agent) to one or more tissue locations. In some embodiments, one or more implantable devices 200 deliver energy and/or an agent while receiving power and/or data from one or more external devices 500. In some embodiments, one or more implantable devices 200 deliver energy and/or an agent (e.g. continuously or intermittently) using an internal power source (e.g. a battery and/or capacitor) without receiving externally supplied power, such as for periods of at least 1 hour, at least 1 day, at least 1 month or at least 1 year. In some embodiments, one or more stimulation parameters are varied (e.g. systematically and/or randomly as described herein), during that period.

Alternatively or additionally, apparatus 10 can be configured as a patient diagnostic apparatus, such as by having one or more implantable devices 200 record a patient parameter (e.g. a patient physiologic parameter) from one or more tissue locations, such as while receiving power and/or data from one or more external devices 500. In some embodiments, during its use, one or more implantable devices 200 at least receives power from one or more external devices 500 (e.g. without also receiving data).

Alternatively or additionally, apparatus 10 can be configured as a patient information recording apparatus, such as by having one or more implantable devices 200 and/or one or more external devices 500 record patient information (e.g. patient physiologic information and/or patient environment information). In some embodiments, one or more implantable devices 200 and/or one or more external devices 500 further collect information (e.g. status information or configuration settings) of one or more of the components of apparatus 10.

In some embodiments, apparatus 10 is configured to deliver stimulation energy to tissue, such as to treat pain. In particular, apparatus 10 can be configured to deliver stimulation energy to tissue of the spinal cord and/or tissue associated with the spinal cord ("tissue of the spinal cord", "spinal cord tissue" or "spinal cord" herein), the tissue including roots, ganglia and/or other nerve tissue. The delivered energy can comprise energy selected from the group consisting of: electrical energy; magnetic energy; electromagnetic energy; light energy such as infrared light energy. visible light energy and/or ultraviolet light energy; mechanical energy; thermal energy such as heat energy and/or cryogenic energy; sound energy such as ultrasonic sound energy (e.g. high intensity focused ultrasound and/or low intensity focused ultrasound) and/or subsonic sound energy; chemical energy; and combinations of one or more of these. In some embodiments, apparatus 10 is configured to deliver to tissue energy in a form selected from the group consisting of: electrical energy such as by providing a controlled (e.g. constant or otherwise controlled) electrical current and/or voltage to tissue; magnetic energy (e.g. magnetic field energy) such as by applying controlled current or voltage to a coil or other magnetic field generating element positioned proximate tissue; and/or electromagnetic energy such as by providing both current to tissue and a magnetic field to tissue. The coil or other magnetic field generating element can surround (e.g. at least partially surround) the target nerve and/or it can be incorporated as part of an anchoring system to the target tissue. Alternatively, or additionally, the magnetic energy can be applied externally and focused to specific target tissue via an implant comprising a coil and/or ferromagnetic materials. In some embodiments, the magnetic energy is configured to induce the application of mechanical energy. Delivered energy can be supplied in one or more stimulation waveforms, each waveform comprising one or more pulses of energy, as described in detail herebelow.

In some embodiments, apparatus 10 is configured as a stimulation apparatus in which external system 50 transmits a power signal to implantable system 20, and implantable system 20 delivers stimulation energy to tissue with a stimulation signal (also referred to as a stimulation waveform), with the power signal and the stimulation signal having one or more different characteristics. The power signal can further be modulated with data (e.g. configuration or other data to be sent to one or more implantable devices 200). In these embodiments, the characteristics of the stimulation signal delivered (e.g. amplitude, frequency, duty cycle and/or pulse width), can be independent (e.g. partially or completely independent) of the characteristics of the power signal transmission (e.g. amplitude, frequency, phase, envelope, duty cycle and/or modulation). For example, the frequency and modulation of the power signal can change without affecting the stimulation signal, or the stimulation signal can be changed (e.g. via external programmer 550), without requiring the power signal to change. In some embodiments, implantable system 20 can be configured to rectify the power signal, and produce a stimulation waveform with entirely difference characteristics (e.g. amplitude, frequency and/or duty cycle) from the rectified power signal. Implantable system 20 can comprise an oscillator and/or controller configured to produce the stimulation signal, such as is described herebelow in reference to FIG. 3. In some embodiments, implantable system 20 is configured to perform frequency multiplication, in which multiple signals are multiplexed, mixed, added, and/or combined in other ways to produce a broadband stimulation signal.

In some embodiments, apparatus 10 is configured such that external system 50 transmits data (e.g. data and power) to implantable system 20, and implantable system 20 recovers (e.g. decodes, demodulates or otherwise recovers) the transmitted data without synchronizing to the carrier and/or data symbol rate of the transmitted signal from external system 50. In some embodiments, the transmitted signal comprises a power signal, and a clock and/or data is recovered without synchronizing to the power signal. In some embodiments, the transmitted signal comprises a clock and/or data signal, and a clock and/or data is recovered without synchronizing to the transmitted clock and/or data signal. In some embodiments, the recovered signal comprises a clock and/or data and a clock and/or data is recovered from the transmission signal without synchronizing to the recovered clock and/or data. Avoiding synchronization reduces power consumption of each implantable device 200, such as by obviating the need for (and avoiding the power consumed by) a frequency locked loop (FLL), phase locked loop (PLL); high frequency clock; and/or crystal oscillator needed to perform the synchronization. Avoiding these components can also be correlated to reduced package size of each implantable device 200 (e.g. avoidance of a relatively large sized crystal oscillator). Asynchronous data transfer between external system 50 and implantable system 20 is also advantageous as it relates to: increased communication data rate; power transfer efficiency; operation with more than one implantable device 200; and combinations of one or more of these. In some embodiments, one or more components of apparatus 10 are of similar construction and arrangement as similar components described in U.S. patent application Ser. No. 13/591,188, titled "Method of Making and Using an Apparatus for a Locomotive Micro-Implant using Active Electromagnetic Propulsion", filed Aug. 21, 2012, the content of which is incorporated herein by reference in its entirety for all purposes. In some embodiments, external system 50 and implantable system 20 provide asynchronous data transfer or are otherwise configured as described in U.S. patent application Ser. No. 13/734,772, titled "Method and Apparatus for Efficient Communication with Implantable Devices", filed Jan. 4, 2013, the content of which is incorporated herein by reference in its entirety for all purposes.

Apparatus 10 can be configured to treat a patient disease or disorder and/or it can be configured to record patient information. Apparatus 10 can be configured to treat pain, such as back pain treated by stimulating dorsal root ganglia and/or other nerves or locations of the spinal cord or other nervous system locations. In some embodiments, apparatus 10 is configured to treat a type of pain selected from the group consisting of: back pain; joint pain; neuropathic pain; tennis elbow; muscle pain; shoulder pain; chronic, intractable pain of the back and/or lower limbs including unilateral or bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations of one or more of these. In some embodiments, apparatus 10 is configured to treat a patient disease or disorder selected from the group consisting of: chronic pain; acute pain; migraine; cluster headaches; urge incontinence; overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations of one or more of these.

Apparatus 10 can be configured to treat heart disease, such as heart failure of a patient. In these embodiments, stimulation of the spinal cord can be performed. In canine and porcine animals with failing hearts, spinal cord stimulation has been shown to reverse left ventricular dilation and improve cardiac function, while suppressing the prevalence of cardiac arrhythmias. In canines, coronary artery occlusion has been associated with increased intracardiac nerve firing, and stimulation at spinal segment T1 has been shown to suppress that nerve firing. Stimulation via apparatus 10 at one or more spinal cord locations can be used to suppress undesired cardiac nerve firing in humans and other mammalian patients. In some embodiments, stimulation via apparatus 10 at multiple spinal cord locations is used to enhance a cardiac treatment. For example, one or more functional elements 260 of one or more implantable devices 200 can be implanted at one or more spinal cord locations. Power and/or data can be transmitted to the one or more implantable devices 200 via one or more external devices 500 of external system 50. One or more stimulation signals can be delivered to spinal cord tissue, such as to treat heart failure or other cardiac disease or disorder. In some embodiments, one or more functional elements 260 are configured to deliver energy (e.g. electrical energy) to tissue to treat heart failure, such as tissue selected from the group consisting of: spinal canal; nerves in the spinal canal; nerves in the epidural space; peripheral nerves; posterior spinal nerve root; dorsal root; dorsal root ganglion; pre-ganglionic tissue on posterior spinal nerve root; post-ganglionic tissue on posterior nerve root; dorsal ramus; grey ramus communicans; white ramus communicans; ventral ramus; and combinations of one or more of these. In some embodiments, one or more functional elements of apparatus 10 (e.g. one or more functional elements 260 of implantable system 20) are used to record a patient parameter, such as a patient heart or spine parameter, and the information recorded is used to adjust the delivered stimulation signals. The at least one heart parameter can comprise a parameter selected from the group consisting of: EKG; blood oxygen; blood pressure; heart rate; ejection fraction; wedge pressure; cardiac output; and combinations of one or more of these.

Apparatus 10 can be configured to pace and/or defibrillate the heart of a patient. One or more functional elements 260 can be positioned proximate cardiac tissue and deliver a stimulation signal as described herein (e.g. based on power and/or data received by implantable system 20 from external system 50). The stimulation signal can be used to pace, defibrillate and/or otherwise stimulate the heart. Alternatively or additionally, apparatus 10 can be configured to record cardiac activity (e.g. by recording EKG, blood oxygen, blood pressure, heart rate, ejection fraction, wedge pressure, cardiac output, lung impedance and/or other properties or functions of the cardiovascular system), such as to determine an onset of cardiac activity dysfunction or other undesired cardiac state. In some embodiments, apparatus 10 is configured to both record cardiac or other information and deliver a stimulation signal to cardiac tissue (e.g. stimulation varied or otherwise based on the recorded information). For example, apparatus 10 can be configured such that external system 50 transmits power and/or data to implantable system 20. Implantable system 20 monitors cardiac activity, and upon detection of an undesired cardiovascular state, implantable system 20 delivers a pacing and/or defibrillation signal to the tissue that is adjacent to one or more functional elements 260 configured to deliver a cardiac stimulation signal.

Apparatus 10 can be configured to perform a diagnostic procedure including measuring one or more patient parameters (e.g. patient physiologic or other patient parameters), such as are described in detail herebelow. In some embodiments, apparatus 10 is configured to measure a physiologic parameter that can be sensed from one or more sensor-based functional elements 260 positioned in subcutaneous tissue. In these embodiments, external system 50 can comprise an external device 500 configured for placement proximate an implantable device 200 implanted in a position to record data from subcutaneous tissue (e.g. blood glucose data). The external device 500 can comprise a wrist band, a wrist watch or an arm band configuration such as when the implantable device 200 is positioned in subcutaneous tissue proximate the patient's wrist or upper arm. The external device 500 can comprise a leg, knee or ankle band configuration, such as when one or more implantable devices 200 are positioned in subcutaneous tissue proximate the patient's ankle, knee or thigh. In some embodiments, external device 500 comprises a band or other attachment device for positioning about the thorax, neck, groin or head. Power and/or data can be sent to the implantable device 200 from the external device 500, and data (e.g. blood glucose data) can be sent to external device 500 (or another component of external system 50) by implantable device 200, such as using a communication configuration described in detail herebelow. In some embodiments, external device 500 comprises a functional element 560 configured to deliver an agent (e.g. insulin or glucose delivered by a needle-based functional element 560), based on the information received from implantable device 200. Alternatively, or additionally, implantable device 200 comprises a functional element 260 configured to deliver an agent (e.g. insulin or glucose delivered by a needle-based functional element 260), based on the information recorded by implantable device 200. Various closed loop sensing and agent delivery combinations and configurations should be considered within the spirit and scope of the present inventive concepts, including but not limited to: sensing a blood parameter such as white blood cell count and delivering a chemotherapeutic or other agent based on the blood parameter; sensing a hormone level and delivering a hormone or a hormone affecting agent; sensing blood pressure and delivering stimulation energy and/or a blood pressure affecting agent; sensing neural activity and delivering stimulation energy and/or a neural affecting agent or other agent based on the neural activity, such as for treating epilepsy; and combinations of one or more of these.

External system 50 can be configured to transmit power and/or data (e.g. implantable system 20 configuration data) to one or more implantable devices 200 of implantable system 20. Configuration data provided by external system 50 (e.g. via one or more antennas 540 of one or more external devices 500) can include when to initiate stimulation delivery (e.g. energy delivery), when to stop stimulation delivery, and/or data related to the value or change to a value of one or more stimulation variables as described hereabove. The configuration data can include a stimulation parameter such as an agent (e.g. a pharmaceutical agent) delivery stimulation parameter selected from the group consisting of: initiation of agent delivery; cessation of agent delivery; amount of agent to be delivered; volume of agent to be delivered; rate of agent delivery; duration of agent delivery; time of agent delivery initiation; and combinations of one or more of these. The configuration data can include a sensing parameter, such as a sensing parameter selected from the group consisting of: initiation of sensor recording; cessation of sensor recording; frequency of sensor recording; resolution of sensor recording; thresholds of sensor recording; sampling frequency of sensor recording; dynamic range of sensor recording; initiation of calibration of sensor recording; and combinations of one or more of these.

External system 50 can comprise one or more external devices 500. External system 50 can comprise one or more antennas 540, such as when a single external device 500 comprises one or more antennas 540 or when multiple external devices 500 each comprise one or more antennas 540. The one or more antennas 540 can transmit power and/or data to one or more antennas 240 of implantable system 20, such as when a single implantable device 200 comprises one or more antennas 240 or when multiple implantable devices 200 each comprise one or more antennas 240. In some embodiments, one or more antennas 540 define a radiation footprint (e.g. a footprint defining a volume, such as a volume of tissue, in which electromagnetic transmissions radiated by antennas 540 can be properly received by antennas 240), such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes.

External system 50 transmits power and/or data with a transmission signal comprising at least one wavelength, $\lambda$. External system 50 and/or implantable system 20 can be configured such that the distance between an external antenna 540 transmitting the power and/or data and one or more implantable antennas 240 receiving the power and/or data transmission signal is equal to between $0.1\lambda$ and $10.0\lambda$, such as between $0.2\lambda$ and $2.0\lambda$. In some embodiments, one or more transmission signals are delivered at a frequency range between 0.1 GHz and 10.6 GHz, such as between 0.1 GHz and 3.0 GHz, between 0.4 GHz and 1.5 GHz, or between 0.902 GHz and 0.928 GHz, or in a frequency range proximate to 866 MHz, or approximately between 863 MHz and 870 MHz.

In addition to transmitting power and/or data to implantable system 20, external system 50 can be further configured to provide information (e.g. patient information and/or apparatus 10 performance information) to one or more other devices, such as tool 60 shown in FIG. 1 and described in detail herebelow.

One or more external devices 500 (singly or collectively external device 500) can be configured to transmit power and/or data (e.g. implantable system 20 configuration data) to one or more implantable devices 200. In some embodiments, one or more external devices 500 are configured to transmit both power and data (e.g. simultaneously and/or sequentially) to one or more implantable devices 200. In some embodiments, one or more external devices 500 are further configured to receive data from one or more implantable devices 200 (e.g. via data transmitted by one or more antennas 240 of one or more implantable devices 200). Each external device 500 can comprise housing 510, power supply 570, a transmitter 530, and/or one or more antennas 540, each described in detail herebelow. Each external device 500 can further comprise one or more functional elements 560, such as a functional element comprising a sensor, electrode, energy delivery element, a magnetic-field generating transducer, and/or any transducer, also described in detail herebelow. In some embodiments, a functional element 560 comprises one or more sensors configured to monitor performance of external device 500 (e.g. to monitor voltage of power supply 570, quality of transmission of power and/or data to implantable system 20, temperature of a portion of an external device 500, and the like).

One or more housings 510 (singly or collectively housing 510) of each external device 500 can comprise one or more rigid and/or flexible materials which surround various components of external device 500 such as antenna 540, transmitter 530 and/or power supply 570 shown in FIG. 1. In some embodiments, a single external device 500 comprises multiple discrete (i.e. separate) housings 510, two or more of which can transfer data or other signals via a wired or wireless connection. In some embodiments, a housing 510 further surrounds an external programmer 550 and/or a power supply 570. In some embodiments, housing 510 comprises both a rigid material and a flexible material. In some embodiments, housing 510 comprises a material selected from the group consisting of: plastic; injection-molded plastic; an elastomer; metal; and combinations of one or more of these. In some embodiments, housing 510 comprises a shielded portion (e.g. shielded to prevent transmission of electromagnetic waves), and an unshielded portion, such as an unshielded portion surrounding antenna 540.

Housing 510 can comprise an adhesive element, such as an adhesive element configured to temporarily attach an external device 500 to the patient's skin. Housing 510 can be constructed and arranged to engage (e.g. fit in the pocket of) a patient attachment device, such as patient attachment device 70 described herebelow.

One or more antennas 540 (singly or collectively antenna 540) can each comprise one or more external antennas. Antenna 540 can comprise one or more polarizable antennas, such as one or more antennas with adjustable polarization. Antenna 540 can comprise an array of antennas, such as an array of antennas configured to: support beam shaping and/or focusing; allow adjustment of the amplitude and/or phase of the transmission signal; increase the radiation footprint; and combinations of one or more of these. An array of antennas 540 can be configured to be selectively activated, such as to improve coupling with one or more implanted antennas 240, such as to adjust for movement of the array of the antennas 540 relative to the implanted antennas 240. Antenna 540 can comprise an array of selectable conductors configured to adjust a radiation pattern and/or an electromagnetic field of a resultant antenna. Antenna 540 can comprise a surface and shield material positioned on the surface, such as when the shield material is positioned on the side facing away from the patient's skin. The shield material can comprise radio-absorptive shield material and/or radio-reflective shield material. One or more antennas 540 can be positioned in a housing 510 that is otherwise void of other components (e.g. void of power supply 570 and transmitter 530), such as when an antenna 540 is positioned within a first housing 510 and communicates with components positioned in a second housing 510.

In some embodiments, a spacer 511 is positioned between antenna 540 and the patient's skin, such as a spacer comprising a thickened portion of housing 510 or a discrete spacer 511 placed on a side of housing 510 (as shown) or on a side of antenna 540. Spacer 511 can comprise one or more materials that match the impedance of antenna 540 to the impedance of the patient's tissue. Spacer 511 can comprise a thickness of between 0.1 cm to 3 cm, such as a thickness between 0.2 cm and 1.5 cm. Spacer 511 can comprise materials which isolate heat (e.g. a spacer 511 comprising thermally insulating material). Alternatively, or additionally, housing 510 can comprise a heat insulating and/or dissipating material. Spacer 511 can comprise a soft or otherwise compressible material (e.g. foam) for patient comfort. Spacer 511 can be inflatable, such as to control the separation distance of an external antenna 540 from the patient's skin. An inflatable spacer 511 can be compartmentalized into several sections with independently controlled air pressure or volume to adjust the separation distance of an external antenna 540 and the patient's skin and/or its angle (e.g. tilt) with respect to the tissue surface.

In some embodiments, antenna 540 comprises a multi-feed point antenna, such as a multi-feed point antenna configured to: support beam shaping and/or focusing; allow adjustment of amplitude and/or phase of a transmission signal; increase the radiation footprint; or combinations of one or more of these.

In some embodiments, antenna 540 comprises one or more antennas selected from the group consisting of: patch antenna; slot antenna; array of antennas; a loop antenna (e.g. a concentric loop antenna); antenna loaded with reactive elements; dipole antenna; polarizable antenna; selectable conductors that form an antenna; and combinations of one or more of these.

Antenna 540 can comprise a major axis between 1 cm and 10 cm, such as a major axis between 2 cm and 5 cm. Antenna 540 can be further configured to receive a signal, such as when an antenna 240 is configured to transmit data to an external device 500. Antenna 540 can be positioned on (e.g. fabricated onto) a substrate, such as a flexible printed circuit board or other printed circuit board (e.g. a single or multiple layer printed circuit board comprising electrical traces connecting components).

A single external antenna 540 can be configured to transmit power and/or data to multiple implantable devices 200 (e.g. each containing one or more antennas 240). In some embodiments, a single external device 500, comprising one or more antennas 540 can be configured to transmit power and/or data to multiple implantable devices 200.

One or more antennas 540 can comprise a multi-turn spiral loop antenna, such as a multi-turn spiral loop antenna configured to desensitize coupling sensitivity and/or boost input voltage. In some embodiments, one or more antennas 540 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

In some embodiments, one or more external devices 500 comprise a first antenna 540 and a second antenna 540. In these embodiments, the first antenna 540 can be similar or dissimilar to the second antenna 540. In some embodiments, a first antenna 540 and a dissimilar second antenna 540 are positioned within a single external device 500 (e.g. within housing 510). In other embodiments, a first antenna 540 is positioned in a first external device 500, and a dissimilar second antenna 540 is positioned in a second external device 500. The similarity or dissimilarity of the antennas can be configured to enhance one or more design and/or performance parameters selected from the group consisting of: implantable device 200 operation depth; polarization; power efficiency; a radiation footprint; directional gain; beam shaping and/or focusing; sensitivity to implantable device 200 placement; patient comfort; patient usability; data transfer; and combinations of one or more of these. In some embodiments, the first antenna 540 can be optimized for a different design parameter than the second antenna 540, and each antenna 540 can be activated independently or simultaneously to realize both benefits. In some embodiments, the first antenna 540 can be similar to the second antenna 540 and placed in an array to increase the radiation footprint or placed in different external locations to operate with multiple implantable devices 200 implanted at different sites.

In some embodiments, a first external antenna 540 and a second external antenna 540 transmit power and/or data to a single implantable antenna 240. In some embodiments, a first antenna 540 and a second antenna 540 can transmit power and/or data to the one or more antennas 240, simultaneously or sequentially. In sequential power and/or data transfers, a first external device 500 comprising a first one or more antennas 540 can be replaced (e.g. swapped) with a second external device 500 comprising a second one or more antennas 540. Alternatively or additionally, sequential power and/or data transfer can be initiated by one or more of the following conditions: when the first external antenna 540 moves (e.g. moves relative to the implanted antenna 240); when a second external device 500 comprising the second antenna 540 is turned on or otherwise activated; when the second antenna 540 provides improved power and/or data transfer to the antenna 240 than is provided by the first antenna 540; and/or when power received from the first antenna 540 decreases (e.g. decreases below a threshold). In some embodiments, an antenna 240 receives power from a first antenna 540 and a second antenna 540, but only receives data from the first antenna 540. In some embodiments, a first antenna (e.g. an antenna 240 or an antenna 540) is driven with a different carrier signal than a second antenna (e.g. an antenna 240 or an antenna 540). The two carrier signals can comprise differences in amplitudes and/or relative phases as compared to each other. Each carrier signal can include a data transmission (e.g. data to be transmitted to an implantable device 200 from an external device 500 or to an external device 500 from an implantable device 200).

One or more transmitters 530 (singly or collectively external transmitter 530) can each comprise one or more external transmitters that drive one or more antennas 540 (e.g. one or more antennas 540 positioned in a single external device 500 or multiple external devices 500). Transmitter 530 is operably attached to antenna 540 and is configured to provide one or more drive signals to antenna 540, such as one or more power signals and/or data signals transmitted to one or more implantable devices 200 of implantable system 20. In some embodiments, transmitter 530 comprises a transmitter that operates in a frequency range between 0.1 GHz and 10.6 GHz, such as a transmitter that operates in a frequency range between 0.1 GHz and 3.0 GHz, between 0.4 GHz and 1.5 GHz, between approximately 0.902 GHz and 0.928 GHz, or in a frequency range proximate to 866 MHz, or approximately between 863 MHz and 870 MHz. Transmitter 530 can comprise a transmitter that produces a transmission signal with a power level between 0.1 W and 4.0 W, such as a transmission signal with a power level between 0.1 W and 2.0 W or between 0.2 W and 1.0 W.

As described herein, one or more external devices 500 can be configured to transmit data (e.g. configuration data) to one or more implantable devices 200, such as via a data transmission produced by transmitter 530 and sent to one or more antennas 540. In some embodiments, a transmitter 530 is configured to perform data modulation comprising amplitude shift keying with pulse width modulation. In these embodiments, the transmitter can be configured to perform multi-level amplitude shift keying. The amplitude shift-keying can be configured to provide adjustable-depth modulation between 0-100% depth, such as between 5-75% depth, or such as between 10-50% depth. In some embodiments, one or more external devices 500 transmit data to one or more implantable devices 200 using time division multiple access (TDMA). In some embodiments, one or implantable devices 200 are independently addressable through unique identification (ID) codes. Alternatively or additionally, transmitter 530 can be configured to transmit one or more data signals with a bandwidth between 1 kHz and 100 MHz, between 0.1 MHz and 100 MHz, or between 1 MHz and 26 MHz.

As described herein, one or more external devices 500 can be configured to transmit power to one or more implantable devices 200, such as via a power transmission produced by transmitter 530 and set to one or more antennas 540. One or more transmitters 530 can deliver power to one or more implantable devices 200 simultaneously or sequentially. In some embodiments, one or more transmitters 530 are configured to adjust the level of power transmitted to one or more implantable devices 200, such as by adjusting one or more duty cycling parameters. In these embodiments, power transmitted can be adjusted to: set a power transfer based on a stimulation level produced by implantable system 20; prevent oversaturation; to reduce interference with implantable system 20 data transmissions (e.g. when one or more implantable devices 200 are further configured to transmit data to external system 50); set a power transfer based on charge information and/or discharge information related to an implantable device 200 (e.g. charge rate and/or discharge rate of an implantable energy storage assembly 270); and combinations of one or more of these. In some embodiments, implantable system 20 comprises a first receiver 230 (e.g. of a first implantable device 200) and a second receiver 230 (e.g. of a second implantable device 200'). One or more transmitters 530 can be configured to transmit a first power transmission to the first receiver 230, and a second power transmission to the second receiver 230. The first power transmission and the second power transmission can be adjusted or otherwise be different, such as to prevent oversaturation.

In some embodiments, transmitter 530 (and/or another component of external system 50) is further configured as a receiver, such as to receive data from implantable system 20. For example, a transmitter 530 can be configured to receive data via one or more antennas 240 of one or more implantable devices 200. Data received can include patient information (e.g. patient physiologic information, patient environment information or other patient information) and/or information related to an implantable system 20 parameter (e.g. an implantable device 200 stimulation parameter and/or other configuration parameter as described herein).

In some embodiments, transmitter 530 comprises a first transmitter to transmit power and/or data to one or more implantable devices 200, and a second transmitter to transmit data to a different device, as described herein. In these embodiments, a second transmitter of transmitter 530 can be configured to transmit data to tool 60 or another device such as an external programmer 550, cell phone; computer; tablet; computer network such as the internet or a LAN; and combinations of one or more of these. In some embodiments, the second transmitter of transmitter 530 comprises a wireless transmitter; a Bluetooth transmitter; a cellular transmitter; and combinations of one or more of these. In some embodiments, a functional element 560 comprises a transmitter such as a Bluetooth transmitter.

Each power supply 570 (singly or collectively power supply 570) can be operably attached to a transmitter 530, and one or more other electrical components of each external device 500. Power supply 570 can comprise a power supplying and/or energy storage element selected from the group consisting of: battery; replaceable battery (e.g. via a battery door of housing 510); rechargeable battery; AC power converter; capacitor; and combinations of one or more of these. In some embodiments, power supply 570 comprises two or more batteries, such as two or more rechargeable batteries, such as to allow the first battery to be replaced (e.g. serially replaced) by the second battery. In some embodiments, power supply 570 is configured to provide a voltage of at least 3V. In some embodiments, power supply 570 is configured to provide a capacity between 1 Watt-hour and 75 Watt-hours, such as a battery or capacitor with a capacity of approximately 5 Watt-hours. In some embodiments, power supply 570 comprises an AC power source.

Each external programmer 550 (singly or collectively external programmer 550 or programmer 550) comprises a programming device configured to control one or more components of apparatus 10. Programmer 550 can comprise a user interface 555. Programmer 550 can send and/or receive commands to and/or from one or more external devices 500 via a wireless or wired connection (wired connection not shown but such as one or more insulated conductive wires). In some embodiments, one or more external devices 500 comprise programmer 550, such as when user interface 555 is integrated into housing 510 of external device 500. In some embodiments, apparatus 10 comprises multiple programmers 550.

External programmer 550 can be configured to adjust one or more parameters of apparatus 10, such as a stimulation parameter (e.g. a stimulation waveform parameter as described herein); a sensing parameter; a therapy parameter; a data recording parameter (e.g. a patient data recording parameter and/or an implantable device 200 data recording parameter); power transfer; data rate; activity of one or more external transmitters 530; activity of one or more external antennas 540; a functional element 260 parameter; a functional element 560 parameter; and combinations of one or more of these, such as is described hereabove. Programmer 550 can be further configured to provide information, such as patient physiologic information recorded by one or more implantable devices 200, or apparatus 10 information, such as performance and/or configuration information (singly or collectively "status information") of one or more external devices 500 and/or implantable devices 200. In some embodiments, the programmer 550 uses information recorded by one or more implantable devices 200, apparatus 10 information, and/or information from external devices 500 to adapt configuration parameters of one or more components of apparatus 10.

In some embodiments, external programmer 550 can be configured to confirm that an adequate power transmission and/or an adequate data transmission has occurred between one or more external devices 500 and one or more implantable devices 200. In these embodiments, programmer 550 can comprise diagnostic assembly 91 described hereinbelow, or otherwise be configured to detect one or more of: power transmission to the implantable system 20 (e.g. to detect power transmission to implantable system 20 below a threshold); power transmission to the implantable system 20 trending in an undesired direction; improper and/or inadequate data transfer to the implantable system 20; and combinations of one or more of these. In some embodiments, the programmer 550 monitors power transfer in real time and adjusts power transmission accordingly to optimize the rectifier 232 efficiency of one or more implantable devices 200. In some embodiments, apparatus 10 can be configured to adjust (e.g. in real time) the power transmission from one or more external devices 500 of external system 50 to one or more implantable devices 200 of implantable system 20, such as to optimize or otherwise improve an efficiency of apparatus 10, such as to improve the efficiency of transmissions between an external device 500 and an implantable device 200. These adjustments can include adjustment to one or more of: power transmission amplitude, duty cycle, frequency, phase, and periodicity.

In some embodiments, programmer 550 and/or another component of apparatus 10 comprises a matching network configured to match the impedance of one or more antennas 540 to one or more transmitters 530. The matching network can comprise an adjustable matching network. The matching network can comprise a directional coupler configured to measure a reflection coefficient. A transmitter 530 can comprise an output, and a programmer 550 can be configured to monitor a standing wave pattern at the output of the transmitter 530.

In some embodiments, external programmer 550 comprises a lookup table of stimulation signal waveform patterns, such as to allow a clinician, patient and/or other operator of apparatus 10 to select a predetermined stimulation pattern. In some embodiments, programmer 550 comprises a set of adjustable stimulation signal parameters configured to be varied to allow an operator to construct customized waveforms, such as to vary one or more stimulation parameters described hereabove. In some embodiments, the programmer 550 is configured to allow an operator to create a customized waveform by specifying an amplitude of one or more discrete pulses or steps of a stimulation signal.

In some embodiments, external programmer 550 comprises a transmitter configured to transmit data to tool 60 or another device such as a cell phone; computer; tablet; computer network such as the internet or a LAN; and combinations of one or more of these. In these embodiments, programmer 550 can comprise a wireless transmitter; a Bluetooth transmitter; a cellular transmitter; and combinations of one or more of these. In some embodiments, external programmer 550 comprises a receiver configured to receive data, or a transceiver configured to both transmit and receive data.

User interface 555 of external programmer 550 can comprise one or more user input components and/or user output components, such as a component selected from the group consisting of: keyboard; mouse; keypad; switch; membrane switch; touchscreen; display; audio transducer such as a speaker or buzzer; vibrational transducer; light such as an LED; and combinations of one or more of these.

In some embodiments, one or more components of external system 50 and/or other external component of apparatus 10, comprises one or more functional elements 560, such as functional elements 560a and/or 560b (singly or collectively functional element 560), shown positioned in programmer 550 and in external device 500, respectively. Each functional element 560 can comprise a sensor, an electrode, an energy delivery element, an agent delivery element, a magnetic field generating transducer, and/or any transducer. In some embodiments, one or more functional elements 560 comprise a transducer selected from the group consisting of: light; light emitting diode; wireless transmitter; Bluetooth device; mechanical transducer; piezoelectric transducer; pressure transducer; temperature transducer; humidity transducer; vibrational transducer; audio transducer; speaker; and combinations of one or more of these. In some embodiments, functional element 560 comprises a needle, a catheter (e.g. a distal portion of a catheter), an iontophoretic element or a porous membrane, such as an agent delivery element configured to deliver one or more agents contained (e.g. one or more agents in a reservoir, such as reservoir 525 described hereinbelow) within an external device 500 and delivered into the patient (e.g. into subcutaneous tissue, into muscle tissue and/or into a blood vessel such as a vein).

In some embodiments, the functional element 560 can comprise an electrode for sensing electrical activity and/or delivering electrical energy. In some embodiments, apparatus 10 is configured to cause stochastic resonance, and the addition of white noise can enhance the sensitivity of nerves to be stimulated and/or boost weak signals to be recorded by the one or more functional elements 260.

In some embodiments, one or more functional elements 560 comprise a sensor, such as a sensor configured to record data related to a patient parameter (e.g. a patient physiologic parameter), an external system 50 parameter and/or an implantable system 20 parameter. In some embodiments, operation of one or more implantable devices 200 (e.g. stimulation energy delivered by one or more implantable devices 200) is configured to be delivered based on the data recorded by one or more sensor-based functional elements 560, such as in a closed-loop energy delivery mode.

Functional element 560 can comprise one or more sensors selected from the group consisting of: electrode; sensor configured to record electrical activity of tissue; blood glucose sensor such as an optical blood glucose sensor; pressure sensor; blood pressure sensor; heart rate sensor; inflammation sensor; neural activity sensor; muscular activity sensor; pH sensor; strain gauge; accelerometer; gyroscope; GPS; respiration sensor; respiration rate sensor; temperature sensor; magnetic sensor; optical sensor; MEMs sensor; chemical sensor; hormone sensor; impedance sensor; tissue impedance sensor; body position sensor; body motion sensor; physical activity level sensor; perspiration sensor; patient hydration sensor; breath monitoring sensor; sleep monitoring sensor; food intake monitoring sensor; urine movement sensor; bowel movement sensor; tremor sensor; pain level sensor; orientation sensor; motion sensor; and combinations of one or more of these.

Functional element 560 can comprise one or more sensors configured to record data regarding a patient parameter selected from the group consisting of: blood glucose; blood pressure; EKG; heart rate; cardiac output; oxygen level; pH level; pH of blood; pH of a bodily fluid; tissue temperature;

inflammation level; bacteria level; type of bacteria present; gas level; blood gas level; neural activity; neural spikes; neural spike shape; action potential; local field potential (LFP); EEG; muscular activity (e.g. as measured using electromyography, EMG); electrical activity produced by skeletal muscles (e.g. as measured using EMG); gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

Functional element 560 can comprise one or more sensors configured to record data representing a parameter of external system 50 or any component of apparatus 10. Functional element 560 can comprise one or more sensors selected from the group consisting of: an energy sensor; a voltage sensor; a current sensor; a temperature sensor (e.g. a temperature of one or more components of external device 500 or programmer 550); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via controller 250 described herebelow) the data recorded by functional element 560 to assess one or more of: power transfer; link gain; power use; energy within power supply 570; performance of power supply 570; expected life of power supply 570; discharge rate of power supply 570; ripple or other variations of power supply 570; matching of antennas 240 and 540; communication error rate between implantable device 200 and external device 500; integrity of transmission between implantable device 200 and external device 500; and combinations of one or more of these.

In some embodiments, one or more functional elements 560 are positioned on a housing 510. A functional element 560 can comprise a body conduction sensor, such as a body conduction sensor configured to record and/or receive data via skin conduction. A functional element 560 can be configured to record data associated with stimulation delivered by one or more implantable devices 200 (e.g. record data associated with stimulation energy delivered by one or more functional elements 260), such as to provide closed loop or semi-closed loop stimulation. A functional element 560 can be configured to record temperature, such as when apparatus 10 is configured to deactivate or otherwise modify the performance of an external device 500 when the recorded temperature (e.g. patient temperature and/or external device 500 temperature) exceeds a threshold.

In some embodiments, external programmer 550 and/or an external device 500 can comprise a temperature sensor, such as functional elements 560a and 560b shown, respectively. The temperature-based functional element 560 can be positioned proximate a portion of programmer 550, housing 510 and/or one or more antennas 540 (e.g. to measure the temperature of one or more portions of a programmer 550 and/or external device 500). In these embodiments, the temperature data recorded by the functional element 560 is used to adjust one or more of: matching network; stimulation level (e.g. stimulation energy delivered by one or more implantable devices 200); power transmission level (e.g. level of power transmitted between one or more external devices 500 and one or more implantable devices 200); and combinations of one or more of these. In some embodiments, the temperature sensor-based functional element 560 is a part of a safety mechanism that deactivates programmer 550 and/or an external device 500 if the recorded temperature exceeds a threshold. Alternatively or additionally, a temperature sensor-based functional element 560 can be configured to measure temperature of the patient, such as when placed on housing 510, such as to adjust energy and/or agent delivery performed by implantable device 200 based on the recorded patient temperature.

Implantable system 20 comprises one or more implantable devices 200, such as one or more implantable devices 200 provided sterile or configured to be sterilized for implantation into the patient. A first implantable device 200 can be of similar or dissimilar construction and arrangement to a second implantable device 200. Each implantable device 200 can be configured to treat a patient (e.g. treat pain of the patient) and/or record patient information, such as by delivering energy and/or an agent to tissue and/or by recording one or more physiologic parameters of tissue.

One or more portions of an implantable device 200 or other component of implantable system 20 can be configured to be visualized or contain a visualizable portion or other visualizable element, such as visualizable element 222 shown. Visualizable element 222 can comprise a material selected from the group consisting of: radiopaque material; ultrasonically reflective material; magnetic material; and combinations of one or more of these. In these embodiments, each implantable device 200 can be visualized (e.g. during and/or after implantation) via an imaging device such as a CT, X-ray, fluoroscope, ultrasound imager and/or MRI.

In some embodiments, implantable system 20 comprises multiple implantable devices 200 (e.g. implantable device 200 and implantable device 200' shown in FIG. 1) and implantable system 20 comprises a "multi-point ready" system, in which the operation (e.g. energy delivery, agent deliver, data recording and/or other function) of the multiple implantable devices 200 is performed simultaneously, asynchronously, and/or sequentially. The implantable devices 200 can be part of a network including one or more external devices 500 (e.g. external device 500 and external device 500' shown in FIG. 1) in which the treating of a patient and/or the recording of patient information relies on operation of the implantable devices 200 at one or more implantation sites in a synchronized, asynchronized, and/or otherwise coordinated way. The synchronization or otherwise coordination can be controlled by a single or multiple external devices 500, which can further be synchronized to a single clock. Each implantable device 200 of implantable system 20 can receive a power signal and/or a data signal from one or more external devices 500. In some embodiments of the multi-point ready implantable system 20, each implantable device 200 comprises a unique ID, such that each implantable device 200 can be individually addressed (e.g. receive unique signals from external system 50). In some embodiments, external system 50 transmits high-bandwidth signals to implantable system 20, such that time-domain multiple access communication can be performed while operating in near real time. In some embodiments, implantable system 20 is configured as a multi-point ready system such that stimulation energy delivered by implantable system 20 is independent of power received by implantable system 20 from external system 50.

Two implantable devices 200, or two discrete components of a single implantable device 200 (e.g. two components comprising or positioned in different housings), can be attached to each other by a connecting filament as defined hereabove. In some embodiments, a connecting filament comprises a user-attachable (e.g. clinician-attachable) connector on at least one end. The filament connector is configured to operably attach to a mating connector on a component (e.g. a housing 210) of an implantable device 200.

Each implantable device 200 is configured to receive power and/or data (e.g. implantable system 20 configuration data) from one or more external devices 500. In some embodiments, one or more implantable devices 200 are configured to receive both power and data (e.g. simultaneously and/or sequentially) from one or more external devices 500. In some embodiments, a single external device 500 sends power and/or data to multiple implantable devices 200. Alternatively or additionally, a single implantable device 200 can receive power and/or data from multiple external devices 500. In some embodiments, a first external device 500 is positioned on or near the patient's skin at a location proximate an implanted first implantable device 200, and a second external device 500 is positioned on or near the patient's skin (generally "on" the patient's skin) at a location proximate an implanted second implantable device 200. In these embodiments, the first external device 500 transmits data and/or power to at least the first implantable device 200 and the second external device 500 transmits data and/or power to at least the second implantable device 200.

Each implantable device 200 can comprise one or more functional elements 260, configured to stimulate, deliver energy to, deliver an agent to, record information from and/or otherwise interface with the patient. Alternatively or additionally, the one or more functional elements 260 can be configured to record patient information. Each implantable device 200 can comprise housing 210, receiver 230, controller 250, energy storage assembly 270 and/or one or more antennas 240, each described in detail herein. Implantable device 200 and controller 250 can be of similar construction and arrangement to the similar components described herebelow in reference to FIG. 3. Each functional element 260 can comprise a sensor and/or any transducer, as described in detail herein. One or more functional elements 260 can be positioned on a lead 265 (e.g. a flexible filament including wires or other conductors that connect each functional element to electronics within housing 210). Each implantable device 200 can comprise one or more leads 265, such as two leads attached to a single housing 210, or a first lead 265 attached to a first housing 210 and a second lead 265 attached to a second housing 210. Each implantable device 200 can further comprise one or more anchor elements 221, as described in detail herebelow.

In some embodiments, one or more implantable devices 200 are further configured to transmit data to one or more external devices 500, such as via one or more antennas 240 transmitting a signal to one or more antennas 540, or otherwise. Data transmitted by an implantable device 200 can comprise patient information (e.g. patient physiologic information recorded by one or more functional elements 260 configured as a physiologic sensor), or implantable device 200 information (e.g. data recorded by one or more functional elements 260 configured as a sensor and positioned in implantable device 200, or other implantable device 200 configuration and/or performance data).

Housing 210 of each implantable device 200 can comprise one or more rigid and/or flexible materials which surround various components, such as antenna 240, energy storage assembly 270, controller 250 and/or receiver 230 as shown in FIG. 1. In some embodiments, one or more functional elements 260 are positioned in, on and/or within housing 210. In some embodiments, housing 210 surrounds a substrate, such as a flexible and/or foldable printed circuit board, such as multiple discrete or continuous printed circuit boards positioned in different planes (e.g. a flexible or foldable printed circuit board).

Housing 210 can comprise one or more shapes or combination of shapes, such as one or more shapes selected from the group consisting of: disc; pill; cylinder; sphere; oblate spheroid; dish-like shape; bowl-like shape; cone; rectangular prism; trapezoidal prism; a portion of a toroid; and combinations of one or more of these.

Housing 210 can comprise a major axis and a minor axis, defined hereabove. In some embodiments, housing 210 comprises a major axis less than or equal to 20 mm, such as a major axis less than or equal to 15 mm, 12 mm or 10 mm. In some embodiments, housing 210 comprises a minor axis less than or equal to 8 mm, such as a minor axis less than or equal to 6 mm, or less than or equal to 5 mm. Housing 210 can comprise a wall thickness between 0.2 mm and 1.0 mm, such as a wall thickness between 0.2 mm and 0.5 mm, such as a wall thickness of approximately 0.3 mm. Housing 210 can comprise a displacement volume less than or equal to 2000 mm$^3$, such as less than or equal to 600 mm$^3$.

Housing 210 can comprise one or more portions that are transmissive to radiofrequency (RF) signals. In some embodiments, housing 210 comprises glass. In some embodiments, housing 210 comprises a material selected from the group consisting of: glass; ceramic; stainless steel; titanium; polyurethane; an organic compound; liquid crystal polymer (LCP); gold; platinum; tungsten; epoxy; a thermoplastic; a thermoset plastic; and combinations of one or more of these. In some embodiments, one or more portions of housing 210 comprises one or more coatings, such as one or more coatings configured to cause or prevent a physiologic reaction and/or a coating configured to block (e.g. shield) an electromagnetic transmission.

Housing 210 can comprise one or more passageways or other feedthroughs, such as for the passage of a lead, wire, optical fiber, fluid delivery tube, mechanical linkage and/or other conduit through a wall of housing 210, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes.

In some embodiments, one or more inner or outer surfaces (or portions of surfaces) of housing 210 includes an insulating and/or shielding layer (e.g. a conductive electromagnetic shielding layer), such as inner coating 219a and/or outer coating 219b shown (singly or collectively coating 219). Coating 219 can comprise an electrically insulating and/or a thermally insulating layer or other coating. In some embodiments, one or more portions of housing 210 comprise an electrically shielding coating 219, while other portions are transmissive to electromagnetic signals such as radiofrequency signals.

In some embodiments, housing 210 comprises an array of feedthroughs, not shown. In some embodiments, housing 210 is surrounded by a covering, such as a flexible and/or non-conductive covering, such as a covering made of an elastomer.

In some embodiments, one or more implantable devices 200 comprises one or more anchor elements configured to secure one or more portions of implantable device 200 to tissue, such as anchor element 221 shown positioned on housing 210. Anchor element 221 can comprise one or more anchoring elements selected from the group consisting of: a sleeve such as a silicone sleeve; suture tab; suture eyelet; bone anchor, wire loops; porous mesh; penetrable wing; penetrable tab; bone screw eyelet; tine; pincers; suture slits; and combinations of one or more of these.

One or more antennas 240 (singly or collectively antenna 240) can be configured to receive power and/or data, and receiver 230 can receive the power and/or data from the one or more antennas 240. Each antenna 240 can comprise one or more implantable antennas, such as one or more antennas positioned within housing 210, and/or one or more antennas electrically attached to a connecting filament. In some embodiments, one or more implantable devices 200 comprise at least two antennas 240, or at least three antennas 240. Antenna 240 can be configured to receive power and/or data from one or more external devices 500, such that an attached receiver 230 receives the power and/or data. In some embodiments, implantable system 20 comprises at least two implantable devices 200, each of which comprise one or more (e.g. two or three) antennas 240 which are positioned within a housing 210 and/or electrically tethered to a housing 210. In some embodiments, an implantable device 200 comprises a first antenna 240 positioned in a first plane and a second antenna 240 positioned in a second plane. The first plane and second plane can be relatively orthogonal planes, or planes oriented between 30° and 90° relative to each other, such as between 40° and 90°, approximately 30°, approximately 45° and/or approximately 60° relative to each other. In some embodiments, an implantable device 200 comprises a first antenna 240 positioned in a first plane, a second antenna 240 positioned in a second plane, and a third antenna 240 positioned in a third plane.

In some embodiments, implantable device 200 comprises one or more antennas 240 positioned on a substrate, such as a printed circuit board (PCB), a flexible printed circuit board and/or a foldable substrate (e.g. a substrate comprising rigid portions and hinged portions). In some embodiments, the substrate can be folded or otherwise pivoted to position the various antennas 240 on differently oriented planes, such as multiple planes oriented between 5° and 90° relative to each other, such as two antennas 240 positioned on two planes oriented between 30° and 90° or between 40° and 90° relative to each other, or three antennas 240 positioned on three planes oriented between 5° and 60° relative to each other. Two or more antennas 240 can be positioned on two or more different planes that are approximately 45° relative to each other, or approximately 60° or approximately 90° relative to each other.

Implantable device 200 can comprise three antennas 240. In some embodiments, a first antenna 240 can comprise an electrical dipole antenna, and the second and third antennas 240 can be positioned in different planes than the first antenna 240. In some embodiments, the three antennas 240 each comprise a loop antenna, such as when each loop antenna is positioned on a different plane. In some embodiments, a first antenna 240 comprises an electrical dipole antenna, and a second antenna 240 and a third antenna 240 each comprise a loop antenna. In these embodiments, the second antenna 240 and the third antenna 240 can be positioned relatively orthogonal to each other (e.g. positioned on two relatively orthogonal planes). In some embodiments, a first antenna (e.g. an electrical dipole antenna) is positioned outside of housing 210, while a second antenna (e.g. a loop antenna) and a third antenna (e.g. a loop antenna) are each positioned on, in and/or within housing 210. In some embodiments, implantable device 200 can comprise one or more antennas 240 in which any combination of antenna types (as described herein) are used in combination.

One or more antennas 240 can comprise an antenna selected from the group consisting of: loop antenna; multiple-turn loop antenna; planar loop antenna; coil antenna; dipole antenna; electric dipole antenna; magnetic dipole antenna; patch antenna; loaded dipole antenna; concentric loop antenna; loop antenna with ferrite core; and combinations of one or more of these. One or more antennas 240 can comprise a loop antenna, such as an elongated loop antenna or a multiple-turn loop antenna.

One or more antennas 240 can comprise a multi-turn spiral loop antenna, such as a multi-turn spiral loop antenna configured to desensitize coupling sensitivity and/or boost input voltage. In some embodiments, one or more antennas 240 comprise multiple concentric loops with varied dimensions, such as concentric loops configured to desensitize coupling sensitivity. In these embodiments, the multiple concentric loops can be: connected in parallel and driven from the same feed point; driven from the same feed point and connected using one or more of a capacitor, inductor, varactor, and combinations of one or more of these; and/or driven from multiple feed points.

One or more antennas 240 can comprise a minor axis and a major axis. In some embodiments, one or more antennas 240 comprise a minor axis between 1 mm and 8 mm, such as between 2 mm and 5 mm. In some embodiments, one or more antennas 240 comprise a major axis between 3 mm and 15 mm, such as between 4 mm and 8 mm. In some embodiments, one or more antennas 240 comprise a major axis above 3 mm, such as between 3 mm and 15 mm, such as when the antenna 240 is positioned outside of housing 210.

One or more antennas 240 can comprise a foldable and/or unfoldable antenna, such as is described in applicant's co-pending U.S. patent application Ser. No. 14/975,358, titled "Method and Apparatus for Minimally Invasive Implantable Modulators", filed Dec. 18, 2015, the content of which is incorporated herein by reference in its entirety for all purposes.

One or more antennas 240 can be positioned inside of housing 210. Alternatively or additionally, one or antennas 240 can be positioned outside of housing 210.

Implantable system 20, one or more implantable devices 200 and/or one or more antennas 240 can be configured to be positioned at a desired depth beneath the patient's skin, such as at a depth between 0.5 cm and 7.0 cm, such as a depth of between 1.0 cm and 3.0 cm.

One or more energy storage assemblies 270 (singly or collectively energy storage assembly 270) can comprise one or more implantable energy storage components, such as one or more batteries (e.g. rechargeable batteries) and/or capacitors (e.g. a supercapacitor). Energy storage assembly 270 can be configured to provide power to one or more of: one or more functional elements 260; controller 250; receiver 230; and combinations of one or more of these. In some embodiments, energy storage assembly 270 further provides power to one or more antennas 240 and/or circuitry configured to transmit data via antenna 240. In some embodiments, energy storage assembly 270 includes digital control for charge/discharge rates, voltage outputs, current outputs, and/or system power distribution and/or management.

Energy storage assembly 270 can comprise one or more capacitors with a single or collective capacitance between 0.01 μF and 10 F, such as a capacitance between 1 μF and 1.0 mF, or between 1 μF and 10 μF. The energy storage assembly 270 can comprise one or more capacitors with capacitance between 1 mF and 10 F, such as when energy storage assembly 270 comprises a super-capacitor and/or an ultra-capacitor. Such large capacitance can be used to store sufficient charge to maintain operation (e.g. maintain delivery of stimulation energy and/or delivery of an agent) without the use (e.g. sufficient proximity) of an associated external device 500, such as is described herebelow in reference to FIG. 2. A capacitor or other energy storage element (e.g. a battery) can be chosen to provide sufficient energy to maintain operation for at least 30 seconds, at least 2 minutes, at least 5 minutes, at least 30 minutes, and up to several hours or more (e.g. during showering, swimming or other physical activity). In some embodiments, energy storage assembly 270 is configured to provide continuous and/or intermittent stimulation energy for at least one charge-balanced pulse (e.g. for the duration of at least one charge-balanced pulse). In some embodiments, a capacitor, battery or other energy storage element is configured to provide stimulation energy without receiving externally supplied power for periods of at least 1 hour, at least 1 day, at least 1 month or at least 1 year. Energy storage assembly 270 can comprise one or more capacitors with a breakdown voltage above 1.0V, such as a breakdown voltage above 1.5V, 4.0V, 10V, or 15V. In some embodiments, energy storage assembly 270 can comprise capacitors distributed outside of housing 210, such as when one or more capacitors are distributed along lead 265. Energy storage assembly 270 can comprise one or more capacitors with low self-leakage, such as to maintain stored energy for longer periods of time.

In some embodiments, energy storage assembly 270 comprises a temporary energy storage component, such as a super-capacitor, configured to store a sufficient quantity of energy to provide uninterrupted stimulation, such as during time periods in which the link gain may be of poor quality or it may be temporarily unavailable (e.g. an external device 500 not being in place such as during a shower, swimming, and the like). An energy storage assembly 270 comprising an ultra-capacitor, super-capacitor or flexible battery can be charged via the wireless power transmission of the present inventive concepts, such as to store a sufficient amount of energy for one or more functional elements 260 to delivery stimulation energy during subsequent (intended or unintended) unavailability of one or more external devices 500 (e.g. an external device 500 is intentionally removed or unintentionally falls off or otherwise loses its position sufficiently proximate one or more implantable devices 200). An energy storage assembly 270 comprising one or more high capacity energy storage components can be beneficial in applications where therapy interruption provides a significant risk or is otherwise relatively unacceptable, such as for life support therapies, cardiac resynchronization therapies, and the like. The high capacity energy storage components of energy storage assembly 270 can be positioned in an assembly positioned within housing 210, on an inner or outer surface of housing 210, within a separate housing, and/or within lead 265.

One or more controllers 250 (singly or collectively controller 250) can be configured to control one or more functional elements 260, such as a functional element 260 comprising a stimulation-based transducer (e.g. an electrode or other energy delivery element) and/or a sensor (e.g. a physiologic sensor and/or a sensor configured to monitor an implantable device 200 parameter). In some embodiments, controller 250 is of similar construction and arrangement to controller 250 described herebelow in reference to FIG. 3. In some embodiments, controller 250 is configured to transmit a stimulation signal (e.g. transmit stimulation energy configured in one or more stimulation waveforms) to one or more functional elements 260 (e.g. one or more functional elements 260 comprising an electrode and/or other energy delivery element), independent of the power signal received by one or more antennas 240 (e.g. independent of power transmitted by external system 50), such as by using energy stored in energy storage assembly 270. In these embodiments, the power signal and/or the RF path for the power signal can be adjusted to optimize power efficiency (e.g. by tuning matching network on transmitter 530 and/or receiver 230; configuring antennas 540 and/or 240 in an array; tuning operating frequency; duty cycling the power signal; adjusting antenna 540 and/or 240 position; and the like), and a stimulation signal can be precisely delivered (e.g. by using energy stored on energy storage assembly 270 and generating stimulation signal locally on the implantable device 200) to ensure clinical efficacy. Also, if the power signal transmission (also referred to as "power link") is perturbed unexpectedly, the stimulation signal can be configured so that it is not significantly affected (e.g. unaffected). In some configurations, the stimulation signal being delivered by one or more implantable devices 200 can be insensitive to interference that may be present. In these embodiments, a power transmission signal and stimulation signal can vary in one or more of: amplitude; changes in amplitude; average amplitude; frequency; changes in frequency; average frequency; phase; changes in phase; average phase; waveform shape; pulse shape; duty cycle; polarity; and combinations of one or more of these.

Controller 250 can receive commands from receiver 230, such as one or more commands related to one or more implantable device 200 configuration parameters selected from the group consisting of: stimulation parameter; data rate of receiver; data rate of data transmitted by the first implantable device 200 at least one implantable antenna 240; functional element 260 configuration; state of controller 250; antenna 240 impedance; clock frequency; sensor configuration; electrode configuration; power management parameter; energy storage assembly parameter; agent delivery parameter; sensor configuration parameter; and combinations of one or more of these.

In some embodiments, one or more functional elements 260 comprise a stimulation element configured to deliver energy (e.g. one or more electrodes configured to deliver monopolar or bipolar electrical energy) to tissue, and controller 250 is configured to control the energy delivery, such as to control one or more stimulation parameters as described herein. Each of these stimulation parameters can be held relatively constant, and/or varied, such as a variation performed in a continuous or intermittent manner. In some embodiments, one or more stimulation parameters are varied in a random or pseudo-random (hereinafter "random") manner, such as a variation performed by apparatus 10 using a probability distribution as described herebelow. In some embodiments, stimulation (e.g. stimulation comprising high frequency and/or low frequency signal components) is varied randomly to eliminate or at least reduce synchrony of neuronal firing with the stimulation signal (e.g. to reduce paresthesia or other patient discomfort). In some embodiments, one or more functional elements 260 comprise a stimulation element configured to stimulate a target (e.g. nerve tissue such as spinal nerve tissue and/or peripheral nerve tissue). The amount of stimulation delivered to the target can be controlled by varying a parameter selected from the group consisting of: functional element 260 size and/or configuration (e.g. electrode size and/or configuration); functional element 260 shape (e.g. electrode shape, magnetic field generating transducer shape or agent delivering element shape); shape of a generated electric field; shape of a generated magnetic field; stimulation signal parameters; and combinations of one or more of these.

In some embodiments, one or more functional elements 260 comprise an element configured to deliver electrical energy to tissue (e.g. one or more electrodes configured to deliver monopolar or bipolar electrical energy), and controller 250 is configured to control charge balance, such as to actively and/or passively control charge balance, as described herebelow. Charge balance can be essential for patient safety in electrical stimulation of nerves or other tissue. Imbalanced stimulation waveforms can cause electrode corrosion and/or dissolution which can lead to deposition of toxic materials in tissue, implant rejection, and nerve damage. The stimulation waveform can be balanced such that net outflow charge approximately equals net inflow charge. With stimulation waveform amplitudes that can vary between 0.01 mA to 15 mA (such as between 0.1 mA and 15 ma, between 0.1 mA and 12 mA, or between 0.1 mA and 10 mA), depending on the treatment, the error in charge balance can be on the order of 0.001% to 0.01%. Alternatively or additionally, controller 250 can comprise AC coupling capacitors that are configured to balance stimulation waveforms passively. The AC coupling capacitance can be fairly large (e.g. greater than 10 µF), in order to pass the stimulation waveform with minimal filtering. In some embodiments, apparatus 10 can be configured to perform active charge balancing. In some embodiments, an implantable device 200 can comprise a precise resistor in series with a stimulation electrode-based functional element 260. The precise resistor can be used to measure outflow and inflow currents, such as when controller 250 comprises an analog to digital converter (ADC). Controller 250 can integrate current over time during a first phase in which stimulation energy is delivered, and during a second phase in which a reverse current is applied (e.g. a reverse current used to balance charge). Controller 250 can be configured to balance the total charge in the two phases, to ensure that the net DC current is approximately zero. The integration can be achieved using an analog integrator and/or a digital summer of controller 250, with controller 250 keeping track of one or more parameters of the pulses delivered (e.g. pulses delivered within a train or a burst). Implantable device 200 can comprise a precise series resistance comprising an on-chip trimmed resistor or an off chip resistor. In some embodiments, implantable device 200 comprises a bank of trimmed resistors that are used to control the net series resistance, such as to adjust resistance based on stimulation amplitude requirements (e.g. to take advantage of the full dynamic range of an ADC of controller 250). In some embodiments, controller 250 comprises a shunt path with an RC-based low pass filter used for both outflow and inflow of current. RC elements of controller 250 can be chosen such that the shunt current is only a fraction of the stimulation current. Since the same RC elements can be used for both outflow and inflow current, the precision required for the RC components can be lower. An ADC can be used to sense the voltage on the capacitor at the end of a stimulation pulse. After the stimulation pulse, the capacitor can be discharged and the polarity of the stimulation current can be reversed and set to any amplitude, until the capacitor is charged to approximately the same voltage (according to the ADC precision) as it was charged during the stimulation pulse. The ADC resolution can be high enough to ensure the residual error is less than what would cause an undesired charge accumulation. ADC resolution requirements can be further reduced by reducing the net capacitance in a shunt RC circuit, to cause accelerated charging of the capacitor. The capacitor can be discharged every time the voltage exceeds a certain predefined threshold, while controller 250 keeps track of the number of times the capacitor has been charged and reset. By resetting the capacitor through a low resistance path, the discharge time can be insignificant compared to the charge time, reducing the error due to discharge period. Since the net charge equivalent to full scale voltage on the ADC can be divided into multiple cycles, the required resolution of the ADC to achieve the same residual error can be divided by the number of cycles.

In some embodiments, controller 250 is configured to produce a stimulation signal comprising a waveform or a waveform pattern (hereinafter stimulation waveform), for one or more functional elements 260 configured as a stimulation element (e.g. such that one or more functional elements 260 deliver stimulation energy comprising or at least resembling that stimulation waveform). Controller 250 can produce a stimulation signal comprising a waveform selected from the group consisting of: square wave; rectangle wave; sine wave; sawtooth; triangle wave (e.g. symmetric or asymmetric); trapezoidal; ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to produce a stimulation signal comprising a waveform including a combination of two or more waveforms selected from the group consisting of: square wave; rectangle wave; sine wave; triangle wave (symmetric or asymmetric); ramp; waveform with exponential increase; waveform with exponential decrease; pulse shape which minimizes power consumption; Gaussian pulse shape; pulse train; root-raised cosine; bipolar pulses; and combinations of one or more of these. In some embodiments, controller 250 is configured to construct a custom waveform (e.g. an operator customized waveform), such as by adjusting amplitude at specified time steps (e.g. for one or more pulses). In some embodiments, controller 250 is configured to generate a waveform including one or more random parameters (e.g. random timing of pulses or random changes in frequency, rate of change or amplitude).

In some embodiments, controller 250 is configured to provide a stimulation signal comprising waveforms and/or pulses repeated at a frequency (e.g. includes a frequency component) between 1.0 Hz and 50 KHz, such as between 10 Hz and 500 Hz, between 40 Hz and 160 Hz and/or between 5 KHz and 15 KHz. In some embodiments, controller 250 is configured to produce a stimulation signal comprising a frequency between 1 Hz and 1000 Hz, such as a stimulation signal with a frequency between 10 Hz and 500 Hz. In some embodiments, controller 250 is configured to produce a stimulation signal comprising a duty cycle between 0.1% and 99%, such as a duty cycle between 1% and 10% or between 1% and 25%. In some embodiments, controller 250 is configured to produce a stimulation signal comprising a frequency modulated stimulation waveform, such as a stimulation waveform comprising a frequency component (e.g. signal) between 1 kHz and 20 kHz. In some embodiments, controller 250 is configured to produce a stimulation signal comprising a mix and/or modulation of low frequency and high frequency signals, which can be of any of the waveform types, shapes and other configurations as described herein. In these embodiments, the stimulation signal can comprise low frequency signals between 1 Hz and 1000 Hz, and high frequency signals between 600 Hz and 50 kHz, or between 1 kHz and 20 kHz. Alternatively or additionally, the stimulation signal can comprise a train of high frequency signals and bursts of low frequency signals, and/or a train of low frequency signals and bursts of high frequency signals. Alternatively or additionally, the stimulation signal can comprise one or more high frequency signals modulated with one or more low frequency signals, such as one or more high frequency signals frequency modulated (FM), amplitude modulated (AM), phase modulated (PM) and/or pulse width modulated (PWM) with one or more low frequency signals. The stimulation signal can cycle among different waveforms shapes at specified time intervals. The stimulation signal can comprise a pseudo random binary sequence (PRBS) non-return-to-zero or return-to-zero waveform, such as with a fixed and/or time-varying pulse width and/or frequency of the pulses.

Controller 250 can comprise a clamping circuit configured to allow fast charging and/or discharging of the energy storage assembly 270, functional element 260 drivers (e.g. electrode drivers) of controller 250, and/or other components of implantable device 200. The clamping circuit can improve pulse shape by offering additional control and/or configuration of rise and fall times in the shape of the waveform (e.g. to create rapid rise or fall times). In some embodiments, the clamping circuit can be configured to limit the rise and/or fall time to be less than or equal to one-tenth (10%) of the pulse width of an applied stimulation pulse (e.g. less than or equal to 1 μs rise and/or fall time for a 10 μs stimulation pulse).

In some embodiments, controller 250 comprises a matching network configured to match the impedance of a first antenna 240 with the impedance of the receiver 230. In these embodiments, controller 250's matching network can be adjustable. Alternatively or additionally, controller 250 can comprise an adjustable loading impedance to stabilize the load seen at an antenna 240 under different operating conditions. In some embodiments, the adjustable loading impedance is controlled according to the charge rate of the energy storage assembly 270.

Controller 250 and/or any other component of each implantable device 200 can comprise an integrated circuit comprising one or more components selected from the group consisting of: matching network; rectifier; DC-DC converter; regulator; bandgap reference; overvoltage protection; overcurrent protection; active charge balance circuit; analog to digital converter (ADC); digital to analog converter (DAC); current driver; voltage driver; digital controller; clock generator; data receiver; data demodulator; data modulator; data transmitter; electrode drivers; sensing interface analog front end; power management circuit; energy storage interface; memory register; timing circuit; and combinations of one or more of these.

One or more receivers 230 (singly or collectively receiver 230) can comprise one or more components, such as demodulator 231, rectifier 232 and/or power converter 233 shown in FIG. 1. In some embodiments, receiver 230 can comprise a DC-DC converter such as a boost converter. Receiver 230 can comprise a data receiver, such as a data receiver including an envelope detector and demodulator and/or an envelope averaging circuit. In some embodiments, one more antennas 240 separately connect to one or more receivers 230. In some embodiments, one or more antennas 240 connect to a single receiver 230, such as via a series connection or a parallel connection.

One or more implantable devices 200 can be configured to transmit a data signal to external system 50. In some embodiments, receiver 230 is configured to drive one or more antennas 240 to transmit data to external system 50 (e.g. to an antenna 540 of an external device 500). Alternatively or additionally, implantable device 200 can be configured to transmit a data signal by having receiver 230 adjust a load impedance to backscatter energy, such as a backscattering of energy which can be detected by external system 50. In some embodiments, data transmission is accomplished by receiver 230 manipulating a signal at a tissue interface, such as to transmit a data signal using body conduction.

In some embodiments, receiver 230 comprises a matching network, such as a matching network configured to detune to prevent oversaturation. For example, implantable system 20 can comprise two or more implantable device 200 each of which includes a receiver 230 comprising a matching network. A first implantable device 200's receiver 230's matching network can be configured to detune based on power received by the second implantable device 200's receiver 230.

Demodulator 231 can comprise circuitry that asynchronously recovers signals modulated on the power signal provided by external system 50, and converts the modulated signals into digital signals. In some embodiments, demodulator 231 asynchronously recovers the modulated signal by comparing a dynamically generated moving average with the envelope, outputting a high voltage when the envelope is greater than the moving average and a low voltage when the envelope is less than the moving average. Data can then be extracted from this resulting digital signal from the width and/or amplitude of the pulses in the signal, according to the encoding method used by external system 50. In some embodiments, demodulator 231 recovers a digital signal that can be used as timing information for an implantable device 200, similar to an on-chip clock. The recovered clock signal can also be used to synchronize an on-chip clock generator of controller 250, such as through the use of a frequency and/or phase locked loop (FLL or PLL).

Rectifier 232 can comprise a power signal rectifier, such as to provide power to the energy storage assembly 270 and/or controller 250. In some embodiments, rectifier 232 comprises one or more self-driven synchronous rectifier (SDSR) stages connected in charge-pump configuration, to boost the voltage from input RF amplitude to the rectifier to a higher voltage. The boosted voltage can directly charge energy storage assembly 270, or be further boosted by a DC-DC converter or boost converter. In some embodiments, rectifier 232 can comprise diode-capacitor ladder stages instead of, or in addition to, SDSR stages. On-chip diodes, such as Schottky diodes, or off-chip diodes can be used in one or more rectifier 232 stages. For maximum efficiency, the rectification elements, such as diodes, can be optimized to minimize forward conduction and/or reverse conduction losses by properly sizing the components and selecting appropriate number of stages based on the input RF voltage and load current.

Power converter 233 can comprise one or more voltage conversion elements such as DC-DC converters that boost or otherwise change the voltage to a desired level. In some embodiments, voltage conversion is achieved with a buck-boost converter, a boost converter, a switched capacitor, and/or charge pumps. One or more power converters 233 can interface with energy storage assembly 270 and charge up associated energy storage components to desired voltages. In some embodiments, power converter 233 receives control signals from controller 250, such as to configure voltages, currents, charge/discharge rates, switching frequencies, and/or other operating parameters of power converter 233.

One or more implantable leads 265 (singly or collectively lead 265) can be attached to one or more housings 210, such as a lead 265 comprising one or more functional elements 260. Lead 265 can comprise one or more functional elements 260 configured as a stimulation element (e.g. an electrode configured to deliver electrical energy in monopolar or bipolar mode or an agent delivery element such as an output port fluidly connected to a reservoir within housing 210). Alternatively or additionally, lead 265 can comprise one or more functional elements 260 configured as a physiologic sensor (e.g. an electrode configured to record electrical activity of tissue or other physiologic sensor as described herein). Alternatively or additionally, lead 265 can comprise one or more functional elements 260 configured to transmit signals through tissue to external system 50, such as through body conduction.

In some embodiments, lead 265 comprises a removable stylet configured to aid in the implantation of lead 265, such as is described in applicant's co-pending International PCT Patent Application Serial Number PCT/US2016/016888, titled "Medical Apparatus including an Implantable System and an External System", filed Feb. 5, 2016; the content of which is incorporated herein by reference in its entirety for all purposes. In some embodiments, implantable system 20 comprises more than one lead 265, comprising one or more functional elements 260 and attached to one or more housings 210 of one or more implantable devices 200. In some embodiments, one or more leads 265 can be attached to a single housing 210.

In some embodiments, lead 265 comprises a diameter between 1 mm and 4 mm, such as a diameter between 1 mm and 2 mm. In some embodiments, lead 265 comprises a length between 3 cm and 60 cm, such as a length between 6 cm and 30 cm. One or more leads 265 can include between 2-64 functional elements 260, such as when a lead 265 comprises between 2 and 64 electrodes, such as between 4 and 32 electrodes. In some embodiments, lead 265 can comprise a paddle lead. In some embodiments, lead 265 comprises a single or multi-lumen catheter, such as when an attached implantable device 200 is configured as an agent delivery apparatus as described herein (e.g. a functional element 260 configured as a catheter comprises at least a portion of lead 265).

One or more functional elements 260 (singly or collectively functional element 260) can comprise one or more sensors, transducers and/or other functional elements. In some embodiments, functional elements 260 comprise at least one sensor and/or at least one transducer (e.g. a single functional element 260 or multiple functional elements 260). In some embodiments, functional element 260 comprises a functional element configured to provide a therapy, such as one or more functional elements 260 configured to deliver an agent to tissue (e.g. a needle or catheter), to deliver energy to tissue and/or to otherwise affect tissue. In some embodiments, functional element 260 comprises one or more functional elements 260 configured to record patient information, such as when functional element 260 comprises one or more sensors configured to measure a patient physiologic parameter, as described herein. In some embodiments, functional element 260 comprises one or more sensors configured to record an implantable device 200 parameter, also as described herein.

One or more functional elements 260 can be positioned on lead 265 as shown in FIG. 1. Alternatively or additionally, one or more functional elements 260 can be positioned on housing 210.

Functional element 260 can comprise one or more functional elements positioned at one or more internal body locations. Functional element 260 can comprise one or more functional elements positioned to interface with (e.g. deliver energy to and/or record a physiologic parameter from) spinal cord tissue, spinal canal tissue, epidural space tissue, spinal root tissue (dorsal or ventral), dorsal root ganglion, nerve tissue (e.g. peripheral nerve tissue, spinal nerve tissue or cranial nerve tissue), brain tissue, ganglia (e.g. sympathetic or parasympathetic) and/or a plexus. In some embodiments, functional element 260 comprises one or more elements positioned proximate and/or within one or more tissue types and/or locations selected from the group consisting of: one or more nerves; one or more locations along, in and/or proximate to the spinal cord; peripheral nerves of the spinal cord including locations around the back; the tibial nerve (and/or sensory fibers that lead to the tibial nerve); the occipital nerve; the sphenopalatine ganglion; the sacral and/or pudendal nerve; brain tissue, such as the thalamus; baroreceptors in a blood vessel wall, such as in the carotid artery; one or more muscles; the medial nerve; the hypoglossal nerve and/or one or more muscles of the tongue; cardiac tissue; the anal sphincter; the dorsal root ganglion; motor nerves; muscle tissue; the spine; the vagus nerve; the renal nerve; an organ; the heart; the liver; the kidney; an artery; a vein; bone; and combinations of one or more of these, such as to stimulate and/or record data from the tissue and/or location in which the functional element 260 is positioned proximate to and/or within. In some embodiments, apparatus 10, implantable device 200 and/or functional element 260 are configured to stimulate spinal nerves, peripheral nerves and/or other tissue as described in applicant's co-pending application International PCT Patent Serial Number PCT/US2016/051177, titled "Apparatus for Peripheral or Spinal Stimulation", filed Sep. 9, 2016.

In some embodiments, functional element 260 comprises one or more sensors configured to record data representing a physiologic parameter of the patient. Functional element 260 can comprise one or more sensors selected from the group consisting of: electrode; sensor configured to record electrical activity of tissue; blood glucose sensor; gas sensor; blood gas sensor; ion concentration sensor; oxygen sensor; pressure sensor; blood pressure sensor; heart rate sensor; cardiac output sensor; inflammation sensor; neural activity sensor; neural spike sensor; muscular activity sensor; EMG sensor, bladder volume sensor, bladder pressure sensor, gastric volume sensor; peristalsis rate sensor; pH sensor; strain gauge; accelerometer; gyroscope; GPS; respiration sensor; respiration rate sensor; flow sensor; viscosity sensor; temperature sensor; magnetic sensor; optical sensor; MEMs sensor; chemical sensor; hormone sensor; impedance sensor; tissue impedance sensor; electrode-tissue interface impedance sensor; body position sensor; body motion sensor; organ motion sensor; physical activity level sensor; perspiration sensor; patient hydration sensor; breath monitoring sensor; sleep monitoring sensor; food intake monitoring sensor; digestion monitoring sensor; urine movement sensor; bowel movement sensor; tremor sensor; pain level sensor; and combinations of one or more of these.

Apparatus 10 and functional element 260 can be configured to record a patient parameter (e.g. patient physiologic and/or patient environment parameter) selected from the group consisting of: blood glucose; blood pressure; EKG;

heart rate; cardiac output; oxygen level; pH level; pH of blood; pH of a bodily fluids; tissue temperature; inflammation level; bacteria level; type of bacteria present; gas level; blood gas level; neural activity; neural spikes; neural spike shape; action potential; local field potential (LFP); EEG; muscular activity (e.g. as measured using EMG); skeletal muscle activity; bladder volume; bladder pressure; gastric volume; peristalsis rate; impedance; tissue impedance; electrode-tissue interface impedance; physical activity level; pain level; body position; body motion; organ motion; respiration rate; respiration level; perspiration rate; sleep level; sleep cycle; digestion state; digestion level; urine production; urine flow; bowel movement; tremor; ion concentration; chemical concentration; hormone level; viscosity of a bodily fluid; patient hydration level; and combinations of one or more of these.

In some embodiments, functional element 260 comprises one or more sensors configured to record data representing a parameter of implantable device 200. In these embodiments, functional element 260 can comprise one or more sensors selected from the group consisting of: an energy sensor; a voltage sensor; a current sensor; a temperature sensor (e.g. a temperature of one or more components of implantable device 200); a contamination detector (e.g. to detect undesired material that has passed through housing 210); an antenna matching and/or mismatching assessment sensor; power transfer sensor; link gain sensor; power use sensor; energy level sensor; energy charge rate sensor; energy discharge rate sensor; impedance sensor; load impedance sensor; instantaneous power usage sensor; average power usage sensor; bit error rate sensor; signal integrity sensor; and combinations of one or more of these. Apparatus 10 can be configured to analyze (e.g. via implantable controller 250, programmer 550 and/or diagnostic assembly 91 described herebelow) the data recorded by functional element 260 to assess one or more of: power transfer; link gain; power use; energy within energy storage assembly 270; performance of energy storage assembly 270; expected life of energy storage assembly 270; discharge rate of energy storage assembly 270; ripple or other variations of energy storage assembly 270; matching of antenna 240 and 540; communication error rate between implantable device 200 and external device 500; integrity of transmission between implantable device 200 and external device 500; and combinations of one or more of these. A functional element 260 can be configured to record temperature, such as when apparatus 10 is configured to deactivate or otherwise modify the performance of an implantable device 500 when the recorded temperature exceeds a threshold.

In some embodiments, one or more functional elements 260 comprise a transducer configured to deliver energy to tissue, such as to treat pain and/or to otherwise stimulate or affect tissue. In some embodiments, functional element 260 comprises a stimulation element, such as one or more transducers selected from the group consisting of: an electrode; an energy delivery element such as an electrical energy delivery element, a light energy delivery element, a laser light energy delivery element, a sound energy delivery element, a subsonic sound energy delivery element and/or an ultrasonic sound delivery element; an electromagnetic field generating element; a magnetic field generating element; a mechanical transducer (e.g. delivering mechanical energy to tissue); a tissue manipulating element; a heat generating element; a cooling (e.g. cryogenic or otherwise heat extracting energy) element; an agent delivery element such as a pharmaceutical drug delivery element; and combinations of one or more of these.

In some embodiments, one or more functional elements 260 comprises a drug or other agent delivery element, such as a needle, port, iontophoretic element, catheter, or other agent delivering element that can be connected to a reservoir of agent positioned within housing 210 (e.g. reservoir 225 described herebelow). In some embodiments, one or more functional elements 260 comprise a drug eluting element configured to improve biocompatibility of implantable system 20.

In some embodiments, one or more functional elements 260 comprise one or more electrodes configured to deliver energy to tissue and/or to sense a patient parameter (e.g. electrical activity of tissue or other patient physiologic parameter). In these embodiments, one or more functional elements 260 can comprise one or more electrodes selected from the group consisting of: microelectrode; cuff electrode; array of electrodes; linear array of electrodes; circular array of electrodes; paddle-shaped array of electrodes; bifurcated electrodes; and combinations of one or more of these.

In some embodiments, apparatus 10 and functional element 260 are configured to both record one or more patient parameters, and also to perform a medical therapy (e.g. stimulation of tissue with energy and/or an agent). In these embodiments, the medical therapy can be performed in a closed-loop fashion, such as when energy and/or agent delivery is modified based on the measured one or more patient physiologic parameters.

In some embodiments, one or more functional elements 260 comprise an agent delivery element, such as a fluid delivery element (e.g. a catheter, a porous membrane, an iontophoretic element or a needle) in fluid communication with a reservoir of the agent positioned within housing 210, such as reservoir 225 described herebelow.

In some embodiments, apparatus 10 comprises tool 60. Tool 60 can comprise a data logging and/or analysis tool configured to receive data from external system 50 or implantable system 20, such as data comprising: diagnostic information recorded by external system 50 and/or implantable system 20; therapeutic information recorded by external system 50 and/or implantable system 20; patient information (e.g. patient physiologic information) recorded by implantable system 20; patient environment information recorded by implantable system 20; and combinations of one or more of these. Tool 60 can be configured to receive data from wired or wireless (e.g. Bluetooth) means. Tool 60 can comprise a tool selected from the group consisting of: a data logging and/or storage tool; a data analysis tool; a network such as a LAN or the Internet; a cell phone; and combinations of one or more of these.

In some embodiments, tool 60 comprises a battery charging assembly, such as an assembly configured to recharge one or more power supplies 570 comprising a rechargeable battery or capacitor.

In some embodiments, tool 60 comprises an implantation tool, such as an introducer or other implantation tool constructed and arranged to aid in the implantation of housing 210, implantable antenna 240, lead 265 and/or one or more functional elements 260.

In some embodiments, lead 265 comprises a paddle lead or other stimulating lead and tool 60 comprises an introducer (e.g. a needle or an extended-width introducer) configured to deliver at least a distal portion of lead 265 into an epidural space of a patient. Tool 60 can comprise an introducer comprising a Tuohy needle, such as a Tuohy needle of 12 gauge or smaller. Tool 60 can comprise a handle for manipulating lead 265. Tool 60 can be configured to place lead 265 at an entry point above the lumbar spinal column (e.g.

between L1 and L2 vertebrae). Tool 60 can include extension tubing used to insert lead 265. Tool 60 can further comprise a tool configured to anchor lead 265, such as when tool 60 comprises sutures, clips, other anchoring elements and/or an anchor securing tool (e.g. a needle or a stapling device), such as to secure lead 265 in subcutaneous tissue. Lead 265 and/or tool 60 can comprise extension tubing used to place lead 265, such as extension tubing that remains in place after removal of an introducer of tool 60. Tool 60 can be configured to place lead 265 against the dura of the spinal cord of the patient.

In some embodiments, tool 60 and/or lead 265 are constructed and arranged to implant lead 265 to stimulate one or more multifidus (MF) muscle fascicles, such as at least three sets of multifidus muscle fascicles. Lead 265 can be secured to a vertebra (e.g. on the transverse process, lamina or vertebral body). Lead 265 can placed via tool 60 such that one or more functional elements 260 (e.g. electrodes) are positioned within the multifidus muscle structures. One or more functional elements 260 can be positioned to deliver electrical energy and/or to otherwise stimulate tissue selected from the group consisting of: muscle motor point(s) or the deep fibers of lumbar multifidus; quadratus lumborum; the erector spinae; psoas major; transverse abdominis; connective tissue such as the annulus or facet capsule; ligaments coupling bony structures of the spine; and combinations of one or more of these. Functional elements 260 can be positioned to: depolarize, hyperpolarize and/or block innervated sections of the muscle that will then propagate an activating and/or inhibiting stimulus along the nerve fibers recruiting muscle tissue remote from the site of stimulation and/or modulate nerve activity (including inhibiting nerve conduction, improving nerve conduction and/or improving muscle activity). In some embodiments, functional elements 260 are positioned to cause transvascular stimulation (e.g. transvascular stimulation from arteries and/or veins in a leg or arm). In some embodiments, functional elements 260 are positioned to stimulate nerve tissue selected from the group consisting of: dorsal ramus nerve; medial branch of dorsal ramus nerve; nervous tissue associated with multifidus muscle; and combinations of one or more of these. In some embodiments, functional elements 260 are configured to deliver stimulation energy to contract the multifidus muscle. In some embodiments, functional elements 260 are configured to stimulate tissue by providing episodic electrical stimulation. In some embodiments, apparatus 10 comprises a tool 60 configured to diagnose a defect in spinal muscle or the motor control system. In some embodiments, apparatus 10 comprises a tool 60 configured to test function of the multifidus muscle, such as when tool comprises an MRI; ultrasound imager; electromyogram; tissue biopsy device; and/or a device configured to test displacement as a function of load for a spine.

In some embodiments, two or more external system 50 components are connected by a connecting filament, such as is described hereabove. Alternatively or additionally, two or more implantable system 20 components are connected by a conduit, such as a connecting filament as described herein. Alternatively or additionally, two more external system 50 components and/or two or more implantable system 20 components transmit information and/or power via a wireless transmitter (e.g. an RF transmitter), magnetic coupling, capacitive coupling and/or other wireless transmission means, Apparatus 10 can include one or more devices, such as patient attachment device 70 shown in FIG. 1, that is used to attach one or more portions of external system 50 to a location on or proximate the patient. In some embodiments, patient attachment device 70 is constructed and arranged as described in applicant's co-pending U.S. patent application Ser. No. 15/385,729, titled "Method and Apparatus for Neuromodulation Treatments of Pain and Other Conditions", filed Dec. 20, 2016, the content of which is incorporated herein by reference in its entirety for all purposes.

Patient attachment device 70 can comprise one or more elements configured to attach one or more external devices 500 at one or more locations on or proximate the patient's skin, that are relatively close to one or more implantable devices 200 that have been implanted in the patient. Patient attachment device 70 can comprise a component selected from the group consisting of: belt; belt with pockets; belt with adhesive, adhesive; strap; strap with pockets; strap with adhesive shoulder strap; shoulder band; shirt; shirt with pockets; clothing; clothing with pockets; epidural electronics packaging; clip; bracelet; wrist band; wrist watch; anklet; ankle bracelet; knee strap; knee band; thigh strap; thigh band; necklace; hat; headband; collar; glasses; goggles; earpiece; behind-the-earpiece; and combinations of one or more of these. In some embodiments, patient attachment device 70 comprises a belt configured to surround at least one antenna 540 (e.g. at least one antenna 540 mounted to or otherwise positioned on a printed circuit board such as a flexible printed circuit board). Patient attachment device 70 can include one or more pockets, such as one or more pockets configured to collectively surround one or more of: external device 500; one or more antennas 540; power supply 570; programmer 550; and combinations of one or more of these. In some embodiments, patient attachment device 70 comprises multiple pockets, such as to allow repositioning of an external antenna 540, programmer 550, external transmitter 530 and/or external power supply 570 to various different locations, such as to improve transmission of power and/or data to one or more implantable devices 200 and/or improve patient comfort. In some embodiments, one or more antennas 540, power supplies 570, and/or transmitters 530 are connected through flexible cables positioned in patient attachment device 70. In some embodiments, the flexible cables are small coax cables that can accommodate the power levels and frequencies of the carried signals. In some embodiments, the one or more antennas 540 are connected to one or more additional components of external device 500 through a single cable with a local power splitting component and/or active matching element that adjusts signal power to each of the one or more antennas 540.

Apparatus 10 can comprise a device configured to operate (e.g. temporarily operate) one or more implantable devices 200, such as trialing interface 80 shown in FIG. 1. Trialing interface 80 can be configured to deliver power to an implantable device 200, deliver data to an implantable device 200, and/or receive data from an implantable device 200. Trialing interface 80 can be configured to interface with one or more implantable devices 200 during an implantation procedure in which one or more implantable device 200 are implanted in a patient (e.g. a sterile clinical procedure). Trialing interface 80 can be configured to be sterilized one or more times. Trialing interface 80 can comprise one or more antennas, such as an antenna similar to antenna 540 of an external device 500. Trial interface 80 can comprise a transmitter, such as a transmitter similar to transmitter 530 of external device 500, and a power supply, such as a power supply similar to power supply 570 of external device 500. In some embodiments, trialing interface is of similar construction and arrangement to the trialing interface described in applicant's co-pending U.S. patent application Ser. No. 15/385,729, titled "Method and Apparatus for Neuromodulation Treatments of Pain and Other Conditions", filed Dec. 20, 2016, the content of which is incorporated herein by reference in its entirety for all purposes. In some embodiments, trialing interface 80 includes a housing to be positioned proximate at least a portion of implantable device 200, such as a housing that surrounds an antenna and a transmitter that is configured to operatively couple to (e.g. transmit power and/or data to) one or more antennas 240 of one or more implantable devices 200.

In some embodiments, one or more implantable devices 200 of implantable system 20 can comprise an implantable transmitter configured to transmit data, such as to transmit data (e.g. stimulation information, patient physiologic information, patient environment information, implantable device 200 performance and/or configuration information, and the like) to one or more external devices 500. In these embodiments, receiver 230 can be configured as both a receiver and a transmitter. One or more implantable devices 200 can be configured to transmit data by sending a signal to (i.e. "driving") one or more antennas 240 or another antenna of implantable device 200. An implantable device 200 can be configured to transmit data using one or more of: load modulation; a signal carrier; and/or body conduction. An implantable device 200 can be configured to adjust the transmission, such as to adjust a data transmission parameter selected from the group consisting of: data rate; pulse width; duration of carrier signal; amplitude of carrier signal; frequency of carrier signal; configurable load; and combinations of one or more of these.

In some embodiments, apparatus 10 comprises a diagnostic assembly, diagnostic assembly 91 shown in FIG. 1. In some embodiments, programmer 550 and/or implantable controller 250 comprise all or a portion of diagnostic assembly 91. Diagnostic assembly 91 can be configured to assess, monitor, determine and/or otherwise analyze patient information and/or implantable device 200 information, such as when one or more functional elements 260 and/or 560 are configured as a sensor configured to record patient information (e.g. patient physiologic information and/or patient environment information) and/or apparatus 10 information (e.g. implantable device 200 information) as described herein. Diagnostic assembly 91 can be configured to analyze communication and/or the power link between an implantable device 200 and an external device 500. In some embodiments, such a communication link analysis can be performed by measuring bit error rate (BER) of a known data stream during communication signal transmission (also referred to as "communication link") measurement phase (e.g. such as during a calibration procedure). The BER can be tracked by the implant controller 250 or programmer 550, such as to monitor and keep track of any trends in the link. This trend can be used to adjust the link and/or provide feedback to an operator of apparatus 10 (e.g. the patient), in case the link cannot be automatically adjusted to compensate for a negative trend (e.g. such that the operator can perform physical re-adjustment of the external system 50). Alternatively or additionally, a power link analysis can be performed by monitoring charge/discharge rate of the implanted energy storage assembly 270. Similar to the communication link, the power link status and/or trending can be monitored and recorded for link adjustment and/or feedback purposes. Diagnostic assembly 91 can be configured to analyze a result of stimulation energy delivered by implantable device 200, such as when a functional element 260 comprises an electrode to record electrical activity of tissue (e.g. in addition to delivering electrical energy to stimulate tissue). A functional element 260 and/or 560 can comprise a sensor configured to record neural activity and/or muscular activity, and the diagnostic assembly configured to analyze the recorded sensor data. In some embodiments, diagnostic assembly 91 can be configured to analyze impedance, such as when a functional element 260 and/or 560 comprises a sensor configured to record data related to impedance, such as when implantable device 200 performs a frequency sweep, performs an impulse response and/or compares voltage and current of a stimulation waveform. In some embodiments, diagnostic assembly 91 is configured to assess the impedance of one or more implantable antennas 240 and/or one or more external antennas 540. In these embodiments, impedance can be assessed by performing a function selected from the group consisting of: performing a frequency sweep; performing an impulse response; comparing voltage and current of a waveform; and combinations of one or more of these.

In some embodiments, diagnostic assembly 91 is configured to test or otherwise assess the link between one or more implantable antennas 240 and one or more external antennas 540 (e.g. during a procedure in which one or more implantable devices 200 are implanted in a patient). In these embodiments, diagnostic assembly 91 can be configured to perform a test prior to anchoring housing 210 to tissue (e.g. prior to initial or final suturing into tissue such as the fascia layer). For example, lead 265 can be implanted at a location to stimulate target tissue (e.g. one or more nerves identified to treat pain or another patient condition). Prior to suturing housing 210 in its permanent location, diagnostic assembly 91 can be configured to confirm that one or more external antenna 540 transmission links to one or more implantable antennas 240 are above an efficiency threshold, for example such that sufficient power will be received by the one or more implantable devices 200. Additionally, the procedure can be performed to optimize or otherwise improve the position of the one or more implantable devices 200 to be implanted and subsequently secured to tissue.

In these link testing embodiments, diagnostic assembly 91 can comprise a handheld assembly (e.g. a sterile assembly comprising a wand or other handheld housing). Diagnostic assembly 91 can be configured to send a simple signal to one or more implantable devices 200 (e.g. a diagnostic assembly 91 with similar power and/or data transmission capabilities as an external device 500). Each implantable device 200 can respond (e.g. via data sent via an implantable antenna 240 or other transmitter) with information related to the quality of the transmission link (e.g. information about the power received by the one or more implantable devices 200). Diagnostic assembly 91 could provide a user interface (e.g. a speaker, a text screen and/or a video display) that provides quality or other information (go/no go information, digital or other discrete level information, and/or analog information). Diagnostic assembly 91 could be further configured to provide information confirming detection of one or more implantable devices 200, status of one or more implantable devices 200 (e.g. parameter level and/or fault detection status), and/or self-diagnostic status (i.e. diagnostic assembly 91 status).

Each implantable device 200 can be configured to specifically identify and/or specifically reply to diagnostic assembly 91 (e.g. in a different form than communications with an external device 500). Each implantable device 200 can be configured to provide information related to one or more of: the charge and/or discharge rate of energy storage assembly 270 (e.g. the charge and/or discharge rate of a capacitor or battery of energy storage assembly 270); or the frequency of a voltage-controlled oscillator that is driven by an unregulated voltage of power converter 233. Diagnostic assembly 91 can be configured to perform numerous performance tests (e.g. of one or more implantable devices 200 or implantation locations for one or more implantable devices 200), prior to completion of the implantation procedure (e.g. prior to closing one or more incisions).

In some embodiments, apparatus 10 is configured to provide a therapy by delivering stimulation energy to tissue, such as electrical energy delivered to tissue by one or more functional elements 260 comprising one or more electrodes. Alternatively or additionally, apparatus 10 can be configured as an agent-delivery apparatus (e.g. a pharmaceutical or other agent delivery apparatus). In some embodiments, apparatus 10 comprises one or more reservoirs for storing the agent, such as reservoir 525 of external device 500 and/or reservoir 225 of implantable device 200, each shown in FIG. 1. Reservoirs 525 and/or 225 can be fluidly connected to one or more functional elements 560 and/or 260, respectively (e.g. via one or more tubes). Reservoirs 525 and/or 225 can comprise one or more chambers (e.g. independent chambers configured to separately contain incompatible drugs or otherwise prevent undesired multiple drug interactions). Reservoirs 525 and/or 225 can comprise a volume (e.g. a volume to store one or more agents) between 0.1 ml and 50 ml, such as between 0.1 ml and 3.0 ml, or between 0.1 ml and 1.0 ml. Reservoirs 525 and/or 225 can comprise pressurized reservoirs or otherwise comprise a fluid pumping mechanism (e.g. a peristaltic mechanism, syringe pump or other fluid pump). Reservoirs 525 and/or 225 and can comprise refillable reservoirs (e.g. when reservoir 225 of an implantable device 200 comprises a valved opening such as a silicone septum or a mechanical valve, either accessible via a needle for refilling). The fluidly attached functional elements 560 and/or 260 can comprise a fluid delivery element selected from the group consisting of: a catheter; a porous membrane; an iontophoretic element; a needle; or combinations of one or more of these. Delivered and/or stored (e.g. in a reservoir) agents can comprise an agent selected from the group consisting of: an analgesic agent such as morphine, fentanyl, lidocaine or other agent delivered to treat pain; a chemotherapeutic agent such as a chemotherapeutic agent delivered systemically (e.g. throughout the blood system of the patient) and/or to a location in or proximate an organ such as the liver or brain to treat cancer; an antibiotic configured to treat or prevent an infection; a hormone such as a hormone delivered intravenously in hormonal therapy; heart medications such as nitroglycerin, a beta blocker or a blood pressure lowering medication; a carbohydrate such as glucose or dextrose delivered to treat a low blood sugar condition; insulin such as to treat a high blood sugar condition; a diabetic medication; a neurological medication; an epilepsy medication; and combinations of one or more of these. In some embodiments, apparatus 10 comprises the one or more agents stored in reservoir 225 and/or 525. In some embodiments, apparatus 10 is constructed and arranged to deliver the agent (e.g. via a catheter-based functional element 560 and/or 260) to a patient location selected from the group consisting of: a vessel; a blood vessel; a vein; an artery; heart; brain; liver; spine; epidural space; intrathecal space; subcutaneous tissue; bone; intraperitoneal space, intraventricular space, and combinations of one or more of these.

In some embodiments, an external device 500 is attached to the patient via a patient attachment device 70 comprising a wrist band, wrist watch, leg band, ankle band or other band configured to position an external device 500 about a limb of the patient (i.e. arm or leg of the patient). In these embodiments, one or more implantable devices 200 are implanted under the skin proximate the intended (limb) location of external device 500 and patient attachment device 70. Apparatus 10 can be configured such that external device 500 comprises one or more antennas 540; one or more implantable devices 200 each comprise one or more antennas 240; and each implantable device 200 one or more antennas 240 receive power and/or data from the one or more antennas 540 of the limb-attached external device 500. The limb-attached external device 500 can comprise one or more reservoirs 525 described hereabove and/or one or more functional elements 560 configured as agent delivery elements and/or sensors. The one or more implantable devices 200 can comprise one or more reservoirs 225 described hereabove and/or one or more functional elements 260 configured as agent delivery elements and/or sensors.

In some embodiments, apparatus 10 comprises an agent delivery apparatus and agent is delivered into the patient (e.g. into a blood vessel, muscle or subcutaneous tissue) by an external device 500 functional element 560 (e.g. a needle) based on signals recorded by an implantable device 200 functional element 260 (e.g. a sensor). Alternatively or additionally, agent can be delivered into the patient (e.g. into a blood vessel, muscle or subcutaneous tissue) by an implantable device 500 functional element 260 (e.g. a needle, catheter, porous membrane or iontophoretic delivery element). The amount of agent delivered by functional element 260 can be based on signals recorded by an implantable device 200 functional element 260 (e.g. a sensor) and/or an external device 500 functional element 560 (e.g. a sensor). External device 500 can provide power to one or more implantable devices 200 and/or it can send data (e.g. sensor data from a functional element 560) to implantable device 500, such as to control agent delivery by implantable device 500.

Apparatus 10 can be configured to prevent an electromagnetic field (e.g. an electromagnetic field produced by one or more devices not included in apparatus 10 and/or other present in the patient environment) from adversely affecting and/or otherwise affecting the patient treatment and/or patient information recording (e.g. patient tissue stimulation and/or patient physiologic information gathering) performed by apparatus 10. Electromagnetic fields from one or more apparatus 10 devices and/or otherwise present in the patient environment can potentially interfere with apparatus 10. The architecture of the wireless signal transmissions of apparatus 10 can be configured to include certain unique and/or identifiable patterns in the signals transmitted by apparatus 10 to confirm (upon receipt) that the signal originated from a component of apparatus 10. Alternatively or additionally, the stimulation signal produced by an implantable device 200 can be created independent from a power signal received from an external device 500, so that any electromagnetic interference in the wireless link does not affect generation and delivery of the stimulation signal. In some embodiments, each implantable device 200 and/or external device 500 includes unique identification codes that are required to be transmitted prior to any changes in stimulation or other implantable device 200 configuration, ensuring correct operation in the presence of interference. Alternatively or additionally, the communication link can incorporate handshaking protocols, confirmation protocols, data encryption and/or scrambling, coding and other security measures to ensure that interfering signals do not adversely affect the implantable system 20 performance (e.g. stimulation). In some embodiments, external system 50 and/or implantable system 20 can incorporate electromagnetic absorptive and/or reflective materials to minimize external interference from other sources and/or minimize the probability of apparatus 10 interfering with other systems. Alternatively or additionally, apparatus 10 can incorporate error detection and protocols for entering an alarm state (e.g. and shutting down normal operation) and/or otherwise ensuring safe operation.

In some embodiments, implantable system 20 of apparatus 10 is configured to perform magnetic field modulation, such as targeted magnetic field neuromodulation (TMFN), electro-magnetic field neuromodulation, such as targeted electro-magnetic field neuromodulation (TEMFN), transcutaneous magnetic field stimulation (TMS), or any combination of these. Each implantable device 200, via one or more of its functional elements 260 (e.g. electrodes) can be configured to provide localized (e.g. targeted) magnetic and/or electrical stimulation. Combined electrical field stimulation and magnetic field stimulation can be applied by using superposition, and can reduce the overall energy requirement. In some embodiments, implantable apparatus 10 comprises one or more functional elements 260 comprising a magnetic field generating transducer (e.g. microcoils or cuff electrodes positioned to partially surround or otherwise be proximate to one or more target nerves). Functional elements 260 comprising microcoils can be aligned with nerves to minimize affecting non-targeted tissue (e.g. to avoid one or more undesired effects to non-target tissue surrounding or otherwise proximate the target tissue). In some embodiments, the target tissue comprises DRG tissue, and the non-target tissue comprises ventral root tissue (e.g. when the stimulation energy is below a threshold that would result in ventral root tissue stimulation).

In some embodiments, external system 50 of apparatus 10 is configured to provide mechanically adjustable alignment of one or more external antennas 540 alignment. Link gain between one or more external antennas 540 and one or more implantable antennas 240 can degrade over time due to physical misalignment of the antennas, relative orientation change between antennas and/or relative angular misalignment between antennas. In order to compensate for misaligned antennas, electrical beam steering can be included in apparatus 10. Antennas comprising a multi-feed antenna structure and/or an array of antennas can be incorporated (e.g. into external antenna 540, implantable antenna 240 or both) for electrical beam steering. Alternatively or additionally, mechanical antenna steering can be implemented to physically realign one or more external antennas 540 with one or more implanted antennas 240 (or vice versa). A substrate of an implantable antenna 240 and/or an external antenna 540 can be flexible and/or rigid (e.g. a substrate comprising polyamide, polyimide, liquid crystal polymer (LCP), Rogers, FR4, or a similar material). One or more antennas 540 can be connected to electronics (e.g. a transmitter, receiver or transceiver) using a flexible waveguide or cable (e.g. 50 ohm 0.047" coaxial cable designed to provide patient comfort) and/or a flexible PCB substrate transmission line. Mechanical or physical realignment of antennas 240 and/or 540 can be accomplished using one or more of: use of motorized positioners, such as a mechanism including one or more small pulleys and/or tensioners used to translate one or more antennas 240 and/or 540 about one or more axes; an actuator (e.g. a piezoelectric actuator) with directional gears configured to translate one or more antennas 240 and/or 540 about one or more axes; a micro-pump with fluid reservoir (e.g. liquid or gas reservoir) configured to hydraulically and/or pneumatically translate one or more antennas 240 and/or 540 about one or more axes, such as by creating a local pressure difference. In some embodiments, a micropump with fluid reservoir can be used to move one or more antennas 240 and/or 540, such as to move an external antenna 540 away from tissue to reduce specific absorption rate (SAR). In these embodiments, external antenna 540 can be positioned in mechanical contact with an expandable reservoir (e.g. a balloon) positioned between external antenna 540 and tissue. The reservoir can be inflated or deflated to control separation distance of the external antenna 540 from the patient's skin surface. In some embodiments, apparatus 10 comprises one or more algorithm positioning algorithms, beam steering functionality and/or mechanical antenna steering as described in applicant's co-pending U.S. patent application Ser. No. 14/975,358, titled "Method and Apparatus for Minimally Invasive Implantable Modulators", filed Dec. 18, 2015, or International PCT Patent Application Serial Number PCT/US2016/016888, titled "Medical Apparatus including an Implantable System and an External System", filed Feb. 5, 2016, the content of each of which is incorporated herein in its entirety for all purposes.

In some embodiments, implantable system 20 of apparatus 10 is configured to provide paresthesia-reduced (e.g. paresthesia-free) high frequency pain management and rehabilitation therapy (e.g. via delivery of a stimulation signal above 600 Hz or 1 kHz, or other stimulation signal resulting in minimal paresthesia). Apparatus 10 can be configured to provide both low frequency (e.g. <1 kHz) stimulation and high frequency stimulation, such as when providing low frequency stimulation to elicit feedback from a patient during intraoperative or other (e.g. post-implantation) stimulation configuration. For example, trialing interface 80 can be used during an intra-operative titration of stimulation configuration using low frequency stimulation (e.g. to position and/or confirm position of one or more functional elements 260, such as to confirm sufficient proximity to target tissue to be stimulated and/or sufficient distance from non-target tissue not to be stimulated). In some embodiments, high frequency stimulation is delivered to reduce pain over extended periods of time, and low frequency stimulation is used in these intraoperative and/or post-implantation titration or other stimulation configuration procedures. Intentional elicitation of paresthesia (e.g. via low frequency stimulation and/or high frequency stimulation) is beneficial during functional element 260 (e.g. electrode) implantation because a patient can provide feedback to the implanting clinician to ensure that the functional elements 260 are positioned close to the target neuromodulation or energy delivery site. This implantation position-optimizing procedure can advantageously reduce the required stimulation energy due to functional elements 260 being closer to target tissue, since a minimum threshold for efficacious stimulation amplitude is proportional to the proximity of functional elements 260 to target tissue (e.g. target nerves). The patient can inform the clinician of the sensation of paresthesia coverage, and the clinician can adjust functional element 260 position to optimize functional element 260 location for efficacious treatment while minimizing unintentional stimulation of non-target tissue (e.g. motor nerves or other nerves which are not causing the patient's pain). These paresthesia-inducing techniques (e.g. using low frequency stimulation and/or high frequency stimulation) can be used during or after implantation of one or more implantable devices 200.

In some embodiments, apparatus 10 is configured to deliver low frequency stimulation energy (e.g. electrical energy comprising a low frequency signal) to stimulate motor nerves, such as to improve tone and structural support (e.g. physical therapy). In these embodiments, apparatus 10 can be further configured to provide high frequency stimulation, such as to treat pain (e.g. suppress and/or control pain). The combined effect can be used not only for pain management but also muscle strengthening and gradual healing of supportive structures. Alternatively or additionally, as described herein, apparatus 10 can be configured to deliver low frequency stimulation energy (e.g. electrical energy) to induce paresthesia, which can also be accompanied by the delivery of high frequency stimulation (e.g. to suppress and/or control pain). In some embodiments, apparatus 10 is configured to deliver low frequency stimulation (e.g. electrical energy comprising a low frequency signal) and burst stimulation, delivered simultaneously or sequentially. The low frequency stimulation and the burst stimulation can be delivered on similar and/or dissimilar functional elements 260 (e.g. similar or dissimilar electrode-based functional elements 260).

As described herein, apparatus 10 can be configured for treating numerous disease and disorders, such as when apparatus 10 is configured to deliver electrical or other stimulation energy to treat pain (e.g. by delivering electrical or other energy to the spine or other neural location). Apparatus 10 can be configured to stimulate tissue with various stimulation waveforms, such as those described herebelow in reference to any of FIGS. 4-30B.

Apparatus 10 can be configured to treat neuropathy, neuralgia and/or other nerve pain that is related to: surgery; trauma; infection (e.g. a herpetic infection); and/or diabetes (e.g. diabetic neuropathy). One or more functional elements 260 can be configured to deliver stimulation energy (e.g. electrical energy, magnetic energy, light energy, thermal energy, sound energy, and/or chemical energy (e.g. energy from a drug or reagent) to nerve tissue such as tissue of the central nervous system and/or peripheral nervous system. One or more leads 265 (each comprising one or more functional elements 260) can be implanted in and/or proximate the spinal cord, the groin and/or a joint such as the hip. For example, apparatus 10 can be configured to treat one or more of: post-surgical neuralgia (e.g. following hernia repair such as a hernia repair including an implanted mesh); headache (e.g. due to occipital neuralgia); post-herpetic neuralgia; chronic pelvic and/or hip pain; knee pain; and combinations of one or more of these.

To treat pain related to hernia or hernia repair, one or more functional elements 260 (e.g. on a lead 265 and/or on a housing 210) can be positioned to stimulate tissue of the peripheral nervous system and/or the central nervous system. In some embodiments, one or more functional elements 260 are positioned to stimulate the cutaneous branch of the ilioinguinal, inguinal and/or genital branch of the genitofemoral nerves. In some embodiments, one or more functional elements 260 are positioned to stimulate corresponding branches of spinal nerves correlating to one or more dermatomes related to pain associated with at least one of hernia or hernia repair.

Hernia or hernia repair can lead to: inguinal pain; ilioinguinal neuralgia; post-traumatic neuropathic pain; ilioinguinal nerve entrapment; neuropathic pain of ilioinguinal origin; post-surgical inguinal pain; genitofemoral pain; genitofemoral neuralgia; genitofemoral nerve entrapment; neuropathic pain of genitofemoral origin; post-surgical genitofemoral pain; iliohypogastric pain; iliohypogastric neuralgia; iliohypogastric nerve entrapment; neuropathic pain of iliohypogastric origin; post-surgical iliohypogastric pain; testicular pain; scrotal pain; penis pain; groin pain; thigh pain; anal pain; rectal pain; perineal pain; abdominal adhesions; pelvic adhesions; scar pain; diffuse polyneuropathy; and combinations of one or more of these.

The apparatus of the present inventive concepts can be configured to stimulate the ilioinguinal nerve, genitofemoral nerve and/or iliohypogastric nerves, such as to ameliorate pain following hernia repair. One or more leads 265 (e.g. one or more leads 265 comprising one or more electrode-based or otherwise stimulation-based functional elements 260) can be inserted over the inguinal region (which may include the inguinal ring) to stimulate any or all three of these nerves (e.g. in a unilateral or bilateral fashion). Both the ilioinguinal and genital branch of the genitofemoral nerves pass through the inguinal ring. The anterior cutaneous iliohypogastric and femoral branch of the genitofemoral nerve can be stimulated at one or more locations proximate but rostral (iliohypogastric) or lateral (genitofemoral) to the inguinal ring. Leads 265 can comprise one or more functional elements 260 comprising cylindrical, paddle, cuff and/or hemi-cuff electrodes (electrodes placed surgically near and/or around these nerves). The nerves can be localized via ultrasound or other imaging modalities. Contrast can be used to image the vessels nearby (e.g. the testicular and/or ovarian vein and/or artery). The genital branch of the genitofemoral nerve can be stimulated in a transvascular manner through the testicular vein and/or artery. The genitofemoral and/or the ilioinguinal nerves can also be stimulated (e.g. transvascularly stimulated) through the femoral vein and/or artery, or via the superficial or deep external pudendal vein and/or artery, and/or via the superficial epigastric vein and/or artery.

The painful areas innervated by the ilioinguinal nerve, genitofemoral nerve and/or iliohypogastric nerves, can also be treated via spinal cord stimulation provided by apparatus 10 in the L1-L5 region of the spinal cord. In some embodiments, direct stimulation of the L1-L2 dorsal root ganglia is provided in a similar treatment. Leads 265 (e.g. percutaneous or paddle) including stimulation-based functional elements 260 can be placed over the dorsal columns, over the dorsal roots and/or in the dorsal root entry zone, in a unilateral, bilateral and/or midline fashion.

To treat occipital neuralgia, also known as C2 neuralgia, one or more functional elements 260 can be positioned to stimulate peripheral nerve tissue to reduce pain. Occipital neuralgia is a medical condition characterized by chronic pain in the upper neck, back of the head and/or behind the eyes (areas corresponding to the locations of the lesser and greater occipital nerves). In some embodiments, one or more leads 265, each comprising one or more functional elements 260, can be implanted transversely, either unilaterally or bilaterally, at the level of the appropriate target cervical nerve (C1, C2, etc.). The C1, 2, 3 cervical roots include the greater occipital nerve which originates primarily from C2, and the lesser occipital nerves. Relevant trigeminal branches include both the supraorbital and supratrochlear nerves from V1, the infraorbital branches from V2, and the superficial temporal nerves from V3. A partial convergence of these two systems occurs at the Trigemino-Cervical Complex (TCC). In some embodiments, one or more functional elements 260 are positioned to stimulate the trigeminal and/or occipital nerves. One or more leads 265 can be anchored to the fascia proximate the tissue to be stimulated.

To treat post-herpetic neuralgia (e.g. neuralgia associated with shingles), one or more functional elements 260 can be positioned to stimulate corresponding branches of the spinal nerves correlating to one or more dermatomes related to the patient's shingles.

In some embodiments, apparatus 10 is configured to treat pelvic, bladder and/or bowel disorders, such as by stimulating sacral, pudendal and/or tibial nerves. In some embodiments, apparatus 10 is configured to treat pelvic pain by stimulating the tibial nerve.

Apparatus 10 can be configured to treat a bladder, bowel or other dysfunction selected from the group consisting of: overactive bladder; urinary urgency; urinary frequency; urinary urgency frequency; urinary urge incontinence; urinary stress incontinence; urge incontinence; stress incontinence; non-obstructive urinary retention; female sexual dysfunction; fecal incontinence; constipation; diarrhea; irritable bowel syndrome; colitis; detrusor instability; detrusor dysfunction; spastic bladder; neurogenic bladder; detrusor sphincter dyssynergia; detrusor hyperreflexia; detrusor areflexia; and combinations of one or more of these.

Apparatus 10 can be configured to treat a pelvic disorder selected from the group consisting of: pelvic pain; painful bladder syndrome; Hunner's ulcers or lesions; interstitial cystitis; pelvic floor dysfunction; endometriosis; vulvodynia; dyspareunia; pelvic adhesions; abdominal adhesions; irritable bowel syndrome; pelvic girdle pain; pudendal nerve entrapment; pudendal neuralgia; dysmenorrhea; Müllerian abnormalities; pelvic inflammatory disease; ovarian cysts; ovarian torsion; Loin pain hematuria syndrome; proctitis; prostatitis; prostadynia; post-abdominal surgical pain; post-pelvic surgical pain; hernia pain; post-hernia surgical pain; anal pain; rectal pain; perineal pain; groin pain; vulvar pain; vaginal pain; clitoral pain; colitis; and combinations of one or more of these.

Apparatus 10 can be configured to treat one or more of the pelvic disorders, bladder dysfunctions and/or and bowel dysfunctions listed above, by stimulating (e.g. using bilateral and/or unilateral stimulation) one or more of the targets listed below.

In some embodiments, the stimulated targets include the sacral nerves (roots) S2, S3 and/or S4. One or more leads 265 (e.g. each including one or more stimulation-delivering functional elements 260) can be positioned to stimulate any or all of the three roots, on a single side or both sides, in any bilateral or unilateral combination. The roots can be accessed, with the patient lying in the prone position, by positioning one or more leads 265 (e.g. percutaneously), with or without the use of fluoroscopy, ultrasound or any other imaging modality, into one/any of the sacral foramen (a) from the posterior aspect of the sacrum. One or more leads 265 can be passed through the foramen to the anterior side of the sacrum, and/or one or more leads 265 can remain inside the foramen(a).

In some embodiments, the sacral roots are approached rostrally, via the sacral canal in a retrograde manner. In these embodiments, one or more leads 265 can be passed through the ligamentum flavum, just caudal to L5 or via any of the intervertebral spaces from L5 to T12, into the spinal canal. One or more leads 265 are then threaded, with or without the aid of visualization (fluoroscopy, ultrasound or other imaging modality), in a caudal (retrograde) manner to enter the sacral canal. One or more leads 265 can be placed along the sacral canal, and each root can be stimulated individually and/or each root can be stimulated in concert, via one or more leads 265 positioned along the internal surface of the sacral canal, and spanning one or more foramina.

In some embodiments, one or more leads 265 are threaded from the spinal canal into each and/or all sacral foramen(a), in an anterior direction. The sacral canal can also be accessed caudally by one or more leads 265, via the sacral hiatus in an anterograde manner.

In some embodiments, the sacral roots (S2, S3 and/or S4) are accessed as they enter the spinal cord at the cauda equina. This access can be achieved by inserting the one or more leads 265 through the ligamentum flavum, at a location just caudal to L5, or via any of the intervertebral spaces from L5 to T12, into the spinal canal. The one or more leads 265 can then be threaded, with or without the aid of visualization (fluoroscopy, ultrasound or other imaging modality), up to the cauda equina, where the S2, S3 and/or S4 roots can be stimulated where they enter the spinal cord, and/or the conus medullaris can be stimulated directly (e.g. in the same location).

In some embodiments, the pudendal nerve is stimulated through one or more different approaches. The pudendal nerve contains both afferent and efferent fibers carried by S2, S3 and S4 roots. The pudendal fibers exit Alcock's canal near the ischial spine, where they spread out to innervate to the bladder wall, perineum, anus, genitals and urethra. Pelvic and voiding disorders can be treated by stimulating pudendal nerve fibers. The fibers can be accessed at the Alcock's canal via various approaches. In one embodiment, a transperineal approach is achieved by positioning the patient in the lithotomy position and inserting the lead 265 midpoint between the ischial tuberosity and the anus. A lead 265 is inserted toward the ischial spine, which can be palpated transvaginally or transrectally. The ischial spine can also be visualized through a number of imaging modalities (e.g. fluoroscopy, x-ray, ultrasound, and the like). In another embodiment, a transvaginal approach is achieved by positioning the patient in the lithotomy position and inserting a lead 265 through the vaginal wall, adjacent to the ischial spine (e.g. through the vaginal wall toward the ischial spine). In another embodiment, a posterior approach is achieved by laying the patient in the prone position and inserting a lead 265 just medial to the ischial tuberosity toward the ischial spine. This insertion can be facilitated by rectal palpation of the ischial spine and through visualization via a number of imaging modalities (e.g. fluoroscopy, x-ray, ultrasound, and the like).

In some embodiments, apparatus 10 is configured to stimulate pudendal afferents, such as by stimulating the dorsal genital nerve. These fibers are located just below the skin on the dorsum of the penis or just rostral to the clitoris. In some embodiments, pudendal afferents are stimulated periurethrally. One or more leads 265 can be inserted alongside the urethra to stimulate the pudendal fibers.

In some embodiments, apparatus 10 is configured to stimulate tibial nerve fibers, such as to treat one or more pelvic disorders (e.g. voiding dysfunction). The tibial nerve can be accessed a few mm below the skin surface in the ankle immediately posterior to the medial malleolus. Lead 265 can comprise a cylindrical SCS-type lead, which can be inserted percutaneously in this location. Alternatively or additionally, a direct (surgical) cut-down can be used to insert a cylindrical lead or to apply a cuff electrode directly to the nerve. The tibial nerve can also be accessed approximately half way up the lower leg adjacent to the tibia. One or more leads 265 can be inserted percutaneously in this location. Alternatively or additionally, a direct cut-down can be used to insert lead 265 (e.g. a cylindrical lead or a cuff electrode and/or hemi-cuff electrode applied directly to the nerve in the mid-shin location). Tibial nerve fibers can be accessed in the popliteal fossa behind the knee, for example percutaneously with a lead 265 comprising a cylindrical lead, and/or via a direct cut-down, for example with a lead 265 comprising either a cylindrical or cuff electrode.

In some embodiments, apparatus 10 and one or more leads 265 are constructed and arranged to stimulate the tibial and/or pudendal nerves via a transvascular approach (i.e. stimulation energy delivered from inside a blood vessel to nerve tissue proximate the blood vessel), such as via the femoral vein and/or artery, each of which provide intraluminal access to many other blood vessels (e.g. using standard interventional techniques). The tibial nerve can be transvascularly stimulated by the popliteal vein and/or artery (e.g. by placing one or more functional elements 260 in the popliteal vein and/or artery), at a location behind the knee. The popliteal vein and/or artery can be intraluminally accessed from the femoral artery and vein. The tibial nerve also passes near the small saphenous vein, where it branches off of the popliteal vein. The posterior tibial vein and/or artery are positioned adjacent to the tibial nerve, from the knee to the foot. One or more leads 265 can utilize one or more of these above locations to stimulate the tibial nerve.

In some embodiments, apparatus 10 and one or more leads 265 are constructed and arranged to stimulate the pudendal nerve and/or sacral roots, such as using a lead 265 placed via the femoral vein and/or artery, which in turn provides intraluminal access to many vessels. One or more leads 265 can be configured to utilize any of the following arteries and veins to stimulate the pudendal nerve and/or the sacral roots. One or more leads 265 can be constructed and arranged to stimulate a target site via a blood vessel selected from the group consisting of: the internal pudendal artery or vein (which branch off of common iliac artery or vein, respectively); the inferior and superior gluteal vein and/or artery; middle rectal, pudendal plexus and internal iliac vein and/or artery; medial and lateral sacral vein and/or artery; uterine and obturator vein and/or artery; and combinations of one or more of these.

In some embodiments, apparatus 10 is configured to treat overactive bladder and/or urinary incontinence (singly or collectively "overactive bladder" herein). In some embodiments, apparatus 10 is configured to treat overactive bladder such as to reduce the effects of overactive bladder and/or to decrease use of one or more medications taken by the patient to treat overactive bladder. In some embodiments, one or more functional elements 260 are positioned to stimulate tissue of the central nervous system or tissue and/or tissue of the peripheral nervous system to treat overactive bladder, such as to stimulate one or more nerves that control and/or are otherwise related to bladder function (e.g. to increase bladder capacity, improve bladder emptying, reduce urge incontinence and/or reduce stress incontinence). For example, one or more functional elements 260 can be positioned to stimulate tibial nerve tissue and/or sacral nerve tissue (e.g. at least the S3 nerve root) to treat overactive bladder. In some embodiments, lead 265 is constructed and arranged to be positioned along one or more locations of the tibial nerve, such as a positioning performed using percutaneous technique (e.g. when lead 265 comprises a cylindrical SCS-type lead) and/or surgical (cut-down) techniques (e.g. when lead 265 comprise a cuff electrode and/or hemi-cuff electrode applied directly to the nerve). The tibial nerve branches off of the sciatic nerve just above the knee, and runs along the length of the tibia, medial and lateral to the tibia. The tibial nerve then passes posterior to the medial malleolus prior to innervating the plantar surface of the foot. Lead 265 can be constructed and arranged to access sites proximate the tibial nerve percutaneously and/or through an incision at the back of the knee in the popliteal fossa, along the tibia or behind the medial malleolus. The housing 210 can be placed anywhere in the leg when stimulating the tibial nerve. Lead 265 can be constructed and arranged to stimulate the tibial nerve through a transvascular approach, via the femoral vein and/or artery, each of which provide intraluminal access to many vessels. The tibial nerve can be accessed by the popliteal artery and vein behind the knee, which are intraluminally accessible from the femoral artery and vein, respectively. The tibial nerve also passes near the small saphenous vein, where it branches off of the popliteal vein. The posterior tibial vein and artery travel adjacent to the tibial nerve from the knee to the foot. One or more leads 265 can be constructed and arranged to utilize any of these locations to transvascularly stimulate the tibial nerve (e.g. transvascularly stimulate the tibial nerve via the popliteal artery, popliteal vein, saphenous vein, posterior tibial artery and/or posterior tibial vein via a lead 265 advanced via the femoral vein and/or artery). In these transvascular embodiments, the housing 210 can be placed near the femoral or popliteal access point at locations in the groin, perineum, scrotum, pelvis, hip, thigh, leg, behind the knee, buttocks, abdomen and/or low back. In the case of sacral nerve stimulation, one or more leads 265 can be inserted through an incision(s) made in the lower back, such that one or more functional elements 260 are positioned proximate (e.g. in contact) with the sacral nerve root(s). The housing 210 can be placed anywhere in the groin, perineum, scrotum, pelvis, hip, thigh, leg, behind the knee, buttocks, abdomen and/or low back. Lead 265 (e.g. a lead 265 comprising a lead extension) can be extended underneath the skin (e.g. tunneled) to a second incision (e.g. across the flank to the lower abdomen, across the midline to the buttocks, or low back), and a third incision can be made (e.g. in the abdomen, back or buttocks) where housing 210 can be inserted and connected to lead 265. Alternatively, housing 210 can be inserted at another internal location. If lead 265 is already connected (e.g. attached in manufacturing) to housing 210, lead 265 can be advanced in the opposite direction, such as from the third incision, to the second incision, to the first incision (if three incisions are made), or housing 210 can be advanced under the tissue from incision 1 to incision 2 or from incision 2 to incision 3. In some embodiments, only 1 or 2 incisions are performed. In some embodiments, such as when lead 265 is already connected (e.g. attached in manufacturing) to housing 210, lead 265 and housing 210 are implanted. In some embodiments, a first lead 265 and a first housing 210 (pre-attached or attachable) are utilized in a dose titration or other "trialing procedure", and a second lead 265 and housing 210 (pre-attached or attachable) are implanted in the patient for subsequent treatment of the patient.

In some embodiments, one or more functional elements 260 are positioned to perform posterior tibial nerve stimulation (PTNS), also referred to as percutaneous tibial nerve stimulation, such as to perform an indirect form of neuromodulation to treat bladder voiding dysfunction. The posterior tibial nerve is derived from the lumbar-sacral nerves (L4-S3), which innervate the bladder detrusor and pelvic floor. In some embodiments, one or more functional elements 260 can be positioned to perform retrograde stimulation of the sacral nerve plexus and restore the balance between bladder inhibitory and excitatory control systems of the bladder. One or more functional elements 260 can be positioned above the ankle, proximate and/or into the tibial nerve. Implantable device 200 can deliver stimulation energy to the functional elements 260 comprising low-voltage electrical stimulation configured to produce sensor and/or motor responses. Apparatus 10 can be configured to provide continuous and/or intermittent stimulation to tissue, such as to modulate transmission of excitatory nerve signals to the bladder muscles. In some embodiments, system 20 is configured to deliver a series of repeated stimulation periods, such as a regimen of approximately: weekly thirty minute sessions of stimulation for twelve weeks. In some embodiments, system 20 is configured to provide daily or hourly sessions that deliver stimulation for between 10 minutes and 60 minutes. In some embodiments, apparatus 10 is configured to achieve an approximate 50% reduction in urinary urge incontinence and/or urinary urgency/frequency episodes.

In some embodiments, apparatus 10 is configured to provide temporary stimulation of tissue to treat overactive bladder, such as by using trialing device 80 described hereabove in reference to FIG. 1, such as to provide power and/or date to one or more implantable devices 200 to confirm acceptable improvement of the patient's overactive bladder (e.g. successful stimulation of one or more sacral nerves, tibial nerves or other tissue), before closing an incision or otherwise fully implanting one or more implantable devices 200. In some embodiments, a temporary stimulation is provided for up to one week or up to one month. In some embodiments, one or more implantable devices 200 are left in place if the temporary stimulation period is successful or unsuccessful (e.g. left implanted due to its small size or otherwise minimal impact on the patient).

In some embodiments, apparatus 10 is configured to stimulate a region of the pelvic floor, such as to: change the reflex thresholds of the bladder muscles responsible for bladder emptying, strengthen and/or otherwise improve the condition of the muscles that maintain closure on the bladder outlet; change the state of the neural pathways, musculature and/or bladder during and beyond the period stimulation; and/or otherwise decrease the severity of urinary incontinence. In some embodiments, one or more functional elements 260 are positioned to stimulate periurethral muscles. In some embodiments, one or more functional elements 260 are positioned to stimulate tissue of the vagina or anus. In some embodiments, one or more functional elements 260 are positioned to stimulate sphincter muscles for controlling the bladder, such as two functional elements 260 positioned on either side of the urethral orifice. In these embodiments, housing 210 can be implanted in suprapubic region or in the perineum. In some embodiments, lead 265 comprises (e.g. on a distal portion) a pessary ring comprising two functional elements 260. In some embodiments, functional elements 260 comprise periurethral electrodes configured to stimulate pudendal afferents.

As described above, apparatus 10 can be configured for treating numerous diseases, disorders or other undesirable patient conditions, such as fecal incontinence. Injury of nerves that sense stool in the rectum can lead to fecal incontinence. In some embodiments, one or more functional elements 260 (e.g. one or more electrical, magnetic, light or other energy delivery elements) of one or more leads 265 and/or one or more implantable devices 200 are configured to stimulate tissue to treat fecal incontinence, such as to treat tissue selected from the group consisting of: sacral nerve tissue; tissue whose stimulation strengthens muscles of the bowel and/or rectum; and combinations of one or more of these. In these fecal incontinence applications, leads 265 can be implanted in a location selected from the group consisting of: the pelvic girdle; the sacral foramina; the lower back; the upper buttock; and combinations of one or more of these, such as to stimulate sacral nerve tissue. Leads 265 can be anchored via lead anchors (silicone or other materials), suture, staples, clips, adhesive and the like, such as an attachment to the underlying fascia of target tissue to be stimulated. In some embodiments, apparatus 10 is configured to treat both fecal incontinence and a bladder disorder such as overactive bladder, such as when one or more functional elements 260 are configured to deliver energy to sacral nerve or other tissue.

In some embodiments, apparatus 10 is configured to treat fecal incontinence, overactive bladder (i.e. overactive bladder and/or urinary incontinence), and/or pelvic disorders, and implantable device 200: comprises between 1 and 16 functional elements 260, such as four or more electrodes; delivers electrical stimulation energy at a range of approximately between 10 Hz and 15 Hz (or a range of between 5 Hz and 25 Hz); delivers electrical stimulation energy with a pulse width of approximately between 180 µsec and 240 µsec (or between 1 µsec and 200 µsec); provides electrical stimulation energy with an amplitude of approximately 0.1V to 8.5V (e.g. providing a current between 0.1 mA to 10 mA, which can be adjusted in increments between 0.01 mA and 0.1 mA), such as an amplitude between 0.4V and 2.0V; delivers continuous electrical stimulation energy; delivers intermittent electrical stimulation energy, such as with a period between 8 seconds and 24 seconds and/or an on time between 8 seconds and 16 seconds; or an on time of several hours followed by an off time of several hours (such as 8 hours of stimulation ON and 16 hours of stimulation OFF or 16 hours on and 8 hours off, and 12 hour on and 12 hours off; delivers monopolar electrical energy; delivers bipolar electrical energy; and combinations of one or more of these.

In some embodiments, apparatus 10 is configured to treat an occipital neuralgia, such as migraine headache, headache and/or cluster headache, and one or more functional elements 260 (e.g. small column paddle electrodes, standard paddle electrodes or other electrodes) are positioned to stimulate nerve tissue selected from the group consisting of: occipital; supraorbital; infraorbital; greater occipital nerve (GON); lesser occipital nerve (LON); both supraorbital and GON; supratroclear; sphenopalantine (SPG); and combinations of one or more of these.

In some embodiments, apparatus 10 is configured to treat neuralgia, such as a neuralgia resulting from surgery (e.g. groin, shoulder, lung and/or amputation), trauma and/or phantom pain, and one or more functional elements 260 are positioned to stimulate nerve tissue.

In some embodiments, apparatus 10 is configured to treat neuralgia, such as a neuralgia resulting from groin surgery (e.g. hernia or other groin surgery), and one or more functional elements 260 are positioned to stimulate nerve tissue selected from the group consisting of: ilioinguinal; genitofemoral; iliohypogastric; and combinations of one or more of these.

In some embodiments, apparatus 10 is configured to treat neuralgia, such as a neuralgia resulting from shoulder surgery, and one or more functional elements 260 are positioned to stimulate axial nerve tissue (e.g. one or more functional elements 260 positioned on a lead 265 implanted in a suprascapular location).

In some embodiments, apparatus 10 is configured to treat neuralgia, such as a neuralgia resulting from lung surgery, and one or more functional elements 260 are positioned to stimulate intercostal nerve tissue.

In some embodiments, apparatus 10 is configured to treat neuralgia, such as a neuralgia associated with carpal tunnel syndrome, and one or more functional elements 260 are positioned to stimulate median nerve tissue.

In some embodiments, apparatus 10 is configured to treat neuralgia, such as a neuralgia associated with temporomandibular joint disorder (TMJ), and one or more functional elements 260 are positioned to stimulate V2 of trigeminal nerve tissue.

In some embodiments, apparatus 10 is configured to treat neuralgia, such as a facial neuralgia, and one or more functional elements 260 are positioned to stimulate trigeminal nerve tissue.

In some embodiments, apparatus 10 is configured to treat neuralgia, such as a leg (sciatic) neuralgia, and one or more functional elements 260 are positioned to stimulate nerve tissue proximal a contributing lesion.

In some embodiments, apparatus 10 is configured to treat pelvic pain, such as interstitial cystitis and/or bladder pain, and one or more functional elements 260 are positioned to stimulate peripheral nervous system tissue (e.g. pudendal tissue and/or S-2, S-3 and/or S-4 roots) and/or central nervous system tissue (e.g. lower spinal cord and/or S3 neural foramen).

In some embodiments, apparatus 10 is configured to treat pelvic pain, such as anal pain, and one or more functional elements 260 are positioned to stimulate peripheral nerve tissue such as pudendal tissue and/or S-2, S-3 and/or S-4 roots.

In some embodiments, apparatus 10 is configured to treat subcutaneous pain, and one or more functional elements 260 (e.g. paddle electrodes) are positioned to stimulate nerve tissue.

In some embodiments, apparatus 10 is configured to treat diabetic neuropathy, such as painful diabetic neuropathy, and one or more functional elements 260 are positioned proximate the lower spinal cord (e.g. to stimulate S3 nerves) or other body location to stimulate nerve tissue.

In some embodiments, apparatus 10 is configured to treat visceral pain, angina and/or other pain, and one or more functional elements 260 are positioned to stimulate the vagus nerve.

In some embodiments, apparatus 10 is configured to treat peripheral vascular disease, diabetic neuropathy and/or other conditions associated with diabetes, such as to treat a disease or disorder selected from the group consisting of: peripheral diabetic neuropathic pain; painful diabetic peripheral neuropathy; peripheral vascular disease; peripheral arterial disease; peripheral artery disease; cardiac autonomic neuropathy; diabetic autonomic neuropathy; diabetic sensory neuropathy; diabetic motor neuropathy; diabetic sensorimotor neuropathy; diabetic muscular atrophy; diabetic neurovascular disease; and combinations of one or more of these. In these embodiments, lead 265 can be positioned proximate a nerve in the foot, leg, arm and/or sacrum (e.g. such that one or more functional elements 260 are positioned proximate the nerve to be stimulated). In some embodiments, lead 265 is positioned to stimulate the dorsal root ganglia to treat diabetic neuropathy (e.g. diabetic neuropathy of the hand and/or foot). Lead 265 can be implanted percutaneously and/or surgically as described herein. Lead 265 and/or one or more functional elements 260 can comprise a paddle electrode, such as one or more paddle electrodes implanted in the foot, leg and/or arm. Lead 265 and/or one or more functional elements 260 can comprise a cuff or hemi-cuff electrode surgically implanted around a nerve in the foot, leg and/or arm. Apparatus 10 can be configured to provide spinal cord stimulation, either through percutaneous insertion of one or more leads 265 in the epidural space or surgical implantation of a lead 265 comprising a paddle lead positioned in the epidural space. Apparatus 10 can be configured to provide transvascular stimulation of nerves in the foot, leg and/or arm, (e.g. to treat diabetic neuropathy) such as when one or more leads 265 are interventionally advanced into the venous or arterial system. Leads 265 can be positioned using percutaneous transforaminal placement in the sacral foramina, such as for treatment of foot or leg disorders. Leads 265 can be constructed and arranged for cephalocaudal insertion (retrograde) into the epidural space or sacral canal, such as for treatment of foot or leg disorders. Leads 265 can be constructed and arranged to provide dorsal root ganglion stimulation, such as for treatment of trunk, neck, head, back, foot, leg, arm and/or hand disorders.

One or more leads 265 (e.g. each including one or more functional elements 260) can be constructed and arranged to stimulate tibial nerve fibers, such as to treat diabetic neuropathy and/or diabetic related maladies of the foot. The tibial nerve can be accessed as described herein.

One or more leads 265 can be configured to stimulate the peroneal nerve or saphenous nerve, such as at one or more locations described herebelow. The peroneal nerve can be accessed percutaneously or surgically behind the knee in the popliteal fossa where it branches off of the sciatic nerve. It can also be accessed as it wraps around the lateral aspect of the knee just prior to diving under the fibularis longus and extensor digitorum longus muscles. The deep fibular nerve (a branch of the peroneal nerve) innervates top medial foot, whereas the superficial fibrular (peroneal) innervates top of both medial and lateral foot. In some embodiments, functional element 260 comprises one or more electrodes positioned in the anterior tibial vein and/or artery to transvascularly stimulate the deep fibular nerve. The saphenous nerve comes off the femoral nerve deep in the thigh. It passes around the medial aspect of the knee medial to the patella. It then runs down the medial shin adjacent to the tibia, gastrocnemius and soleus muscles where it can be accessed surgically or percutaneously. It then surfaces just as it warps around the anterior aspect of the medial malleolus where it supplies the medial posterior foot in front of heel. The medial sural cutaneous nerve comes off of the tibial at the popliteal fossa, then runs down the back of the calf (over the gastrocnemius) and wraps around the posterior aspect of the lateral malleolus before innervating the lateral aspect of the sole and heel. In some embodiments, the saphenous nerve is transvascularly stimulated by positioning one or more functional elements 260 in a blood vessel selected from the group consisting of: femoral vein; femoral artery; great saphenous vein; great saphenous artery; and combinations of one or more of these. In some embodiments, the sural nerve is stimulated. In these embodiments, the sural nerve can be transvascularly stimulated by positioning one or more functional elements 260 in the saphenous vein.

One or more leads 265 can be configured to stimulate the median nerve, ulnar nerve and/or radial nerve. The median nerve can be accessed percutaneously in the upper arm lateral to the brachial vein and/or artery, but medial to the biceps muscle, whereas the ulnar nerve runs medial to the brachial artery in the upper arm. The median nerve passes through the anterior aspect of the elbow under the bicipital aponeurosis. The ulnar nerve runs medial and posterior to the medial epicondyle of the humerus. The median nerve can also be accessed in the wrist just proximal to the palm and the palmar carpal ligament. The ulnar nerve can be accessed just proximal to the palmar carpal ligament adjacent to the pisiform. The radial nerve can be accessed percutaneously just as it passes anterior to the lateral epicondyle. In some embodiments, apparatus 10 can be configured to transvascularly stimulate at least one of a median nerve, an ulnar nerve or a radial nerve, and functional element 260 can comprise one or more electrodes positioned in a vessel selected from the group consisting of: brachial vein; brachial artery; basilic vein; basilic artery; deep vein of the arm; deep artery of the arm; and combinations of one or more of these. In some embodiments, apparatus 10 can be configured to transvascularly stimulate at least one of a median nerve or an ulnar nerve, and functional element 260 can comprise one or more electrodes positioned in a vessel selected from the group consisting of: brachial vein; brachial artery; and combinations of one or more of these. In some embodiments, apparatus 10 can be configured to transvascularly stimulate the radial nerve, and functional element 260 can comprise one or more electrodes positioned in a vessel selected from the group consisting of: deep vein of arm; deep artery of arm; basilic vein; radial collateral vein; radial collateral artery; medial collateral vein; medial collateral artery; radial vein; radial artery; and combinations of one or more of these. In some embodiments, apparatus 10 can be configured to transvascularly stimulate the medial cutaneous nerve, and functional element 260 can comprise one or more electrodes positioned in the basilic vein. In some embodiments, apparatus 10 is configured to transvascularly stimulate the ulnar nerve, and functional element 260 can comprise one or more electrodes positioned in a vessel selected from the group consisting of: ulnar collateral vein; ulnar collateral artery; ulnar vein; ulnar artery; and combinations of one or more of these. In some embodiments, apparatus 10 is configured to transvascularly stimulate the median nerve, and functional element 260 can comprise one or more electrodes positioned in a vessel selected from the group consisting of: brachial vein; brachial artery; ulnar vein; ulnar artery; and combinations of one or more of these.

As described herein, one or more leads 265 can be positioned to stimulate the spinal cord, such as via percutaneous insertion of a lead 265 in the epidural space or surgical implantation of the lead 265 (e.g. a paddle lead) in the epidural space. A lead 265 can be placed such that one or more functional elements 260 (e.g. one or more electrodes) are positioned from T5-S5, such as to capture the area of pain or reduced circulation of the leg or foot. One or more functional elements 260 of one or more leads 265 can be positioned from C2 to T8, such as to capture the area of pain or reduced circulation of the arm or hand. One or more leads 265 can be placed along the midline, unilaterally and/or bilaterally over the dorsal columns, in the gutter (over dorsal roots) and/or in the dorsal root entry zone. Leads 265 can span several vertebral levels or they can be positioned to span a single level.

One or more functional elements 260 (e.g. one or more electrodes attached to one or more leads 265) can be positioned to transvascularly stimulate one or more nerves, such as one or more nerves in the foot, leg and/or arm, such as when the one or more functional elements 260 are implanted within one or more blood vessels of the venous and/or arterial system.

In the leg, the tibial nerve, sacral roots and/or deep fibular nerve can be stimulated, such as when a lead 265 accesses the tissue to be stimulated through a transvascular approach, such as via the femoral vein and/or artery, as described herein. The deep fibular nerve can be stimulated by one or more functional elements 260 positioned in the anterior tibial vein and/or the anterior tibial artery. In the arm, the median nerve, ulnar nerve, superior ulnar nerve, medial cutaneous nerve and/or radial nerve can be stimulated, such as when lead 265 accesses the tissue to be stimulated through a transvascular approach, such as via the brachial vein and/or artery, the basilic vein and/or artery, and/or the deep vein and/or artery.

One or more functional elements 260 (e.g. one or more electrodes attached to one or more leads 265) can be positioned to stimulate dorsal root ganglia that supply the following nerves (e.g. to treat the leg and/or foot): common peroneal (L4-S2); tibial (L4-S3); femoral (L2-L4); and combinations of one or more of these. One or more functional elements 260 (e.g. one or more electrodes attached to one or more leads 265) can be positioned to stimulate dorsal root ganglia that supply the following nerves (e.g. to treat the hand and/or arm): radial (C5-T1); median (C5-T1); ulnar (C7-T1); and combinations of one or more of these. In these embodiments, one or more leads 265 can be passed through the intervertebral foramina, either unilaterally or bilaterally, at a single vertebral level or at multiple vertebral levels.

In some embodiments, apparatus 10 is configured to treat post-amputation pain, such as to treat a disease or disorder selected from the group consisting of: phantom limb pain; phantom stump pain; acute and persistent stump pain; limb pain; neuroma; Morton's neuroma; neurilemoma; neurolemoma; Schwann cell tumor; phantom limb itch; phantom limb sensations; and combinations of one or more of these. Apparatus 10 can be configured to treat the conditions associated with post-amputation pain (i.e., stump pain), such as by using a high frequency alternating current (HFAC) block approaches. In these embodiments, one or more leads 265 can be implanted such that one or more functional elements 260 stimulate one or more nerves in the leg, arm and/or sacrum. One or more leads 265 can be surgically implanted, such as when lead 265 comprises a paddle electrode positioned near a nerve in the foot, leg or arm and/or a cuff electrode or hemi-cuff electrode positioned to at least partially surround a nerve in the foot, leg or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg or arm, such as when one or more functional elements 260 are implanted within a vein or artery. One or more leads 265 can be implanted using percutaneous transforaminal placement in the sacral foramina, such as for treatment of leg stump pain. One or more leads 265 can be implanted using cephalocaudal insertion (retrograde) into the epidural space or sacral canal, such as for treatment of leg stump pain. One or more leads 265 can be positioned to perform dorsal root ganglion stimulation and/or block, such as for treatment of leg and/or arm stump pain.

In some embodiments, apparatus 10 is configured to treat occipital and/or headache (HA) pain, such as when apparatus 10 is configured to treat a disease or disorder selected from the group consisting of: occipital neuralgia; cervicogenic headache; tension headache; chronic and episodic migraine headache; tension headache; hemicrania continua; trigeminal autonomic cephalalgias (TACs); chronic and episodic cluster headache; chronic and episodic paroxysmal hemicranias; short-lasting unilateral neuralgiform headache attacks with conjunctival injection and tearing (SUNCT); short-lasting unilateral neuralgiform headache attacks with cranial autonomic symptoms (SUNA); long-lasting autonomic symptoms with hemicrania (LASH); post-traumatic headache; and combinations of one or more of these.

Apparatus 10 can be configured to treat the conditions associated with headache pain and/or occipital neuralgia by stimulating one or more nerves in the head, such as one or more nerves selected from the group consisting of: greater and/or lesser occipital nerve (e.g. which arise from C2 and C3); the greater and/or lesser auricular nerves (e.g. which also arise from C2/C3); the third (least) occipital nerve (e.g. which arises from C3); and combinations of one or more of these. The infraorbital or supraorbital nerves can be access subcutaneously below and above the eye, respectively. Apparatus 10 can be configured to stimulate auriculotemporal, supratrochlear and/or sub-occipital nerves. To stimulate any of these nerves, lead 265 (e.g. a cylindrical SCS-type lead) can be inserted percutaneously either subcutaneously or under the muscle. Alternatively, surgical (e.g. direct cut-down) can be performed to insert lead 265 (e.g. a cylindrical lead, a paddle lead, a cuff or hemi-cuff electrode) proximate, one and/or around these nerves. Alternatively or additionally, the nerves can be accessed transvascularly as described herein (e.g. when one or more functional elements 260 are implanted in a blood vessel). Housing 210 can be implanted anywhere in the head under the skin, including: behind the ear, back of the head, the neck, in the face, and the like, where an one or more external devices 500 can be positioned in, on and/or within a hat, headband, glasses, goggles, earpiece, necklace, patch, and the like. Apparatus 10 can be configured to treat headache pain and/or occipital neuralgia by stimulating tissue in the cervical spinal cord (C2-C3), for example proximate the location the nerve enters the cord from the foramen. One or more leads 265 can be placed over the dorsal columns, in the gutter, over the dorsal root entry zone and/or out in the foramen at the dorsal root ganglion. In some embodiments, the trigeminal and pterygopalatine ganglia are accessed by inserting one or more leads 265 through the face or the roof of the mouth. In these embodiments, housing 210 can be placed anywhere in the head under the skin, as described herein.

In some embodiments, apparatus 10 is configured to treat post-herpetic neuralgia, such as to treat a disease or disorder selected from the group consisting of: shingles; herpes zoster; zoster; zona; varicella zoster virus infection; zoster sine herpete; fever blisters; herpes zoster blisters; herpes zoster rash; and combinations of one or more of these. In some embodiments, apparatus 10 is configured to treat post-herpetic neuralgia using high frequency alternating current (HFAC) block approaches. In these embodiments, one or more leads 265 can be implanted such that one or more functional elements 260 stimulate one or more nerves in the leg, arm, torso and/or sacrum. One or more leads 265 can be surgically implanted, such as when lead 265 comprises a paddle electrode positioned near a nerve in the foot, leg, torso and/or arm and/or a cuff electrode or hemi-cuff electrode positioned to at least partially surround a nerve in the foot, leg, torso or arm. One or more leads 265 can be positioned to stimulate the spinal cord, such as via a percutaneous insertion of the leads 265 in the epidural space or surgical implantation of the lead 265 (e.g. a paddle lead) in the epidural space. One or more leads 265 can be positioned to provide transvascular stimulation of nerves in the leg, torso and/or arm, such as when one or more functional elements 260 are implanted within a vein or artery. One or more leads 265 can be implanted using percutaneous transforaminal placement in the sacral foramina, such as for treatment of leg or foot pain. One or more leads 265 can be implanted using cephalocaudal insertion (retrograde) into the epidural space or sacral canal, such as for treatment of leg or foot pain. One or more leads 265 can be positioned to perform dorsal root ganglion stimulation and/or block, such as for treatment of leg, torso and/or arm pain.

In some embodiments, apparatus 10 is configured to treat angina, such as to treat a disease or disorder selected from the group consisting of: angina; chest pain caused by reduced blood flow to the heart muscle; chest pain associated with coronary artery disease such as squeezing, pressure, heaviness, tightness or pain in the chest; recurring angina pectoris; acute angina pectoris; chronic angina pectoris; acute coronary syndrome; chest pain; coronary artery spasms; microvascular angina; Prinzmetal's angina; angina inversa; stable or common angina; unstable angina; variant angina; and combinations of one or more of these.

In some embodiments, apparatus 10 is configured to treat carpal tunnel syndrome, such as to treat a disease or disorder selected from the group consisting of: median nerve entrapment; tingling and/or numbness in fingers or hand; median nerve irritation or compression; narrowing of the carpal tunnel; and combinations of one or more of these.

In some embodiments, apparatus 10 is configured to treat erectile dysfunction (ED), such as to treat a disease or disorder selected from the group consisting of: impotence; male sexual dysfunction; inability to develop or maintain an erect penis; cardiogenic ED; vasculogenic ED; diabetic ED; neurogenic ED; traumatic ED; post-prostatectomy ED; hormonal ED; hyopogonadism; pharmacological ED; and combinations of one or more of these.

In some embodiments, apparatus 10 is configured to treat complex regional pain syndrome (CRPS), such as to treat a disease or disorder selected from the group consisting of: CRPS type 1; CRPS type 2; reflex sympathetic dystrophy; causalgia; reflex neurovascular dystrophy; amplified musculoskeletal pain syndrome; systemic autonomic dysregulation; neurogenic edema; musculoskeletal pain; and combinations of one or more of these.

Figure 2:
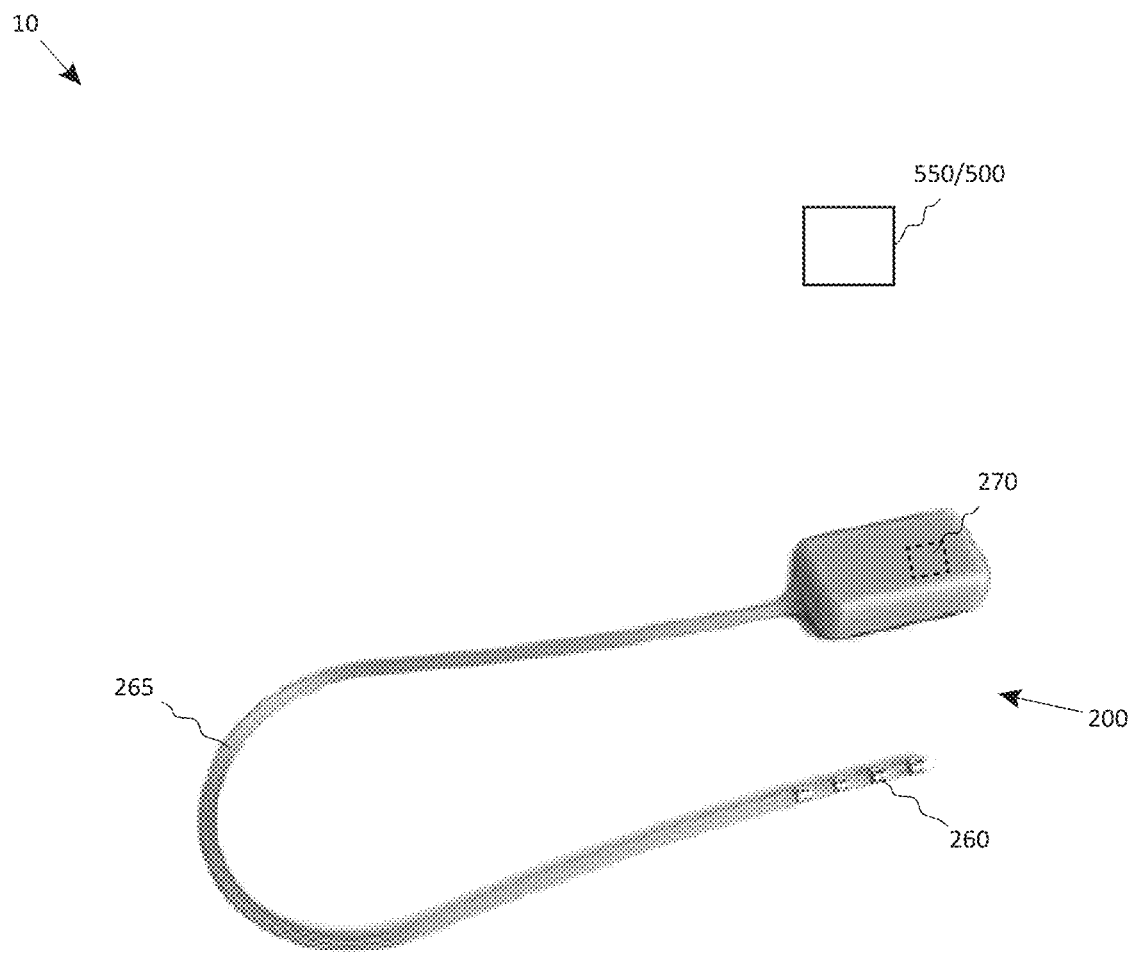
FIG. 2 is a perspective view of a system for stimulating tissue, consistent with the present inventive concepts.

In some embodiments, apparatus 10 is configured as described herebelow in reference to FIG. 2, such as when implantable device 200 has an internal battery or other power supply such that stimulation (e.g. stimulation energy and/or a stimulation agent) can be delivered to one or more locations within a patient for an extended time period (e.g. at least 1 hour, at least 1 day, at least 1 month or at least 1 year), without receiving a power transmission (e.g. as described herein from an external device such as external device 500) during that time period. In some embodiments, at least a portion of a single pulse of energy (e.g. at least a single phase) is delivered by implantable device 200 using energy provided by an internal power supply such as a battery or a capacitor. In these embodiments, data can be transmitted by one or more of an external device 500 and/or programmer 550, such as to activate or modify stimulation being delivered, with or without also transmitting power.

Figure 3:
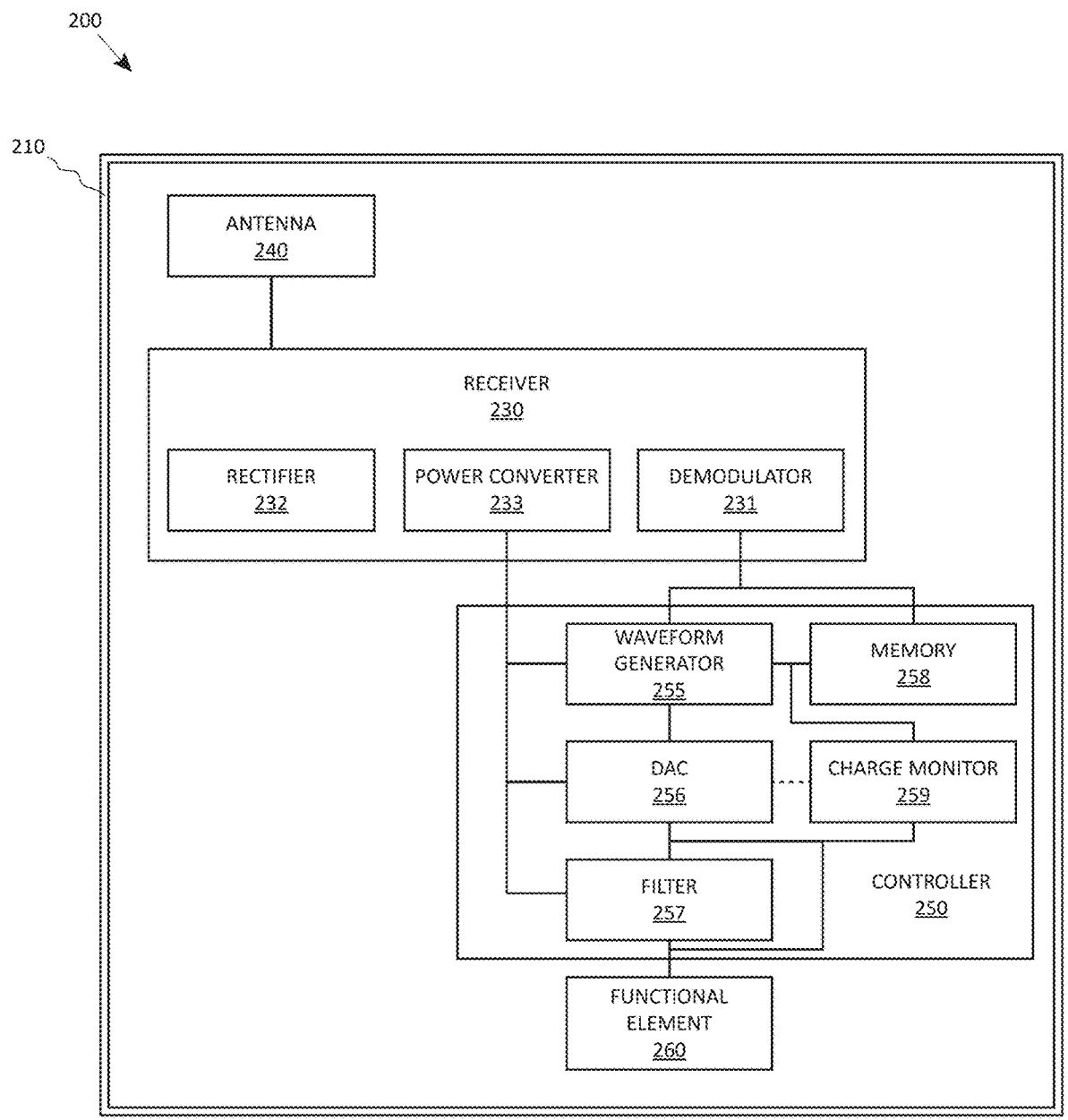
FIG. 3 is a schematic view of circuitry and other componentry of an implantable device, consistent with the present inventive concepts.

In some embodiments, implantable device 200 comprises one or more components configured to receive transmitted power (e.g. via an external device 500), receive transmitted data (e.g. via an external device 500 and/or programmer 550) and/or deliver stimulation (e.g. deliver stimulation energy and/or a stimulation agent) as described herebelow in reference to FIG. 3.

In some embodiments, one or more implantable devices 200 are configured to deliver stimulation energy (e.g. via one or more functional elements 260 comprising an electrode) with a stimulation waveform comprising one or more high frequency signals (e.g. a signal comprising one or more high frequency components). For example, one or more implantable devices 200 can deliver one or more stimulation waveforms comprising one or more signals above 600 Hz, such as one or more signals above 1.0 kHz, 1.2 kHz, 5 kHz, 10 kHz or 25 kHz.

In these embodiments, the delivered stimulation waveform can be configured to be void of (i.e. not include) one or more lower frequency signals, such as by not including any signals at a frequency below 100 Hz, below 500 Hz, below 1000 Hz, below 1200 Hz or below 1500 Hz.

One or more implantable devices 200 can be configured to deliver stimulation energy with a stimulation waveform that varies over time. In some embodiments, one or more stimulation parameters of the stimulation waveform are randomly varied over time, such as by using a probability distribution as described herein. Each stimulation waveform can comprise one or more pulses, such as a group of pulses that are repeated at regular and/or irregular intervals. In some embodiments, a pulse can comprise delivery of electrical energy, such as electrical energy delivered in one or more phases (e.g. a pulse comprising at least a cathodic portion and an anodic portion). In some embodiments, single or groups of pulses are provided at time-varying modes of repetition (e.g. regular intervals for a period, then a period of irregular intervals) or at regular intervals with occasional (random) spurious pulses inserted (creating a single irregular event in an otherwise regular series). Non-limiting examples of waveform variations include: a variation in frequency (e.g. frequency of one or more signals of the waveform); variation of a signal amplitude; variation of interval time period (e.g. at time period between pulses or a time period between pulse trains); variation of a pulse width; multiple piecewise or continuous variations of one of more stimulation parameters in a single pulse (e.g. multi-step, multi-amplitude in one "super-pulse"); variation of pulse symmetry (e.g. via active drive, passive recovery and/or active-assisted passive recovery); variation of stimulation energy over a time window and/or overlapping time windows; variation of the power in the frequency spectrum of the stimulation waveform; and combinations of one or more of these. In some embodiments, apparatus 10 and/or implantable device 200 can be configured to vary a stimulation waveform "systematically" such as a variation performed temporally (e.g. on predetermined similar or dissimilar time intervals) and/or a variation performed based on a parameter, such as a measured parameter that can be based on a signal produced by a sensor of implantable device 200 or another component of apparatus 10. Alternatively or additionally, apparatus 10 and/or implantable device can be configured to vary a stimulation waveform randomly, such as is described herein. Random variation shall include discrete or continuous variations that can be selected from a distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. Random pulses or groups of pulses can be generated based on randomly varying one or more stimulation signal parameters as described herein. One or more stimulation parameters can be varied randomly through the use of one or more probability distributions, as described herebelow.

In some embodiments, the amplitude of a signal delivered by one or more implantable devices 200 is adjusted to prevent discomfort to the patient (e.g. paresthesia or other undesired condition) from the stimulation signal. In some embodiments, the amplitude of the stimulation signal can be ramped (e.g. up and/or down), a single time or multiple times (e.g. continuously or intermittently). In some embodiments, a titration procedure can be performed to "set" one or more stimulation parameters based on avoiding patient discomfort.

In some embodiments, one or more implantable devices 200 (e.g. as described hereabove in reference to FIG. 1 or 2) are configured to deliver stimulation energy (e.g. via one or more functional elements 260 comprising an electrode) with a stimulation waveform comprising a waveform pattern as described herebelow in reference to any one or more of FIGS. 4-30B. The stimulation waveforms delivered can be configured to treat various conditions of a patient. Each stimulation waveform can comprise a series of continuous pulses, intermittent pulses, and/or spurious pulses (e.g. occasional events in an otherwise continuous stream). Each pulse can comprise a pulse train that is repeatedly delivered by implantable device 200, the train comprising one or more cathodic pulses and/or one or more anodic pulses. In some embodiments, implantable device 200 delivers a multiphasic pulse comprising at least two cathodic pulses and/or anodic pulses, with or without any time between each pulse. For example, implantable device 200 can deliver a biphasic pulse comprising a cathodic pulse followed by an anodic pulse, a triphasic pulse comprising a cathodic pulse followed by an anodic pulse followed by a second cathodic pulse, or any series of two or more cathodic and/or anodic pulses. In some embodiments, delivered pulses are exponential in nature (e.g. comprise an exponential portion), such as dynamic return pulses that exceed a minimum current (e.g. at least 1 mA, 10 mA or 50 mA) for a short duration (e.g. for approximately 1 μsec), and then decay to lower current levels (e.g. a level of approximately 100 nA), with a time constant on the order of 1 μsec to 100 μsec, such as is described herebelow in reference to FIG. 29B.

The stimulation waveforms delivered by implantable device 200 can comprise one or more high frequencies (e.g. as described herein). The stimulation waveform frequency or other stimulation parameter can be set and/or adjusted (hereinafter "adjusted") to optimize therapeutic benefit to the patient and minimize undesired effects (e.g. paresthesia or other patient discomfort). In some embodiments, a stimulation waveform is adjusted based on a signal produced by a sensor of apparatus 10 (e.g. a sensor of implantable device 200, such as a functional element 260 configured as a sensor or other sensor of implantable device 200 as described hereabove). Adjustment of a stimulation waveform parameter can be performed automatically by the implantable device 200 and/or via an external device 500 and/or programmer 550).

In some embodiments, a pulse shape can be varied, such as a pulse shape comprising: a sinusoidal geometry; a square geometry (e.g. a waveform comprising a square wave); a rectangular geometry; a triangular geometry; (e.g. symmetric or asymmetric); a trapezoidal geometry; a sawtooth geometry; a ramped geometry; an exponential geometry; a piece-wise step function geometry; a root-raised cosine geometry; and combinations of one or more of these.

In some embodiments, a charge recovery phase (e.g. anodal phase) is varied by implantable device 200, such as is described herebelow in reference to FIGS. 29 and 29A-D.

Inter-pulse gap, the time between one or more pulses (e.g. a biphasic or other multiphasic pulse that is repeated continuously), can be varied systematically and/or randomly by implantable device 200. In some embodiments, inter-pulse gap between one or more pulses comprises zero time (i.e. a first pulse is immediately followed by a similar or dissimilar second pulse). In some embodiments, inter-pulse gap is varied systematically, such as on a routine basis (i.e. temporally) and/or varied based on a signal produced by a sensor of apparatus 10. Alternatively or additionally, inter-pulse gap can be varied randomly, such as a random variation based on a distribution (e.g. a probability distribution with a pre-determined shape) as described herebelow.

In some embodiments, implantable device 200 delivers a stimulation waveform comprising a series of frequency modulated (FM) pulses, such that the frequency of stimulation varies. Implantable device 200 can be configured to deliver a frequency modulated stimulation waveform comprising a carrier signal, at a carrier frequency, that is modulated continuously between a first frequency and a second frequency. For example, implantable device 200 can deliver a stimulation waveform that modulates between 2.0 kHz and 3.0 kHz every second (e.g. comprising a carrier signal at 2.5 kHz that is modulated at 1 Hz) with a modulation range (the excursion from the carrier signal) of +/−500 Hz. In some embodiments, implantable device 200 can deliver a stimulation waveform that comprises: a carrier frequency between 1 kHz and 50 kHz, a modulation frequency between 0.1 Hz and 10 kHz and/or a modulation range between 1 Hz and the carrier frequency.

In some embodiments, implantable device 200 delivers a stimulation waveform comprising a series of amplitude modulated (AM) pulses, such that the amplitude of stimulation varies (e.g. varying the amplitude of the voltage and/or current of the stimulation signal). The amplitude of delivered current can be varied in a single amplitude modulated sweep, such as a sweep from 2 mA to 3 mA. In some embodiments, amplitude of a signal can be varied continuously, such as when current is varied between 2 mA and 3 mA every second (e.g. a signal comprising a modulation frequency of 1 Hz). In these embodiments, the depth of modulation would be 33%, where depth of modulation is equal to 1-[lower range/upper range]. In some embodiments, amplitude of delivered current fluctuates between 1 mA and 3 mA (i.e. a depth of modulation of 66%), while in other embodiments, current fluctuates between 0 mA and 3 mA (e.g. a depth of modulation of 100%). In some embodiments, implantable device 200 is configured to deliver an amplitude modulated signal comprising: a carrier frequency between 1 Khz and 50 kHz; a modulation frequency between 0.1 Hz and the carrier frequency and/or a depth of modulation between 0.1% and 100%.

Figure 1A:
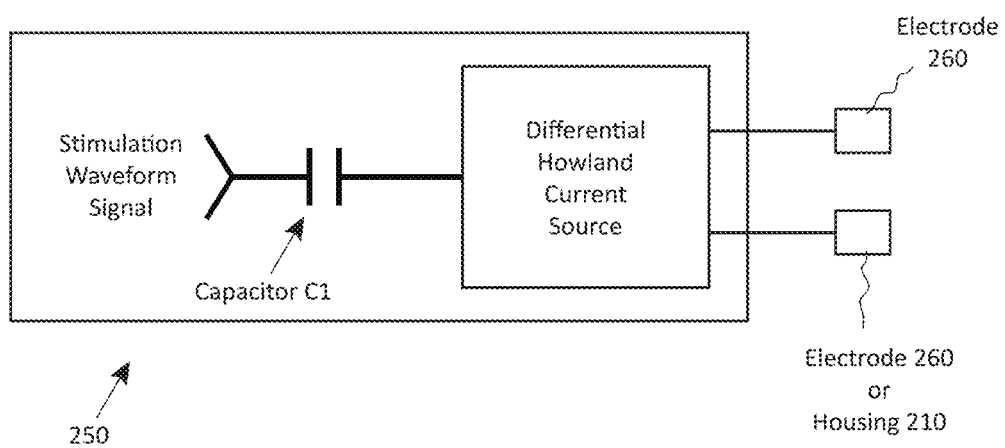
FIG. 1A is a schematic view of a controller comprising a capacitively coupled current source, consistent with the present inventive concepts.

In some embodiments, implantable device 200 delivers a stimulation waveform comprising delivery of continuously balanced analog current waveforms, for example from a differential Howland current source. In these embodiments, there are not independent pulses, but rather there is true analog frequency and amplitude modulation. Periods of delivering stimulation (or presence of balanced differential analog stimulation) and periods of no stimulation (e.g. a quiescent period) can be included. In some embodiments, controller 250 comprises one or more reconfigurable stimulation blocks including one or more Howland or other current sources, as shown in FIG. 1A. The one or more current sources (e.g. two or more current sources) can each be attached to a functional element 260 (e.g. in a monopolar configuration when the current source is also connected to housing 210 or in a bipolar configuration when the current source is connected to a pair of functional elements 260). Alternatively, controller 250 can comprise one or more current sources that are attached to a matrix of switches that selectively connect the one or more current sources to multiple functional elements 260 (e.g. connect a single current source to 2, 4, 8, 12 or 16 electrodes). In some embodiments, controller 250 is configured such that a stimulation waveform signal provided to the current source passes through a capacitor (e.g. capacitor C1 shown), the capacitor providing DC balance.

Figure 30A:
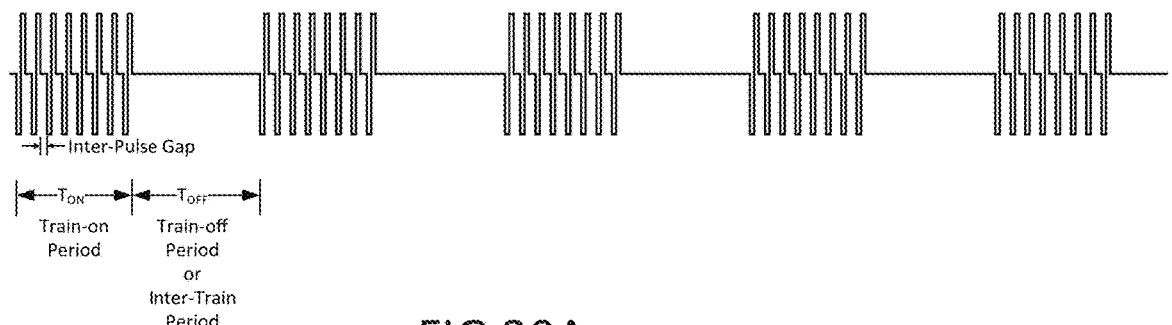
FIG. 30A is a chart of a stimulation waveform comprising multiple pulse trains of biphasic pulses, consistent with the present inventive concepts.

In some embodiments, implantable device 200 delivers a stimulation waveform comprising delivery of multiple trains of pulses that are delivered intermittently, a "burst stimulation" waveform as defined hereabove. For example, implantable device 200 can be configured to deliver a series or train of five pulses, each with a 1 msec pulse width. The each of the five pulses can be separated by an inter-pulse gap of 4 msec, creating a train-on period of 16 msec. These five pulses can be repeated every 25 msec (the "inter-train period"). In some embodiments, implantable device 200 can be configured to deliver a burst stimulation waveform comprising a pulse width between 5 μsec and 1 μmsec. Implantable device 200 can deliver a train or burst stimulation waveform comprising pulses with constant pulse widths and/or varying pulse widths, such as when the pulse widths (and/or other stimulation parameters) are varied randomly and/or systematically. Implantable device 200 can deliver a train or burst stimulation waveform with a varied or constant pulse shape selected from the group consisting of: sinusoid; square, rectangle; triangle (symmetric or asymmetric); trapezoid; sawtooth; ramp (e.g. a linear ramp); exponential curve; piece-wise step function; and combinations of one or more of these. Implantable device 200 can deliver a train or burst stimulation waveform with an inter-pulse gap less than inter-train period (e.g. as shown in FIG. 30A). The inter-pulse gap can be relatively constant or it can be varied, such as when implantable device 200 randomly varies the inter-pulse gap or varies the inter-pulse gap systematically. In some embodiments, the inter-pulse gap between any two pulses within a pulse train (or burst) can be varied between 0.1 μsec and the inter-train period (or inter-burst period). Implantable device 200 can deliver a train stimulation waveform with an inter-pulse gap between 1 μsec and 1 second. Implantable device 200 can deliver a burst stimulation waveform with an inter-train period between 1 μsec and 1 second. Implantable device 200 can deliver a burst stimulation waveform with an inter-burst period between 20 μsec and 24 hours. The inter-burst period can be relatively constant or it can be varied, such as when implantable device 200 randomly varies the inter-burst period or varies the inter-burst period systematically. In some embodiments, inter-burst period is varied by the user, such as via a user using controller 550. In these embodiments, user activation can be regulated with one or more safeguards or other limits such as those incorporated into patient controlled analgesia devices. The inter-train period can be varied between 1 μsec and 24 hours. Implantable device 200 can deliver a train or burst stimulation waveform with a train-on period (the time between the onset of a first pulse in a pulse train to the end of the last pulse in a pulse train) between 10 μsec and 24 hours. The train-on and/or burst-on period can be relatively constant or it can be varied, such as when implantable device 200 randomly varies the train-on and/or burst-on period or varies the train-on and/or burst-on period systematically. Implantable device 200 can deliver a train or burst stimulation waveform with a train or burst envelope selected from the group consisting of: cosine; cosine-squared; sine; square; rectangle; triangle (symmetric or asymmetric); trapezoid: sawtooth; ramp (e.g. linear ramp); and combinations of one or more of these. Implantable device 200 can deliver a train and/or burst stimulation waveform with a train ramp duration or burst ramp duration between 1 μsec to 10 minutes.

Implantable device 200 can deliver a train and/or burst stimulation waveform with a depth of modulation between train and/or bursts of between 1% and 99%. For example, between some or all of the trains and/or bursts (burst-off or train-off periods), a signal may be present and may contain the same or different elements contained in the train-on and/or burst-on period. These burst-off or train-off periods may comprise a quiescent period as described herein. The amplitude of the signal contained in these quiescent period may be from 0% to 99% of the signal amplitude during the train-on and/or burst-on period, such as a signal with an amplitude less than 50% of the signal amplitude during the train-on and/or burst-on period or another amplitude below a neuronal excitation threshold.

In some embodiments, apparatus 10 is configured to deliver stimulation energy to dorsal root ganglion and/or spinal cord tissue to treat a condition such as pain. In these and other embodiments, apparatus 10 can be configured to provide a stimulation waveform comprising: a combination of low frequency stimulation (e.g. electrical energy comprising a low frequency signal) and burst stimulation; burst stimulation (e.g. burst stimulation alone); a combination of low frequency stimulation and high frequency stimulation; a combination of low frequency stimulation, high frequency stimulation and burst stimulation; and combinations of one or more of these. The stimulation energy provided by apparatus 10 can be delivered to tissue via one or more functional elements 260, such as two or more electrodes which deliver similar or dissimilar stimulation waveforms simultaneously and/or sequentially. Each of the stimulation waveforms can comprise one or more pulses comprising an entire phase or at least a portion of a phase at a superthreshold level. Alternatively or additionally, each of the stimulation waveforms can comprise one or more pulses comprising an entire phase or at least a portion of a phase at a subthreshold level.

Figure 35:
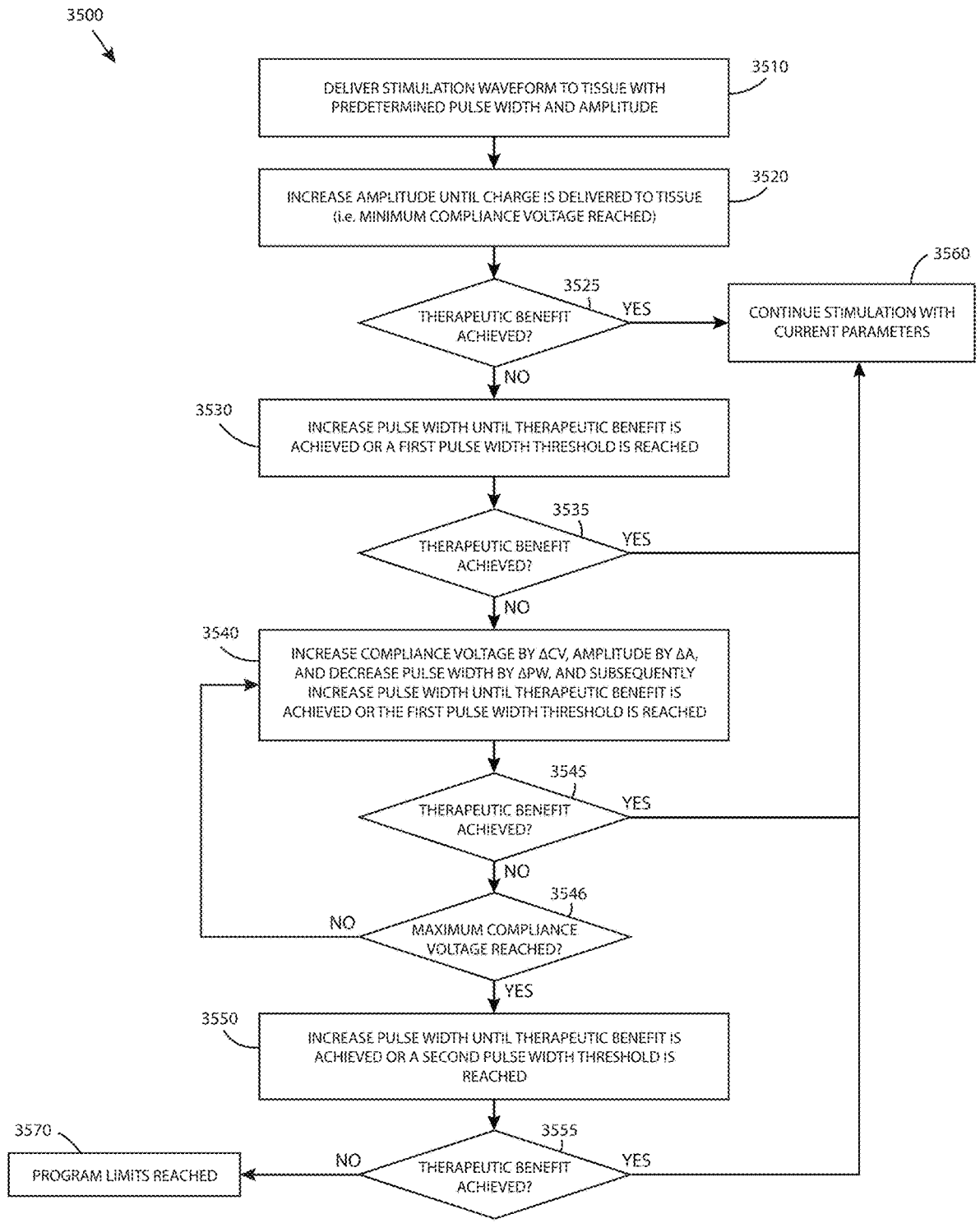
FIG. 35 is a flow chart of a method of varying parameters of stimulation waveforms to increase charge to be delivered to a patient via a therapeutic device, consistent with the present inventive concepts.
Figure 36A:
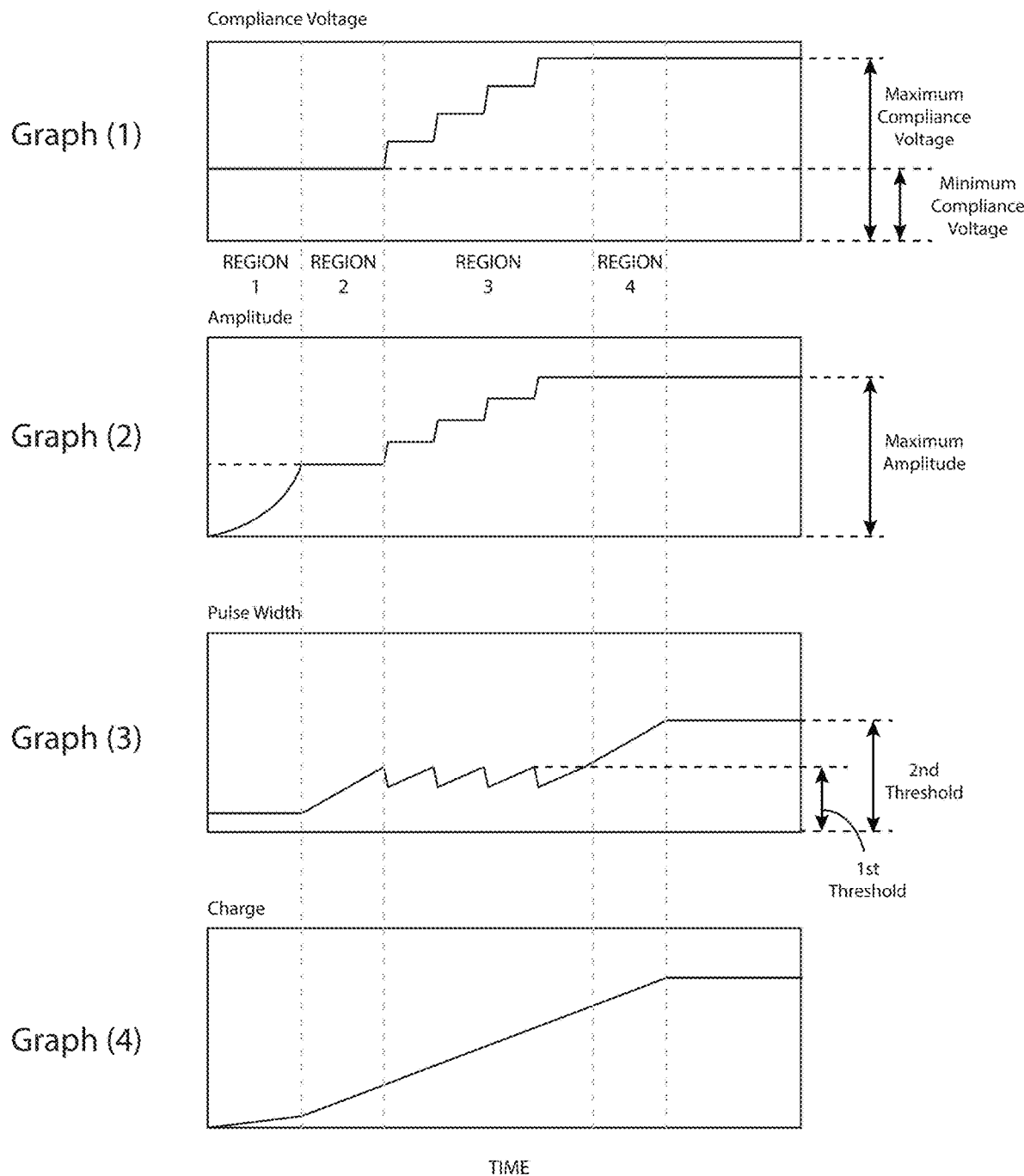
FIG. 36A illustrates graphs of the stimulation waveform parameter variation described above in the method of FIG. 35, consistent with the present inventive concepts.

In some embodiments, apparatus 10 is configured to vary one or more stimulation parameters as described herebelow in reference to FIGS. 35, 36A and/or 36B. The stimulation parameters can be varied to optimize (e.g. balance the benefits of) therapeutic benefit, system efficiency, stimulation efficiency, avoidance and/or reduction of paresthesia, and/or reduction of charge. In some embodiments, apparatus 10 is configured to deliver one or more stimulation waveforms as described herebelow, such as is described in reference to FIGS. 37A-B.

Referring now to FIG. 2, a perspective view of a system for stimulating tissue is illustrated, consistent with the present inventive concepts. Apparatus 10 comprises at least one implantable device 200, and an external control device such as external device 500 and/or programmer 550. Apparatus 10, implantable device 200, external device 500 and/or programmer 550 can be of similar construction and arrangement to similar components of apparatus 10 described hereabove in reference to FIG. 1. Implantable device 200 can comprise an implantable battery, capacitor or other power source (e.g. energy storage assembly 270 shown and described hereabove in reference to FIG. 1), such as a power source configured to provide stimulation energy that is delivered by one or more electrode-based functional elements 260 of lead 265. Implantable device 200 and energy storage assembly 270 can be configured to deliver stimulation energy for a prolonged period of time (e.g. at least 1 hour, at least 1 day, at least 1 month or at least 1 year), without receiving a wired or wireless power transmission from another source (e.g. the wireless power transmission described hereabove from an external device such as external device 500) during that time period. In some embodiments, energy storage assembly 270 can comprise a battery or capacitor configured to provide (e.g. store) at least 1 mWh of energy, or at least 1 Wh of energy. In some embodiments, energy storage assembly 270 is configured to provide less than 1 mWh of energy (e.g. to provide short term power in embodiments where implantable device 100 receives wired or wireless power from a separate device). In some embodiments, implantable device 200 is configured to deliver one or more stimulation waveforms comprising a waveform shape as described hereabove in reference to FIG. 1, or as described herebelow in reference to any one or more of FIGS. 4-30B. In some embodiments, the implantable device 200 of FIG. 2 is configured to deliver one or more stimulation waveforms in which one or more stimulation parameters are varied, such as via a random variation as described herein. In some embodiments, external device 500 and/or programmer 550 wirelessly transmits data (e.g. programming commands) through the patient's skin, to one or more implantable devices 200 that have been implanted. In some embodiments, external device 500 wirelessly transmits power (e.g. via an RF signal or inductive coupling) through the patient's skin to one or more implantable devices 200 that have been implanted, such as a power transfer that occurs at intervals of at least one day, one week, one month or one year. Alternatively, external device 500 transmits power to one or more implantable devices 200 relatively continuously, as described hereabove in reference to FIG. 1.

Referring now to FIG. 3, a schematic view of circuitry and other componentry of an implantable device is illustrated, consistent with the present inventive concepts. Implantable device 200 comprises implantable housing 210, implantable antenna 240, implantable receiver 230, implantable controller 250, and implantable functional element 260. While antenna 240 and functional element 260 are shown positioned within housing 210, either or both (as well as one or more other components of implantable device 200) can be positioned outside of housing 210, such as when either or both are positioned within a second housing. Implantable device 200 and any of its components can be of similar construction and arrangement to implantable device 200 described hereabove in reference to FIGS. 1 and/or 2. Implantable antenna 240 can comprise one or more antennas, and functional element 260 can comprise one or more functional elements, such as one or more electrodes configured to deliver stimulation energy as described herein. Receiver 230 comprises demodulator 231, rectifier 232 and power converter 233, each of which can also be of similar construction and arrangement as described hereabove in reference to FIG. 1.

Antenna 240 is configured to receive data from an external device, such as external device 500 and/or programmer 550 described hereabove, such as data used to adjust a stimulation waveform. Receiver 230 receives a data transmission captured by antenna 240 and demodulates the transmission into data via demodulator 231.

In some embodiments, antenna 240 is further configured to receive power from one or more external devices 500. In these embodiments, a power transmission captured by antenna 240 is rectified by rectifier 232, and the rectified signal is received by power converter 233. In some embodiments, power converter 233 comprises an energy storage element such as a battery or capacitor, such as energy storage assembly 270 described hereabove in reference to FIG. 1. Power converter 233 provides power to various components of implantable device 200 requiring power.

Implantable device 200 of FIG. 3 further comprises controller 250 which can comprise waveform generator 255. Alternatively or additionally, an external device, such as external device 500 described hereabove, can comprise all or a portion of waveform generator 255. Waveform generator 255 can be operably attached to power converter 233 (e.g. to receive power) and demodulator 231 (e.g. to receive programming or other data received from an external device, such as external device 500 described herein). Waveform generator 255 is configured to produce a stimulation waveform based on various input parameters, such as a parameter received via demodulator 231. Alternatively or additionally, waveform generator 255 can receive parameter information via a memory module of controller 250, such as memory 258 shown. Memory 258 can be pre-programmed with various parameter data (e.g. a stimulation table) and/or it can receive parameter data from demodulator 231 (e.g. information received from an external device 500 and stored for later use). Memory 258 can receive energy from power converter 233 (power connection not shown for illustrative clarity).

Waveform generator 255 can include various digital and/or analog electronic components used to produce a stimulation waveform, such as one or more components selected from the group consisting of: timers; oscillators; crystals; transistors; amplifiers; semiconductors; chopping circuits; diodes; switches; voltage references; level shifters; current sources; current mirrors; digital logic; capacitors; resistors; transmission line elements; tunable components; and combinations of one or more of these.

Waveform generator 255 can produce a stimulation waveform comprising one or more signals, and each signal can be based on one or more stimulation parameters as described herein. Each of the stimulation parameters can comprise a constant value (e.g. a constant amplitude or frequency) or a varying value (e.g. a value that varies over time in a predetermined and/or random manner). In some embodiments, waveform generator 255 varies one or more stimulation parameters based on a probability distribution as described herein (e.g. a probability distribution maintained within memory 258). Waveform generator 255 can produce a stimulation waveform based on an amplitude parameter, such as the amplitude of one or more pulses that varies over time. Waveform generator 255 can produce a stimulation waveform based on a pulse width parameter, such as a pulse width of one or more pulses of a pulse train. Waveform generator 255 can produce a stimulation waveform based on a timing (e.g. frequency) of pulse delivery parameter, such as the timing between the delivery of individual pulses or the timing of delivery between pulse trains. Waveform generator 255 can produce a stimulation waveform based on a carrier frequency and/or a modulation frequency, each of which can be varied (e.g. randomly varied) or held constant. Waveform generator 255 can produce a stimulation waveform based on a modulation depth parameter (e.g. a parameter that controls the modulation depth of a carrier pulse train). The modulation depth can vary between 0% and 100% of the carrier's maximum amplitude.

In some embodiments, waveform generator 255 produces a waveform comprising a signal which is at least partially based on a parameter whose level is randomly generated by waveform generator 255 (e.g. via a pseudo-random sequence generator or utilizing a probability distribution as described herein). Waveform generator 255 can generate and/or memory 258 can store information regarding interpulse timing information and/or other stimulation parameter information.

In some embodiments, memory 258 comprises a stimulation table which can store various stimulation waveform parameter information, such as one or more stimulation parameters used to determine an individual pulse shape, magnitude or duration of a pulse, and/or the shape, magnitude or duration of a pulse train or burst. In some embodiments, the stimulation table or other information stored in memory 258 is updated via data wirelessly received from an external device 500.

In some embodiments, waveform generator 255 produces a stimulation waveform selected from the group consisting of: pulses with relatively constant amplitude and pulse width; amplitude modulated pulses (e.g. via one or more modulation frequency and/or modulation depth parameters); pulse width modulated pulses (e.g. where the pulse width is maintained within a predetermined range); amplitude and pulse width modulated pulses (e.g. where either or both parameters are varied); multiple pulses with random interpulse gaps between two or more pulses (e.g. where timing between pulses is randomly changed or changed based on a probability distribution as described herebelow); and combinations of one or more of these. In some embodiments, waveform generator 255 produces a stimulation waveform comprising pulse width modulated pulses, and while the pulse width is varied, the overall charge of each pulse is held constant. In some embodiments, waveform generator 255 produces a stimulation waveform comprising one or more random pulses, but the timing of the pulses is maintained within a constrained, predetermined range (e.g. using a probability distribution as described herebelow), such as to ensure a "locus" of frequency.

In some embodiments, memory 258 is manufactured with all the parameters necessary for waveform generator 255 to produce the stimulation waveforms that implantable device 200 will deliver to tissue via the electrode-based functional elements 260. Alternatively or additionally, an external device (such as external device 500 and/or programmer 550) can transmit data (e.g. wirelessly transmit data via antenna 240 and demodulator 231) to waveform generator 255 and/or memory 258. The transmitted data can include data related to one or more stimulation waveform parameters. In some embodiments, some or all the waveform parameter information are received from an external device. In other embodiments, some or all the waveform parameter information are present in memory 258 (e.g. manufactured into memory 258 such that implantable device 200 can autonomously generate the waveform without information from an external device). In yet other embodiments, some of the waveform parameter information is manufactured into memory 258, and other waveform parameter information is received from an external device. For example, memory 258 can store waveform parameter information for a period of time and/or for a fixed number of pulses, and an external device can transmit new waveform parameter information (e.g. to be stored in memory 258) to generate subsequent waveforms to be delivered after the period of time has expired and/or the fixed number of pulses have been delivered. Implantable device 200 can be configured to simultaneously or sequentially, in any order, deliver some stimulation waveforms based on parameters stored in memory 258, and to deliver other waveforms based on parameters received from an external device. Methods of storing and receiving parameter information can be selected based on bandwidth of communication, power consumption of the implantable device 200, timing resolution, and the like.

In some embodiments, waveform generator 255 is configured to produce a waveform as described herebelow in reference to one or more of FIGS. 4-30B. In some embodiments, apparatus 10 is configured such that stimulation waveforms are delivered by one or more implantable devices 200, and each implantable device 200 stores the information (e.g. in memory 258) upon which the stimulation is based, such that each implantable device 200 can autonomously generate the delivered stimulation waveforms. Alternatively or additionally, one or more implantable devices 200 can receive waveform information from an external device 500, such that a stimulation waveform delivered by an implantable device 200 is fully or at least partially based on the information received from an external device 500, as described hereabove. In some embodiments, information received from an external device 500 updates information stored in memory 258 of implantable device 200. In some embodiments, patient, clinician or other user interaction with an external device 500 causes one or more stimulation waveforms to be adjusted, such as when stimulation waveforms delivered by an implantable device 200 adjusts dynamically between different modes of stimulation (e.g. changes to pulses, pulses trains, constant charge characteristic, optimized burst characteristic, and the like), the adjustments occurring in any order and in any combination.

Implantable device 200 can further comprise a digital-to-analog converter of controller 250, DAC 256 shown, which receives a digital signal from waveform generator 255 and converts that signal to an analog signal. DAC 256 can be attached to a source of power, power converter 233.

Controller 250 can further comprise a filter, filter 257 shown, which can receive the analog signal produced by DAC 256 and apply a filter to that signal prior to delivering the signal to one or more electrode-based functional elements 260. In some embodiments, filter 257 is configured to at least filter DC signals from reaching functional element 260 (e.g. when filter 257 comprises a capacitor). Filter 257 can be attached to a source of power, power converter 233.

In some embodiments, controller 250 comprises a mechanism, charge monitor 259 as shown, which can be configured to track total charge delivered to tissue and recovered from tissue (e.g. via active and/or passive charge recovery) and produce charge status information. Controller 250 can adjust a stimulation parameter (e.g. as described herein) of one or more pulses or pulse trains of stimulation energy based on the charge monitored by charge monitor 259. Charge monitor 259 can track charge delivered by one or more electrode-based functional elements 260, such that an implantable device 200 can generate future stimulation pulses that compensate to achieve a satisfactory charge balance. In some embodiments, information gathered by charge monitor 259 can be transmitted to an external device 500, such as when external 500 provides information to an implantable device 200 regarding one or more compensating pulses to be delivered.

Figure 29:
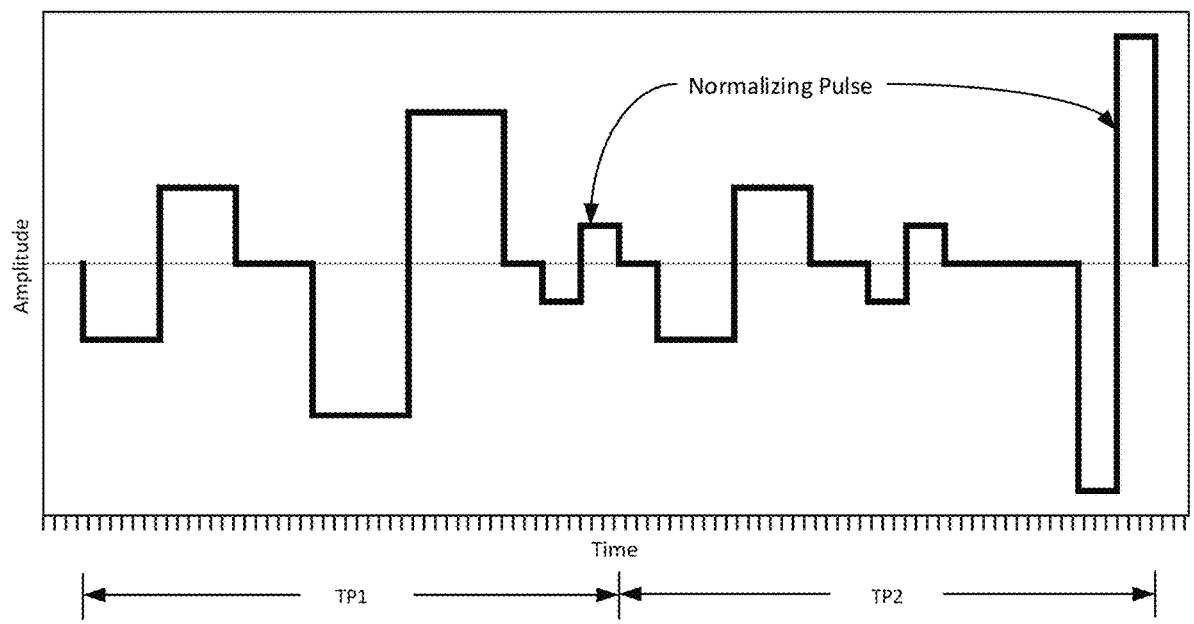
FIG. 29 is a chart of a stimulation waveform comprising a time period in which charge is desired to be kept constant, consistent with the present inventive concepts.

In some embodiments, one or more mechanisms of apparatus 10 is configured to provide "charge constancy" in which, for one or more time intervals (e.g. defined time intervals), charge is maintained constant while varying one or more stimulation parameters (e.g. as defined herein such as pulse width, amplitude and/or inter-pulse gap). In some embodiments, charge constancy comprises maintaining a minimum level of charge delivered over a pre-determined time period (e.g. for a particular patient), such as when one (or more) stimulation parameters is varied randomly and one (or more) other stimulation parameters is varied to achieve charge constancy (e.g. to maintain a minimum charge delivered in a time period or to maintain a balanced charge in a time period). Varying of the one or more stimulation parameters by apparatus 10 can be based on implantable device 200 or other apparatus 10 component capabilities, or by a patient constraint such as a patient constraint based on psychophysics principles. Referring additionally to FIG. 29, a time period TP is determined in which charge is desired to be kept constant. Within each time period TP (e.g. time periods TP1 and TP2 shown), stimulation pulses delivered by an implantable device 200 can comprise any amplitude, pulse width and/or interval between pulses (e.g. pulses can comprise one or more stimulation parameters that are randomly generated as described herein). Near the end of each time period TP, a "normalizing pulse" (e.g. comprising one or more pulses as shown) can be delivered, the normalizing pulse resulting in the desired charge constancy. In some embodiments, a normalizing pulse charge balances one or more pulses that include one or more randomly varied stimulation parameters. The time periods TP can range from 100 μsec to 10 seconds, such as a time period TP of approximately 1 msec. Apparatus 10 can be configured to achieve charge constancy using active recovery, passive recovery or both.

Figure 29A:
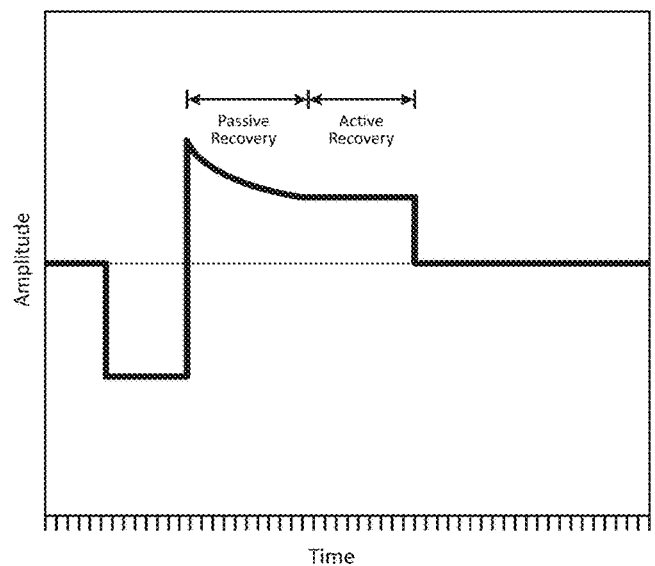
FIG. 29A is a chart of a stimulation waveform comprising a biphasic signal configured for combined active and passive charge recovery, consistent with the present inventive concepts.
Figure 29B:
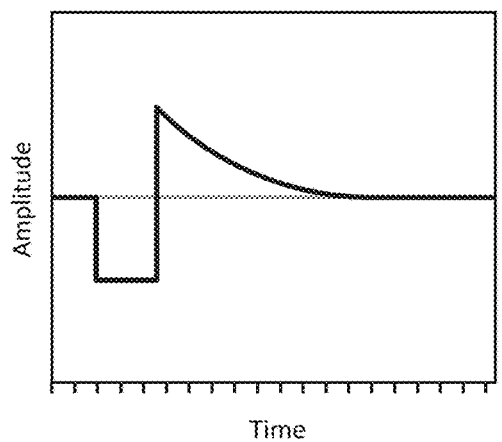
FIG. 29B is a chart of a stimulation waveform comprising a biphasic signal configured for passive charge recovery, consistent with the present inventive concepts.
Figure 29C:
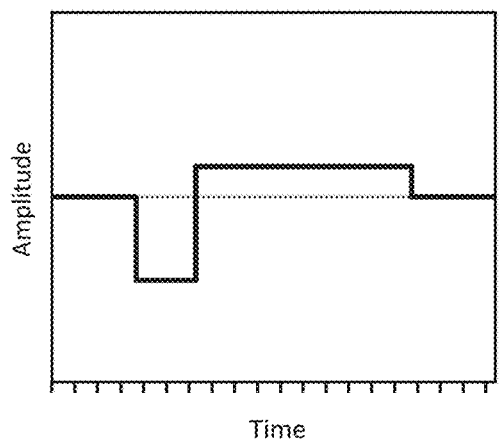
FIG. 29C is a chart of a stimulation waveform comprising a biphasic signal comprising a relatively low ratio of the two biphasic pulses.
Figure 29D:
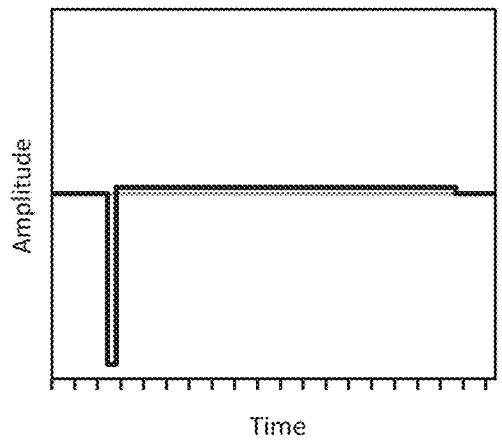
FIG. 29D is a chart of a stimulation waveform comprising a biphasic signal comprising a relatively high ratio of the two biphasic pulses.

In some embodiments, a charge recovery (e.g. anodal phase) is varied to maintain charge balance, such as a charge recovery performed by one or more implantable devices 200. Referring additionally to FIGS. 29A-D, charge recovery can be accomplished through delivery of a biphasic signal, comprising sequential pairs (symmetric or asymmetric) of cathodic and anodic pulses. Alternatively or additionally, charge recovery can be accomplished over repeated series of two, three or more pulses whose charge delivery balances to zero. Alternatively or additionally, charge can be recovered not by balancing charge over a series of pulses (i.e. netting to zero), but by a separate mechanism. Charge recovery can be passive and/or exponential in nature. In some embodiments, charge recovery is accomplished with a combination of passive and active recovery (also referred to as active-assisted passive recovery), in which an active pulse is delivered during the otherwise passive recovery period to decrease the time required to achieve charge balance. In some embodiments, active-assisted passive recovery may comprise an initial passive recovery phase followed by an analog or digital measurement or calculation of the remaining charge and then delivering an active pulse that precisely recovers the residual charge. In FIG. 29A, charge recovery is accomplished via a combination of passive recovery and active recovery. In FIG. 29B, charge recovery is limited to passive charge recovery. In some embodiments, a relatively slow DC charge recovery can be employed wherein the time in which stimulation current is delivered is less than the time in which charge is recovered, for example a an asymmetric configuration comprising a relatively small ratio as shown in FIG. 29C (e.g. charge recovery time approximately 4 to 10 times stimulation energy delivery time) or a relatively high ratio as shown in FIG. 29D (e.g. charge recovery time approximately 100 to 1000 times the stimulation energy delivery time. For example, a single stimulation pulse of 1 mA for μsec can be accompanied by a charge recovery pulse of 100 nA for 1 second.

Randomization of one or more stimulation parameters by apparatus 10 can be configured to elicit one or more neurostimulation effects selected from the group consisting of: synchronized superthreshold neuronal activation (e.g. via high amplitude pulses occasionally far apart in time); stochastic activation (a series of superthreshold pulses close enough in time to activate neurons but too fast to allow pulse-for-pulse synchrony of stimulation and action potential); sub-paresthesia neuronal stimulation; and combinations of one or more of these. Apparatus 10 can be configured to automatically, semi-automatically and/or manually assess one or more stimulation parameters to allow the patient to receive optimized therapy (e.g. optimized pain control based on the patient's own perceptual experience). In some embodiments, apparatus 10 is configured to deliver superthreshold stimulation comprising stimulation pulses delivered above a threshold whereupon (e.g. after a suitable relaxation period) delivery of a single superthreshold pulse elicits a response (e.g. an action potential) from one or more neurons.

In some embodiments, apparatus 10 is configured to provide "therapeutic constancy" in which, for one or more time intervals (e.g. defined time intervals), a therapeutic benefit measure is maintained constant while varying one or more stimulation parameters. For example, a target amount of current to be delivered to achieve a therapeutic benefit can be greater at lower pulse widths than at higher pulse widths. Accordingly, as an alternative to maintaining constant charge over a time period TP, a therapeutic measure can be maintained over each time period TP, such as a therapeutic measure based on strength-duration information as described in Lee et al, "Predicted effects of pulse width programming in spinal cord stimulation: a mathematical modeling study" Apr. 29, 2011. Therapeutic benefit can be related to a cumulative stimulation pulse target comprising the amount of charge delivered in a time period TP. Within each time period TP, stimulation pulses delivered by an implantable device 200 can comprise any amplitude, pulse width and/or interval between pulses (e.g. pulses can comprise one or more stimulation parameters that are randomly generated as described herein). Near the end of each time period TP, a "residual therapy pulse" is delivered that achieves the desired therapeutic constancy. Similar to the "charge constancy" embodiments described hereabove, the time periods TP can range from 100 μsec to 10 seconds, such as a time period TP of approximately 1 msec. In some embodiments, strength-duration information is measured for the patient (e.g. at initial use), and the information is stored in memory 258 and/or in external system 50. The stored information can be used to set or adjust one or more stimulation parameters, such as when used to maintain therapeutic constancy in subsequent therapy provided to the patient (e.g. pain management). In some embodiments, the stored strength-duration or other therapeutic threshold information is stored and used in any adjustment of a stimulation parameter during use (e.g. to set a minimum, maximum or target value for one or more stimulation parameters).

In some embodiments, apparatus 10 is configured to provide "compliance optimization" in which, for example, voltage compliance is maintained. Voltage compliance (e.g. the maximum voltage a current source requires to source stimulation current) is an important aspect of each implantable device 200 as it relates to efficiency and power consumption. Apparatus 10 can be configured to achieve optimal compliance voltage by setting the voltage (e.g. the voltage at or between two or more electrode-based functional elements 260) to be equal to the stimulation current times the tissue impedance. A minimum voltage level can be maintained during delivery of a stimulation pulse. In scenarios where the compliance voltage required for a therapy is less than the minimum that can be achieved by apparatus 10 (e.g. as might be encountered during high frequency and burst stimulation), apparatus 10 can be configured to reduce pulse width such that the current levels required are increased in order to deliver the same amount and/or other target amount of charge. Apparatus 10 can be configured such that the pulse width and/or current of stimulation pulses are selected to keep the compliance voltage at an optimized level. As described above, apparatus 10 can be configured to gather and/or use strength-duration information, such as to set and/or adjust voltage, current and/or other stimulation parameters. In some embodiments, one or more functional elements 260 comprise a sensor (e.g. one or more electrodes), and implantable device 200 is configured to measure tissue impedances periodically (e.g. at the start of delivering a group of stimulation pulses), such as to automatically adjust pulse widths and current to provide compliance optimization. In these embodiments, applicable compliance voltages range from greater than 0V (e.g. 0.1V minimum) to approximately 16V, such as compliance voltages between 1V and 5V.

Figure 30B:
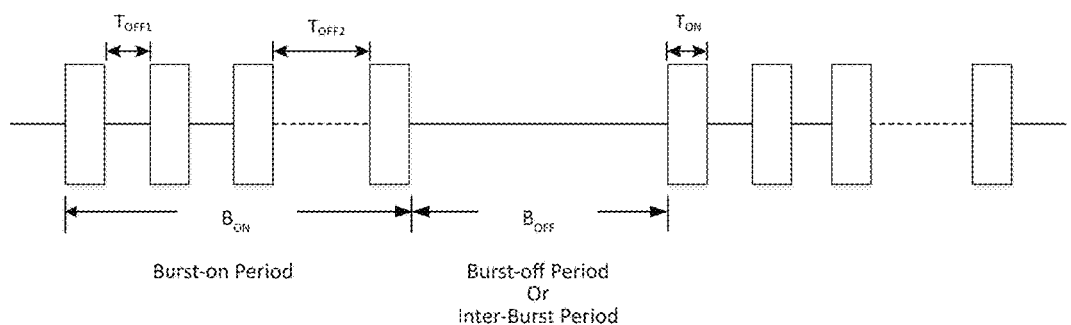
FIG. 30B is a chart of a stimulation waveform comprising bursts, consistent with the present inventive concepts.

In some embodiments, apparatus 10 is configured to provide "compliance optimized burst", for example when one or more implantable devices 200 deliver a repeated series of short stimulation pulses comprising voltage compliance optimized narrow pulses providing reduced power consumption while providing therapeutic efficacy (i.e. the amplitude is held constant at the optimal compliance voltage, while varying the pulse width). Referring additionally to FIGS. 30A and 30B, stimulation waveforms comprising multiple trains are illustrated, consistent with the present inventive concepts. In FIG. 30A, apparatus 10 can deliver a series of narrow pulses (e.g. between 2 and 1000 pulses, 8 biphasic pulses shown) for a train-on period $T_{ON}$ (e.g. a time period of between 1 μsec to 100 msec), after which no energy is delivered for a train-off period $T_{OFF}$ (e.g. a time period of between 1 μsec to 100 msec). While the trains of FIG. 30A are illustrated as comprising multiple bi-phasic pulses (pulses comprising alternating phases of energy delivery), in some embodiments, a train comprises two or more sequential pulses in one phase followed by one or more pulses in the opposite phase, such as is described herebelow in reference to FIG. 25 or 25A. In some embodiments, apparatus 10 is configured to deliver triphasic or other multiphasic pulses. In some embodiments, apparatus 10 is configured to deliver a series of monophasic pulses, as described herebelow in reference to FIGS. 37A-B. In these embodiments, a charge recovery pulse in an opposite phase (to the therapeutic stimulation pulses) can be delivered. Alternatively or additionally, charge recovery can be achieved by passive means (e.g. one or more stimulation-delivering electrodes, functional elements 260, are allowed to simply discharge into tissue, such as by being electrically connected together such that the accumulated charge discharges in an opposite direction to the stimulation pulse), without actively delivering a pulse of opposite polarity.

In some embodiments, apparatus 10 is configured to deliver a train comprising multiple pulses with an inter-pulse gap of at least 1 msec, such as to cause synchronous firing of one or more neurons (i.e. neuronal action potentials are generated by one or more neurons as a result of each delivered pulse).

In some embodiments, apparatus 10 is configured to deliver a train comprising multiple pulses with an inter-pulse gap less than 1 msec or less than 0.67 msec, such as to cause stochastic (random) firing of one or more neurons (e.g. one pulse can be delivered within the refractory period of an action potential generated by a previous pulse). Apparatus 10 can be configured to cause this random firing of action potentials in spinal cord neurons, such as to provide a therapy such as pain reduction.

In some embodiments, an inter-phase gap, an inter-pulse gap, a train-off period and/or a burst-off period is set to zero time, such as a systematic or random reduction to zero time that occurs between two phases, two pulses, two trains or two bursts.

In some embodiments, apparatus 10 is configured to provide compliance optimized burst by delivering stimulation comprising a repeated cycle of "burst-on" periods $B_{ON}$ followed by "burst-off" periods $B_{OFF}$, as shown in FIG. 30B. Each burst-on period $B_{ON}$ can comprise one or more sets of $T_{ON}$ and $T_{OFF}$ periods. Each burst-on period $B_{ON}$ can comprise between 2 and 1000 $T_{ON}$ periods (e.g. between 2 and 1000 pairs of $T_{ON}$ and $T_{OFF}$ periods, or trains, four trains shown in FIG. 30B). The various train periods $T_{ON}$ can be similar or different (similar or different number of pulses, lengths of time, and the like). The inter-train period between trains can be similar or different (e.g. in FIG. 30B $T_{OFF1}$ is less than $T_{OFF2}$). Each burst-off period $B_{OFF}$ can comprise a time period between 1 μsec and 10 seconds.

In some embodiments, apparatus 10 is configured to deliver a stimulation waveform (e.g. a compliance optimized burst waveform) comprising one, two or more parameters selected from the group consisting of: one or more train-on periods with a duration of approximately 790 μsec; one or more pulses each comprising at least two phases of approximately 10 μsec each; one or more inter-phase gaps each with a duration of approximately 10 μsec; one or more inter-pulse gaps each with a duration of approximately 10 μsec; a train-off period with a duration of approximately 910 μsec; an inter-pulse gap with a duration of approximately 10 μsec; a pulse width of approximately 30 μsec; a pulse train comprising approximately 10 pulses; a burst-on period of approximately 8.5 msec; a burst-off period of approximately 16.5 msec; and combinations of one or more of these.

In some embodiments, apparatus 10 is configured to deliver a stimulation waveform (e.g. a compliance optimized burst waveform) comprising one, two or more parameters selected from the group consisting of: one or more train-on periods with a duration of approximately 8 msec; one or more pulses each comprising at least two phases of approximately 10 μsec each; one or more pulses each with a pulse width of approximately 30 μsec; one or more inter-phase gaps each with a duration of approximately 10 μsec; one or more inter-pulse gaps each with a duration of approximately 90 μsec; a burst-on period of approximately 8 msec; a burst-off period of approximately 17 msec; and combinations of one or more of these.

In some embodiments, apparatus 10 is configured to deliver a stimulation waveform (e.g. a compliance optimized burst waveform) comprising one, two or more parameters selected from the group consisting of: one or more train-on periods with a duration of approximately 1.45 msec; one or more pulses each comprising at least two phases of approximately 10 μsec each; one or more pulses each with a pulse width of approximately 90 μsec; one or more inter-phase gaps each with a duration of approximately 20 μsec; one or more inter-pulse gaps each with a duration of approximately 90 μsec; a train-off period of approximately 1.55 msec; a burst-on period of approximately 12 msec; a burst-off period of approximately 18 msec; and combinations of one or more of these.

In some embodiments, apparatus 10 is configured to deliver a stimulation waveform (e.g. a compliance optimized burst waveform) comprising one, two or more parameters selected from the group consisting of: one or more train-on periods with a duration of approximately 1.45 msec; one or more pulses each comprising at least two phases of approximately 10 μsec each; one or more pulses each with a pulse width of approximately 90 μsec; one or more inter-phase gaps each with a duration of approximately 20 μsec; one or more inter-pulse gaps each with a duration of approximately 90 μsec; a train-off period of approximately 1.55 msec; a burst-on period of approximately 12 msec; a burst-off period of approximately 13 msec; and combinations of one or more of these.

In some embodiments, apparatus 10 is configured to deliver a stimulation waveform (e.g. a compliance optimized burst waveform) comprising one, two or more parameters selected from the group consisting of: one or more train-on periods with a duration between 700 μsec and 1.1 msec; one or more pulses each comprising at least two phases of between 5 μsec and 15 μsec each; one or more pulses each with a pulse width of between 30 μsec and 90 μsec; one or more inter-phase gaps each with a duration of between 10 μsec and 30 μsec; one or more inter-pulse gaps each with a duration of between 1 μsec and 100 μsec; a train-off period of between 900 μsec and 1.7 msec; a burst-on period of between 8 msec and 12 msec; a burst-off period of between 8 msec and 18 msec; and combinations of one or more of these.

In some embodiments, during the $T_{OFF}$ and/or $B_{OFF}$ periods (each quiescent periods as defined herein), non-zero energy is delivered, such as a delivery of monophasic or multiphasic (e.g. biphasic, triphasic, etc.) sub-threshold pulses (e.g. of insufficient magnitude to elicit a neuronal response). These sub-threshold pulses delivered during a quiescent period can comprise a pulse width as short as 1 μsec in duration, a frequency between 0.1 Hz and 100 KHz and/or a delivery pattern with inter-pulse gap between 0.1 msec and 10 seconds. In some embodiments, the duration, frequency and/or inter-pulse gap varies randomly, such as via a probability distribution as described herebelow. In some embodiments, a stimulation waveform comprises a burst at a first frequency and a first amplitude (constant or varying), combined with one or more bursts at a different frequency and/or a different amplitude. In these embodiments, one or more frequencies can be a high frequency and one or more frequencies can be a low frequency (e.g. to achieve the benefits of both high and low frequency stimulation). In some embodiments, during the $T_{OFF}$ and/or $B_{OFF}$ periods, energy is delivered with an amplitude, frequency and/or other configuration that does not result in paresthesia, such as a delivery of monophasic or multiphasic (e.g. biphasic, triphasic, etc.) pulses that do not elicit paresthesia (sub-paresthesia energy is delivered).

Figure 30C:
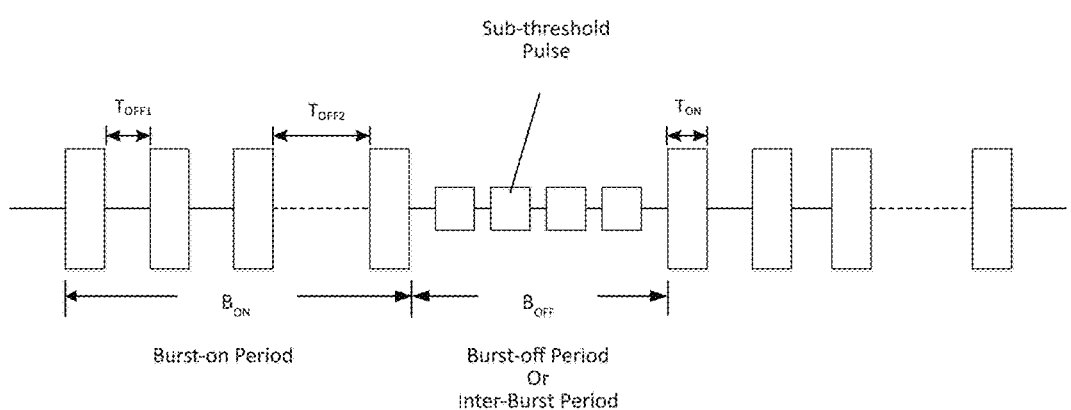
FIG. 30C is a chart of a stimulation waveform comprising bursts with a burst-off period in which sub-threshold energy is delivered, consistent with the present inventive concepts.

In some embodiments, apparatus 10 is configured to deliver burst stimulation in which one or more burst-off periods comprise delivery of energy at a level insufficient to cause neuronal firing. For example, a stimulation waveform can include one or more sub-threshold pulses that are delivered during a burst-off period as shown in FIG. 30C. The burst-off periods can comprise a duration between 1 msec and 5 seconds.

Figure 38:
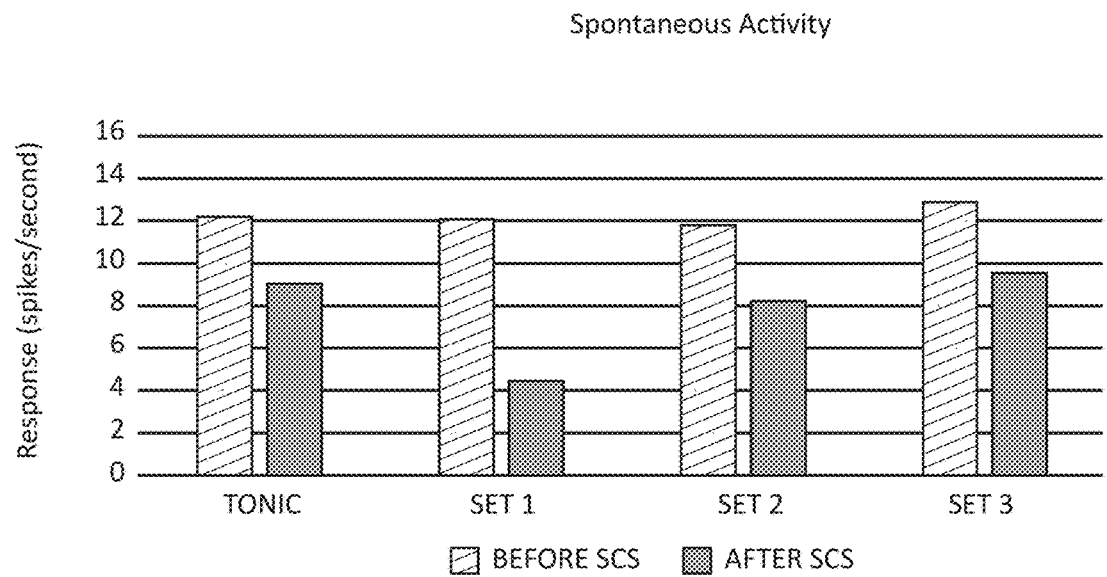
FIGS. 38 and 39 are charts of results of pre-clinical experiments in a murine model of neuropathic pain; consistent with the present inventive concepts.
Figure 39:
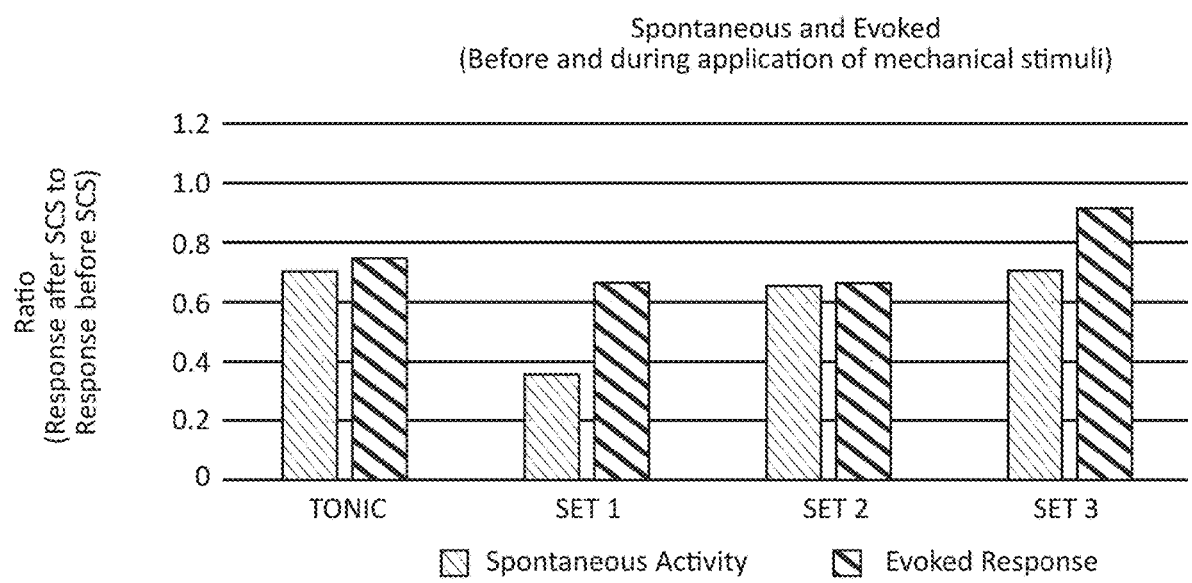

In some embodiments, apparatus 10 is configured to deliver a stimulation waveform comprising a parameter set selected from Table 1 herebelow. SET 1 and SET 2 each comprise pulses with a relatively short inter-pulse gap (e.g. approximately 10 μsec-30 μsec), which can be implemented to increase system efficiency, while SET 3 comprises a longer inter-pulse gap (e.g. approximately 100 μsec), which can be implemented to improve efficacy of treatment. SET 3 can be configured to cause different physiologic responses (e.g. targeting different fibers by the use of broader pulses widths, such as a pulse width of approximately 100 μsec versus 30 μsec). Apparatus 10 can be configured to stimulate spinal cord neurons, which in turn can affect the activity of wide dynamic range (WDR) neurons in the dorsal horn of the spinal cord. These WDR neurons receive multiple inputs from a variety of pathways responsible for modulating pain in the central nervous system and play a significant role in the propagation of pain information up the spinal cord to the brain. Activation of the dorsal column fibers excites supraspinal brain stem relays that transmit descending information, modulating the release of neurotransmitters in the spinal cord, which modulate the WDR cells. Applicant has performed pre-clinical experiments in a murine model of neuropathic pain, comparing SET 1, SET 2, and SET 3 to a spinal cord stimulation waveform comprising standard tonic stimulation. Wide dynamic range (WDR) neurons were identified, and both evoked and spontaneous activity was recorded. Evoked activity was generated through use of a nociception assay, in particular the Von Frey assay. Mechanical stimuli, in particular Von Frey fibers applied to the bottom of the subject's paw, were used to create the evoked activity. FIG. 38 illustrates the effects of spinal cord stimulation on spontaneous (non-evoked) WDR activity, as recorded from a neuron of a representative murine subject tested. The testing of FIG. 38 includes spinal cord stimulation performed using tonic stimulation, as well as spinal cord stimulation using waveforms comprising the parameters of SET 1, SET 2 and SET 3. In the example murine subject of FIG. 38, the waveform comprising the parameters of SET 1 resulted in the largest inhibition relative to each of Tonic, SET 2 and SET 3. FIG. 39 illustrates varied effects of the same spinal cord stimulation waveforms for both spontaneous activity and evoked activity. The effect is shown as a ratio of activity prior to spinal cord stimulation to activity after spinal cord stimulation. Ratios less than 1 indicate a suppression of activity due to the particular spinal cord stimulation waveform. As shown in FIG. 39, spinal cord stimulation in the form of (i.e. comprising the parameters of) Tonic, SET 1, SET 2 and SET 3 all inhibited WDR activity in this example neuron of a representative murine subject tested. SET 1 elicited the largest inhibition of spontaneous activity, whereas SET 2 resulted in a similar inhibition to that achieved with SET 1 in terms of the evoked response. SET 1 resulted in the largest inhibition of evoked activity in a majority of murine subjects tested (a quantity of 7).

TABLE 1

| Spinal Cord Stimulation Parameter Set | Pulse Width (μsec) | Inter-Pulse Gap (μsec) | Train-On Period (msec) | Train-Off Period (msec) | Burst-On Period (msec) | Burst-Off Period (msec) |
|---|---|---|---|---|---|---|
| SET 1 | 30 | 30 | 2 | 0.9 | 13.5 | 11.5 |
| SET 2 | 30 | 10 | 1.33 | 0.9 | 10.2 | 14.8 |
| SET 3 | 100 | 50 | 1.5 | 0.9 | 11.1 | 13.9 |

Referring now to FIGS. 4-30B, a series of stimulation waveforms and/or stimulation waveform parameter information is illustrated, consistent with the present inventive concepts. In each figure, the amplitude shown can correlate to a voltage or current delivered by one or more electrode or other electrical energy-based functional elements 260 of one or more implantable devices 200 as described above in reference to FIGS. 1, 2 and/or 3. Alternatively, the amplitude shown can represent an intensity of non-electrical energy, such as the intensity of: magnetic energy; electromagnetic energy; light energy; sound energy such as ultrasound energy; mechanical energy such as vibrational energy; thermal energy such as heat energy or cryogenic energy; chemical energy; and combinations of one or more of these. In some embodiments, electrical stimulation energy is delivered by one or more functional elements 260 in a monopolar fashion (e.g. when a housing such as housing 210, or other portion of implantable device 200 acts as a return electrode). Alternatively or additionally, stimulation energy is delivered by one or more functional elements 260 in a bipolar or other multi-polar fashion (e.g. when one or more electrode-based functional elements 260 act as a return electrode). In some embodiments, the stimulation waveforms described herebelow are used to treat a disease or disorder of the patient, such as to treat pain as described herein. In some embodiments, one or more implantable devices 200 are configured to deliver stimulation energy while varying (e.g. randomly varying) one or more stimulation parameters, such as to avoid or at least limit neuronal synchronization, such as to avoid or at least reduce paresthesia and/or to improve therapy (e.g. improve pain relief). For example, inter-pulse gap can be varied, such as a random variation based on a distribution as described herebelow.

Each of the waveforms illustrated in the figures described herebelow can comprise intermittent or otherwise varied delivery of energy, such as intermittent or otherwise varied delivery of: electrical energy, magnetic energy, sound energy (e.g. ultrasound energy), light energy, thermal energy (e.g. heat energy and/or cryogenic energy) and/or chemical energy. Variations can be performed systematically or randomly (e.g. randomly based on a probability distribution as described herein). In some embodiments, one or more functional elements 260 deliver electrical energy with a current between 100 nA and 40 mA, such as stimulation delivered with a current between 0.5 mA and 10 mA. In some embodiments, electrical energy is delivered by delivering a voltage whose absolute value is less than 20V (e.g. a voltage between −20V and +20V), such as a voltage with an absolute value ranging between 0.1V and 15V, such as between 1V and 15V. In some embodiments, current and/or voltage are varied between zero (or another minimum value that doesn't elicit a neuronal response) and the above ranges. In some embodiments, current and/or voltage are varied between the above ranges and a maximum (e.g. a maximum greater than the above ranges). In some embodiments, a group of pulses (or two or more phases of a single pulse) comprise asymmetric pulses (or asymmetric single pulse phases) with amplitudes and/or pulse widths with ratios between 1:1 and 10,000:1, such as a ratio of approximately 2:1, 3:1, 10:1, or 100:1. In some embodiments, one or more pulses of a stimulation waveform have a pulse width between 1 μsec and 10 msec, such as a duration between 10 μsec and 300 μsec.

Each of the probability distributions illustrated in the figures described herebelow can comprise any discrete or continuous probability distribution. In some embodiments, apparatus 10 utilizes a probability distribution equivalent to or similar to a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these.

Figure 4:
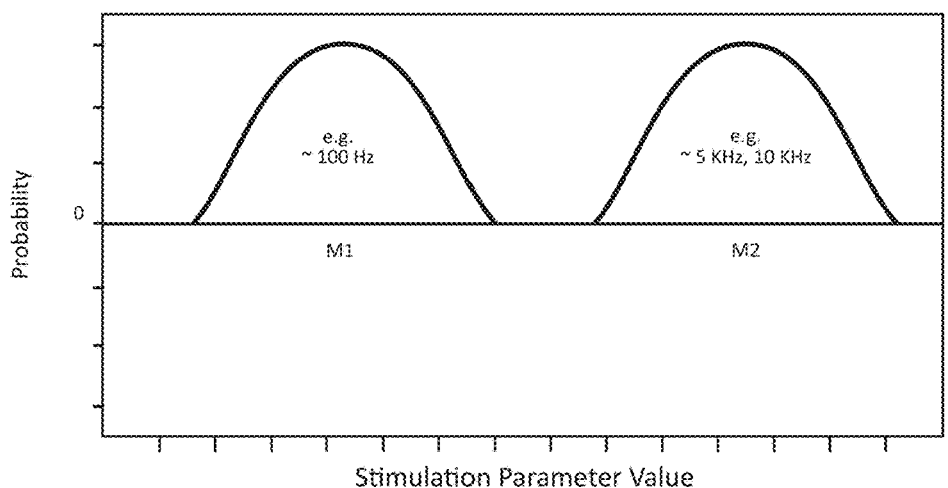
FIGS. 4-6 are charts of a first probability distribution, a burst and/or train stimulation waveform, and a second probability distribution, respectively, consistent with the present inventive concepts.
Figure 5:
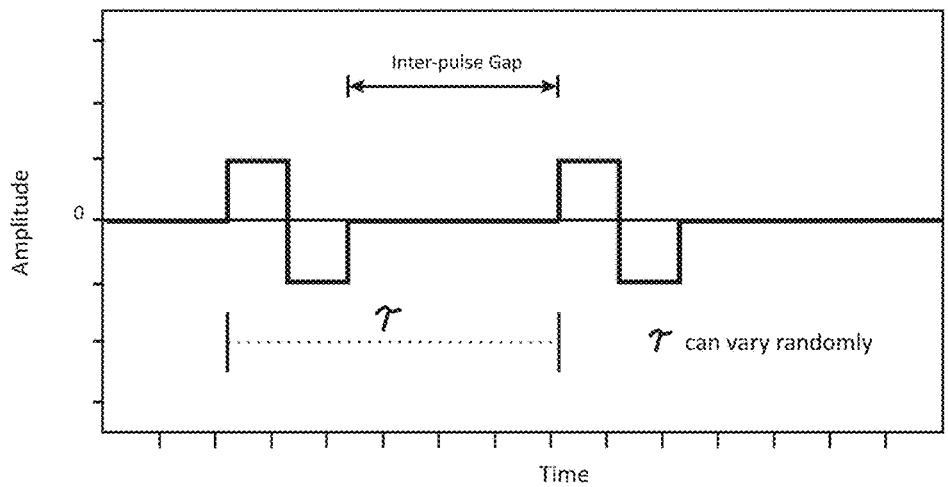
Figure 6:
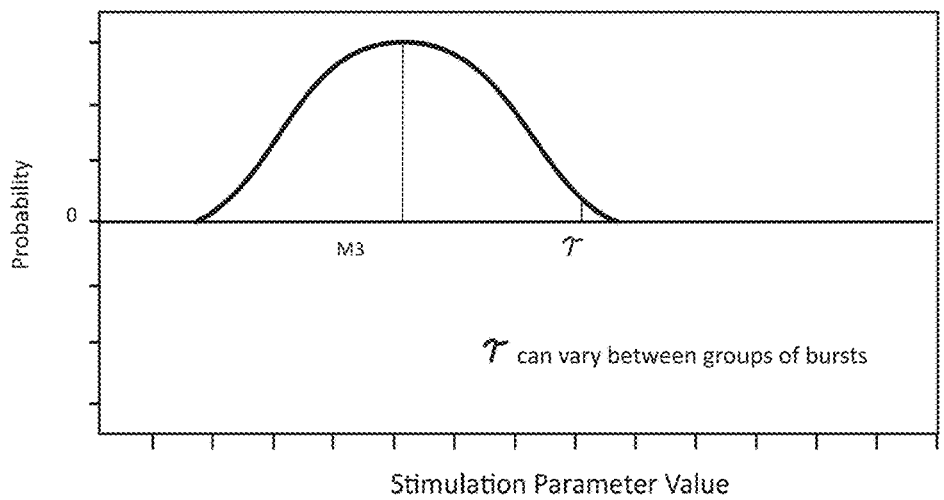
Figure 7:
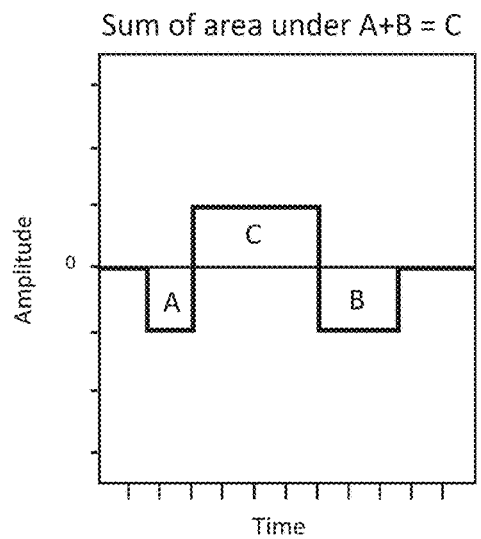
FIGS. 7-10 are charts of four stimulation waveforms, each comprising a multiphasic pulse train, consistent with the present inventive concepts.
Figure 10:
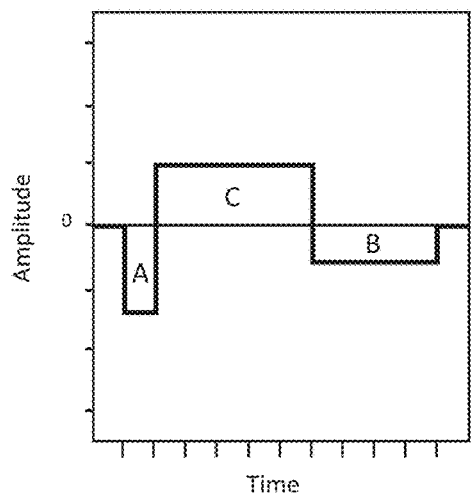
Figure 8:
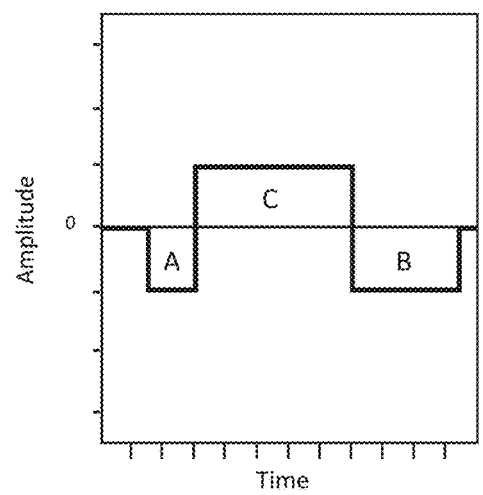

Referring now to FIGS. 4-6, charts of a first probability distribution, a burst and/or train stimulation waveform, and a second probability distribution, respectively, are illustrated, consistent with the present inventive concepts. In FIG. 4, distributions M1 and M2 are shown. Distribution M1 can comprise a low frequency peak, such as a peak of approximately 100 Hz as shown, although other low frequency peaks could be utilized, such as approximately 10 Hz, 50 Hz, 200 Hz, 300 Hz, or 1000 Hz. Distribution M2 can comprise a high frequency peak, such as a high frequency peak of approximately 1 kHz or 10 kHz as shown, although other peaks could be utilized, such as peaks of approximately 5 kHz, 7.5 kHz, 12.5 kHz or 15.0 kHz. In some embodiments, a distribution includes multiple peaks, such as multiple peaks above 5 kHz or above 10 kHz. In FIG. 6, a distribution M3 is shown. Distribution M3 can have a relatively low frequency peak or a relatively high frequency peak as described in reference to FIG. 4. In FIG. 5, a pair of cathodic and anodic pulses is repeated at a time period Tau, which correlates to the inter-pulse gap shown. Tau can vary randomly or systematically, as described herein. In some embodiments, Tau is varied by sampling from the distributions M1 and/or M2 shown in FIG. 4 and/or the distribution M3 shown in FIG. 6, such as to generate randomly varying pulses or pulse trains or bursts whose variations are based on distributions about a high and/or low frequency. In some embodiments, one or more other frequency-based or non-frequency based stimulation parameters (e.g. amplitude, frequency, pulse-shape, inter-pulse gap, inter-train period and/or inter-burst period) is varied based on a distribution, such as a distribution of similar or dissimilar shapes and values to distributions M1, M2 and M3 shown in FIGS. 4 and 6, but containing values applicable to other (non-frequency based) stimulation parameter variables. In some embodiments, one or more probability distributions are shifted during use (e.g. to greater or lower values or other change in distribution), such as a distribution shifted based on patient feedback received in a patient diagnostic procedure in which patient discomfort (e.g. paresthesia) or therapeutic efficacy (e.g. pain relief) are assessed.

Referring now to FIGS. 7-10, charts of four stimulation waveforms, each comprising a multiphasic pulse train, are illustrated, consistent with the present inventive concepts. FIGS. 7-10 illustrate triphasic waveforms in which the areas A+B=C as shown in each figure (while containing different amplitudes, durations and/or shapes for each pulse), such as to maintain charge balance. In some embodiments, one or more stimulation parameters of the waveforms of FIGS. 7-10 are varied randomly, as described herein.

Figure 11:
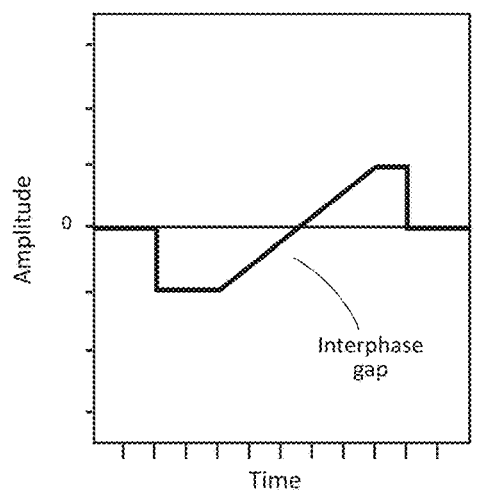
FIGS. 11 and 12 are charts of two stimulation waveforms comprising a biphasic pulse train including an inter-phase gap, consistent with the present inventive concepts.
Figure 9:
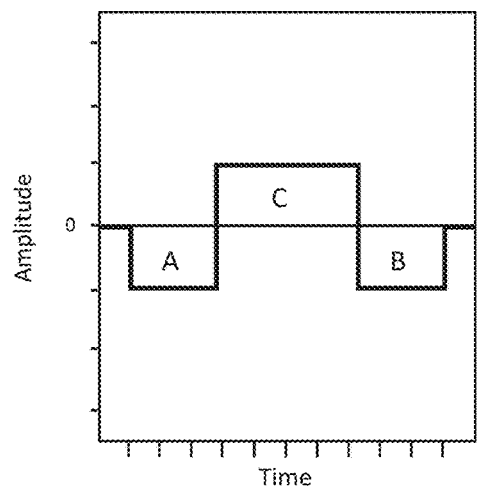
Figure 12:
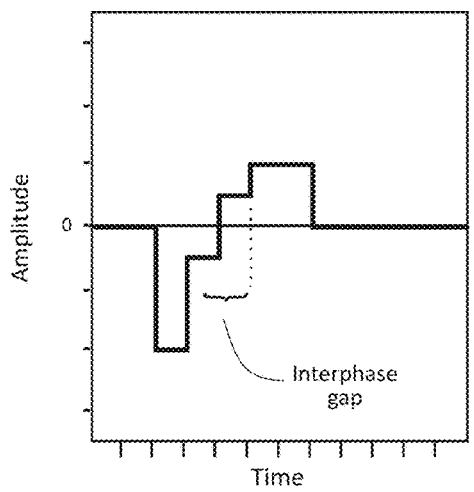

Referring now to FIGS. 11 and 12, charts of two stimulation waveforms comprising a biphasic pulse train including an inter-phase gap, are illustrated, consistent with the present inventive concepts. FIGS. 11 and 12 illustrate biphasic waveforms with different inter-phase gaps configured as shown in each figure. While the inter-phase gaps of FIGS. 11 and 12 have been shown separating two pulses of a biphasic pulse train, it should be appreciated that the same or similar inter-phase gaps can be incorporated between pulses of triphasic or other multiphasic pulse trains. In some embodiments, one or more stimulation parameters of the waveforms of FIGS. 11-12 are varied randomly, as described herein.

Figure 13:
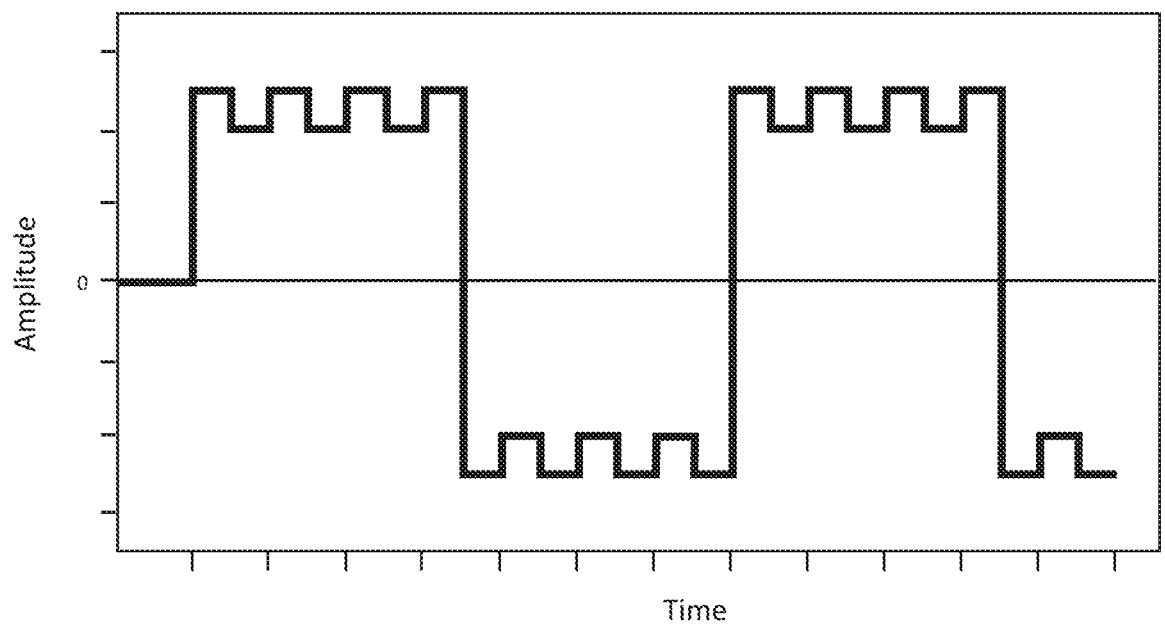
FIG. 13 is a chart of a stimulation waveform comprising a signal amplitude modulated with a square wave, consistent with the present inventive concepts.

Referring now to FIG. 13, a chart of a stimulation waveform comprising a signal amplitude modulated with a square wave is illustrated, consistent with the present inventive concepts. The stimulation waveform can comprise a carrier signal at a first frequency that is modulated by a higher frequency signal (both the carrier and modulation shown as square waves). For example, the carrier signal can comprise a frequency between 0.01 Hz and 1500 Hz. The amplitude modulating signal can comprise a frequency between 1 Hz and 100 kHz. Although the waveforms of FIG. 13 are shown as a square-wave carrier modulated by a square wave signal, other shaped signals can be used for the carrier and/or modulation signal, such as a signal with a shape selected from the group consisting of: sinusoid; square; rectangle; triangle (symmetric or asymmetric); trapezoid; sawtooth; ramp; piece-wise step function; and combinations of one or more of these. The pulse widths of the carrier and/or modulation signal can be varied, such as a variance performed randomly or systematically, as described herein. In some embodiments, one or more stimulation parameters of the waveform of FIG. 13 are varied randomly, as described herein.

Figure 14:
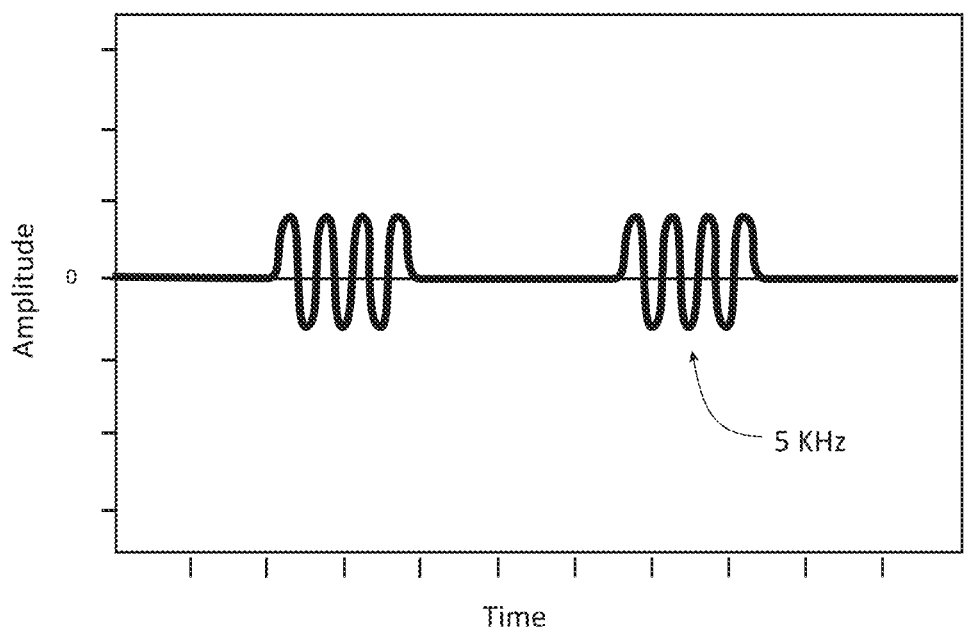
FIG. 14 is a chart of a stimulation waveform comprising a repeating burst, consistent with the present inventive concepts.

Referring now to FIG. 14, a chart of a stimulation waveform comprising a repeating burst is illustrated, consistent with the present inventive concepts. The waveform of FIG. 14 can represent bursts delivered at a frequency ranging between 10 Hz and 100 kHz. Each burst can comprise a sinusoid (as shown), such as a sinusoid with a frequency of approximately 5 kHz. In some embodiments, the delivered sinusoid or other shaped waveform has a frequency between 100 Hz and 100 kHz. While the waveform shown is a sinusoid, other waveform shapes can be delivered, such as a waveform with a shape selected from the group consisting of: sinusoid; square; rectangle; triangle (symmetric or asymmetric); trapezoid; sawtooth; ramp; and combinations of one or more of these. The burst comprises multiple pulses delivered intermittently (e.g. with a non-zero inter-pulse gap). In some embodiments, a repeated pulse train is delivered with a stimulation parameter selected from the group consisting of: 3 to 6 pulses in each train; pulse widths of approximately 1 msec; inter-pulse gap of approximately 4 msec; inter-train period of approximately 25 msec; a train-on period of approximately 16 msec; and combinations of one or more of these. In some embodiments, a stimulation waveform comprises one or more pulses that remain constant and/or one or more pulses that are varied (e.g. one or more stimulation parameters are varied randomly and/or systematically). The pulses can comprise a pulse width of between 5 μsec and 1 msec. The inter-pulse gap can comprise a time between 20 μsec to 1 sec, and can vary by a magnitude between 0.1 μsec to 1 msec. The inter-burst period can comprise a time between 20 μsec and 24 hours, and can vary by a magnitude between 1 μsec and 24 hours. In some embodiments, a burst comprises a burst envelope, such as when a burst-on period comprises a shape selected from the group consisting of: cosine; cosine-squared; sine; trapezoid; ramp; square; rectangular; triangular; and combinations of one or more of these. The burst can comprise a burst ramp duration (the time from the onset of the burst until the burst envelope reaches full amplitude) of between 1 μsec and 10 minutes. In some embodiments, one or more stimulation parameters of the waveform of FIG. 14 are varied randomly, as described herein.

Figure 15:
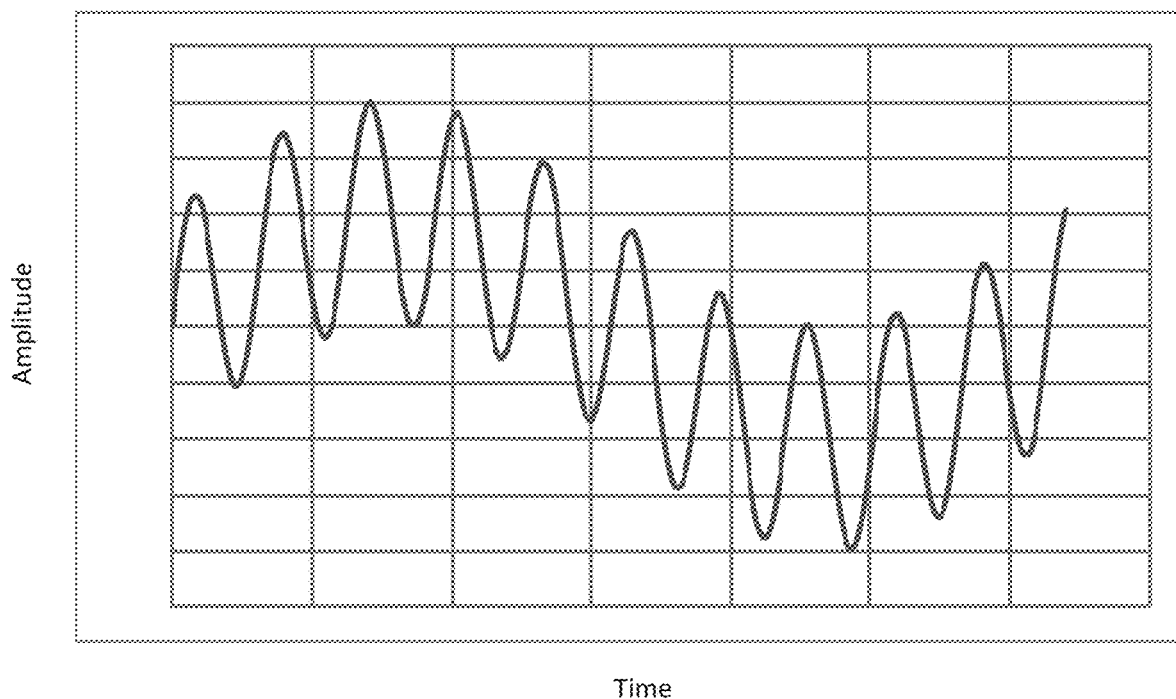
FIGS. 15 and 16 are charts of two stimulation waveforms, each comprising an amplitude modulated stimulation signal, consistent with the present inventive concepts.
Figure 16:
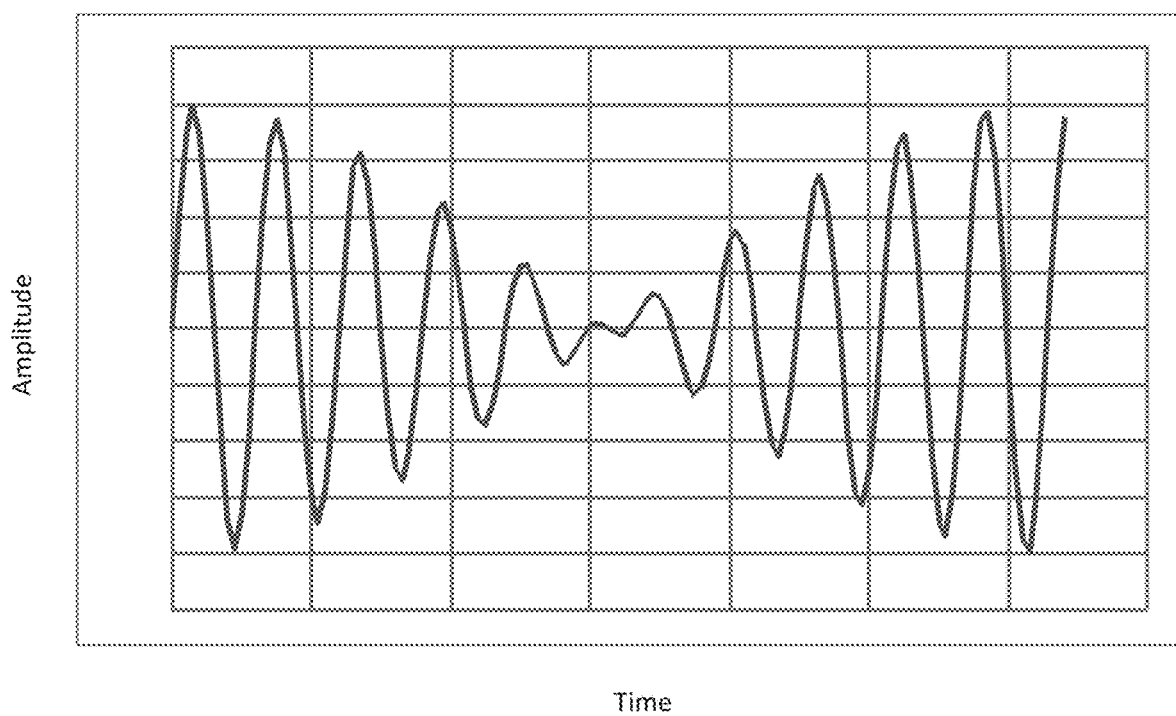

Referring now to FIGS. 15 and 16, charts of two stimulation waveforms, each comprising an amplitude modulated stimulation signal, are illustrated, consistent with the present inventive concepts. The stimulation waveform of FIG. 15 includes a high frequency carrier signal and a low frequency signal disposed on the high frequency carrier. The stimulation waveform of FIG. 16 includes a high frequency carrier signal modulated with a low frequency envelope. The low frequency component can range from 0.01 Hz to 1500 Hz, and the high frequency component can range from 1 Hz to 100 kHz. In some embodiments, the high frequency component comprises a frequency of approximately 10 kHz and the low frequency component comprises a frequency of approximately 40 Hz. While the stimulation waveform of FIGS. 15 and 16 are shown as a sine wave, alternatively it can comprise a waveform geometry selected from the group consisting of: square; rectangle; triangle (symmetric or asymmetric); trapezoid; sawtooth; ramp; and combinations of these. In some embodiments, the stimulation waveform comprises a biphasic pulse at a frequency of approximately 10 kHz (e.g. a sinusoidal shape or square-wave shape with a pulse width of approximately 30 μsec) with a low frequency sinusoidal envelope between approximately 40 Hz and 100 Hz. In some embodiments, one or more stimulation parameters of the waveforms of FIGS. 15-16 are varied randomly, as described herein.

Figure 17:
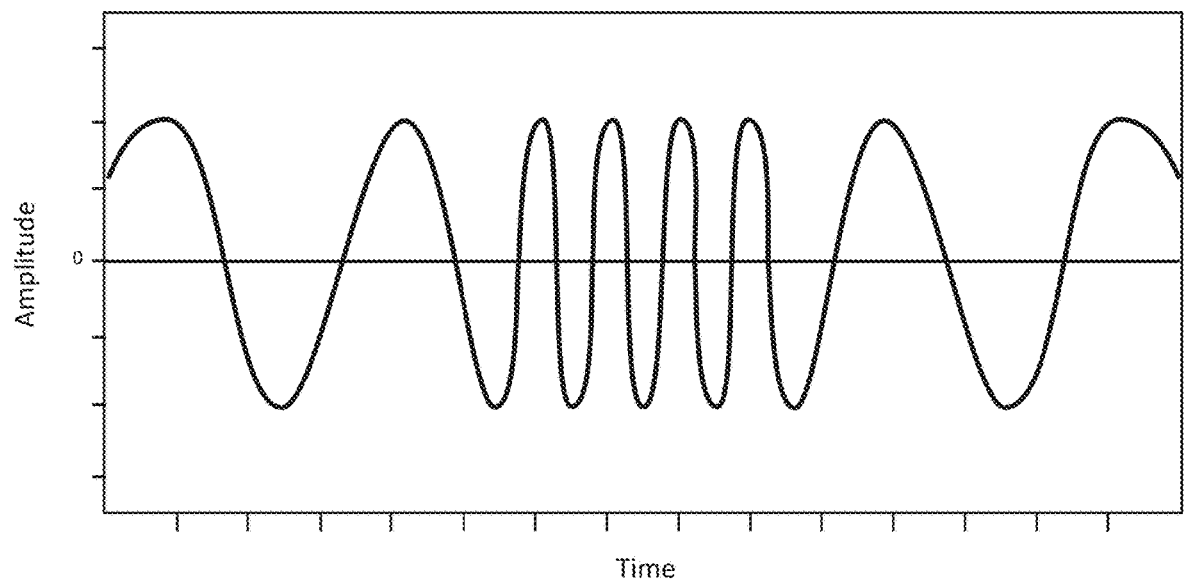
FIGS. 17 and 18 are charts of two stimulation waveforms, each comprising a frequency modulated stimulation signal, consistent with the present inventive concepts.
Figure 18:
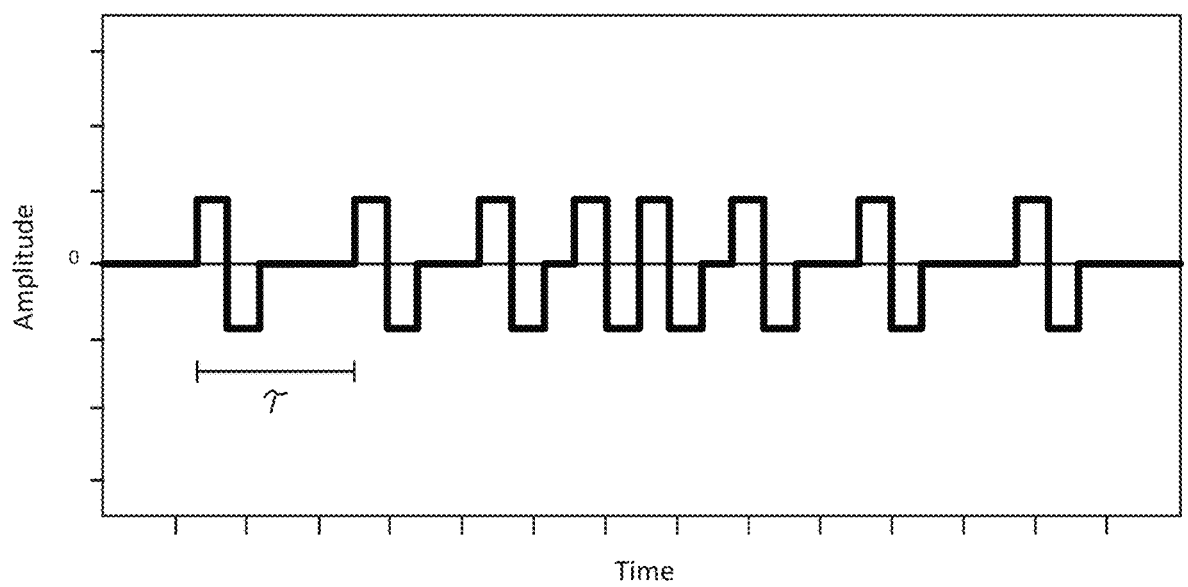

Referring now to FIGS. 17 and 18, charts of two stimulation waveforms, each comprising a frequency modulated stimulation signal, are illustrated, consistent with the present inventive concepts. The stimulation waveform of FIG. 17 includes a sinusoidal signal in which the instantaneous frequency is varied systematically (e.g. temporally varies or varies based on a signal produced by a sensor, as described herein). The stimulation waveform of FIG. 18 includes square wave pulses in which the frequency varies (e.g. varied systematically and/or randomly). In some embodiments, the amplitude of the stimulation signal is also varied (e.g. systematically and/or randomly). In these embodiments, the amplitude variation can be performed independent of the frequency modulation. While the stimulation waveforms of FIGS. 17 and 18 are shown as a sine wave and square wave, respectively, they can comprise various shapes, such as a shape selected from the group consisting of: rectangle; triangle (symmetric or asymmetric); trapezoid; sawtooth; ramp; and combinations of one or more of these. In some embodiments, one or more stimulation parameters of the waveforms of FIGS. 17-18 are varied randomly, as described herein.

Figure 19:
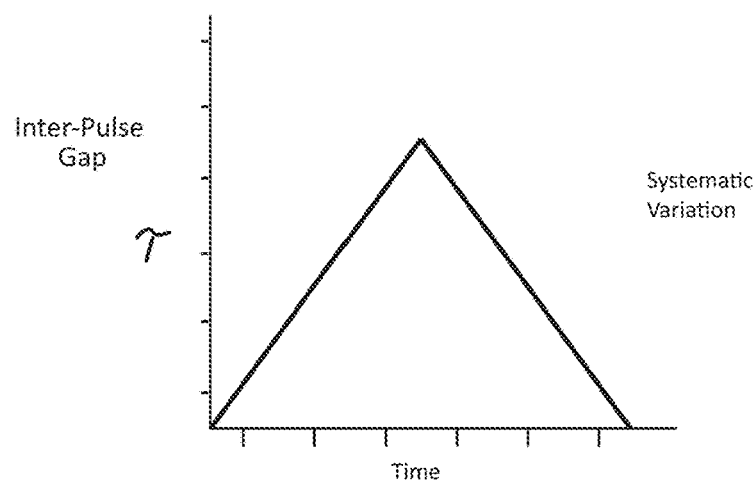
FIGS. 19-21 are charts of a first inter-pulse gap, a second inter-pulse gap, and a probability distribution, respectively, consistent with the present inventive concepts.
Figure 20:
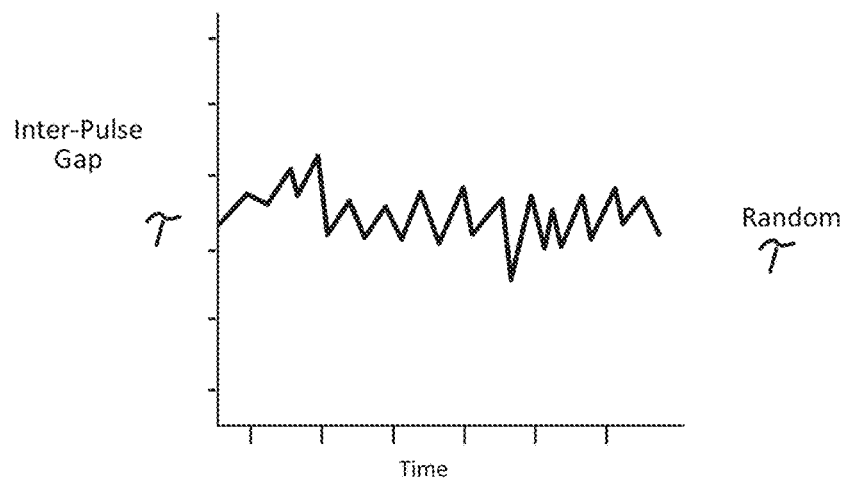
Figure 21:
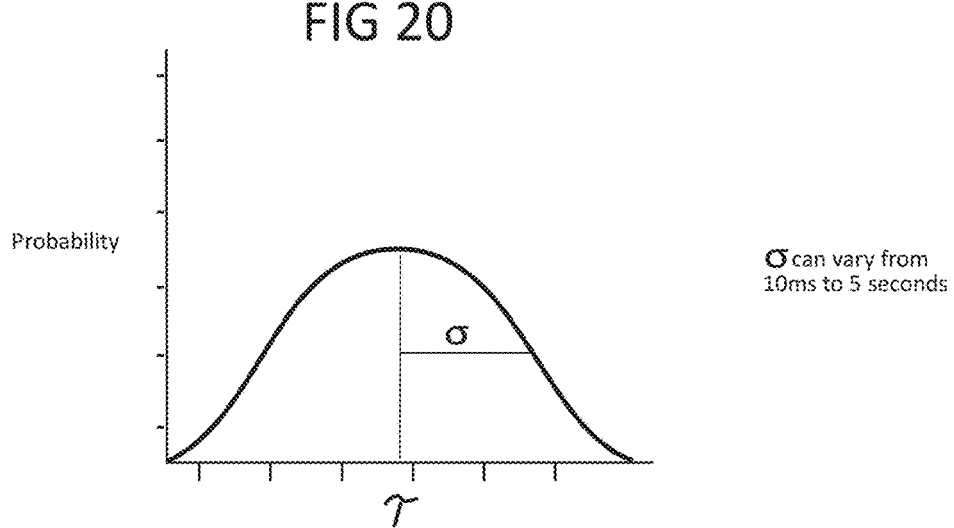

Referring now to FIGS. 19-21, charts of a first inter-pulse gap, a second inter-pulse gap, and a probability distribution, respectively, are illustrated, consistent with the present inventive concepts. In FIG. 19, an inter-pulse gap (represented by Tau) varies with time, as shown in the chart. Alternatively, Tau can vary with time, in any predetermined manner (e.g. as determined by one or more algorithms of implantable device 200 or apparatus 10). In FIG. 20, an example of a random variation of Tau over time is shown. In FIG. 21, a probability distribution for varying Tau is shown, where (sigma) is defined as 1 standard deviation. As described above, the probability distribution used can be any discrete or continuous probability distribution, such as a probability distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations of one or more of these. In some embodiments, pulse width can be varied in a similar manner to that shown for varying inter-pulse gaps in FIGS. 19-21.

Figure 22:
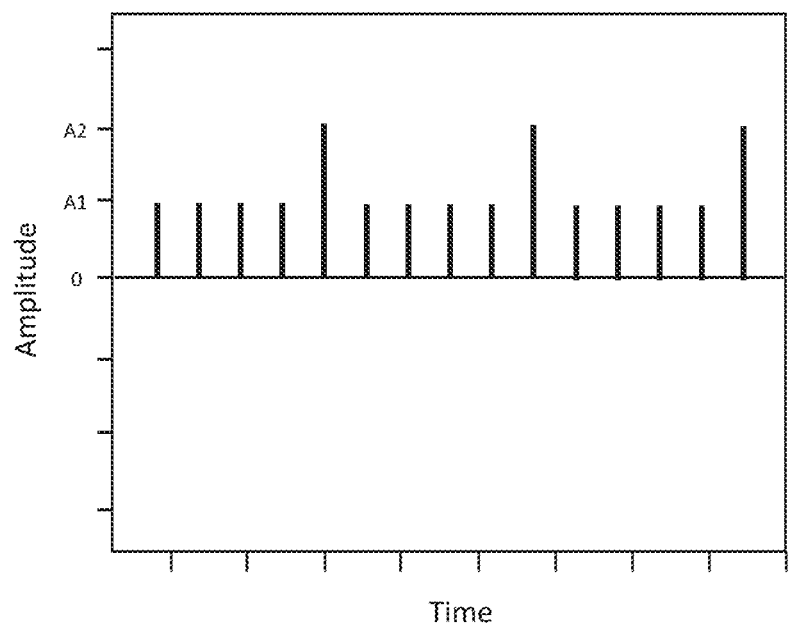
FIG. 22 is a chart of a stimulation waveform comprising a train of pulses at different amplitudes, consistent with the present inventive concepts.

Referring now to FIG. 22, a chart of a stimulation waveform comprising a train of pulses at different amplitudes is illustrated, consistent with the present inventive concepts. The stimulation waveform of FIG. 22 comprises a repeating series of pulse trains (including one or more pulses at a first amplitude A1 (four shown), and one or more pulses at a second, higher amplitude A2 (one shown). In some embodiments, each of the pulses is delivered at a relatively high frequency, such as a frequency of at least 1 kHz, such as a frequency of approximately 10 kHz. In some embodiments, the pulses delivered at amplitude A1 are delivered at a high frequency (e.g. approximately 10 kHz) and the pulses delivered at amplitude A2 are delivered at a lower frequency (e.g. less than 1 kHz). Each pulse can have similar or dissimilar amplitude and/or pulse width. In some embodiments, one or more pulses of the stimulation waveform have a pulse width between 1 μsec and 10 msec, such as a duration between 10 μsec and 300 μsec. In alternative embodiments, a pulse train is delivered comprising multiple pulses at the higher amplitude A2 and a lesser number of pulses (e.g. one) at the lower amplitude A1, such as is described herebelow in reference to FIG. 24. In some embodiments, charge is held constant by co-varying pulse width and amplitude of A1 and/or A2. In some embodiments, one or more stimulation parameters of the waveform of FIG. 22 are varied randomly, as described herein.

Figure 23:
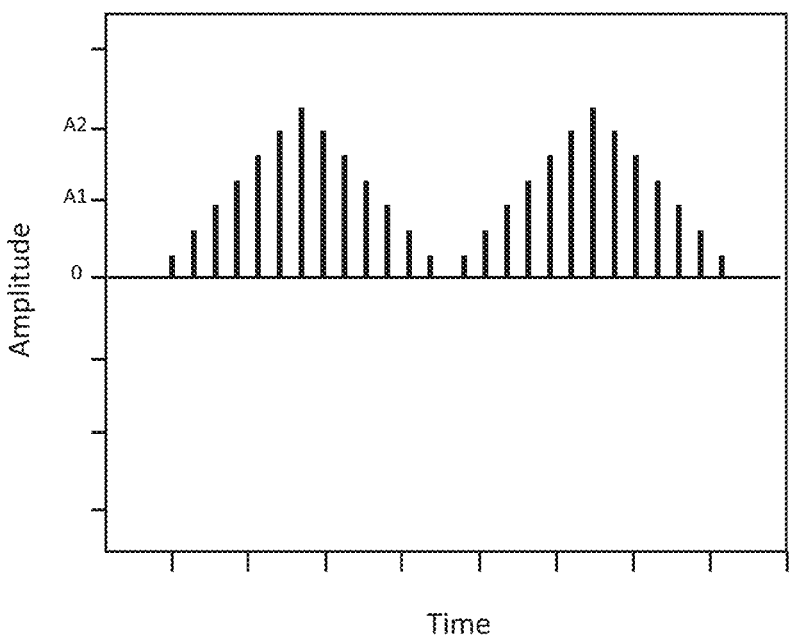
FIG. 23 is a chart of a stimulation waveform comprising a series of pulses modulated by a triangle wave, consistent with the present inventive concepts.

Referring now to FIG. 23, a chart of a stimulation waveform comprising a series of pulses modulated by a triangle wave is illustrated, consistent with the present inventive concepts. The stimulation waveform of FIG. 23 comprises a repeating series of a group of pulses that are modulated by a triangle wave. In some embodiments, the pulses are delivered at a high frequency, such as a frequency of at least 1 kHz, such as a frequency of approximately 10 kHz. In some embodiments, one or more pulses of the stimulation waveform have a pulse width between 1 μsec and 10 msec, such as a duration between 10 μsec and 300 μsec. In some embodiments, one or more stimulation parameters of the waveform of FIG. 23 are varied randomly, as described herein.

Figure 24:
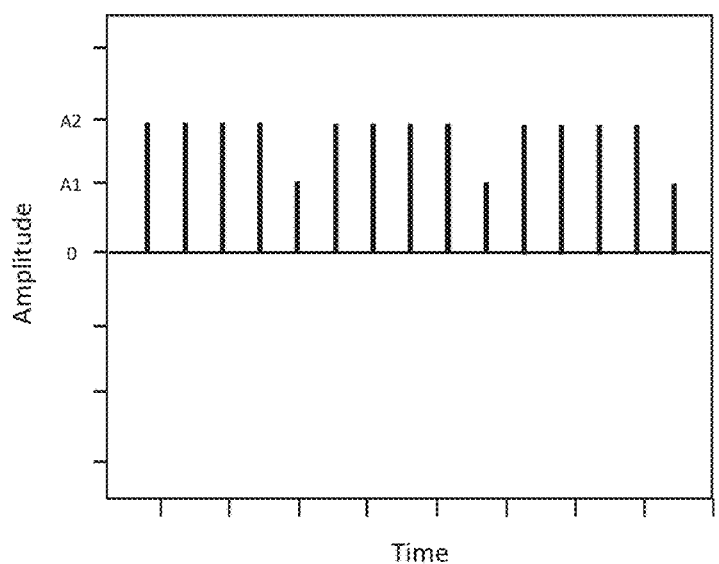
FIG. 24 is a chart of a stimulation waveform comprising a train of pulses at multiple amplitudes, consistent with the present inventive concepts.

Referring now to FIG. 24, a chart of a stimulation waveform comprising a train of pulses at multiple amplitudes is illustrated, consistent with the present inventive concepts. The stimulation waveform of FIG. 24 comprises a repeating series of a group of pulses including one or more pulses at a first amplitude A2 (four shown), and one or more pulses at a second, lower amplitude A1 (one shown). In some embodiments, each of the pulses is delivered at a relatively high frequency, such as a frequency of at least 1 kHz, such as a frequency of approximately 10 kHz. In some embodiments, the pulses delivered at amplitude A2 are delivered at a high frequency (e.g. approximately 10 kHz) and the pulses delivered at amplitude A1 are delivered at a lower frequency (e.g. approximately between 10 Hz and 5 kHz). In some embodiments, one or more pulses of the stimulation waveform have a pulse width between 1 μsec and 10 msec, such as a duration between 10 μsec and 300 μsec. In some embodiments, one or more stimulation parameters of the waveform of FIG. 24 are varied randomly, as described herein.

Figure 25:
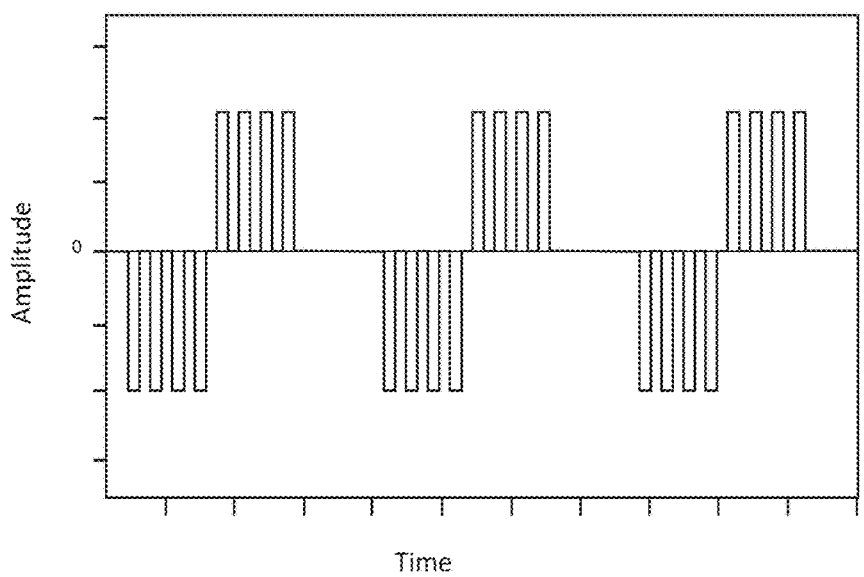
FIG. 25 is a chart of a stimulation waveform comprising a series of sequential pulses in a single phase followed by pulses in an opposite phase, consistent with the present inventive concepts.
Figure 25A:
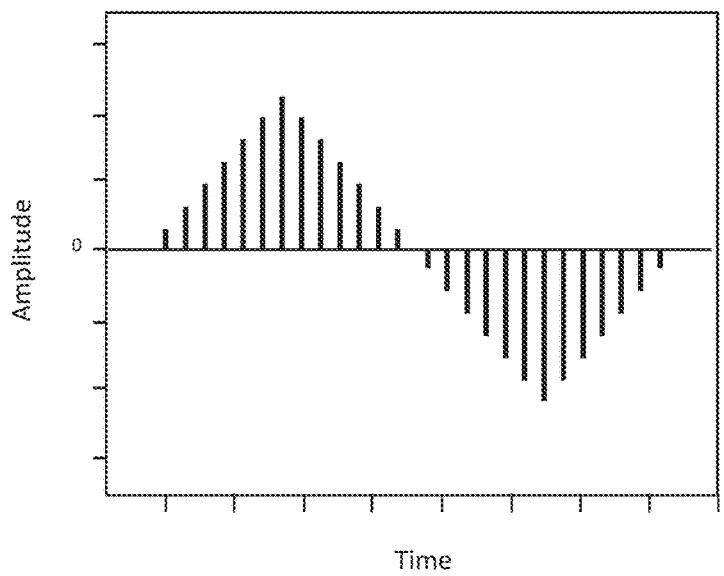
FIG. 25A is a chart of a stimulation waveform comprising a series of pulses modulated by a triangle wave and including multiple sequential pulses in a single phase followed by multiple sequential pulses in the opposite phase, consistent with the present inventive concepts.

Referring now to FIG. 25, a chart of a stimulation waveform comprising a series of sequential pulses in a single phase followed by a series of pulses in an opposite phase is illustrated, consistent with the present inventive concepts. Apparatus 10 can be configured to deliver two or more pulses in one phase (e.g. four cathodic phase pulses as shown) after which one or more pulses in the opposite phase (e.g. the four anodic phase pulses as shown) are delivered. In some embodiments, multiple pulses in the same phase comprise the same amplitude and pulse width, as shown in FIG. 25. Alternatively, two or more pulses in the same phase can comprise different amplitudes and/or different pulse widths. In some embodiments, the stimulation waveform comprises a repeating series of a group of cathodic pulses and anodic pulses (as shown) that are modulated by a triangle wave, as shown in FIG. 25A. In some embodiments, a different modulation shape is applied. In some embodiments, the total charge in one period of the wave (such as a triangle wave or any other wave described herein) is balanced. In some embodiments, each pulse in the wave represents a biphasic charge-balanced pulse (negative pulses may or may not include phase reversals of the biphasic pulse). In some embodiments, the pulses are delivered at a high frequency, such as a frequency of at least 1 kHz, such as a frequency of approximately 10 kHz. In some embodiments, one or more pulses of the stimulation waveform have a pulse width between 1 μsec and 10 msec, such as a duration between 10 μsec and 300 μsec. In some embodiments, one or more stimulation parameters of the waveform of FIG. 25 are varied randomly (e.g. the number of sequential pulses in the same phase are varied randomly), as described herein.

Figure 26:
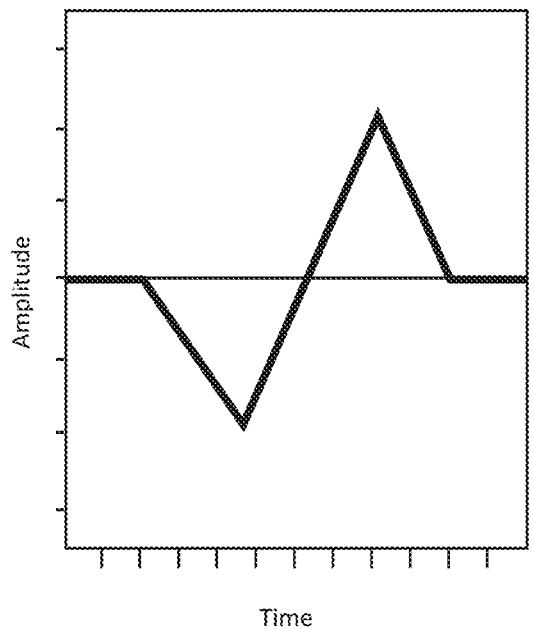
FIG. 26 is a chart of a stimulation waveform comprising a triangle wave, consistent with the present inventive concepts.

Referring now to FIG. 26, a chart of a stimulation waveform comprising a triangle wave is illustrated, consistent with the present inventive concepts. The shape of delivered pulses can be configured to influence the onset and/or patient perception of neural activation (such as via the shape of the triangle wave shown). In some embodiments, one or more pulses of the stimulation waveform have a pulse width between 1 μsec and 10 msec, such as a duration between 10 μsec and 300 μsec. In some embodiments, one or more stimulation parameters of the waveform of FIG. 26 are varied randomly, as described herein.

Figure 27:
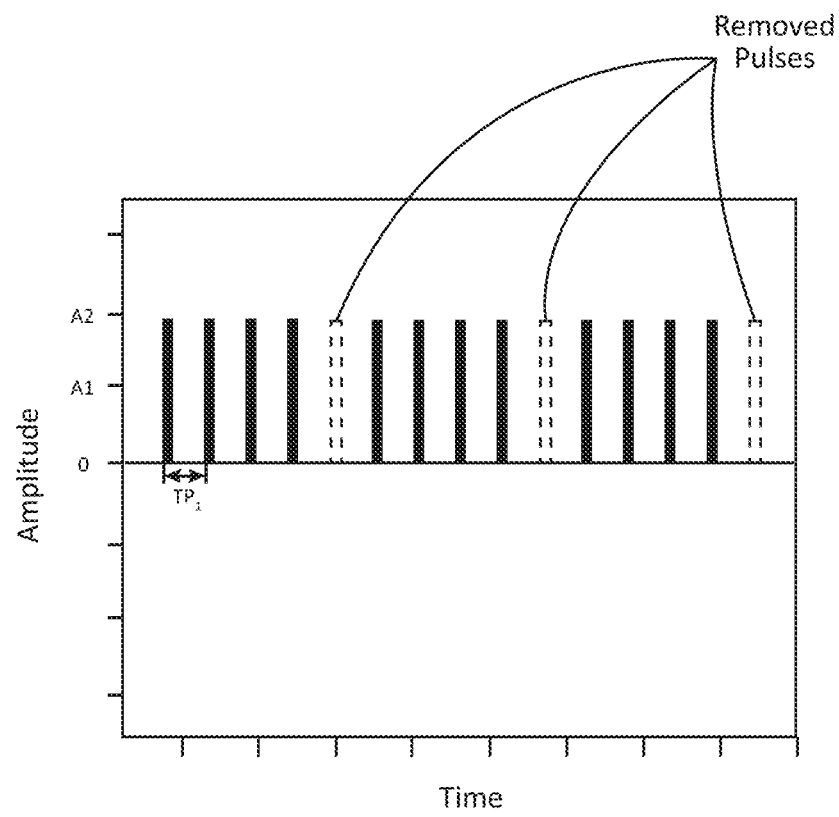
FIG. 27 is a chart of a stimulation waveform comprising a set of planned pulses with one or more pulses removed, consistent with the present inventive concepts.

Referring now to FIG. 27, a chart of a stimulation waveform comprising a set of planned pulses with one or more pulses removed is illustrated, consistent with the present inventive concepts. The apparatus of the present inventive concepts (e.g. apparatus 10 described herein) can be configured to provide a "planned series of pulses" comprising a set of multiple pulses scheduled to be delivered on a regular basis (e.g. at constant frequency), or any timing pattern as pre-determined by an apparatus of the present inventive concepts (e.g. determined by an algorithm and/or library of pulse delivery timing information). The apparatus can be further configured to remove one or more pulses from the planned series, such as one or more pulses removed randomly, such as a random removal based on a probability distribution as described herein. The stimulation waveform of FIG. 27 comprises a set of pulses that represents a planned series of pulses that have had 3 pulses removed (as shown). The planned series of pulses each have an amplitude A2, and are planned to be delivered at a frequency equal to 1/TP$_1$. While the timing, pulse width and amplitude of the planned series of pulses is shown as relatively constant, in some embodiments one or more of these variables varies between two or more planned pulses.

In some embodiments, one or more other stimulation parameters of the stimulation waveform of FIG. 27 are also varied (e.g. via a random or systematic variation), such as by varying the timing, pulse width, pulse shape and/or amplitude of one or more of the pulses planned to be delivered (e.g. whether delivered or not). In some embodiments, as an alternative to or in addition to removing one or more pulses from a planned series of pulses, one or more pulses are added to a planned series of pulses, such as is described herebelow in reference to FIGS. 28A and 28B.

Figure 28A:
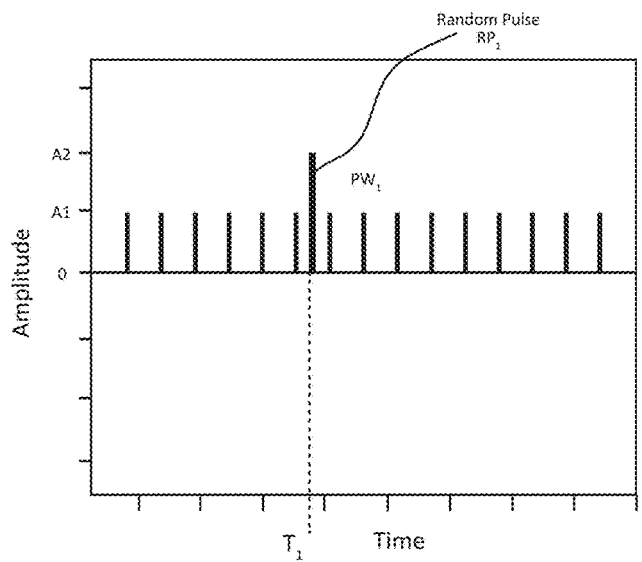
FIG. 28A is a chart of a stimulation waveform comprising a set of planned pulses with one or more pulses added, consistent with the present inventive concepts.
Figure 28B:
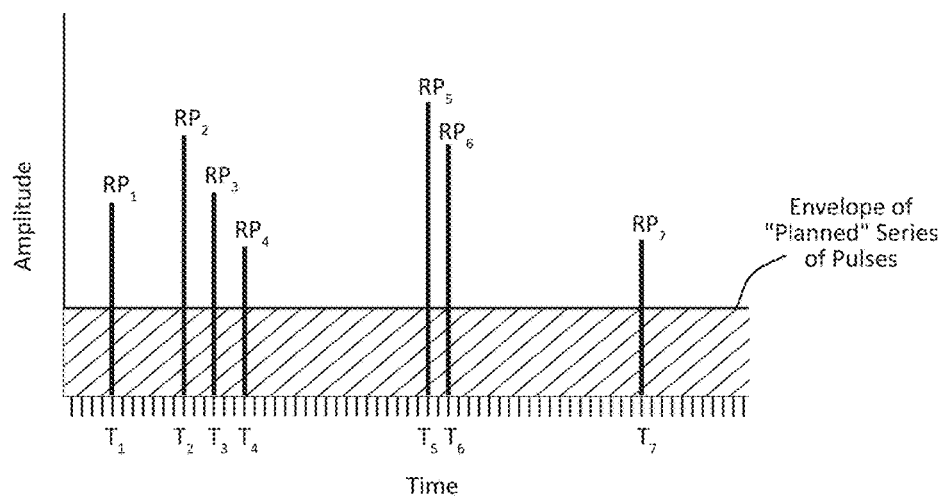
FIG. 28B is a chart of a stimulation waveform comprising a set of planned pulses with multiple pulses added, consistent with the present inventive concepts.

Referring now to FIG. 28A, a chart of a stimulation waveform comprising a set of planned pulses with one or more pulses added is illustrated, consistent with the present inventive concepts. The apparatus of the present inventive concepts (e.g. apparatus 10 described herein) can be configured to provide a "planned series of pulses" as described hereabove in reference to FIG. 27. The apparatus can be further configured to add one or more pulses to the planned series, such as one or more pulses added randomly, such as a random addition based on a probability distribution as described herein. The stimulation waveform of FIG. 28A comprises a set of pulses that represents a planned series of pulses that have had a pulses added (as shown). The planned series of pulses each have an amplitude A1 and are planned to be delivered at a frequency equal to 1/TP$_1$. A random pulse RP$_1$ is delivered at time T$_1$. Random pulse RP$_1$ comprises a pulse with a pulse width PW$_1$ and amplitude A2. The amplitude and pulse width of the random pulse RP$_1$ can be similar or dissimilar to the amplitude and/or pulse width of one or more of the planned pulses. Referring now to FIG. 28B, in some embodiments, multiple random pulses are added to a planned set of pulses, such as the random pulses RP$_1$, RP$_2$, RP$_3$, RP$_4$, RP$_5$, RP$_6$, RP$_7$ shown. The multiple random pulses RP$_{1-7}$ can comprise different timing (as shown), pulse width, pulse shape and/or amplitude (as shown), such as a random timing of delivery, random pulse width, random pulse shape, random amplitude and/or other stimulation parameter that is randomly set. Each randomly determined stimulation parameter can be randomly determined by the apparatus of the present inventive concepts based on a probability distribution as described herein.

In some embodiments, one or more other stimulation parameters of the stimulation waveforms of FIGS. 28A and/or 28B are also varied (e.g. via a random or systematic variation), such as by varying the timing, pulse width, pulse shape and/or amplitude of one or more of the pulses planned to be delivered. In some embodiments, as an alternative to or in addition to adding one or more pulses to a planned series of pulses, one or more pulses are removed from a planned series of pulses, such as is described hereabove in reference to FIG. 27.

Figure 31:
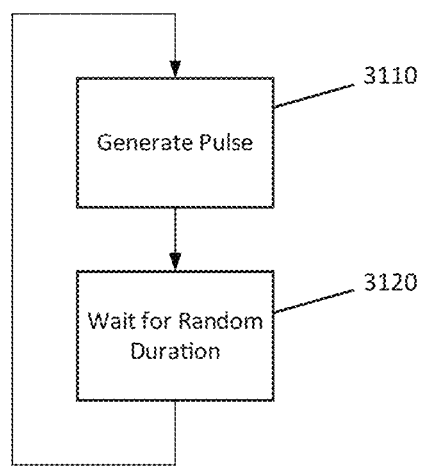
FIG. 31 is a flow chart of a method of generating a stimulation pulse or pulse train comprising randomly varying inter-pulse gaps, consisting with the present inventive concepts.

Referring now to FIG. 31, a flow chart of a method of generating a stimulation pulse or pulse train comprising randomly varying inter-pulse gaps is illustrated, consisting with the present inventive concepts. In Step 3110, a pulse of a stimulation waveform is generated, such as a pulse generated by an implantable device 200 of apparatus 10 described herein. The generated pulse can comprise a single pulse, or a set of multiple pulses. In Step 3120, a wait period is performed, wherein the duration of the wait period is randomly generated, such as a wait period based on a probability distribution as described hereabove. In some embodiments, the wait period is randomly generated by the implantable device (e.g. via controller 250 of implantable device 200 described hereabove). Alternatively or additionally, the wait period can be randomly generated by an external device (e.g. external device 500), and the wait period can be wirelessly transmitted to the implantable device delivering the stimulation pulses.

Figure 32:
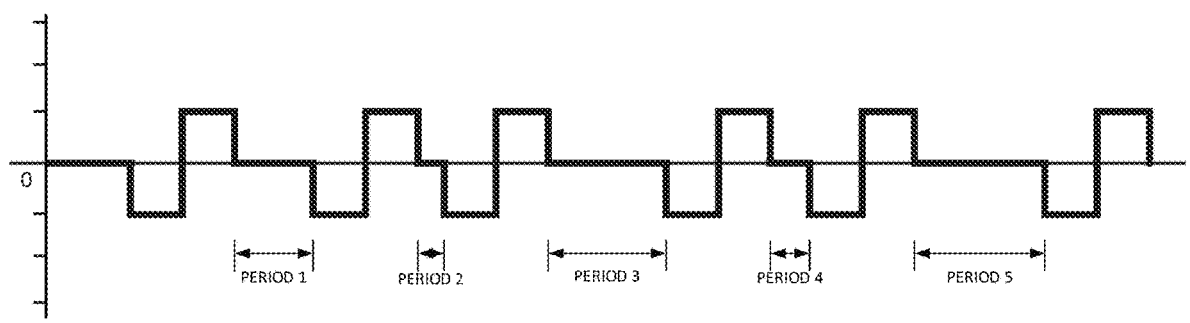
FIG. 32 is a chart of a stimulation waveform comprising varying inter-pulse gaps, consistent with the present inventive concepts.

After the wait period duration is met, Step 3110 is repeated (the wait period correlating to an inter-pulse gap for the next pulse), such as is shown in FIG. 32. Periods 1, 2, 3, 4 and 5 each comprise randomly different inter-pulse gap durations. Steps 3110 and 3120 can be repeated many times, such as to create a series of stimulation pulses that is delivered over hours or days.

While the embodiment shown in FIGS. 31 and 32 illustrate randomly varying inter-pulse gaps, a similar method can be employed to generate random pulse widths, randomly varying frequencies and/or other stimulation parameter that is varied randomly. Variations of one or more stimulation parameters can be performed sequentially or simultaneously.

Figure 33:
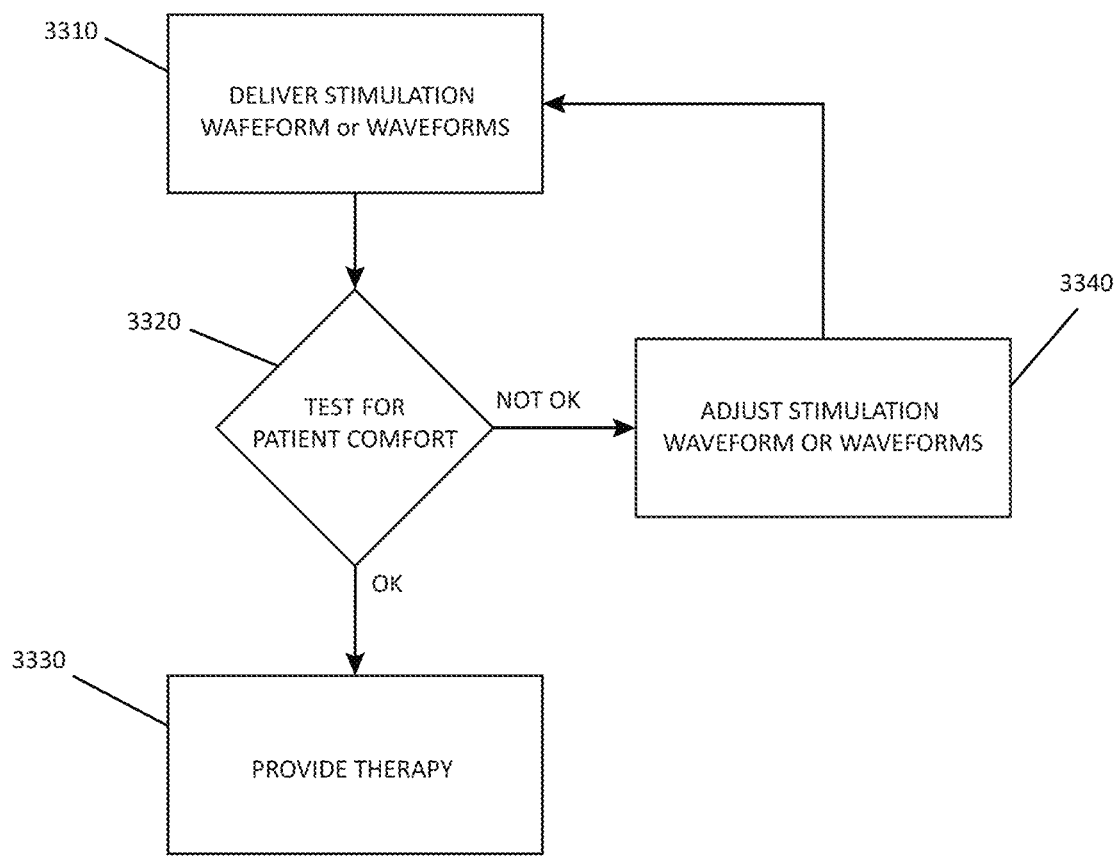
FIG. 33 is a flow chart of a method for selecting a stimulation waveform or waveforms to be delivered to a patient, consistent with the present inventive concepts.

Referring now to FIG. 33, a flow chart of a method for selecting a stimulation waveform or waveforms to be delivered to a patient is illustrated, consistent with the present inventive concepts. In Step 3310, stimulation energy is delivered via one or more stimulation waveforms, a first stimulation waveform, such as via an implantable device 200 of the present inventive concepts. In Step 3320, the patient is tested (e.g. in a verbal interrogation or autonomously by the patient) to assess patient comfort. If the patient comfort level is determined to be acceptable (e.g. an acceptable level of paresthesia and/or pain relief is achieved), Step 3330 is performed in which therapy is provided (e.g. pain control therapy) using the first stimulation waveform. If the patient comfort level is determined to not be acceptable, Step 3340 is performed, in which a different waveform or waveforms, a second stimulation waveform, is determined. Step 3310 is then repeated, in which the modified waveform (the second waveform) is delivered to the patient, and Step 3320 is repeated in which the patient is tested for comfort. If unacceptable, a second modification creating a third stimulation waveform is generated (in Step 3340) and delivered (in Step 3310), and so on until an acceptable stimulation waveform results.

In some embodiments, one or more of the delivered stimulation waveforms comprise one or more randomly varying stimulation parameters (e.g. randomly varying frequency, inter-pulse gap, inter-train period, inter-burst period, pulse shape, and/or amplitude), each of which can be randomly determined using a probability distribution (as described herein). The probability distribution can be configured to provide random variations in one or more stimulation parameters that reduce paresthesia or another undesired patient condition, such as by avoiding accommodation (habituation) by creating a stochastic pulse train. The stochastic nature of action potentials, in this case, can diminish paresthesia by minimizing temporal summation of neural activity. Paresthesia can also be controlled by the apparatus of the present inventive concepts performing a function selected from the group consisting of: incorporating patient feedback; monitoring evoked potentials; using data provided by positional sensors; adjusting stimulation based upon known heuristics; and combinations of one or more of these. In some embodiments, since a patient can be more sensitive to paresthesia or other discomfort while sitting (as compared to standing, lying down and/or walking), apparatus 10 can shift a probability distribution (e.g. toward lower or higher values) while the patient is standing, lying down and/or walking, and/or it can shift a probability distribution while the patient is sitting (e.g. a different shift such as a greater shift or a shift in an opposite direction). In these embodiments, a first probability distribution can be replaced with a second, different probability distribution (e.g. in Step 3340), such as a replacement that reduces paresthesia or otherwise achieves a satisfactory patient comfort level. Alternatively or additionally, the probability distribution can be adjusted (e.g. in Step 3340), such as an adjustment to the probability distribution that results in reduced paresthesia or otherwise achieves a satisfactory patient comfort level. In some embodiments, threshold levels of one or more stimulation parameters are identified (about which the patient transitions from discomfort to comfort). In these embodiments, one or more of these thresholded parameters can be set to a level including a safety margin (e.g. a safety margin percentage under or otherwise away from the threshold level(s) that caused patient discomfort, such as a safety margin percentage of 10%, 20% or 50%).

In some embodiments, a stimulation waveform comprises amplitude modulated (AM) signals comprising a high frequency carrier with low frequency modulation. In some embodiments, a stimulation waveform comprises frequency modulated (FM) signals configured to avoid accommodation (habituation) by creating a continuously varying pulse train (e.g. a waveform comprising one or more stimulation parameters that are randomly varied as described herein). In some embodiments, a first electrode (e.g. a first functional element 260) delivers stimulation energy at a first frequency (e.g. a high frequency), and a second electrode (e.g. a second functional element 260) delivers stimulation at a second, different frequency (e.g. a low frequency). In some embodiments, a stimulation waveform comprises a first train and/or burst of pulses, followed by one or more subsequent trains and/or bursts of pulses. The subsequent trains and/or burst of pulses can comprise one or more different stimulation parameters than the first train and/or burst of pulses, such as a difference in frequency, amplitude, inter-pulse gap, inter-train period, inter-burst period and/or pulse shape. In each of these embodiments, multiple different pulses or pulse trains can be provided, such as to provide therapeutic benefit from each, such as a different therapeutic benefit from each. Alternatively or additionally, the differences can be configured to avoid accommodation (habituation), such as to avoid or at least reduce paresthesia, other patient discomfort and/or other undesirable condition.

Figure 34:
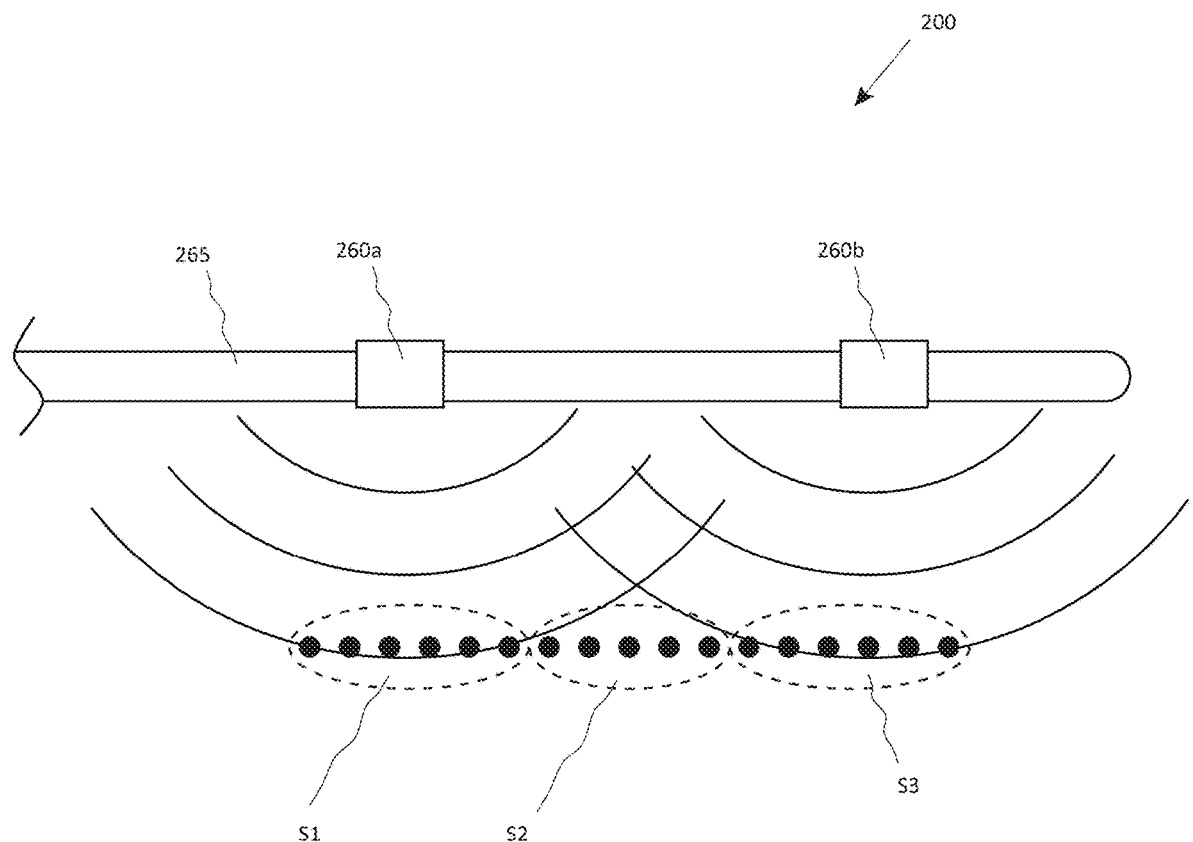
FIG. 34 is an anatomical view of a stimulation portion of an implantable device, consistent with the present inventive concepts.

Referring now to FIG. 34, an anatomical view of a stimulation portion of an implantable device is illustrated, consistent with the present inventive concepts. Apparatus 10 of the present inventive concepts can be configured to deliver significant stimulation energy to two or more areas of target tissue (e.g. stimulation energy delivered to two or more areas of the spinal cord associated with pain of the patient) while avoiding or at least reducing stimulation to non-target tissue including areas intervening between the two or more areas in which stimulation is intended (e.g. tissue in which significant stimulation energy would cause an adverse effect). Lead 265 comprises at least two electrode-based functional elements, 260a and 260b as shown. In alternative embodiments, lead 265 comprises two leads, one comprising functional element 260a and the other comprising functional element 260b. Implantable device 200 can deliver stimulation energy via functional elements 260a and 260b in an interleaved fashion as shown, to effectively deliver sufficient energy to tissue site S1 and S3 while delivering minimal (e.g. subthreshold) energy to tissue site S2.

Figure 34A:
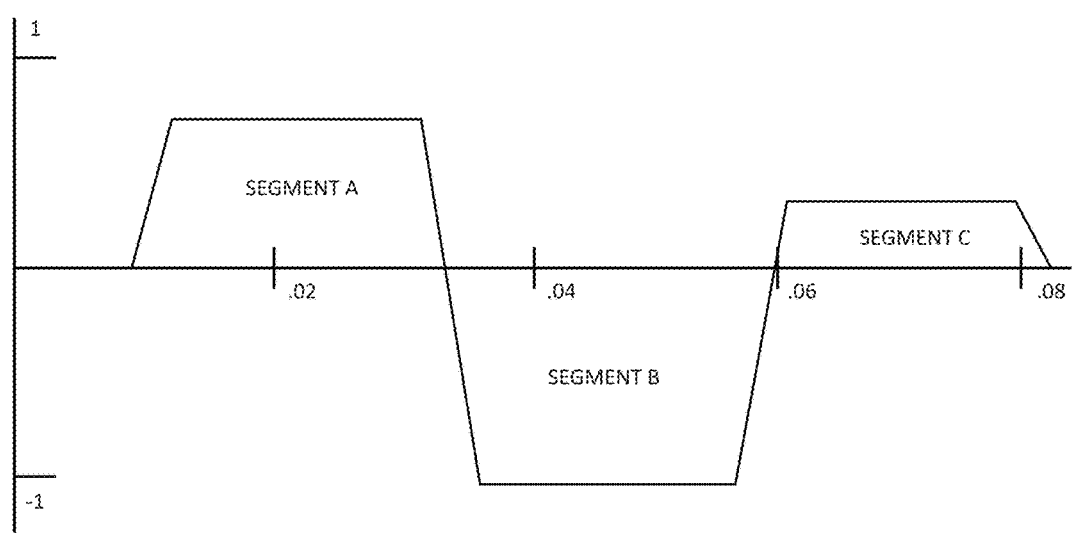
FIG. 34A is a chart of a stimulation waveform configured to avoid surpassing an excitation threshold within a particular tissue site, consistent with the present inventive concepts.

In this configuration, biphasic stimulation at sufficiently high frequencies can result in delivery of stimulation energy to tissue (e.g. neurons) above a threshold level (e.g. a stimulation threshold). For example, after delivery of a first pulse, subsequent pulses delivered quickly (i.e. at high frequency) can cause additional charge to accumulate (e.g. on the neuronal membrane), due to time between pulses being too short to allow complete decay of the charge. In these instances, excitation from energy delivered by functional element 260a combined with the excitation from energy delivered by functional element 260b may result in exceeding one or more neuron's (e.g. within site S2) excitation threshold. In some embodiments, implantable device 200 is configured to avoid surpassing an excitation threshold level of neurons within site S2 by delivering a triphasic stimulation pulse (e.g. as shown in FIG. 34A), via functional elements 260a and/or 260b. In these embodiments, charge on the membrane of neurons in site S2 can be maintained closer to the resting potential, thereby decreasing likelihood of exciting those neurons, even when both functional elements 260a and 260b deliver energy (e.g. since the amplitude of segment A and segment C of the triphasic stimulation is reduced, thereby preventing accumulation of charge that would surpass the excitation threshold). In some embodiments, pulses comprising four or more phases are delivered, allowing reduced amplitude in each to avoid charge accumulation that would cause undesired tissue stimulation (e.g. stimulation of non-target tissue). In some embodiments, one or more stimulation parameters of the waveform of FIG. 34A are varied randomly, as described herein.

Referring now to FIG. 35, a flow chart of a method of varying parameters of stimulation waveforms to increase charge to be delivered to a patient via a therapeutic device is illustrated, consistent with the present inventive concepts. Variation of parameters as described herebelow minimizes power consumption while delivering effective therapy, while also simplifying the patient's experience and minimizing programming time. Method 3500 comprises a series of steps of varying the parameters of stimulation waveforms via a therapeutic device, such as via apparatus 10 described hereabove, improving system efficiency while providing a therapeutic benefit to patient. In Step 3510, stimulation energy is delivered to patient tissue via a stimulation waveform comprising one or more stimulation waveforms as described hereabove (e.g. a series of pulses in which the amplitude and/or pulse width are varied). In some embodiments, at least voltage is controlled, and the voltage amplitude is varied as described herein. Alternatively or additionally, current can be controlled, and the current amplitude can be varied as described herein.

The initial stimulation waveform delivered in Step 3510 comprises an initial, predetermined pulse width and amplitude (e.g. a low or minimum pulse width and amplitude), and a "set compliance voltage" (e.g. the magnitude of the compliance voltage at the present time). In Step 3510, the set compliance voltage can be set to the minimum compliance voltage enabled by the system, as described herein. In Step 3520, amplitude of the stimulation waveform is increased (e.g. linearly, exponentially and/or step-wise increased, thereby increasing charge delivered to patient tissue), while the patient is tested for therapeutic benefit (e.g. continuously tested via verbal interrogation or autonomously by the patient), until a desired therapeutic benefit (e.g. relatively pain-free) is achieved, or until the amplitude (e.g. voltage and/or current amplitude of the stimulation waveform) has reached the maximum enabled by the set compliance voltage. In Step 3525, a decision is made (e.g. via an algorithm of software and/or hardware), based on the outcome of Step 3520. If therapeutic benefit has been achieved, Step 3560 is performed in which stimulation of patient tissue continues with the current parameters (the parameters in place when the desired therapeutic benefit was achieved). Otherwise, if therapeutic benefit has not been achieved (e.g. the amplitude has reached a maximum enabled by the set compliance voltage), Step 3530 is performed. In Step 3530, the pulse width of the stimulation waveform is increased (e.g. linearly, exponentially and/or step-wise increased), while the patient is tested for therapeutic benefit (as described hereabove) until a desired therapeutic benefit is achieved, or until a first pulse width threshold is reached (e.g. a pulse width threshold determined by a minimum desired inter-pulse gap, as described herein).

In Step 3535, a decision is made (e.g. via an algorithm of software and/or hardware), based on the outcome of Step 3530. If therapeutic benefit has been achieved in Step 3530, Step 3560 is performed in which stimulation of patient tissue continues with the current parameters (the parameters in place when the desired therapeutic benefit was achieved). Otherwise, if therapeutic benefit has not been achieved, and the first pulse width threshold has been reached, Step 3540 is performed. In Step 3540, the set compliance voltage is increased by an increment $\Delta CV$, the amplitude of the stimulation waveform is increased by an increment $\Delta A$, and the pulse width of the stimulation waveform is decreased by an increment $\Delta PW$. In some embodiments, $\Delta CV$ comprises an increase in compliance voltage, such as a step increase of between 0.2 V and 1.5V (e.g. a step increase of 0.5V or 1.0V). In some embodiments, $\Delta A$ comprises an increase in amplitude that results in an amplitude that correlates (e.g. maximizes efficiency) with the newly increased set compliance voltage (e.g. the maximum amplitude enabled by the newly set compliance voltage). In some embodiments, $\Delta PW$ comprises a decrease in pulse width that results in charge delivered to patient tissue by the initial waveform of Step 3540 approximating the charge delivered to patient tissue by the final waveform of Step 3530 (e.g. pulse width is decreased to compensate for increased amplitude, keeping charge constant). Subsequent to the compliance voltage increase $\Delta CV$, amplitude increase $\Delta A$, and pulse width decrease $\Delta PW$, the pulse width can be increased (e.g. linearly, exponentially and/or step-wise increased), while the patient is tested for therapeutic benefit (as described hereabove) until a desired therapeutic benefit is achieved, or the first pulse width threshold is reached (again).

In Step 3545, if therapeutic benefit has been achieved, Step 3560 is performed in which stimulation of patient tissue continues with the current parameters (the parameters in place when therapeutic benefit was achieved). Otherwise, if therapeutic benefit has not been achieved, Step 3546 is performed. In Step 3546, if the maximum compliance voltage has not been reached, Step 3540 is then repeated in which the compliance voltage is (again) increased (e.g. by $\Delta CV$ or another increment as described hereabove), the amplitude of the stimulation waveform is increased (e.g. by $\Delta A$ or another increment as describe hereabove), and pulse width is decreased (e.g. by $\Delta PW$ or another increment as described hereabove). Otherwise, if the maximum compliance voltage has been reached, Step 3550 is performed. In Step 3550, the pulse width of the stimulation waveform is increased (e.g. linearly, exponentially and/or step-wised increased above the first pulse width threshold), and the patient is tested for therapeutic benefit (as described hereabove) until a desired therapeutic benefit is achieved or until a second pulse width threshold is reached. In Step 3555, if therapeutic benefit has been achieved, Step 3560 is performed in which stimulation of patient tissue continues with the current parameters (the parameters in place when therapeutic benefit was achieved). Otherwise, if therapeutic benefit has not been achieved and the second pulse width threshold has not been reached, Step 3570 is performed. Step 3570 can include notifying the patient and/or other operator (e.g. a clinician) that a maximum charge level of the system has been achieved, provide a prompt to increase and/or decrease one or more thresholds of apparatus 10, and/or indicate that a different therapeutic program should be selected.

Referring now to FIG. 36A, graphs of the stimulation waveform parameter variations described above in the method of FIG. 35 are illustrated, consistent with the present inventive concepts. The top graph (1) illustrates the compliance voltage (V) being varied over time, wherein a minimum compliance voltage and a maximum compliance voltage are shown. Compliance voltage can comprise an optimal level (i.e. maximum current multiplied by the impedance, plus circuit drop out) in order to minimize power consumption. Compliance voltage can comprise a minimum voltage (e.g. a starting voltage correlating to the minimum compliance voltage supported by implantable system 200 hardware) between 1V and 5V, and a maximum voltage of approximately 15V (e.g. a maximum voltage supported by the power supply and other circuitry of implantable system 200). Graph (2) illustrates the amplitude being varied over time, wherein a maximum amplitude is shown. Graph (3) illustrates pulse width being varied over time, wherein a first pulse width threshold and a second pulse width threshold are utilized. Pulse width can comprise a minimum of approximately 10 μsec, and/or a first threshold of approximately 100 μsec. Additionally, the pulse width can comprise a second threshold of approximately 200 μsec. For biphasic pulses (pulses comprising alternating phases of energy delivery) the effective pulse width can comprise a double pulse width due to a recovery pulse of equal width and opposite polarity following the stimulating pulse. Graph (4) illustrates charge being varied over time, as determined by the varying of parameters shown in graphs (1), (2), and (3). Each of graphs (1), (2), (3) and (4) include multiple time portions, Regions 1-4 shown. In Region 1, amplitude is varied while pulse width is maintained constant. In Regions 2 and 4, pulse width is varied while amplitude is maintained constant. In Region 3, amplitude is increased with a decreased pulse width, after which the pulse width is increased, the two steps performed in an alternating fashion. Regions 1, 2, 3 and 4 correspond to steps 3520, 3530, 3540 and 3550, respectively, described hereabove in reference to FIG. 35. In some embodiments, a stimulation apparatus of the present concepts, apparatus 10 described herein, increases charge by varying stimulation parameters as described in reference to any of Regions 1-4, in any order, with each Region performed one or more times. In some embodiments, charge is decreased by decreasing amplitude and/or pulse width, in a similar but reverse fashion to that described in steps 3520, 3530, 3540 and 3550.

Figure 36B:
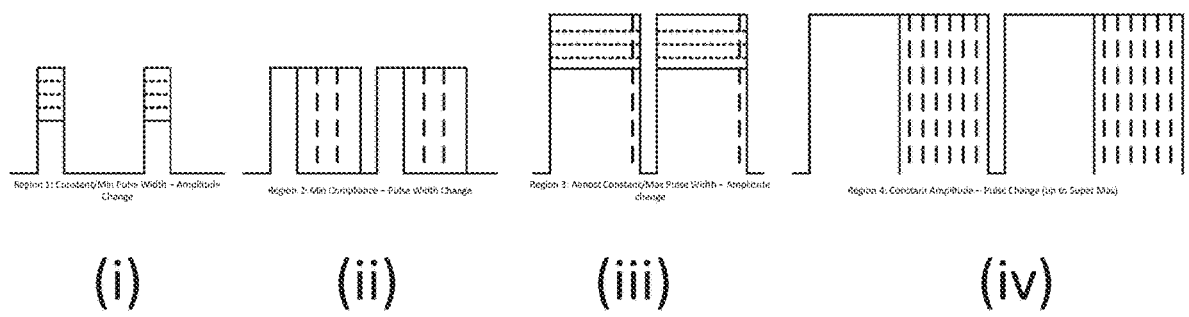
FIG. 36B illustrates charts of a stimulation waveform in accordance with the method of varying the parameters as described above in FIG. 35, consistent with the present inventive concepts.

Referring additionally to FIG. 36B, charts of a stimulation waveform in accordance with the method of varying the parameters as described above in FIG. 35 are illustrated, consistent with the present inventive concepts. Charts (i), (ii), (iii) and (iv) represent superimposed changes in pulses of a stimulation waveform in which amplitude and/or pulse width are varied to increase charge delivered to tissue to achieve a therapeutic benefit (e.g. to achieve sufficient pain relief). Chart (i) illustrates a stimulation waveform comprising one or more pulses (two shown) at a first amplitude and pulse width, onto which subsequent pulses are superimposed with increasing amplitude (amplitude increases shown in dotted lines) and the same pulse width. Such an amplitude increase and constant pulse width can be performed as described hereabove in reference to Step 3520 of FIG. 35.

Chart (ii) illustrates a stimulation waveform comprising one or more pulses (two shown) at a first amplitude and pulse width, onto which subsequent pulses are superimposed. The subsequent pulses have the same amplitude and increasing pulse width (pulse width increases shown in dotted lines). In some embodiments, the first amplitude of Chart (ii) comprises the maximum amplitude of Chart (i). The constant amplitude and pulse width increases of Chart (ii) can be performed as described hereabove in reference to Step 3530 of FIG. 35. In Chart (ii), the increasing of pulse width correlates to a corresponding change in the inter-pulse interval.

Chart (iii) illustrates a stimulation waveform comprising one or more pulses (two shown) at a first amplitude and pulse width, onto which subsequent pulses are superimposed. The subsequent pulses alternatingly increase amplitude while decreasing pulse width, and then increase pulse width while maintaining the most recent amplitude. In some embodiments, the first amplitude of Chart (iii) comprises the maximum amplitude of Chart (i) and/or Chart (ii), and the first pulse width of Chart (iii) comprises the maximum pulse width of Chart (ii). The alternating change to amplitude and pulse width of Chart (iii) can be performed as described hereabove in reference to Step 3540 of FIG. 35.

Chart (iv) illustrates a stimulation waveform comprising one or more pulses (two shown) at a first amplitude and pulse width onto which subsequent pulses are superimposed. The subsequent pulses have the same amplitude and increasing pulse width (pulse width increases shown in dotted lines). In some embodiments, the first amplitude of Chart (iv) comprises the maximum amplitude of Chart (iii). The constant amplitude and pulse width increases of Chart (iv) can be performed as described hereabove in reference to Step 3550 of FIG. 35. In Chart (iv), the increasing of pulse width correlates to a corresponding change in the inter-pulse interval. In some embodiments, pulse width can increase up to 200 μsec (i.e. second threshold for the pulse width).

While the embodiments described hereabove in reference to FIGS. 35, 36A and 36B have described a particular order of varying parameters (e.g. amplitude and pulse width), any of the described steps can be performed in any order. For example, in a first step pulse width can be increased while maintaining constant amplitude (e.g. as described hereabove in reference to Step 3530 of FIG. 35, Region 2 of FIG. 36A and/or Chart (ii) of FIG. 36B). In a subsequent, second step, amplitude can be increased while maintaining a constant pulse width (e.g. as described hereabove in reference to Step 3520 of FIG. 35, Region 1 of FIG. 36A and/or Chart (i) of FIG. 36B). Alternatively or additionally, a step in which amplitude and/or pulse width are alternatingly increased and/or decreased (e.g. as described in reference to Step 3540 of FIG. 35, Region 3 of FIG. 36A and/or Chart (iii) of FIG. 36B) can be performed.

In some embodiments, apparatus 10 provides multiple stimulation paradigms (e.g. multiple different waveforms) configured to deliver therapies for multiple, different patient conditions. For example, spinal cord stimulation devices include programs (made available to a patient or other user) that routinely include stimulation paradigms for more than one anatomical area (e.g. more than one anatomical area causing pain), such as when stimulation paradigms are provided to treat the lower back and leg. Due to stimulation device operational constraints, different stimulation paradigms often include (e.g. when treating multiple anatomical areas simultaneously) a common set of one or more stimulation parameters, for example a common rate (e.g. pulse rate). In some instances, it may not be desirable to utilize common stimulation parameters, such as if a particular anatomical area is better treated with a different set of stimulation parameters than a different anatomical area. In some embodiments, apparatus 10 comprises multiple stimulation paradigms (i.e. multiple waveforms with one or more stimulation parameters that are different between waveforms), and the patient chooses the particular stimulation paradigm to be delivered (e.g. to improve pain relief or other therapeutic result).

Apparatus 10 can be configured to provide a user interface program comprising multiple sub-programs. Each sub-program can be configured to treat one or more anatomical locations of the patient. The sub-program associated with each anatomical area can comprise the same or similar stimulation paradigm (e.g. the same or similar set of stimulation parameters). In some embodiments, rate is constant between sub-programs, while other stimulation parameters are varied. For example, a first sub-program can include a tonic stimulation waveform configured to treat two anatomical areas (e.g. back and leg) and a second sub-program can be a non-tonic stimulation waveform configured to treat a single anatomical area (e.g. back or leg). In some embodiments, apparatus 10 comprises a program that can cycle through multiple sub-programs (e.g. automatically), and each sub-program can include adjustable stimulation parameters (e.g. stimulation parameters adjustable by the patient, a clinician, and/or other user of apparatus 10). The cycling through the sub-programs can occur on a pulse-by-pulse basis (e.g. one pulse at a time), on a block of pulses basis, and/or on a time duration basis (e.g. a time duration for each sub-program comprising minutes, hours, and/or days). Sets of sub-programs that are configured to treat more than one anatomical area can be sequentially and/or simultaneously performed to treat all or a subset of the anatomical areas available for treatment. In some embodiments, apparatus 10 is configured to switch between sub-programs rapidly, for example switching between sub-programs within time periods between 50 μsec and 1 second, or for example changing between sub-programs at rates between 10 Hz and 10 kHz.

Figure 37A:
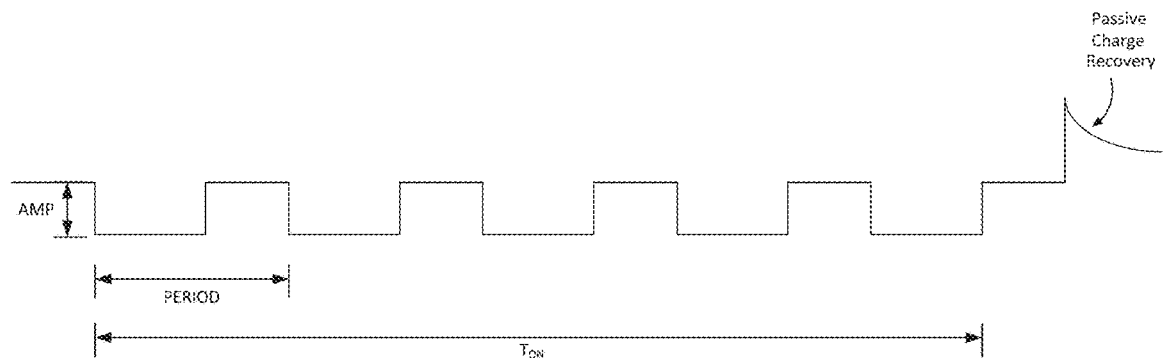
FIGS. 37A and 37B are stimulation waveforms comprising multiple trains of monophasic pulses, consistent with the present inventive concepts.
Figure 37B:
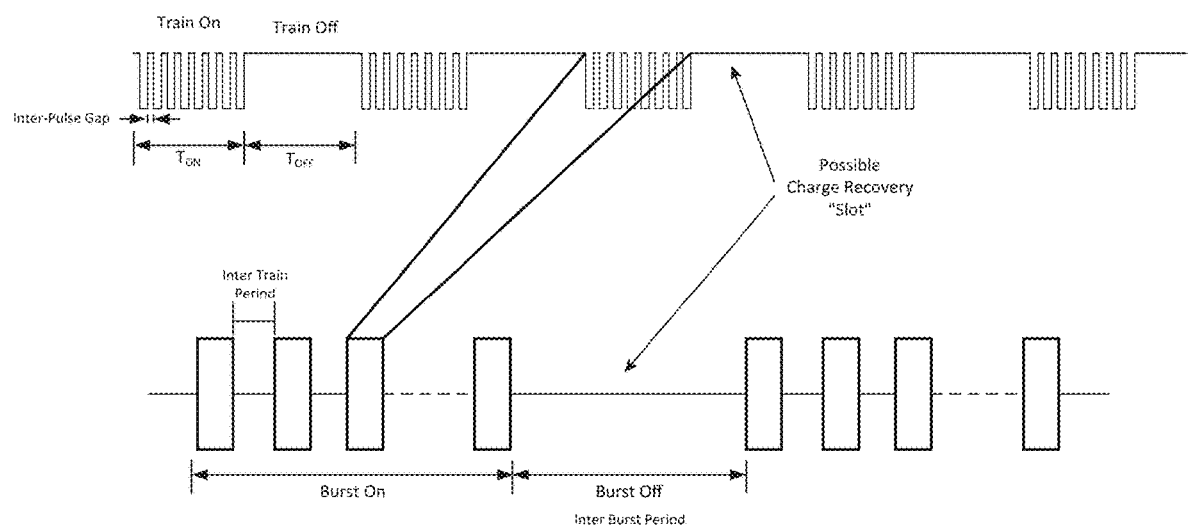

Referring now to FIGS. 37A and 37B, stimulation waveforms comprising multiple trains of monophasic pulses are illustrated, consistent with the present inventive concepts. In some embodiments, the stimulation apparatus of the present inventive concepts, apparatus 10 described herein, is configured to deliver one or more stimulation waveforms as described in reference to FIGS. 37A-B. In FIG. 37B, a stimulation waveform comprises a series of narrow pulses (e.g. between 2 and 1000 pulses, eight monophasic pulses shown) for a train-on period $T_{ON}$ (e.g. a time period of between 1 μsec to 100 msec), after which no energy is delivered for a train-off period $T_{OFF}$ (e.g. a time period of between 1 μsec to 100 msec). As illustrated in FIG. 37A, train-on period $T_{ON}$ can comprise a series of monophasic pulses (5 monophasic pulses shown), after which a charge recovery (e.g. a passive charge recovery) pulse is delivered. The monophasic pulses can comprise an amplitude between 0.01 mA and 20 mA, such as an amplitude between 0.05 mA and 20 mA, or between 0.5 mA and 2.5 mA.

In some embodiments, apparatus 10 is configured to provide a stimulation waveform comprising a compliance optimized burst by delivering one or more stimulation waveforms comprising a repeated cycle of "burst-on" periods $B_{ON}$ followed by "burst-off" periods $B_{OFF}$, as shown. Each burst-on period $B_{ON}$ can comprise one or more sets of $T_{ON}$ and $T_{OFF}$ periods. Each burst-on period $B_{ON}$ can comprise between 2 and 1000 $T_{ON}$ periods (e.g. between 2 and 1000 pairs of $T_{ON}$ and $T_{OFF}$ periods, or trains, five trains shown). The various train periods $T_{ON}$ can be similar or different (similar or different number of pulses, lengths of time, and the like). Each burst-off period $B_{OFF}$ can comprise a time period between 1 μsec and 10 seconds. Each burst-off period $B_{OFF}$ can comprise a charge recovery slot, into which a charge recovery pulse in the opposite phase can be delivered. Alternatively or additionally, charge recovery can be achieved by passive means (e.g. one or more stimulation-delivering electrodes, functional elements 260, are allowed to simply discharge into tissue, such as by being electrically connected together such that the accumulated charge discharges in an opposite direction to the stimulation pulse), without actively delivering a pulse of opposite polarity. In some embodiments, the stimulation waveforms described in FIGS. 37A-B comprise one or more parameters described hereabove in reference to Table 1. In some embodiments, stimulation parameters (e.g. amplitude and/or pulse width) of the stimulation waveforms described in FIGS. 37A-B are varied as described hereabove in reference to FIGS. 35, 36A and/or 36B.

Figure 40:
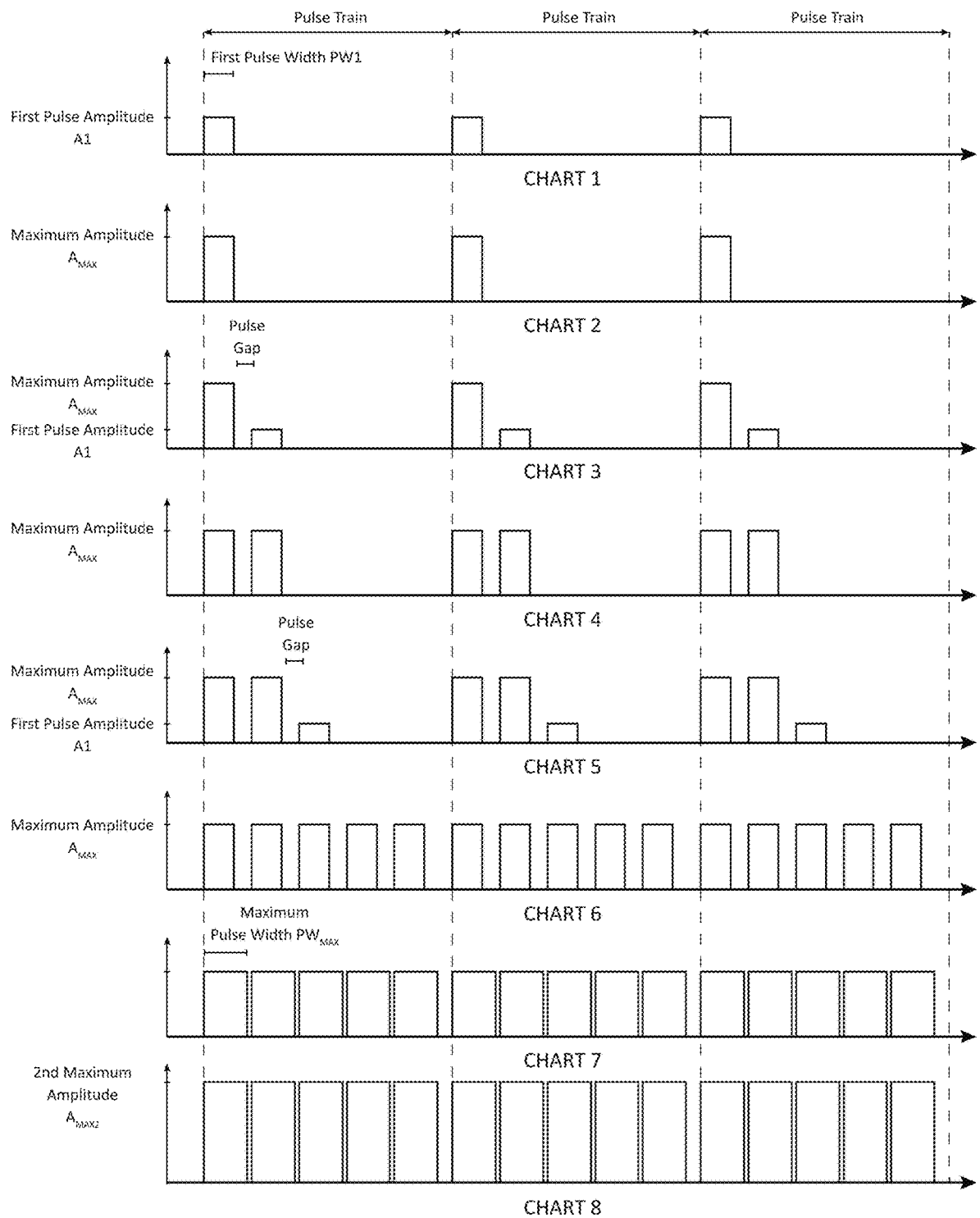
FIG. 40 is a series of charts of varied stimulation waveforms, consistent with the present inventive concepts.

Referring now to FIG. 40, a series of charts of varied stimulation waveforms is illustrated, consistent with the present inventive concepts. Each variation can be used to increase charge to be delivered to a patient by a stimulator such as implantable stimulator 100 described herein. Variation of parameters as described herebelow minimizes power consumption while delivering effective therapy, while also simplifying the patient's experience (e.g. minimizing programming complexity) and reducing programming time, such as has been described hereabove in reference to FIG. 35. Charts 1-8 of FIG. 40 represent the amplitude and pulse width of successive pulse trains of a varied stimulation waveform (3 pulse trains shown in each chart). Chart 1 illustrates a stimulation waveform comprising a single pulse per pulse train, each pulse at a first amplitude, A1, and a pulse width $PW_1$. In order to increase charge delivered via the stimulation waveform of Chart 1, the amplitude of each pulse can be increased, as shown in Chart 2. The amplitude can be increased to a level $A_{MAX}$, in which a compliance threshold and/or other amplitude limiting factor is reached. Amplitude $A_{MAX}$ can be predetermined (e.g. based on a stimulator architecture limitation) or determined at the time of use (e.g. based on the level of one or more other system parameters).

After amplitude $A_{MAX}$ (of the single pulse of each pulse train) has been reached, charge can be further increased by adding a second pulse to the pulse train, as shown in Chart 3. Also as shown in Chart 3, the added pulse can have the same pulse width, $PW_1$, as the first pulse and a minimum amplitude, such as amplitude A1 (of the single pulse of Chart 1). Alternatively, the added pulse can have a different pulse width and/or a different amplitude as compared to the first pulse of each train. The added pulse can be delivered at a predetermined pulse gap from the first pulse. In order to further increase charge delivered, the amplitude of the added, second pulse can be increased (e.g. while the first pulse remains unchanged), as shown in Chart 4. The amplitude can be increased to the previous amplitude limit, $A_{MAX}$, as shown in Chart 4, or to another amplitude limit (e.g. a predetermined or other limit). The adding of another pulse as shown in Chart 3, and/or the increase in amplitude of that added pulse as shown in Chart 4, can be repeated to further increase the charge delivered, until a predetermined maximum number of pulses are added to the pulse trains, and/or the maximum amplitude of each pulse is reached. In Chart 5, a third pulse is added to each pulse train, at amplitude A1. Subsequently, the third pulse's amplitude can be increased (e.g. to $A_{MAX}$), after which a fourth pulse can be added, and so on, until a maximum number of pulses have been sequentially added and subsequently each pulse amplitude increased (e.g. to $A_{MAX}$ before the next pulse is added, as shown in Chart 6).

After a maximum number of pulses have been added to the pulse trains (e.g. as limited by the pulse width of the pulses and the period of the pulse train), and each are at a maximum allowed amplitude (as shown in Chart 6), the pulse width of the pulses can be increased to increase the charge delivered. The pulse width of each pulse can be increased sequentially (e.g. starting with the first pulse, then second, and so on to the last pulse added, as needed), or simultaneously, until a maximum pulse width is reached, $PW_{MAX}$, for each pulse of the pulse train, as shown in Chart 7. The maximum pulse width $PW_{MAX}$ can comprise a pulse width less than the cumulative time of the original pulse width plus the pulse gap between the successive pulses (e.g. to avoid pulse overlap).

After $PW_{MAX}$ is reached, with the pulses at $A_{MAX}$, in order to further increase charge delivered the amplitude of the pulse train can be increased to a second maximum, $A_{MAX2}$, as shown in Chart 8. This stimulation waveform variation described in reference to Charts 1-8 of FIG. 40 can be reversed to decrease the charge delivered. While the stimulation waveform variations of FIG. 40 have been described in a particular order to increase charge (e.g. modification of Chart 2 performed before modification of chart 3, and so on), charge increases can be performed in any order. In some embodiments, decreases in charge are performed sequentially (e.g. change from Chart X to Chart X-1), however charge decreases can also be performed in any order.

The pulse trains of FIG. 40 are shown with no gap between each pulse train, in other words the train-off period is zero, such as is described hereabove in reference to FIGS. 30A-C. In some embodiments, the train-off period can be non-zero, and can be varied, such as to vary the amount of charge delivered over time. The multiple pulse trains (3 shown in each Chart of FIG. 40), can be considered a burst, or part of a burst. Each burst can be separated by a burst-off period, such as a burst-off period that is varied to vary the amount of charge delivered over time, also as described hereabove in reference to FIGS. 30A-C.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A medical apparatus for a patient, comprising:
an implantable system,
wherein the implantable system comprises an implantable device comprising:
at least one implantable functional element configured to generate therapeutic stimulation energy and comprising at least one electrode to deliver the therapeutic stimulation energy to tissue of the patient; and
an implantable controller configured to provide a therapeutic stimulation waveform to the at least one implantable functional element, the therapeutic stimulation waveform comprising one or more therapeutic stimulation parameters,
wherein the therapeutic stimulation energy that is generated and delivered to the tissue of the patient by the at least one electrode comprises the provided therapeutic stimulation waveform,
wherein the therapeutic stimulation waveform comprises bursts of trains of pulses, and
wherein each train comprises a series of pulses and each burst comprises a series of trains,
each train having a train-on period from a beginning of a first pulse of said train to an end of a last pulse of said train, wherein there is a train-off quiescent period between an end of one train and a beginning of a next train, and
each burst having a burst-on period from a beginning of a first pulse of a first train of said burst to an end of a last pulse of a last train of said burst, wherein there is a burst-off quiescent period between an end of one burst and a beginning of a next burst, and
wherein the therapeutic stimulation waveform comprises a plurality of waveform parameters including the train-on period, the train-off quiescent period, the train-off quiescent period, the burst-on period, and the burst-off quiescent period, said waveform parameters being selected to effect treatment of the patient.

2. The medical apparatus according to claim 1, wherein the train-on period is between 1 μsec and 100 msec.

3. The medical apparatus according to claim 1, wherein the train-off period is between 1 μsec and 100 msec.

4. The medical apparatus according to claim 1, wherein the burst-on period is between 8 msec and 12 msec.

5. The medical apparatus according to claim 1, wherein the burst-off period is between 8 msec and 18 msec.

6. The medical apparatus according to claim 1, wherein the therapeutic stimulation waveform comprises a series of monophasic pulses.

7. The medical apparatus according to claim 1, wherein the therapeutic stimulation waveform comprises a biphasic pulse.

8. The medical apparatus according to claim 1, wherein one or more of the apparatus or the therapeutic stimulation waveform are configured to reduce paresthesia.

9. The medical apparatus according to claim 8, wherein the apparatus is configured to reduce paresthesia by performing a function selected from the group consisting of: incorporating patient feedback; monitoring evoked potentials; using data provided by positional sensors; adjusting stimulation based upon known heuristics; and combinations thereof.

10. The medical apparatus according to claim 8, wherein the apparatus is configured to randomly vary at least one of the one or more therapeutic stimulation parameters to reduce paresthesia.

11. The medical apparatus according to claim 8, wherein the therapeutic stimulation waveform comprises an inter-pulse gap that is varied.

12. The medical apparatus according to claim 11, wherein the inter-pulse gap is varied randomly.

13. The medical apparatus according to claim 1, wherein the therapeutic stimulation waveform comprises an inter-pulse gap with a first duration and an inter-train period with a second duration, and wherein the first duration is less than the second duration.

14. The medical apparatus according to claim 1, wherein the therapeutic stimulation waveform comprises an inter-pulse gap with a duration between 1 μsec and 1 second.

15. The medical apparatus according to claim 14, wherein the therapeutic stimulation waveform comprises an inter-pulse gap with a duration between 1 μsec and 100 μsec.

16. The medical apparatus according to claim 1, wherein the therapeutic stimulation waveform comprises an inter-phase gap with a duration between 10 μsec and 30 μsec.

17. The medical apparatus according to claim 1, wherein the therapeutic stimulation waveform comprises pulses with a pulse width between 1 μsec and 10 msec.

18. The medical apparatus according to claim 17, wherein the therapeutic stimulation waveform comprises pulses with a pulse width between 10 μsec and 300 μsec.

19. The medical apparatus according to claim 18, wherein the therapeutic stimulation waveform comprises pulses with a pulse width between 30 μsec and 90 μsec.

20. The medical apparatus according to claim 1, wherein the therapeutic stimulation waveform comprises a high frequency carrier signal modulated with a low frequency envelope.

21. The medical apparatus according to claim 1, wherein the therapeutic stimulation waveform comprises an envelope with a shape selected from the group consisting of: cosine; cosine-squared; sine; square; rectangle; triangle; symmetric triangle; asymmetric triangle; trapezoid; sawtooth; ramp; linear ramp; and combinations thereof.

22. The medical apparatus according to claim 1, wherein the therapeutic stimulation waveform comprises a duty cycle between 0.1% and 99%.

23. The medical apparatus according to claim 22, wherein the therapeutic stimulation waveform comprises a duty cycle between 1% and 25%.

24. The medical apparatus according to claim 1, wherein the apparatus is configured to randomly vary one or more therapeutic stimulation parameters.

25. The medical apparatus according to claim 24, further comprising a probability distribution, and wherein the apparatus is configured to randomly vary the one or more therapeutic stimulation parameters based on the probability distribution.

26. The medical apparatus according to claim 25, wherein the probability distribution comprises a distribution selected from the group consisting of: a uniform distribution; an arbitrary distribution; a gamma distribution; a normal distribution; a log-normal distribution; a Pareto distribution; a Gaussian distribution; a Poisson distribution; a Rayleigh distribution; a triangular distribution; a statistic distribution; and combinations thereof.

27. The medical apparatus according to claim 25, wherein the apparatus is configured to randomly vary the one or more therapeutic stimulation parameters to elicit a neurostimulation effect selected from the group consisting of: synchronized superthreshold neuronal activation; stochastic activation; sub-paresthesia neuronal stimulation; and combinations thereof.

28. The medical apparatus according to claim 1, wherein the train-on period has a duration between 700 µsec and 1.1 msec.

29. The medical apparatus according to claim 1, wherein the train-off period between trains has a duration between 900 µsec and 1.7 msec.

30. The medical apparatus according to claim 1, wherein one or more of the apparatus or the therapeutic stimulation waveform are configured to treat pain.

31. The medical apparatus according to claim 30, wherein the one or more of the apparatus or the therapeutic stimulation waveform are configured to treat pain selected from the group consisting of: back pain; joint pain; neuropathic pain; tennis elbow; muscle pain; shoulder pain; chronic, intractable pain of the back; chronic intractable pain of the lower limbs; unilateral pain; bilateral pain; neuropathic groin pain; perineal pain; phantom limb pain; complex regional pain syndrome; failed back surgery syndrome; cluster headaches; migraines; inflammatory pain; arthritis; abdominal pain; pelvic pain; and combinations thereof.

32. The medical apparatus according to claim 1, wherein one or more of the apparatus or the therapeutic stimulation waveform are configured to treat a disease or disorder selected from the group consisting of: chronic pain; acute pain; migraine; cluster headaches; urge incontinence; overactive bladder; fecal incontinence; bowel disorders; tremor; obsessive compulsive disorder; depression; epilepsy; inflammation; tinnitus; high blood pressure; heart failure; carpal tunnel syndrome; sleep apnea; obstructive sleep apnea; dystonia; interstitial cystitis; gastroparesis; obesity; mobility issues; arrhythmia; rheumatoid arthritis; dementia; Alzheimer's disease; eating disorder; addiction; traumatic brain injury; chronic angina; congestive heart failure; muscle atrophy; inadequate bone growth; post-laminectomy pain; liver disease; Crohn's disease; irritable bowel syndrome; erectile dysfunction; kidney disease; and combinations thereof.

33. The medical apparatus according to claim 1, wherein the waveform parameters are selected to effect treatment of the patient while minimizing an undesired condition of the patient in response to the therapeutic stimulation energy.

34. The medical apparatus according to claim 33, wherein the undesired condition comprises paresthesia.

* * * * *